US010494620B2

(12) United States Patent
Doudna et al.

(10) Patent No.: US 10,494,620 B2
(45) Date of Patent: *Dec. 3, 2019

(54) METHODS AND COMPOSITIONS FOR MODIFYING A SINGLE STRANDED TARGET NUCLEIC ACID

(71) Applicant: The Regents of the University of California, Oakland, CA (US)

(72) Inventors: Jennifer A. Doudna, Oakland, CA (US); Samuel H. Sternberg, Oakland, CA (US); Mitchell O'Connell, Oakland, CA (US); Benjamin Oakes, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/002,602

(22) Filed: Jun. 7, 2018

(65) Prior Publication Data

US 2018/0273922 A1 Sep. 27, 2018

Related U.S. Application Data

(63) Continuation of application No. 15/036,298, filed as application No. PCT/US2014/069730 on Dec. 11, 2014, now Pat. No. 9,994,831.

(60) Provisional application No. 61/915,432, filed on Dec. 12, 2013.

(51) Int. Cl.
*C12N 9/22* (2006.01)
*C12N 15/113* (2010.01)
*C12P 19/34* (2006.01)
*C12Q 1/6874* (2018.01)

(52) U.S. Cl.
CPC .............. *C12N 9/22* (2013.01); *C12N 15/113* (2013.01); *C12P 19/34* (2013.01); *C12Q 1/6874* (2013.01)

(58) Field of Classification Search
None
See application file for complete search history.

(56) References Cited

U.S. PATENT DOCUMENTS

| 8,697,359 | B1 | 4/2014 | Zhang | |
| 9,267,135 | B2 | 2/2016 | Church et al. | |
| 2014/0068797 | A1* | 3/2014 | Doudna | C12N 15/102 800/18 |
| 2015/0353905 | A1* | 12/2015 | Weiss | C07K 14/195 435/348 |
| 2016/0024524 | A1 | 1/2016 | Joung et al. | |

FOREIGN PATENT DOCUMENTS

WO WO 2014/093595 6/2014

OTHER PUBLICATIONS

Mali et al. (2013) Cas9 as a versatile tool for engineering biology. Nature Methods, 10(10):957-963 (Year: 2013).*
Ran et al. (2013) Genome engineering using the CRISPR-Cas9 system. Nature Protocols, 8(11):2281-2308 (Year: 2013).*
Auer et al., "Highly efficient CRISPR/Cas9-mediated knock-in in zebrafish by homology-independent DNA repair," Genome Res. Oct. 31, 2013.
Chen et al., "LncRNADisease: a database for long-non-coding RNA-associated diseases," Nucleic Acids Res. Nov. 1, 2013; 41(20): e19.
Cheng et al., "Multiplexed activation of endogenous genes by CRISPR-on, an RNA-guided transcriptional activator system," Cell Res. Oct. 2013; 23(10): 1163-71.
Cho et al., "Heritable Gene Knockout in *Caenorhabditis elegans* by Direct Injection of Cas9-sgRNA Ribonucleoproteins," Genetics. Nov. 2013; 195(3): 1177-80.
Chylinski et al., "The tractRNA and Cas9 families of type II CRISPR-Cas immunity systems," RNA Biol. May 2013; 10(5): 726-37.
Cong et al., "Multiplex genome editing using CRISPR/Cas Systems"; Science, Jan. 3, 2013, vol. 339, No. 6121, pp. 819-823. Entire document.
Dicarlo et al., "Genome engineering in *Saccharomyces cerevisiae* using CRISPR-Cas systems," Nucleic Acids Res. Apr. 2013; 41(7): 4336-43.
Dickinson et al., "Engineering the Caenorhabditis elegans genome using Cas9-triggered homologous recombination," Nat Methods. Oct. 2013; 10(10): 1028-34.
Ebina et al., "Harnessing the CRISPR/Cas9 system to disrupt latent HIV-1 provirus," Sci Rep. 2013: 3:2510.
Fujii et al., "Efficient generation of large-scale genome-modified mice using gRNA and CAS9 endonuclease," Nucleic Acids Res. Nov. 1, 2013 ; 41(20): e187.
Gasiunas, et al.; "Cas9-crRNA ribonucleoprotein complex mediates specific DNA cleavage for adaptive immunity in bacteria." PNAS, E2579-E2586 (2012).

(Continued)

*Primary Examiner* — Neil P Hammell
(74) *Attorney, Agent, or Firm* — Bozicevic Field & Francis, LLP; Paula A. Borden

(57) ABSTRACT

The present disclosure provides compositions and methods for binding and/or cleaving a single stranded target nucleic acid. Subject compositions include a Cas9 polypeptide, a guide nucleic acid, and a PAMmer. A subject PAMmer is a single stranded oligonucleotide having a protospacer adjacent motif (PAM) sequence and at least one of: a specifity segment positioned 5' of the PAM sequence, and an orientation segment positioned 3' of the PAM sequence. In some embodiments, the Cas9 polypeptide is a variant Cas9 polypeptide having reduced nuclease activity relative to a corresponding wild type Cas9 polypeptide. In some cases, methods of binding are for visualizing single stranded target nucleic acids using a detectable label. In some cases, methods of binding are for isolating, collecting, and/or analyzing at least one of: (i) bound single stranded target nucleic acids; and (ii) polypeptides associated with bound single stranded target nucleic acids.

22 Claims, 55 Drawing Sheets

Specification includes a Sequence Listing.

(56) References Cited

OTHER PUBLICATIONS

Hou et al., "Efficient genome engineering in human pluripotent stem cells using Cas9 from *Neisseria meningitides*," Proc Natl Acad Sci U S A. Sep. 24, 2013; 110(39): 15644-9.

Hsu et al., "DNA targeting specificity of RNA-guided Cas9 nucleases," Nat Biotechnol. Jul. 21, 2013, vol. 31, pp. 827-832. Entire document.

Hu et al., "Heritable gene-targeting with gRNA/Cas9 in rata," Cell Res. Nov. 2013, 23(11): 1322-5.

Jiang et al., "Demonstration of CRISPR/CAs0/sgRNA-mediated targeted gene modification in Arabidopsis, tobacco, sorghum and rice," Nucleic Acids Res. Nov. 1, 2013; 41(20): 3188.

Jinek et al., "A programmable dual-RNA-guided DNA endonuclease in adaptive bacterial immunity" Science, Jun. 28, 2012, vol. 337, No. 6096, pp. 816-821. Entire document.

Jinek et al., "RNA-programmed genome editing in human cells," eLIFE. 2013; 2:e00471.

Larson et al., "CRISPR interference (CRISPRi) for sequence-specific control of gene expression," Nat Protoc. Nov. 2013; 8(11): 2180-96.

Ma et al., "A Guide RNA Sequence Design Platform for the CRISPR/Cas9 System for Model Organism Genomes," Biomed Red Int. 2013; 2013: 270805.

Mali et al., "Cas9 as a versatile tool for engineering biology," Nat Methods, Oct. 2013; 10(10): 957-63.

Nakayama et al., "Simple and efficient CRISPR/Cas9-mediated targeted mutagenesis in Xenopus tropicalis," Genesis. Dec. 2013; 51(12): 835-43.

O'Connell et al., "Programmable RNA recognition and cleavage by CRISPR/Cas9," Nature, Sep. 28, 2014, vol. 516, No. 7530. pp. 263-266. Entire document.

Pattanyak et al., "High-through-put profiling of off-target DNA cleavage reveals RNA-programmed Cas9 nuclease specificity," Nat Biotechnol. Sep. 2013; 31(9): 839-43.

Q99ZW2 (*Streptococcus pyogenes* CRISPR-associated endonuclease Cas9/Csn1, NCB I Reference Sequence, priority to Nov. 28, 2006).

Qi et al., "Repurposing CRISPR as an RNA-Guided Platform for Sequence-Specific Control of Gene Expression," Cell. 2013 Fen 28; 152(5): 1173-83.

Ran et al., "Double nicking by RNA-guided CRISPR Cas9 for enhanced genome editing specificity," Cell. Sep. 12, 2013; 154(6):1380-9.

Ran et al., "Genome engineering using the CRISPR-Cas9 system," Nat Protoc. Nov. 2013; 8(11): 2281-308.

Sampson, et al.; "A CRISPR-CAS System Mediates Bacterial Innate Immune Evasion and Virulence"; Nature; vol. 497, No. 7448, pp. 254-257 (May 9, 2013).

Sampson, et al.; "Exploiting CRISPR/CAS systems for biotechnology," Bioessays, 36:34-38 (Year: 2013).

Sternberg et al., "DNA interrogation by the CRISPR RNA-guided endonuclease Cas9," Nature, Jan. 29, 2014, vol. 507, No. 7490, p. 62-67. Entire document.

Upadhyay et al., "RNA-Guided Genome Editing for Target Gene Mutations in Wheat," G3 (Bethesda). Dec. 9, 2013; 3(12): 2233-8.

Walsh et al., "A variant CRISPR-Cas9 system adds versatility to genome engineering," Proc Natl Acad Sci U S A. Sep. 24, 2013; 110(39): 15514-5.

Wang et al., "One-step generation of mice carrying mutations in multiple genes by CRISPR/Cas-mediated genome engineering," Cell. May 9, 2013: 153(4): 910-8.

WP 011 054416 (*Streptococcus pyogenes* type II CRISPR RNA-guided endonuclease Cas9, NCB I Reference Sequence, priority to May 15, 2013, 1 page).

Xie et al., "RNA-guided genome editing in plants using a CRISPR-Cas system," Mol Plant. Oct. 9, 2013.

Yang et al., "One-step generation of mice carrying reporter and conditional alleles by CRISPR/Cas-mediated genome engineering," Cell. Sep. 12, 2013; 154(6): 1370-9.

Sampson, et al.; "Author Correction: A CRISPR/Cas system mediates bacterial innate immune evasion and virulence"; Nature; vol. 570, 2 pages (Jun. 13, 2019).

Mate, et al.; "Structure-based Analysis of the Metal-dependent Mechanism of H-N-H Endonucleases"; The Journal of Biological Chemistry; vol. 279, Issue of Aug. 13, pp. 34763-34769 (2004).

Pommer, et al.; "Enzymological characterization of the nuclease domain from the bacterial toxin colicin E9 from *Escherichia coli*"; Biochem. J.; vol. 334, pp. 387-392 (1998).

Pommer, et al.; "Mechanism and Cleavage Specificity of the H-N-H Endonuclease Colicin E9"; J. Mol. Biol.; vol. 314, pp. 735-749 (2001).

* cited by examiner

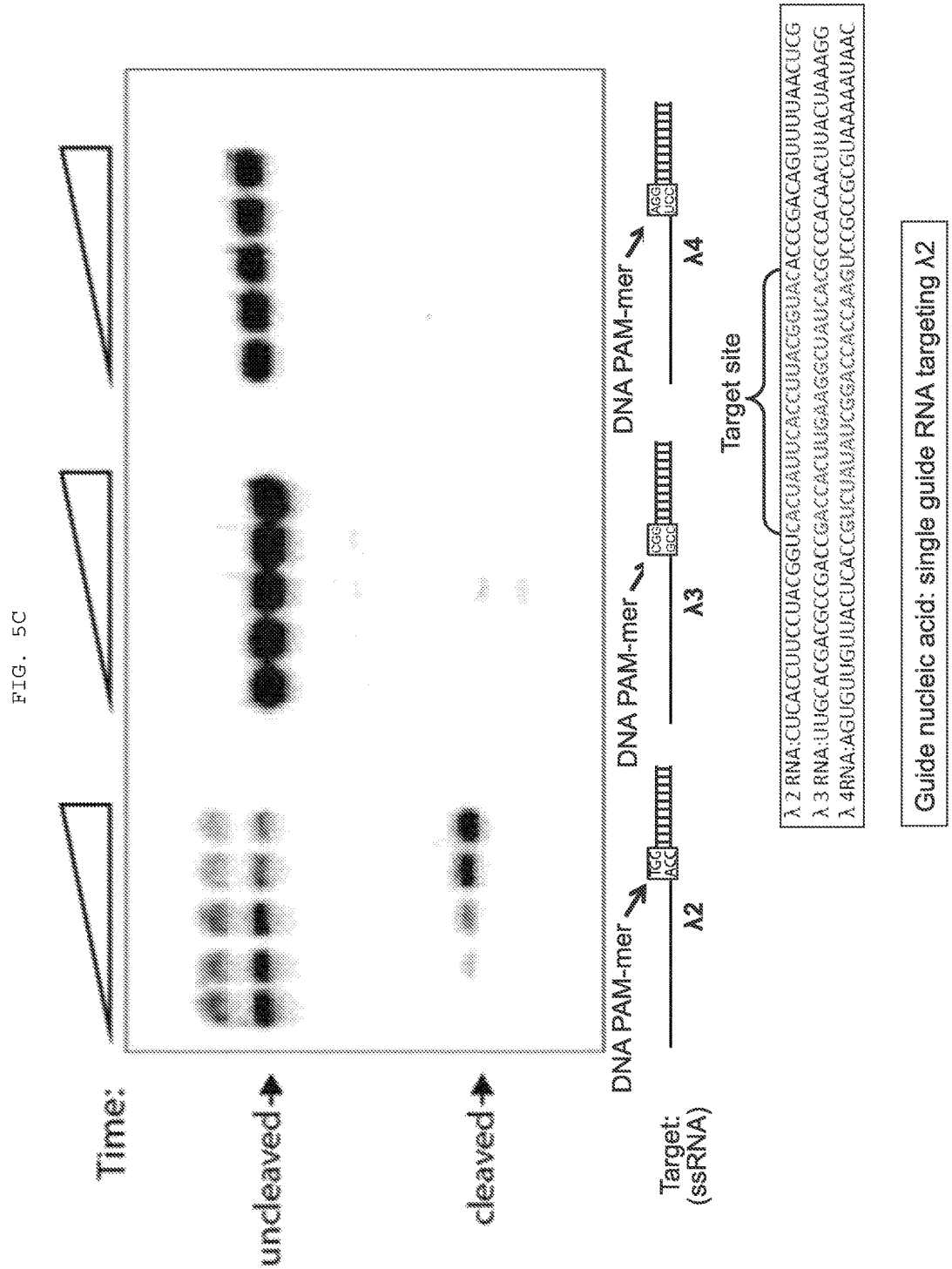

FIG. 9A

Cas9/Csn1 Streptococcus pyogenes motifs
              *
1 MDKKYSIGLDIGTNSVGWAVITDDYKVPSKKLKGLGNTDRHGIKKNLIGALL
  FDSGETAEATRLKRTARRRYTRRKNRICYLQEIFSNEMAKVDDSFFHRLEE
  SFLVEEDKKHERHPIFGNIVDEVAYHEKYPTIYHLRKKLADSTDKVDLRLIYL
  ALAHMIKFRGHFLIEGDLNPDNSDVDKLFIQLVQTYNQLFEENPINASRVDA
  KAILSARLSKSRRLENLIAQLPGEKKNGLFGNLIALSLGLTPNFKSNFDLAED
  AKLQLSKDTYDDDLDNLLAQIGDQYADLFLAAKNLSDATLLSDILRVNSEITK
  APLSASMIKRYDEHHQDLTLLKALVRQQLPEKYKEIFFDQSKNGYAGYIDGG
  ASQEEFYKFIKPILEKMDGTEELLAKLNREDLLRKQRTFDNGSIPYQIHLGEL
  HAILRRQEDFYPFLKDNREKIEKILTFRIPYYVGPLARGNSRFAWMTRKSEE
  TITPWNFEEVVDKGASAQSFIERMTNFDKNLPNEKVLPKHSLLYEYFTVYN
  ELTKVKYVTEGMRKPAFLSGEQKKAIVDLLFKTNRKVTVKQLKEDYFKKIEC
  FDSVEISGVEDRFNASLGTYHDLLKIIKDKDFLDNEENEDILEDIVLTLTLFED
  REMIEERLKTYAHLFDDKVMKQLKRRRYTGWGRLSRKLINGIRDKQSGKTI
  LDFLKSDGFANRNFMQLIHDDSLTFKEDIQKAQVSGQGDSLHEHIANLAGS
2 PAIKKGILQTVKVVDELVKVMGRHKPENIVIEMARENQTTQKGQKNSRERM
  KRIEEGIKELGSDILKEYPVENTQLQNEKLYLYYLQNGRDMYVDQELDINRL
3 SDYDVDHIVPQSFLKDDSIDNKVLTRSDKNRGKSDNVPSEEVVKKMKNYW
  RQLLNAKLITQRKFDNLTKAERGGLSELDKVGFIKRQLVETRQITKHVAQILD
4 SRMNTKYDENDKLIREVRVITLKSKLVSDFRKDFQFYKVREINNYHHAHDAY
  LNAVVGTALIKKYPKLESEFVYGDYKVYDVRKMIAKSEQEIGKATAKYFFYS
  NIMNFFKTEITLANGEIRKRPLIETNGETGEIVWDKGRDFATVRKVLSMPQV
  NIVKKTEVQTGGFSKESILPKRNSDKLIARKKDWDPKKYGGFDSPTVAYSVL
  VVAKVEKGKSKKLKSVKELLGITIMERSSFEKDPIDFLEAKGYKEVRKDLIIKL
  PKYSLFELENGRKRMLASAGELQKGNELALPSKYVNFLYLASHYEKLKGSP
  EDNEQKQLFVEQHKHYLDEIIEQISEFSKRVILADANLDKVLSAYNKHRDKPI
  REQAENIIHLFTLTNLGAPAAFKYFDTTIDRKRYTSTKEVLDATLIHQSITGLY
  ETRIDLSQLGGD

FIG. 9B

Cas9/Csn1 Streptococcus pyogenes

Domains

1 MDKKYSIGLDIGTNSVGWAVITDDYKVPSKKLKGLGNTDRHGIKKNLIGAL
LFDSGETAEATRLKRTARRRYTRRKNRICYLQEIFSNEMAKVDDSFFHRLE
ESFLVEEDKKHERHPIFGNIVDEVAYHEKYPTIYHLRKKLADSTDKVDLRLI
YLALAHMIKFRGHFLIEGDLNPDNSDVDKLFIQLVQTYNQLFEENPINASRV
DAKAILSARLSKSRRLENLIAQLPGEKKNGLFGNLIALSLGLTPNFKSNFDLA
EDAKLQLSKDTYDDDLDNLLAQIGDQYADLFLAAKNLSDATLLSDILRVNSEI
TKAPLSASMIKRYDEHHQDLTLLKALVRQQLPEKYKEIFFDQSKNGYAGYID
GGASQEEFYKFIKPILEKMDGTEELLAKLNREDLLRKQRTFDNGSIPYQIHL
GELHAILRRQEDFYPFLKDNREKIEKILTFRIPYYVGPLARGNSRFAWMTRK
SEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKI
ECFDSVEISGVEDRFNASLGTYHDLLKIIKDKDFLDNEENEDILEDIVLTLTLF
EDREMIEERLKTYAHLFDDKVMKQLKRRRYTGWGRLSRKLINGIRDKQSG
KTILDFLKSDGFANRNFMQLIHDDSLTFKEDIQKAQVSGQGDSLHEHIANLA
2 GSPAIKKGILQTVKVVDELVKVMGRHKPENIVIEMARENQTTQKGQKNSR
ERMKRIEEGIKELGSDILKEYPVENTQLQNEKLYLYYLQNGRDMYVDQEL
DINRLSDYDVDHIVPQSFLKDDSIDNKVLTRSDKNRGKSDNVPSEEVVKK
MKNYWRQLLNAKLITQRKFDNLTKAERGGLSELDKVGFIKRQLVETRQIT
KHVAQILDSRMNTKYDENDKLIREVRVITLKSKLVSDFRKDFQFYKVREIN
NYHHAHDAYLNAVVGTALIKKYPKLESEFVYGDYKVYDVRKMIAKSEQEIG
KATAKYFFYSNIMNFFKTEITLANGEIRKRPLIETNGETGEIVWDKGRDFATV
RKVLSMPQVNIVKKTEVQTGGFSKESILPKRNSDKLIARKKDWDPKKYGGF
DSPTVAYSVLVVAKVEKGKSKKLKSVKELLGITIMERSSFEKDPIDFLEAKGY
KEVRKDLIIKLPKYSLFELENGRKRMLASAGELQKGNELALPSKYVNFLYLA
SHYEKLKGSPEDNEQKQLFVEQHKHYLDEIIEQISEFSKRVILADANLDKVL
SAYNKHRDKPIREQAENIIHLFTLTNLGAPAAFKYFDTTIDRKRYTSTKEVLD
ATLIHQSITGLYETRIDLSQLGGD

FIG. 10

|  | Motif 1 | Motif 2 | Motif 4 |
|---|---|---|---|
| S. pyogenes | ...IGLDIGTNSVGWAVI... | ...IVIEMARE... | ...HHAHDAYL... |
| L. pneumophila | ...IGIDLGGKFTGVCLS... | ...MMQRLAYE... | ...SHAIDATL... |
| G. proteobacterium | ...IAIDLGAKFTGVALY... | ...IIEHIARK... | ...SHVVDAVC... |
| L. innocua | ...IGLDIGTNSVGWAVL... | ...IVVEMARE... | ...HHAHDAYL... |
| L. gasseri | ...VGLDVGTNSCGWVAM... | ...IAIEFTRD... | ...HHAIDAYL... |
| E. rectale | ...LALDIGIASVGWAIL... | ...IVIEMPRD... | ...HHAVDAML... |
| S. lugdunensis | ...LGLDIGITSVGYGLI... | ...IIIELARE... | ...HHAEDALI... |
| M. synoviae | ...IGFDLGVASVGWSIV... | ...VVIEMARE... | ...HHAVDASI... |
| M. mobile | ...LGLDLGIASVGWCLT... | ...IVVEVTRS... | ...HHAEDAYF... |
| W. succinogenes | ...LGVDLGISSLGWAIV... | ...VHFELARE... | ...HHAVDAII... |
| F. columnare | ...LGLDLGTNSIGWAIR... | ...IHIEMARE... | ...HHTIDAIT... |
| F. succinogenes | ...LGLDLGTNSIGWAVV... | ...IHLELGRD... | ...HHAMDAIV... |
| B. fragilis | ...LGLDLGTNSIGWALV... | ...IRVELARE... | ...HHAMDALT... |
| A. cellulolyticus | ...LGVDVGERSIGLAAV... | ...IVVELARG... | ...HHAVDAVV... |
| B. dentium | ...IGIDVGLMSVGLAAI... | ...VQIEHVRE... | ...HHAVDAAV... |

|  | Motif 3 |
|---|---|
| S. pyogenes | ...DVDHIVPQSFLKD------DSIDNKVLTRSDKN... |
| L. pneumophila | ...EIDHIYPRSLSKKHFGVIFNSEVNLIYCSSQGN... |
| G. proteobacterium | ...EIDHIIPRSLTGRTKKTVFNSEANLIYCSSKGN... |
| L. innocua | ...DIDHIVPQSFITD------NSIDNLVLTSSAGN... |
| L. gasseri | ...DIDHILPQSFIKD------DSLENRVLVKKAVN... |
| E. rectale | ...EIDHIIPRSISFD------DARSNKVLVYRSEN... |
| S. lugdunensis | ...EVDHIIPRSVSFD------NSYHNKVLVKQSEN... |
| M. synoviae | ...EIDHVIPYSKSAD------DSWFNKLLVKKSTN... |
| M. mobile | ...DIDHIVPRSISFD------DSFSNLVIVNKLDN... |
| W. succinogenes | ...EIDHILPRSRSAD------DSFANKVLCLARAN... |
| F. columnare | ...DIEHTIPRSISQD------NSQMNKTLCSLKFN... |
| F. succinogenes | ...EIEHVIPQSLYFD------DSFSNKVICEAEVN... |
| B. fragilis | ...DIEHIIPQARLFD------DSFSNKTLEARSVN... |
| A. cellulolyticus | ...ELDHIVPRTDGG------SNRHENLAITCGACN... |
| B. dentium | ...EMDHIVPRKGVGS------TNTRVNLAAACAACN... |

FIG. 12A

```
                    1                                    36
    L. innocua   (1) GUUUUAGAGCUAUGUUAUUUUGAAUGCUAACAAAAC
    S. pyogenes  (1) GUUUUAGAGCUAUGCUGUUUUGAAUGGUCCCAAAAC
      S. mutans  (1) GUUUUAGAGCUGUGUUGUUUCGAAUGGUUCCAAAAC
 S. thermophilus1 (1) GUUUUAGAGCUGUGUUGUUUCGAAUGGUUCCAAAAC
```

FIG. 12B

```
                     1                                     37
      C. jejuni   (1) AUUUUACC-AUAAAGAAAUUUAAAAAGGGACUAAAAC
      S. pyogenes (1) GUUUUAGA-GCUAUGCUGUUUUGAAUGGUCCCAAAAC
      F. novicida (1) GUUUCAGUUGCUGAAUUAUUGGUAAACUACUGUUAG
       M. mobile  (1) GUUUUGGU-GUAGUAUCAUUCUUAUGUAUUCUUAAAC
  N. meningitidis (1) GUUGUAGC-UCCCUUUCUCAUUUCGCAGUGCUACAAU
     P. multocida (1) GUUGUAGU-UCCCUCUCUCAUUUCGCAGUGCUACAAU
 S. thermophilus2 (1) GUUUUUGU-ACUCUCAAGAUUUAAGUAACUGUACAAC
```

*Streptococcus pyogenes*

Base-pairing *in vivo* (crRNA /tracrRNA)

```
                          crRNA (targeter)
                              ↓
         5'— variable 20nt -GUUUUAG--AGCUAUGCUGUUUG-3'
                           •|||||•   |||||||||||
  AGCCACGGUGAAAAAGUUCAACUAUUGCCUGAUCGGAAUAAAAUUGAACGAUACGACAAA-5'
  G |||||||
    UCGGUGCUUUUUUU-3'
                              ↑
                        tracrRNA (activator)
```

Example of a single guide nucleic acid

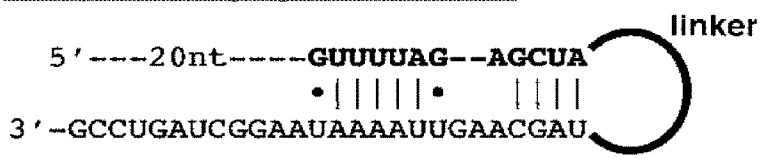

*Listeria innocua*

Base-pairing *in vivo* (crRNA /tracrRNA)

Example of a single guide nucleic acid

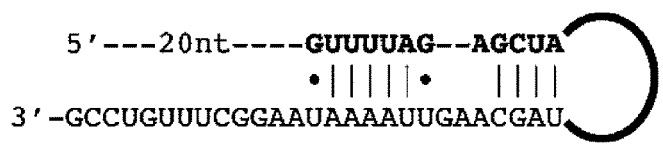

FIG. 15A

| Fusion Partner (for RNA targets) | Exemplary Function |
|---|---|
| Splicing factors (e.g., RS domains) | Allow Cas9 to affect splicing choices |
| Translation factors (e.g., initiation, elongation, release, etc.) (e.g., eIF4G) | Allow sequence specific recruitment of the ribosome to particular messages independent of the presence of a 5' cap structure |
| RNA methylases | Methylation of RNA targets |
| RNA deaminases (e..g, ADAR (adenosine deaminase acting on RNA)) | Deamination of RNA targets (e.g,. A to I and/or C to U editing of RNA targets |
| helicases | Unwind secondary structure (duplexes) |
| RNA-binding proteins | |

FIG. 15B

| Protein name | Function |
|---|---|
| Transcriptional Activators | |
| GAL4 | Transcription activation |
| VP16 | Transcription activation |
| VP64 | Transcription activation |
| p65 subdomain (NFkB) | Transcription activation |
| Transcriptional repressors | |
| KRAB | Transcription repression |
| Mad mSIN3 interaction domain (SID) | Transcription repression |
| the ERF repressor domain (ERD) | Transcription repression |
| Histone lysine methyltransferases (KMT) | |
| KMT1 family: SUV39H1, SUV39H2, G9A, ESET/SETDB1, and homologs (Clr4, Su(var)3-9) | Heterochromatin formation/transcription repression |
| KMT2 family: hSET1A, hSET1B, MLL1 to 5, ASH1, and homologs (Trx, Trr, Ash1) | Transcription activation |
| KMT3 family: SYMD2, NSD1 | Transcription activation |
| KMT4: DOT1L and homologs | Transcription activation |
| KMT5 family: Pr-SET7/8, SUV4-20H1, and homologs (PR-set7, Suv4-20, Set9) | DNA damage response, transcription repression |
| KMT6: EZH2 | Polycomb silencing |
| KMT8: RIZ1 | Transcription repression |
| Histone lysine demethylates (KDM) | |
| KDM1: LSD1/BHC110 and homologs (SpLsd1/Swm1/Saf110, Su(var)3-3) | Transcription activation and repression, heterochromatin formation |
| KDM3 family: JHDM2a/b | Androgen receptor gene activation, spermatogenesis |
| KDM4 family: JMJD2A/JHDM3A, JMJD2B, JMJD2C/GASC1, JMJD2D, and homologs (Rph1) | Transcription elongation, transcription repression, heterochromatin formation, genome integrity |
| KDM5 family: JARID1A/RBP2, JARID1B/PLU-1, JARID1C/SMCX, JARID1D/SMCY, and homologs (Lid, Jhn2, Jmj2) | Transcription repression |
| KDM6 family: UTX, JMJD3 | Transcription activation |

FIG. 15C

| Protein name | Function |
|---|---|
| Histone lysine acetyltransferases (KAT) | |
| KAT2 family: hGCN5, PCAF, and homologs (dGCN5/PCAF, Gcn5) | Transcription activation, DNA repair |
| KAT3 family: CBP, p300, and homologs (dCBP/NEJ) | Transcription activation, DNA repair |
| KAT4: TAF1 and homologs (dTAF1) | Transcription activation |
| KAT5: TIP60/PLIP, and homologs | Transcription activation, DNA repair |
| KAT6: MOZ/MYST3, MORF/MYST4, and homologs (Mst2, Sas3, CG1894) | Transcription activation and elongation, DNA replication |
| KAT7: HBO1/MYST2, and homologs (CHM, Mst2) | Transcription, DNA replication |
| KAT8: HMOF/MYST1, and homologs (dMOF, CG1894, Sas2, Mst2) | Chromatin boundaries, dosage compensation, DNA repair |
| KAT13 family: SRC1, ACTR, P160, CLOCK, and homologs | Transcription activation |
| Histone lysine deacetylases | |
| Class I: HDAC1, HDAC2, HDAC3, HDAC8, and its homologs (Rpd3, Hos1, Cir6) | Transcription repression, heterochromatin formation |
| Class IIa: HDAC4, HDAC5, HDAC7, HDAC9, and its homologs (Hda1, Cir3 etc.) | Transcription repression, heterochromatin formation |
| Class III: SIRT1, SIRT2, and its homologs (Sir2, Hst1, Hst2, Hst3, Hst4) | Transcription repression, heterochromatin formation |
| Class IV: HDAC11 | Transcription repression |
| DNA methylases (adenosine or cytosine modification) | |
| Dam (E. coli) | Restriction system |
| Dcm (E. coli) | Restriction system |
| M. SssI (Spiroplasma sp) | Restriction system |
| DNMT1 | Transcription repression, imprinting, heterochromatin formation |
| DNMT3a/DNMT3b, MET1, DRM3 (plants), and homologs | Transcription repression, imprinting, heterochromatin formation |
| Chromomethylases e.g. ZMET2, CMT1, CMT2 (plants) | Transcription repression, imprinting, heterochromatin formation |
| DNA demethylases | |
| AID/Apobec deaminase family: AID | Transcription activation, genome integrity |
| TET dioxygenase family: TET1 | Transcription activation, genome integrity |
| DEMETER glycosylase family: DME, DML1, DML2, ROS1 | Transcription activation, genome integrity |

FIG. 15D

| Protein name | Function |
|---|---|
| Boundary elements | |
| CTCF | Chromatin insulation, heterochromatin spreading suppression |
| Periphery recruitment elements | |
| Lamin A | Transcription repression |
| Lamin B | Transcription repression |
| Protein docking elements | |
| FKBP/FRB (S. pombe) | rapamycin dependent recruitment |
| Pil1/Aby1 (E. coli) | ABA dependent recruitment |

FIG. 16D

PAM binding loop in SpyCas9

```
Ana  243  . . . . . . . . . . . . . . . . . . . . . . . . . . . . . . . . . . . . . . SRVAPDP
Nme  233  . . . . . . . . . . . . . . . . . . . . . . . . . . . . . . . . . . . . . . SGDAVQK
Cje  224  . . . . . . . . . . . . . . . . . . . . . . . . . . . . . . . . . . . . . . ALKDFSH
Tde  449  FPDRCWVVKKEKSPSGKTTPWNFFDHIDKEKTAEAFITS
Sth  438  . . . AWSIRKR. . . NEKITPWNFEDVIDKESSAEAFINR
Smu  438  . . . AWLSRKS. . . ADKITPWNFDEIVDKESSAEAFINR
Sag  439  . . . AWMTRKT. . . DDSIRPWNFEDLVDKEKSAEAFIHR
Spy  438  . . . AWMTRKS. . . EETITPWNFEEVVDKGASAQSFIER
``` ertion in AnaCas9)          PAM binding loop2 in SpyCas9

```
Ana  878  FSKRKKTDSDRDETPFGAIAVRGFV. . . EI. . GPSIH
Nme  899  . . . . . . EPFYKYDKAGNRTQQVKAVRV. . EQVQK
Cje  801  . . . . . . . . . . . . . . . SYGKEGVLKALEL. . . . . . . . .
Tde  1108 . . LGQ. . HPLKKEGPFSNISKYGYNKVSAAYTLIEYEEK
Sth  1125 . . NSNENL. . VGAKEYLDPKKYGYAGISNSFTVLVKGTIE
Smu  1094 . . NSDKLIPRKTKKFYWDTKKYGFDSPIVAYSILVIADIE
Sag  1113 . . NSDKLIPRKTKDIYLDPKKYGFDSPIVAYSVLVVADIK
Spy  1115 . . NSDKLIARKK. . . DWDPKKYGFDSPTVAYSVLVVAKVE
```

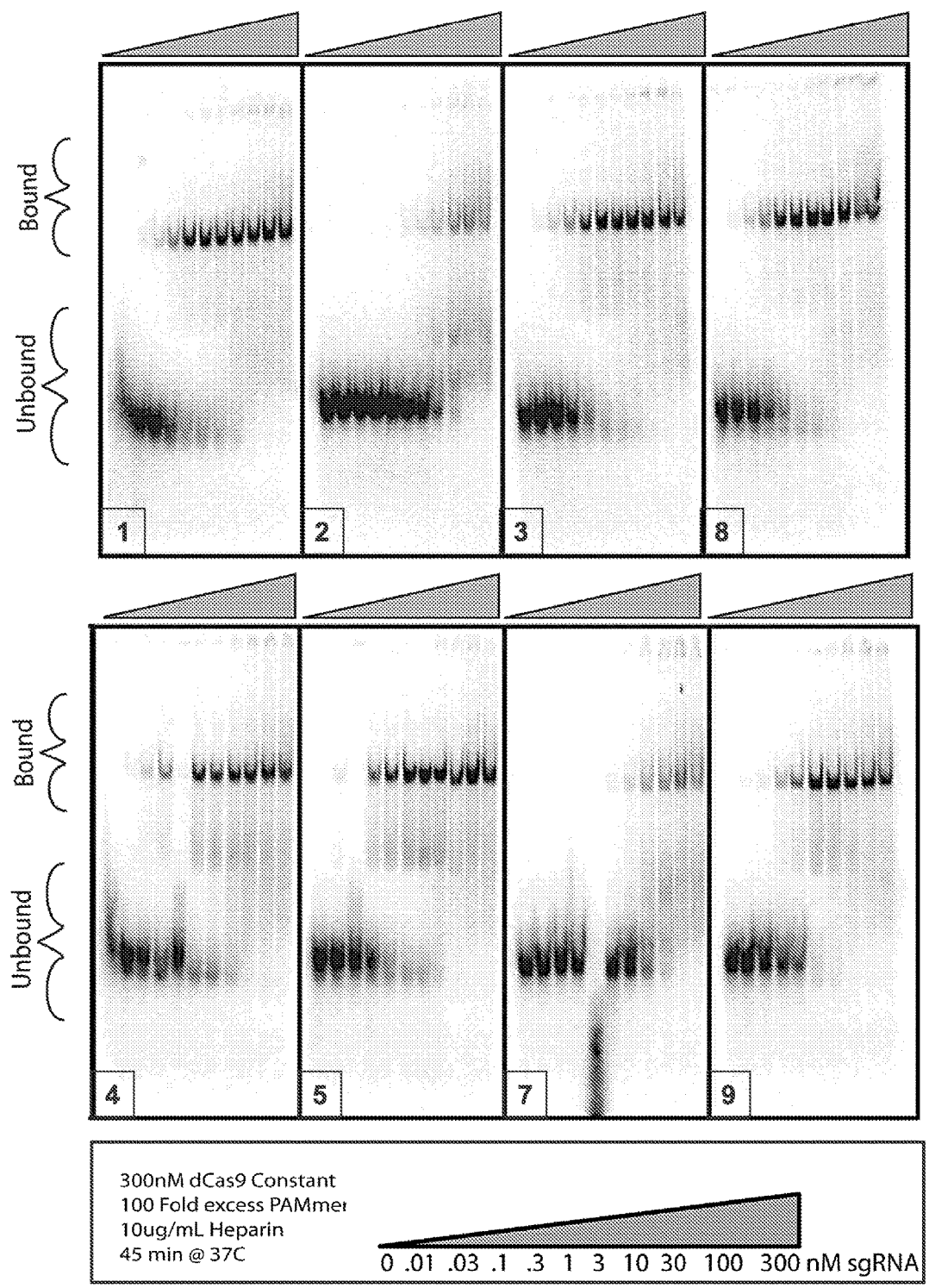

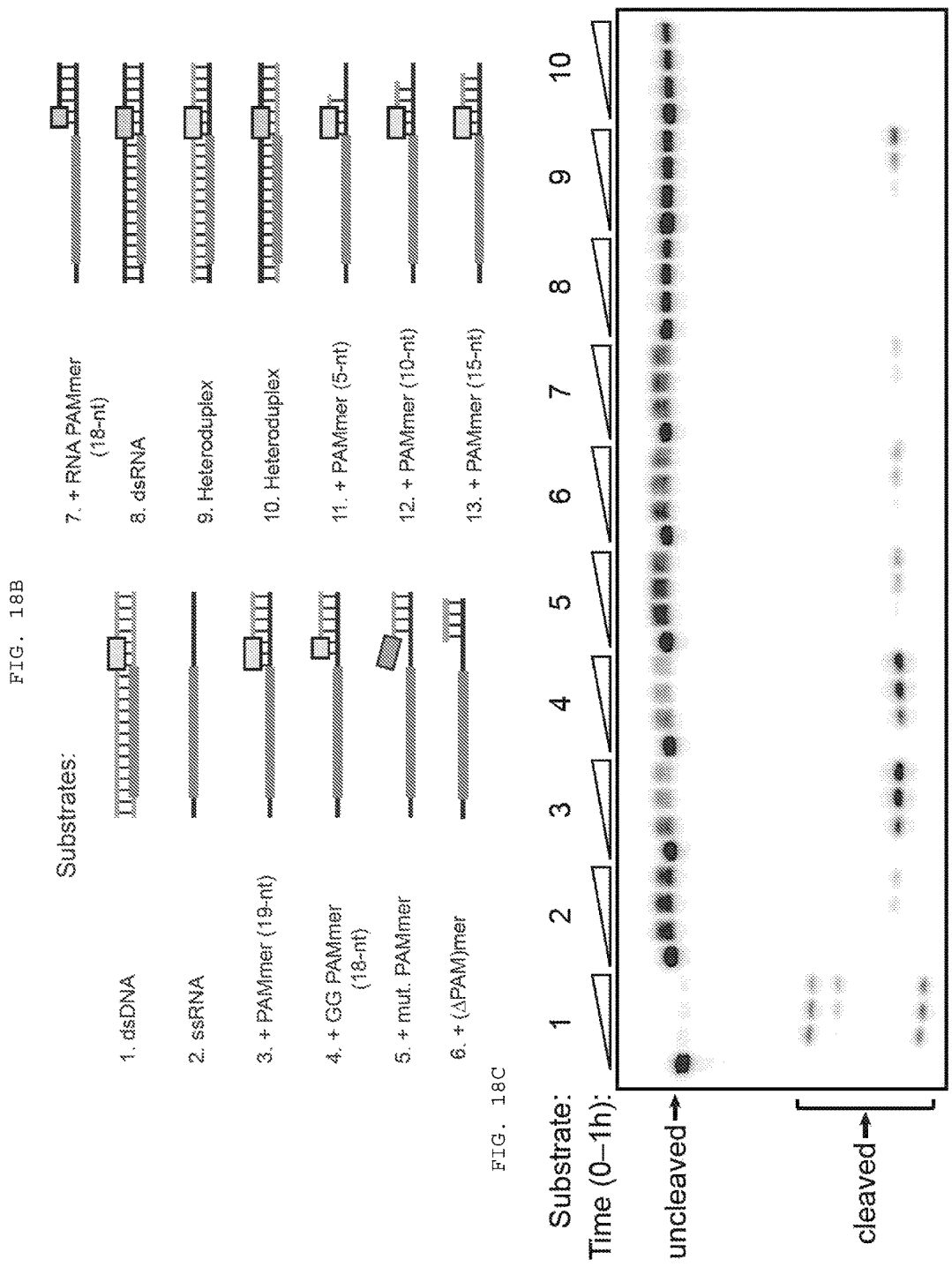

FIG. 18D
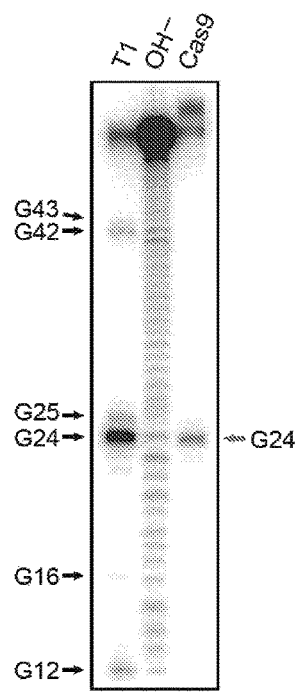
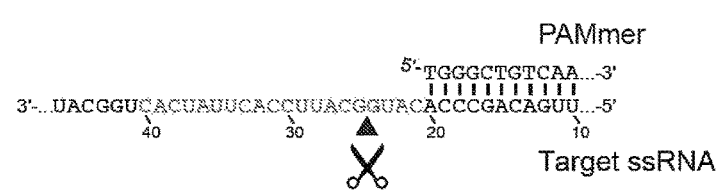
FIG. 18E
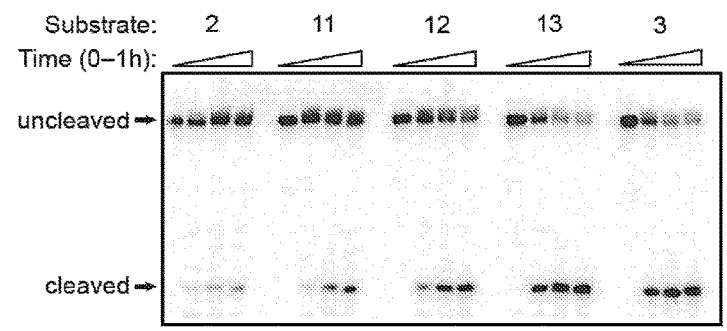

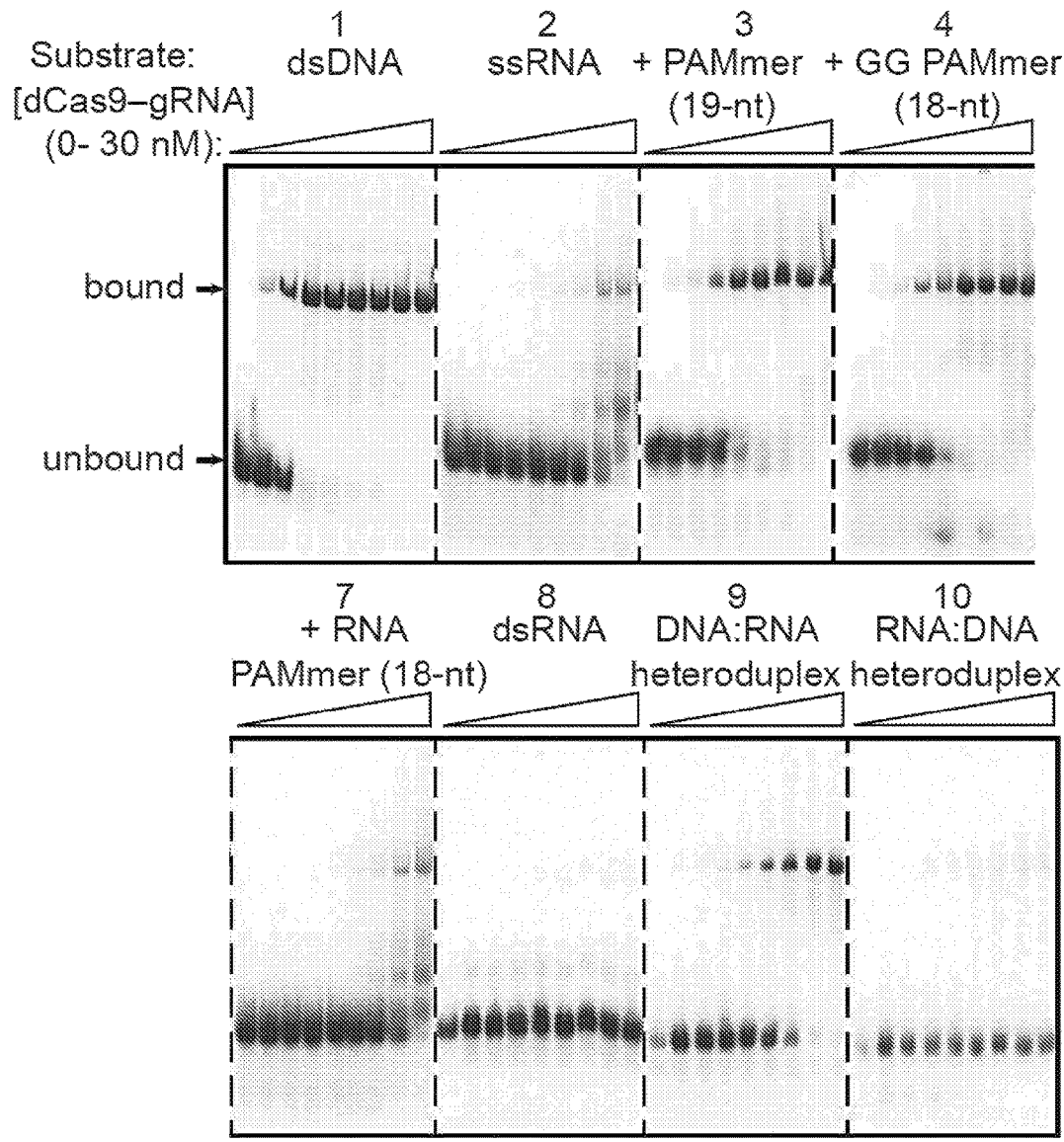

ssRNA + mismatched PAMmer non-PAM dsDNA transcription

Substrates:

1. PAM dsDNA
2. non-PAM dsDNA
3. ssRNA + PAMmer
4. ssRNA + PAMmer, mismatched
5. ssRNA + PAMmer, mismatched & 5'-extended FIG. 21E
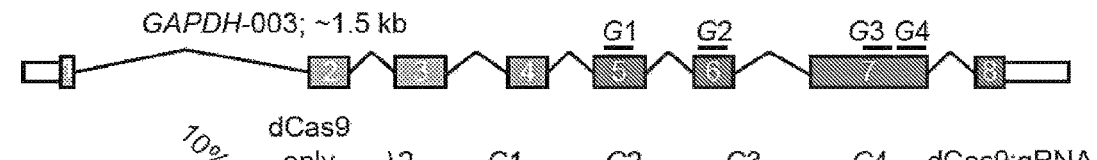
FIG. 21F
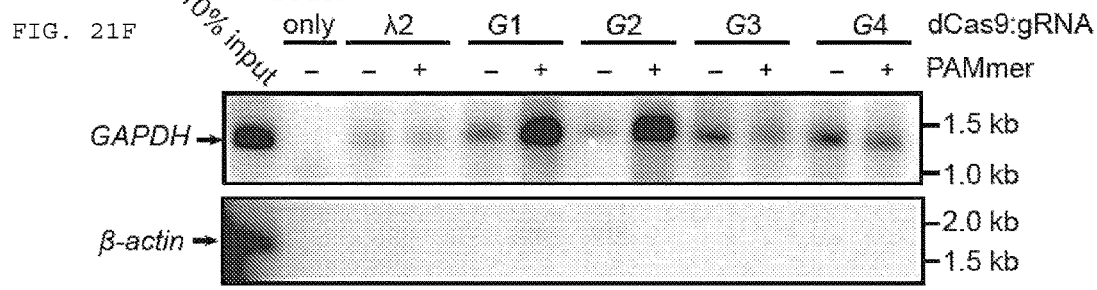
FIG. 21G
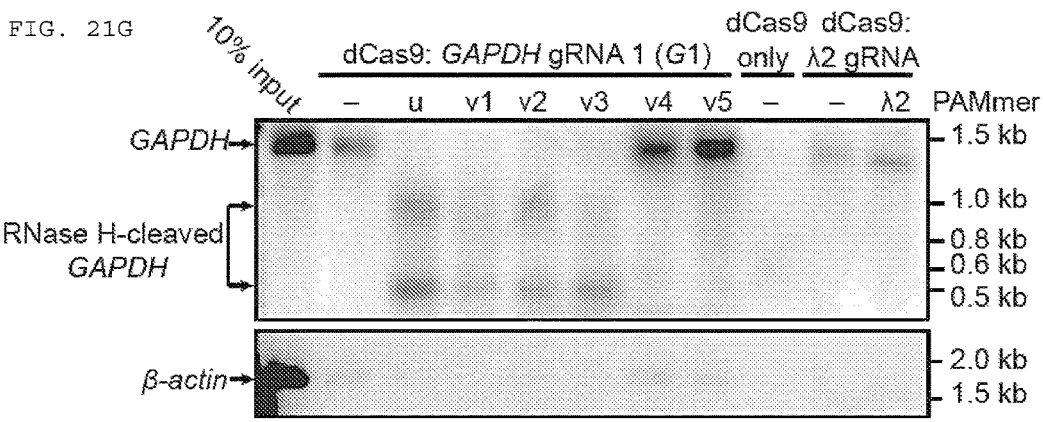
FIG. 21H
```
         5' extension PAM    3' anchor
u:   ATGACCTAGGGGCTCCCCCCTGCAAA
v1:  AUGACCTAGGGGCTCCCCCCUGCAAA
v2:  ATGACCUAGGGGCTCCCCCCTGCAAA
v3:  ATGACCUAGGGGCUCCCCCCTGCAAA
v4:  ATGACCTAGGGGCTCCCCCCUGCAAA
v5:  ATGACCTAGGGGCUCCCCCCTGCAAA
```

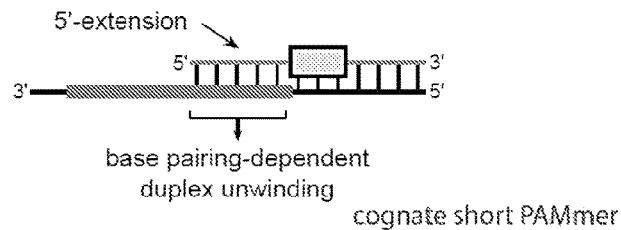
FIG. 24
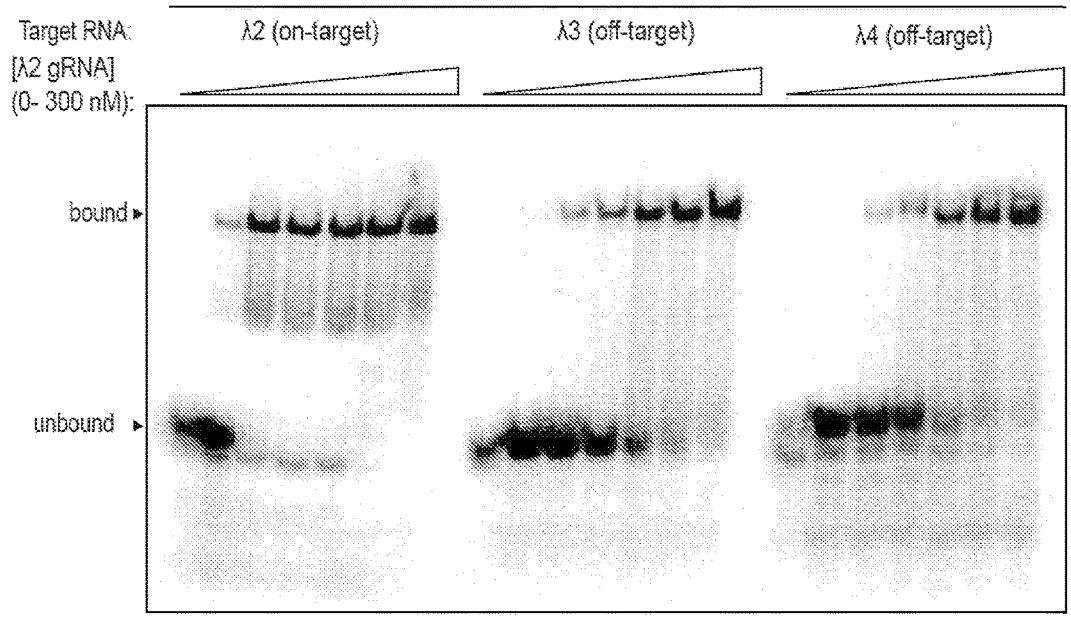
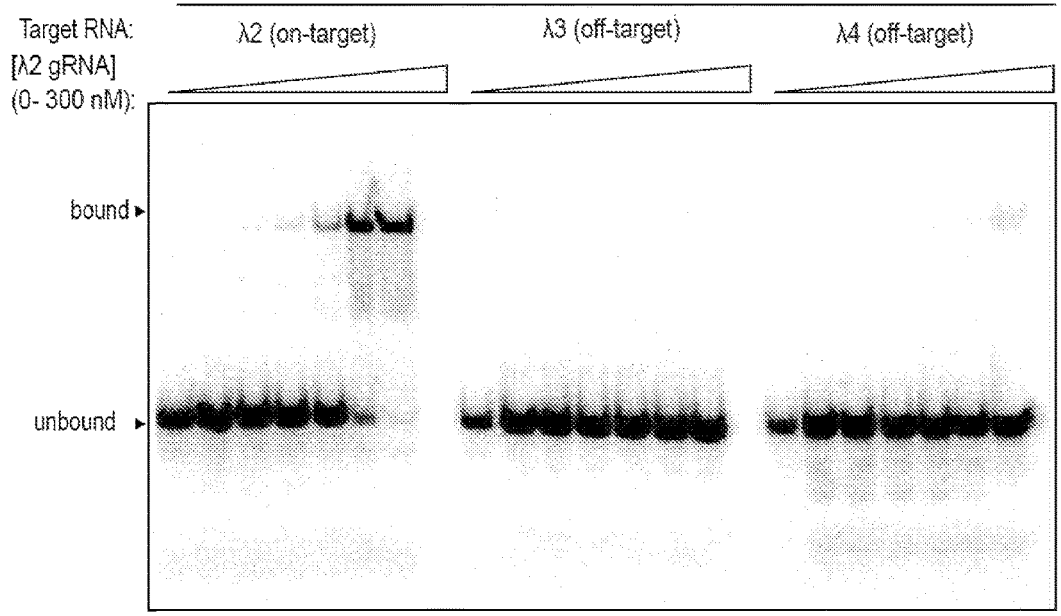

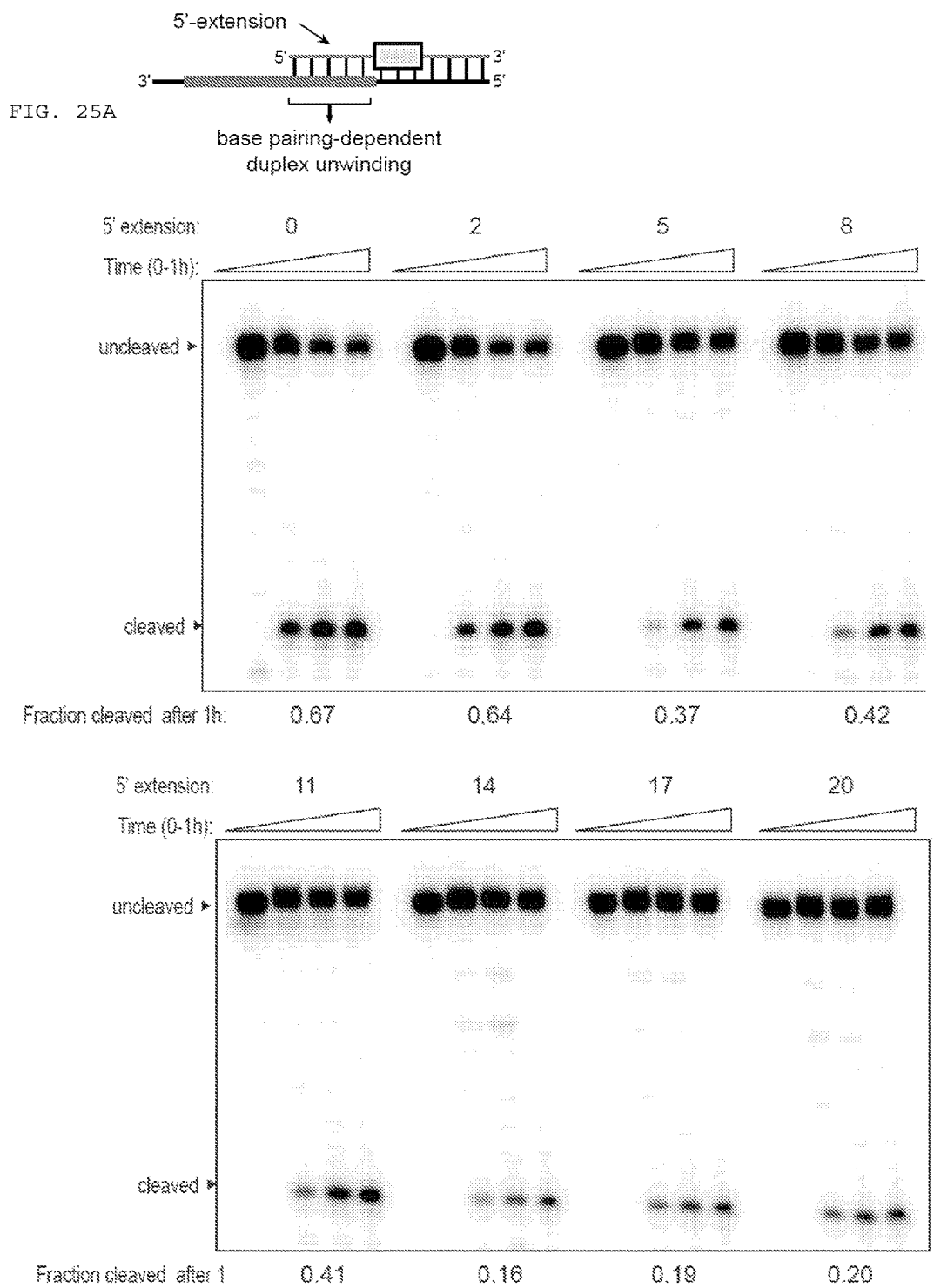

FIG. 26A
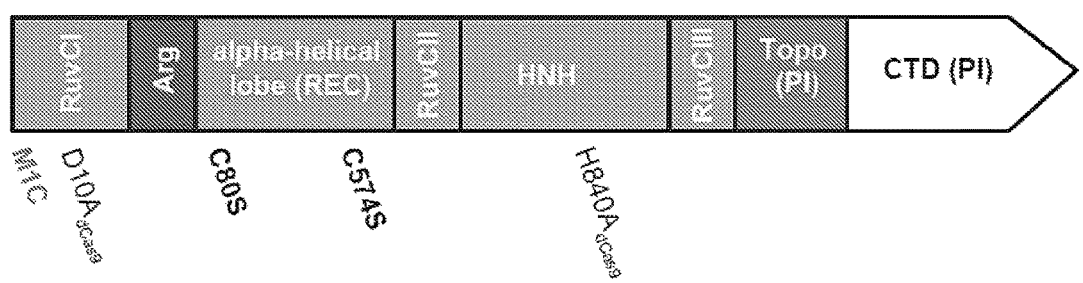
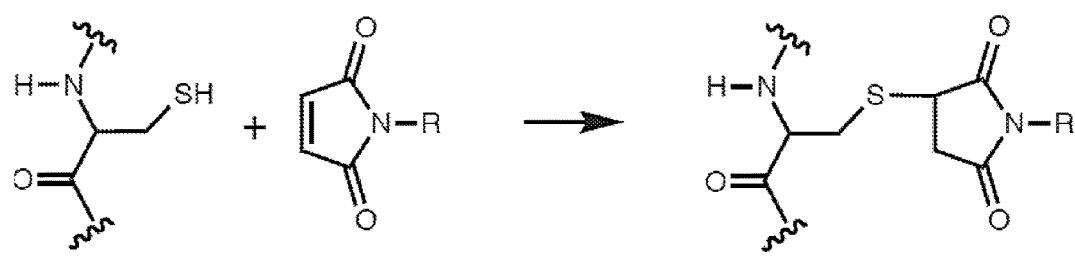
R = 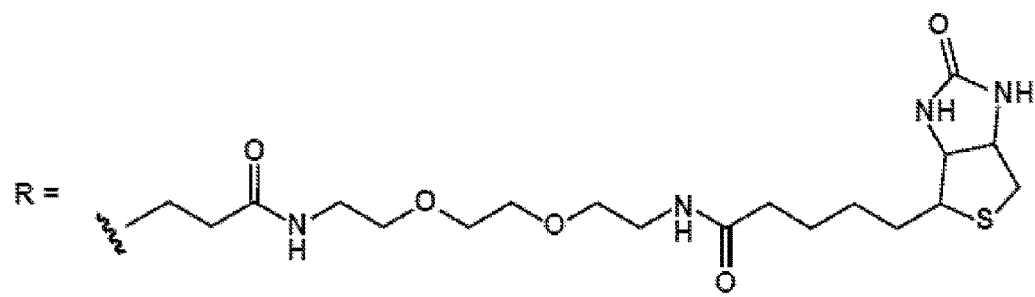

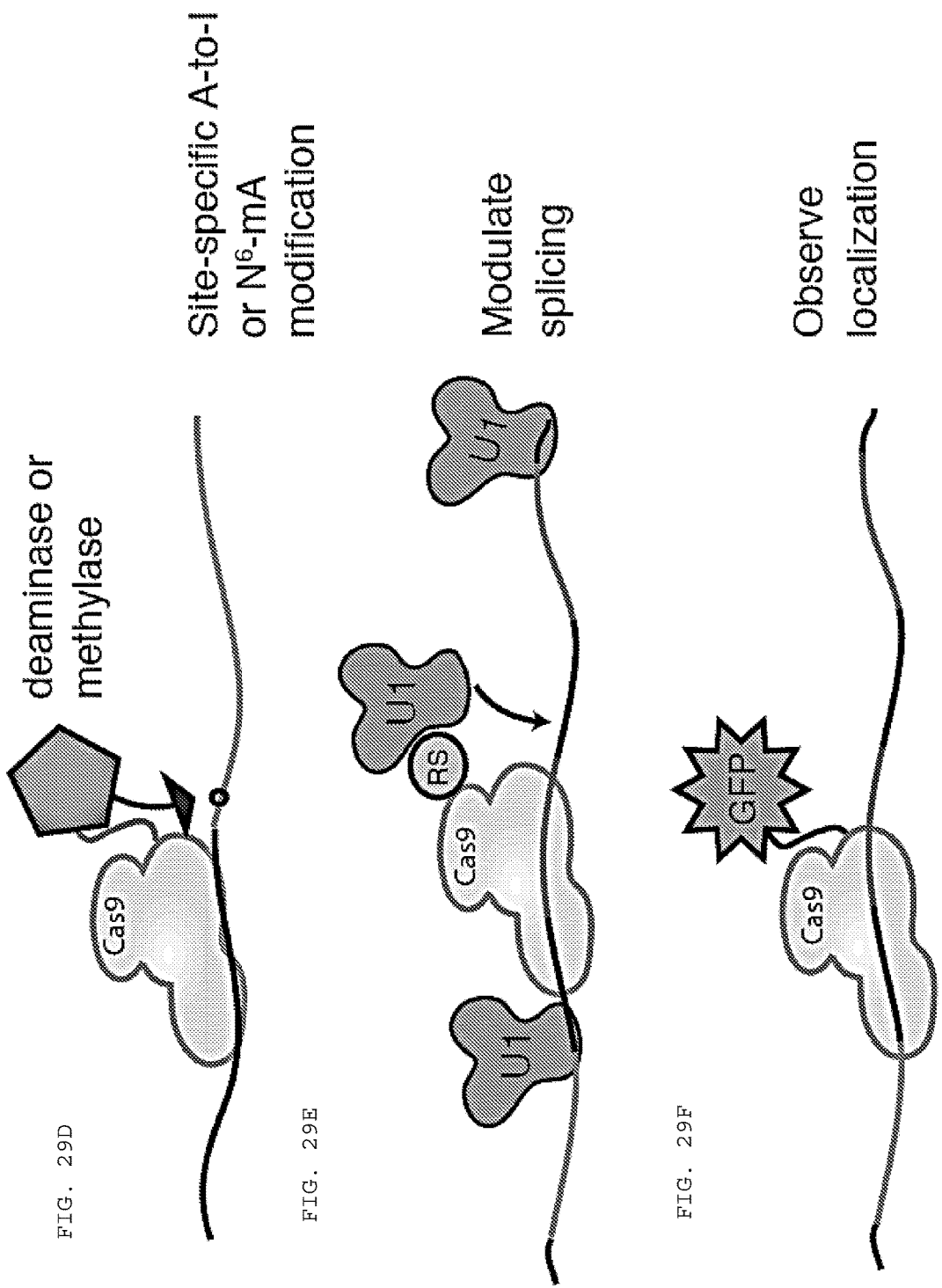

METHODS AND COMPOSITIONS FOR MODIFYING A SINGLE STRANDED TARGET NUCLEIC ACID

CROSS-REFERENCE

This application is a continuation of U.S. patent application Ser. No. 15/036,298, filed May 12, 2016, now U.S. Pat. No. 9,994,831, which claims the benefit of U.S. Provisional Patent Application No. 61/915,432, filed Dec. 12, 2013, which applications are incorporated herein by reference in their entirety.

INCORPORATION BY REFERENCE OF SEQUENCE LISTING PROVIDED AS A TEXT FILE

A Sequence Listing is provided herewith as a text file, "BERK-232CON_SEQ LISTING_ST25.txt" created on Apr. 10, 2019 and having a size of 7,722 KB. The contents of the text file are incorporated by reference herein in their entirety.

INTRODUCTION

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. In Type II CRISPR-Cas systems, Cas9 functions as an RNA-guided endonuclease that uses a dual-guide RNA consisting of crRNA and trans-activating crRNA (tracrRNA) for target recognition and cleavage by a mechanism involving two nuclease active sites that together generate double-stranded DNA breaks (DSBs).

RNA-programmed Cas9 has proven to be a versatile tool for genome engineering in multiple cell types and organisms. Guided by a dual-RNA complex or a chimeric single-guide RNA, Cas9 generates site-specific DSBs within double-stranded DNA (dsDNA) target nucleic acids, which are repaired either by non-homologous end joining (NHEJ) or homologous recombination (HR). Thus, the Cas9 system provides a facile means of modifying genomic information. Catalytically inactive Cas9 alone or fused to transcriptional activator or repressor domains can be used to alter transcription levels at sites within double-stranded DNA (dsDNA) target nucleic acids by binding to the target site without cleavage.

The systematic interrogation of genomes and genetic reprogramming of cells involves targeting sets of genes for expression or repression. Currently the most common approach for targeting arbitrary genes for regulation is to use RNA interference (RNAi). This approach has limitations. For example, RNAi can exhibit significant off-target effects and toxicity. Furthermore, this mode of repression relies on the function of a number of endogenous host proteins and therefore can lead to phenotypic effects distinct from the intended effect.

There is a need in the art for methods of controlling the expression of RNA (e.g., mRNA, rRNA, tRNA, microRNA, etc.) with minimal off-target effects and in a manner that does not depend on host proteins. Additionally, there is a need in the art for a technology that allows precise targeting of nuclease activity (or other protein activities such as binding) to single stranded target nucleic acids (e.g., ssRNA, ssDNA, mRNA, rRNA, tRNA, microRNA, etc.). Cas9 can require the presence of a protospacer adjacent motif (PAM) sequence in the target nucleic acid that is adjacent to the targeted sequence. There is a need in the art for methods that facilitate the sequence-specific targeting of Cas9 to a target site within a target nucleic acid in a manner that does not depend on the presence of a PAM sequence in the target nucleic acid.

LITERATURE

Chylinski et al., RNA Biol. 2013 May; 10(5):726-37; Jinek et al., Science. 2012 Aug. 17; 337(6096):816-21; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4): 910-8; Auer et. al., Genome Res. 2013 Oct. 31; Chen et. al., Nucleic Acids Res. 2013 Nov. 1; 41(20):e19; Cheng et. al., Cell Res. 2013 October; 23(10):1163-71; Cho et. al., Genetics. 2013 November; 195(3):1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. al., Nat Methods. 2013 October; 10(10):957-63; Nakayama et. al., Genesis. 2013 December; 51(12):835-43; Ran et. al., Nat Protoc. 2013 November; 8(11):2281-308; Ran et. al., Cell. 2013 Sep. 12; 154(6):1380-9; Upadhyay et. al., G3 (Bethesda). 2013 Dec. 9; 3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9.

SUMMARY

The present disclosure provides compositions and methods for binding and/or cleaving a single stranded target nucleic acid. A method of cleaving includes contacting a singled stranded target nucleic acid with (or introducing into a cell) a Cas9 polypeptide, a guide nucleic acid (e.g., a dual guide RNA, a single guide RNA, an RNA/DNA hybrid guide RNA, etc.), and a PAMmer. A subject PAMmer is a single stranded oligonucleotide having a protospacer adjacent motif (PAM) sequence and at least one of: (i) a specificity segment, positioned 5' of the PAM sequence, having a nucleotide sequence that is complementary to a first target nucleotide sequence in the target nucleic acid (i.e., the target site); and (ii) an orientation segment, positioned 3' of the PAM sequence, having a nucleotide sequence that is complementary to a second target nucleotide sequence in the target nucleic acid (i.e., the orientation site). A method of binding includes contacting a singled stranded target nucleic acid with (or introducing into a cell): (i) a variant Cas9 polypeptide having reduced or undetectable nuclease activity relative to a corresponding wild type Cas9 polypeptide; and (ii) a guide nucleic acid. In some cases, a method of binding includes contacting a singled stranded target nucleic acid with (or introducing into a cell): (i) a variant Cas9 polypeptide having reduced or undetectable nuclease activity relative to a corresponding wild type Cas9 polypeptide; (ii) a guide nucleic acid; and (iii) a PAMmer. In some cases, methods of binding are for visualizing single stranded target nucleic acids using a detectable label. In some cases, methods of binding are for isolating, collecting, and/or analyzing at least one of: (i) bound single stranded target nucleic acids; and (ii) polypeptides associated with bound single stranded target nucleic acids. In some cases, methods of binding are for isolating, collecting, and/or analyzing bound single stranded target nucleic acids. In some cases, methods of binding are for isolating, collecting, and/or analyzing a polypeptide (e.g., polypeptides) associated with bound single stranded target nucleic acids.

In some cases, the sequence of the target nucleic acid that is targeted by the specificity segment of a PAMmer is within 20 or less nucleotides (nt) of the sequence targeted by the orientation segment of the PAMmer (e.g., 18 or less nt, 16 or less nt, 14 or less nt, 12 or less nt, 10 or less nt, 9 or less nt, 8 or less nt, 7 or less nt, 6 or less nt, 5 or less nt, 4 or less nt, 3 or less nt, 2 or less nt, 1 nt, or 0 nt). In some cases, the sequence targeted by the specificity segment of a PAMmer is immediately adjacent to the sequence targeted by the orientation segment of the PAMmer. In some embodiments, 20 or less nt are present in the target nucleic acid between the sequence targeted by the specificity segment of the PAMmer and the sequence targeted by the orientation segment of the PAMmer (e.g., 18 or less nt, 16 or less nt, 14 or less nt, 12 or less nt, 10 or less nt, 9 or less nt, 8 or less nt, 7 or less nt, 6 or less nt, 5 or less nt, 4 or less nt, 3 or less nt, 2 or less nt, 1 or less nt, or no nt).

In some cases, the sequence of the target nucleic acid that is targeted by the orientation segment of a PAMmer is within 20 or less nucleotides (nt) of the sequence targeted by the targeting segment of the guide nucleic acid (e.g., 18 or less nt, 16 or less nt, 14 or less nt, 12 or less nt, 10 or less nt, 9 or less nt, 8 or less nt, 7 or less nt, 6 or less nt, 5 or less nt, 4 or less nt, 3 or less nt, 2 or less nt, 1 or less nt, or no nt). In some cases, the sequence targeted by the orientation segment of a PAMmer is immediately adjacent to the sequence targeted by the targeting segment of the guide nucleic acid. In some embodiments, 20 or less nt are present in the target nucleic acid between the sequence targeted by the targeting segment of the guide nucleic acid (i.e., the target site) and the sequence targeted by the orientation segment of the PAMmer (e.g., 18 or less nt, 16 or less nt, 14 or less nt, 12 or less nt, 10 or less nt, 9 or less nt, 8 or less nt, 7 or less nt, 6 or less nt, 5 or less nt, 4 or less nt, 3 or less nt, 2 or less nt, 1 or less nt, or no nt).

In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). In some cases, a Cas9 polypeptide is conjugated to a PAMmer. In some cases, a guide nucleic acid is conjugated to a PAMmer. In some cases, a guide nucleic acid is a DNA/RNA hybrid guide nucleic acid where the segment that is complementary to a target nucleic acid (i.e., the targeting segment) has DNA and the segment that interacts with a Cas9 polypeptide (i.e., the protein-binding segment) has RNA. The subject methods can be performed outside of a cell in vitro, inside of a cell in vitro or ex vivo, and/or inside of a cell in vivo. Also provided are kits and libraries for performing the disclosed methods.

FEATURES

The present disclosure features a method of cleaving a single stranded target nucleic acid, the method comprising: contacting the single stranded target nucleic acid with: (i) a Cas9 polypeptide comprising an amino acid sequence having 75% or more amino acid sequence identity to amino acids 7-166 or 731-1003 of the S. pyogenes Cas9 amino acid sequence (SEQ ID NO:8), or to a corresponding portion in the Cas9 amino acid sequence set forth in any of SEQ ID NOs:1-7, 9-259, and 795-1346; (ii) a guide nucleic acid, or a nucleic acid encoding the same, wherein the guide nucleic acid comprises: (a) a first segment that comprises a nucleotide sequence that is complementary to a first target nucleotide sequence in the single stranded target nucleic acid, and (b) a second segment that forms a double-stranded RNA duplex and interacts with the Cas9 polypeptide; and (iii) a PAMmer, or a nucleic acid encoding the same, wherein the PAMmer is a single stranded oligonucleotide comprising: (a) a protospacer adjacent motif (PAM) sequence, and at least one of: (b.i) a specificity segment comprising a nucleotide sequence that is complementary to the first target nucleotide sequence, wherein the specificity segment is positioned 5' of the PAM sequence; and (b.ii) an orientation segment comprising a nucleotide sequence that is complementary to a second target nucleotide sequence in the target nucleic acid, wherein the orientation segment is positioned 3' of the PAM sequence. In some cases, the contacting is carried out outside of a cell in vitro. In some cases, the contacting is in a cell in vitro or ex vivo. In some cases, the contacting is in a cell in vivo. In any of the above-mentioned embodiments, in some cases, the guide nucleic acid is a DNA/RNA hybrid nucleic acid and the first segment of the guide nucleic acid comprises DNA. In any of the above-mentioned embodiments, in some cases, the guide nucleic acid is a guide RNA. In any of the above-mentioned embodiments, in some cases, the guide nucleic acid is a dual guide nucleic acid. In any of the above-mentioned embodiments, in some cases, the guide nucleic acid is a single guide nucleic acid. In some cases, the second segment of the guide nucleic acid comprises a nucleotide sequence with 60% or more identity over a stretch of 8 or more contiguous nucleotides to a nucleotide sequence set forth in any of SEQ ID NOs: 431-682, or a complement thereof. In some cases, the single stranded target nucleic acid is a single stranded RNA (ssRNA). In some cases, the target ssRNA is selected from: mRNA, rRNA, tRNA, non-coding RNA (ncRNA), long non-coding RNA (lncRNA), and microRNA (miRNA). In some cases, the target ssRNA is mRNA and the method results in reduced production of a protein encoded by the mRNA. In some cases, the single stranded target nucleic acid is from a virus. In some cases, the single stranded target nucleic acid is single stranded DNA (ssDNA). In some cases, the Cas9 polypeptide is a variant Cas9 polypeptide that comprises a D10A mutation of the S. pyogenes Cas9 amino acid sequence (SEQ ID NO:8) or the corresponding mutation in the amino acid sequence set forth in any of SEQ ID NOs: 1-7, 9-256, and 795-1346. In some cases, the PAMmer is covalently linked to the guide nucleic acid. In some cases, the PAMmer is covalently linked to the Cas9 polypeptide. In some cases, the PAMmer comprises an orientation segment. In some cases, the PAMmer does not comprise a specificity segment. In some cases, the PAM sequence is the 5' end of the PAMmer. In some cases, the PAMmer comprises a specificity segment. In some cases, the PAMmer does not comprise an orientation segment. In some cases, the PAM sequence is the 3' end of the PAMmer. In some cases, wherein the PAM sequence is GG. In some cases, the PAM sequence is 5'-NGG-3' and N can be any nucleotide. In some cases, the target nucleic acid: (i) does not have a nucleotide sequence that is complementary to the PAM sequence at a position within 10 nucleotides of the 3' end of the specificity segment of the PAMmer; or (ii) does not have a nucleotide sequence that is complementary to the PAM sequence at a position within 10 nucleotides of the 5' end of the orientation segment of the PAMmer. In some cases, 10 or fewer nucleotides are present in the target nucleic acid between the first and second target nucleotide sequences. In some cases, 2 or 3 nucleotides are present in the target nucleic acid between the first and second target nucleotide sequences.

The present disclosure features a method of binding a single stranded target nucleic acid, the method comprising: contacting the single stranded target nucleic acid with: (i) a variant Cas9 polypeptide, or a nucleic acid encoding the same, having reduced nuclease activity relative to a corresponding wild type Cas9 polypeptide, wherein the variant Cas9 polypeptide comprises an amino acid sequence having 75% or more amino acid sequence identity to amino acids 7-166 or 731-1003 of the *S. pyogenes* Cas9 amino acid sequence (SEQ ID NO:8), or to a corresponding portion in the Cas9 amino acid sequence set forth in any of SEQ ID NOs:1-7, 9-259, and 795-1346; and (ii) a guide nucleic acid, or a nucleic acid encoding the same, wherein the guide nucleic acid comprises a protein-binding segment that forms a double-stranded RNA duplex and interacts with the Cas9 polypeptide, wherein said contacting produces a variant-Cas9/target complex. In some cases, the method further comprises contacting the single stranded nucleic acid with a PAMmer, or a nucleic acid encoding the same, wherein the PAMmer is a single stranded oligonucleotide comprising: (a) a protospacer adjacent motif (PAM) sequence, and at least one of: (b.i) a specificity segment comprising a nucleotide sequence that is complementary to a first target nucleotide sequence, wherein the specificity segment is positioned 5' of the PAM sequence; and (b.ii) an orientation segment comprising a nucleotide sequence that is complementary to a second target nucleotide sequence in the target nucleic acid, wherein the orientation segment is positioned 3' of the PAM sequence. In some cases, the variant Cas9 polypeptide comprises at least one of: (i) an H840A mutation of the *S. pyogenes* Cas9 amino acid sequence (SEQ ID NO:8) or the corresponding mutation in the amino acid sequence set forth in any of SEQ ID NOs: 1-7, 9-256, and 795-1346; and (ii) W476A and W1126A mutations of the *S. pyogenes* Cas9 amino acid sequence (SEQ ID NO:8) or the corresponding mutation in the amino acid sequence set forth in any of SEQ ID NOs: 1-7, 9-256, and 795-1346. In some cases, the variant Cas9 polypeptide comprises at least one of: (i) D10A and H840A mutations of the *S. pyogenes* Cas9 amino acid sequence (SEQ ID NO:8) or the corresponding mutations in the amino acid sequence set forth in any of SEQ ID NOs: 1-7, 9-256, and 795-1346; and (ii) W476A and W1126A mutations of the *S. pyogenes* Cas9 amino acid sequence (SEQ ID NO:8) or the corresponding mutation in the amino acid sequence set forth in any of SEQ ID NOs: 1-7, 9-256, and 795-1346. In some cases, the variant Cas9 polypeptide comprises a detectable label. In some cases, the detectable label is a fluorescent protein. In some cases, the guide nucleic acid comprises a detectable label. In some cases, the detectable label of the guide nucleic acid is a fluorescent dye. In some cases, the detectable label of the guide nucleic acid is an indirect detectable label. In some cases, the indirect detectable label of the guide nucleic acid is a nucleotide sequence that specifically binds a labeling protein. In some cases, the labeling protein comprises a second detectable label. In some cases, the second detectable label of the labeling protein is a fluorescent protein. In some cases, the variant Cas9 polypeptide comprises a fusion partner with an enzymatic activity, and the single stranded target nucleic acid is modified as a result of the method. In some cases, in any of the above-mentioned embodiments of a method of the present disclosure, the method further comprises: isolating the variant-Cas9/target complex; releasing the single stranded target nucleic acid from the variant-Cas9/target complex; and collecting and/or analyzing the released single stranded target nucleic acid and/or a polypeptide associated with the single stranded target nucleic acid.

The present disclosure features a hybrid guide nucleic acid comprising: (i) a first segment comprising a DNA nucleotide sequence that is complementary to a first target sequence in a target nucleic acid; and (ii) a second segment that comprises RNA, forms a double-stranded RNA duplex, and interacts with a Cas9 polypeptide, wherein the Cas9 polypeptide comprises an amino acid sequence having 75% or more amino acid sequence identity to amino acids 7-166 or 731-1003 of the *S. pyogenes* Cas9 amino acid sequence (SEQ ID NO:8), or to a corresponding portion in the Cas9 amino acid sequence set forth in any of SEQ ID NOs:1-7, 9-259, and 795-1346. In some cases, the second segment of the hybrid guide nucleic acid comprises a nucleotide sequence with 60% or more identity over a stretch of 8 or more contiguous nucleotides to a nucleotide sequence set forth in any of SEQ ID NOs: 431-682, or a complement thereof. In some cases, the hybrid guide nucleic acid is a dual guide nucleic acid. In some cases, the hybrid guide nucleic acid is a single guide nucleic acid. In some cases, the guide nucleic acid is covalently linked to a PAMmer, wherein the PAMmer is a single stranded oligonucleotide comprising: a protospacer adjacent motif (PAM) sequence, and at least one of: (i) a specificity segment comprising a nucleotide sequence that is complementary to the first target nucleotide sequence in a single stranded target nucleic acid, wherein the specificity segment is positioned 5' of the PAM sequence; and (ii) an orientation segment comprising a nucleotide sequence that is complementary to a second target nucleotide sequence in the single stranded target nucleic acid, wherein the orientation segment is positioned 3' of the PAM sequence.

The present disclosure features a composition, comprising: a PAM-modified Cas9 polypeptide, wherein the PAM-modified Cas9 polypeptide is a Cas9 polypeptide that is conjugated to a PAMmer, wherein: (i) the PAMmer is a single stranded oligonucleotide comprising: (a) a protospacer adjacent motif (PAM) sequence, and at least one of: (a.i) a specificity segment comprising a nucleotide sequence that is complementary to the first target nucleotide sequence in a single stranded target nucleic acid, wherein the specificity segment is positioned 5' of the PAM sequence, and (a.ii) an orientation segment comprising a nucleotide sequence that is complementary to a second target nucleotide sequence in the single stranded target nucleic acid, wherein the orientation segment is positioned 3' of the PAM sequence; and (ii) the Cas9 polypeptide comprises an amino acid sequence having 75% or more amino acid sequence identity to amino acids 7-166 or 731-1003 of the *S. pyogenes* Cas9 amino acid sequence (SEQ ID NO:8), or to a corresponding portion in the Cas9 amino acid sequence set forth in any of SEQ ID NOs:1-7, 9-259, and 795-1346.

The present disclosure features a composition, comprising: (i) a PAMmer, or a nucleic acid encoding the same, wherein the PAMmer is a single stranded oligonucleotide comprising: (a) a protospacer adjacent motif (PAM) sequence, and at least one of: (a.i) a specificity segment comprising a nucleotide sequence that is complementary to the first target nucleotide sequence in a single stranded target nucleic acid, wherein the specificity segment is positioned 5' of the PAM sequence, and (a.ii) an orientation segment comprising a nucleotide sequence that is complementary to a second target nucleotide sequence in the single stranded target nucleic acid, wherein the orientation segment is positioned 3' of the PAM sequence; and at least one of: (ii) a guide nucleic acid, or a nucleic acid encoding the same, wherein the guide nucleic acid comprises: (a) a first segment that comprises a nucleotide sequence that is complementary to a first target sequence in a single stranded target nucleic acid, and (b) a second segment that forms a double-stranded RNA duplex and interacts with a Cas9 polypeptide, wherein the Cas9 polypeptide comprises an amino acid sequence having 75% or more amino acid sequence identity to amino acids 7-166 or 731-1003 of the S. pyogenes Cas9 amino acid sequence (SEQ ID NO:8), or to a corresponding portion in the Cas9 amino acid sequence set forth in any of SEQ ID NOs:1-7, 9-259, and 795-1346; and (iii) a Cas9 polypeptide, wherein the Cas9 polypeptide comprises an amino acid sequence having 75% or more amino acid sequence identity to amino acids 7-166 or 731-1003 of the S. pyogenes Cas9 amino acid sequence (SEQ ID NO:8), or to a corresponding portion in the Cas9 amino acid sequence set forth in any of SEQ ID NOs:1-7, 9-259, and 795-1346. In some cases, the guide nucleic acid is a guide RNA. In some cases, the guide nucleic acid is a DNA/RNA hybrid guide nucleic acid, wherein the first segment of the guide nucleic acid comprises DNA. In some cases, the guide nucleic acid is a dual guide nucleic acid. In some cases, the guide nucleic acid is a single guide nucleic acid. In some cases, the second segment of the guide nucleic acid comprises a nucleotide sequence with 60% or more identity over a stretch of 8 or more contiguous nucleotides to a nucleotide sequence set forth in any of SEQ ID NOs: 431-682, or a complement thereof. In some cases, the PAM sequence is the 5' end of the PAMmer. In some cases, the PAM sequence is GG. In some cases, the PAM sequence is 5'-NGG-3' and N can be any nucleotide. In some cases, 10 or fewer nucleotides are present in the target nucleic acid between the first and second target sequences. In some cases, 2 or 3 nucleotides are present in the target nucleic acid between the first and second target sequences. In any of the above-described embodiments, a composition of the present disclosure comprises a Cas9 polypeptide, or a nucleic acid encoding the same. In some cases, the Cas9 polypeptide is a variant Cas9 polypeptide having reduced nuclease activity relative to a corresponding wild type Cas9 polypeptide.

The present disclosure features a kit comprising: (i) a guide nucleic acid, or a nucleic acid encoding the same, wherein the guide nucleic acid comprises: (a) a first segment comprising a nucleotide sequence that is complementary to a first target sequence in a target nucleic acid, and (b) a second segment that forms a double-stranded RNA duplex, and interacts with a Cas9 polypeptide, wherein the Cas9 polypeptide comprises an amino acid sequence having 75% or more amino acid sequence identity to amino acids 7-166 or 731-1003 of the S. pyogenes Cas9 amino acid sequence (SEQ ID NO:8), or to a corresponding portion in the Cas9 amino acid sequence set forth in any of SEQ ID NOs:1-7, 9-259, and 795-1346; and (ii) a PAMmer, or a nucleic acid encoding the same, wherein the PAMmer is a single stranded oligonucleotide comprising: (a) a protospacer adjacent motif (PAM) sequence, and at least one of: (a.i) a specificity segment comprising a nucleotide sequence that is complementary to the first target nucleotide sequence in a single stranded target nucleic acid, wherein the specificity segment is positioned 5' of the PAM sequence, and (a.ii) an orientation segment comprising a nucleotide sequence that is complementary to a second target nucleotide sequence in the single stranded target nucleic acid, wherein the orientation segment is positioned 3' of the PAM sequence.

The present disclosure features a library comprising: Two or more targeting pairs, wherein each targeting pair comprises: (i) a guide nucleic acid, or a nucleic acid encoding the same, wherein the guide nucleic acid comprises: (a) a first segment comprising a nucleotide sequence that is complementary to a first target sequence in a target nucleic acid, and (b) a second segment that forms a double-stranded RNA duplex, and interacts with a Cas9 polypeptide, wherein the Cas9 polypeptide comprises an amino acid sequence having 75% or more amino acid sequence identity to amino acids 7-166 or 731-1003 of the S. pyogenes Cas9 amino acid sequence (SEQ ID NO:8), or to a corresponding portion in the Cas9 amino acid sequence set forth in any of SEQ ID NOs:1-7, 9-259, and 795-1346; and (ii) a PAMmer, or a nucleic acid encoding the same, wherein the PAMmer is a single stranded oligonucleotide comprising: (a) a protospacer adjacent motif (PAM) sequence, and at least one of: (a.i) a specificity segment comprising a nucleotide sequence that is complementary to the first target nucleotide sequence in a single stranded target nucleic acid, wherein the specificity segment is positioned 5' of the PAM sequence, and (a.ii) an orientation segment comprising a nucleotide sequence that is complementary to a second target nucleotide sequence in the single stranded target nucleic acid, wherein the orientation segment is positioned 3' of the PAM sequence.

The present disclosure features a method of cleaving a single stranded target nucleic acid, the method comprising: contacting the single stranded target nucleic acid with: (i) a Cas9 polypeptide; (ii) a guide nucleic acid comprising: (a) a targeting segment comprising a nucleotide sequence that is complementary to a first target nucleotide sequence in the single stranded target nucleic acid, and (b) a protein-binding segment comprising two stretches of nucleotides that hybridize with one another to form a double-stranded RNA duplex that interacts with the Cas9 polypeptide; and (iii) a PAMmer, wherein the PAMmer is a single stranded oligonucleotide comprising: (a) a protospacer adjacent motif (PAM) sequence, and (b) at least one of: (i) an orientation segment, positioned 3' of the PAM sequence, comprising a nucleotide sequence that is complementary to a second target nucleotide sequence in the target nucleic acid; and (ii) a specificity segment, positioned 5' of the PAM sequence, comprising a nucleotide sequence that is complementary to said first target nucleotide sequence. In some cases, the single stranded target nucleic acid is a single stranded RNA (ssRNA). In some cases, the target ssRNA is selected from: mRNA, rRNA, tRNA, non-coding RNA (ncRNA), long non-coding RNA (lncRNA), and microRNA (miRNA). In some cases, the target ssRNA is mRNA and the method results in reduced production of a protein encoded by the mRNA. In some cases, the single stranded target nucleic acid is single stranded DNA (ssDNA). In some cases, the single stranded target nucleic acid is from a virus. In some cases, the PAMmer is covalently linked to the guide nucleic acid. In some cases, the PAMmer is covalently linked to the Cas9 polypeptide. In some cases, the PAMmer comprises an orientation segment. In some cases, the PAMmer does not comprise a specificity segment. In some cases, the PAM sequence is the 5' end of the PAMmer. In some cases, the PAMmer comprises a specificity segment. In some cases, the PAMmer does not comprise an orientation segment. In some cases, the PAM sequence is the 3' end of the PAMmer. In some cases, the PAMmer comprises an orientation segment and a specificity segment. In some cases, the PAMmer comprises a detectable label (e.g., a fluorescent label). In some cases, the PAM sequence is GG. In some cases, the PAM sequence is 5'-NGG-3' and N can be any nucleotide. In some cases, said contacting is outside of a cell in vitro. In some cases, said contacting is in a cell in vitro or ex vivo. In some cases, said contacting is in a cell in vivo. In some cases, the guide nucleic acid is a DNA/RNA hybrid nucleic acid and the first segment of the guide nucleic acid comprises DNA. In some cases, the guide nucleic acid is a guide RNA. In some cases, the guide nucleic acid is a dual guide nucleic acid, wherein the two stretches of nucleotides that hybridize with one another are present on separate nucleic acid molecules. In some cases, the guide nucleic acid is a single guide nucleic acid, wherein the two stretches of nucleotides that hybridize with one another are present on the same nucleic acid molecule and are covalently linked by intervening nucleotides. In some cases, the target nucleic acid: (i) does not have a nucleotide sequence that is complementary to the PAM sequence at a position within 10 nucleotides of the 3' end of the specificity segment of the PAMmer; or (ii) does not have a nucleotide sequence that is complementary to the PAM sequence at a position within 10 nucleotides of the 5' end of the orientation segment of the PAMmer. In some cases, 10 or less nucleotides are present in the target nucleic acid between the first and second target nucleotide sequences. In some cases, 2 or 3 nucleotides are present in the target nucleic acid between the first and second target nucleotide sequences.

The present disclosure features a method of binding a single stranded target nucleic acid, the method comprising: contacting the single stranded target nucleic acid with: (i) a variant Cas9 polypeptide having an amino acid mutation that results in reduced nuclease activity relative to a corresponding wild type Cas9 polypeptide; and (ii) a guide nucleic acid comprising: (a) a targeting segment comprising a nucleotide sequence that is complementary to a first target nucleotide sequence in the single stranded target nucleic acid, and (b) a protein-binding segment comprising two stretches of nucleotides that hybridize with one another to form a double-stranded RNA duplex that interacts with the Cas9 polypeptide, wherein said contacting produces a variant-Cas9/target complex. In some cases, the method further comprising contacting the single stranded traget nucleic acid with a PAMmer, wherein the PAMmer is a single stranded oligonucleotide comprising: (a) a protospacer adjacent motif (PAM) sequence, and (b) at least one of: (i) an orientation segment, positioned 3' of the PAM sequence, comprising a nucleotide sequence that is complementary to a second target nucleotide sequence in the target nucleic acid; and (ii) a specificity segment, positioned 5' of the PAM sequence, comprising a nucleotide sequence that is complementary to said first target nucleotide sequence. In some cases, the PAMmer comprises a detectable label. In some cases, the PAMmer comprises an orientation segment and a specificity segment. In some cases, the variant Cas9 polypeptide comprises at least one of: (i) an H840A mutation of the S. pyogenes Cas9 amino acid sequence (SEQ ID NO:8) or the corresponding mutation in the amino acid sequence set forth in any of SEQ ID NOs: 1-7, 9-256, and 795-1346; and (ii) W476A and W1126A mutations of the S. pyogenes Cas9 amino acid sequence (SEQ ID NO:8) or the corresponding mutation in the amino acid sequence set forth in any of SEQ ID NOs: 1-7, 9-256, and 795-1346. In some cases, the variant Cas9 polypeptide comprises at least one of: (i) D10A and H840A mutations of the S. pyogenes Cas9 amino acid sequence (SEQ ID NO:8) or the corresponding mutations in the amino acid sequence set forth in any of SEQ ID NOs: 1-7, 9-256, and 795-1346; and (ii) W476A and W1126A mutations of the S. pyogenes Cas9 amino acid sequence (SEQ ID NO:8) or the corresponding mutation in the amino acid sequence set forth in any of SEQ ID NOs: 1-7, 9-256, and 795-1346. In some cases, the variant Cas9 polypeptide comprises a detectable label. In some cases, the detectable label of the Cas9 polypeptide is a fluorescent protein. In some cases, the guide nucleic acid comprises a detectable label. In some cases, the detectable label of the guide nucleic acid is a directly detectable label. In some cases, the detectable label of the guide nucleic acid is an indirectly detectable label. In some cases, the indirectly detectable label of the guide nucleic acid is a nucleotide sequence that specifically binds a labeling protein. In some cases, the variant Cas9 polypeptide comprises a fusion partner with an enzymatic activity, and the single stranded target nucleic acid is modified as a result of the method. In some cases, the method further comprises: isolating the variant-Cas9/target complex; releasing the single stranded target nucleic acid from the variant-Cas9/target complex; and collecting and/or analyzing the released single stranded target nucleic acid and/or a polypeptide associated with the single stranded target nucleic acid.

The present disclosure features a hybrid guide nucleic acid, comprising: (i) a targeting segment comprising a DNA nucleotide sequence that is complementary to a first target nucleotide sequence in a target nucleic acid (i.e., a targeting segment comprising deoxyribonucleotides having a nucleotide sequence that is complementary to a first target nucleotide sequence in a target nucleic acid); and (ii) a protein-binding segment that comprises RNA, forms a double-stranded RNA duplex, and interacts with a Cas9 polypeptide (i.e., a protein-binding segment comprising two stretches of ribonucleotides that hybridize with one another to form a double-stranded RNA duplex that interacts with a Cas9 polypeptide). In some cases, the protein-binding segment of the hybrid guide nucleic acid comprises a nucleotide sequence with 60% or more identity over a stretch of 8 or more contiguous nucleotides to a nucleotide sequence set forth in any of SEQ ID NOs: 431-682, or a complement thereof. In some cases, the hybrid guide nucleic acid is a dual guide nucleic acid (i.e., where two stretches of ribonucleotides that hybridize with one another are present on separate nucleic acid molecules). In some cases, the hybrid guide nucleic acid is a single guide nucleic acid (e.g., where two stretches of RNA nucleotides that hybridize with one another are present on the same nucleic acid molecule and are covalently linked by intervening nucleotides). In some cases, the guide nucleic acid is covalently linked to a PAMmer, wherein the PAMmer is a single stranded oligonucleotide comprising: a protospacer adjacent motif (PAM) sequence, and at least one of: (i) an orientation segment, positioned 3' of the PAM sequence, comprising a nucleotide sequence that is complementary to a second target nucleotide sequence in the target nucleic acid; and (ii) a specificity segment, positioned 5' of the PAM sequence, comprising a nucleotide sequence that is complementary to said first target nucleotide sequence.

Thus, the present disclosure features a hybrid guide nucleic acid, comprising: (i) an activator nucleic acid that comprises a duplex forming segment having an RNA nucleotide sequence; and (ii) a targeter nucleic acid that comprises (a) a targeting segment having a DNA nucleotide sequence that is complementary to a first target nucleotide sequence in a target nucleic acid, and (b) a duplex forming segment having an RNA nucleotide sequence, wherein the duplex forming segments of the activator and the targeter nucleic acids hybridize with one another to form a double-stranded RNA duplex that interacts with a Cas9 polypeptide. In some cases, the hybrid guide nucleic acid is a dual guide nucleic acid (i.e., where the activator and the targeter nucleic acids are separate nucleic acid molecules). In some cases, the hybrid guide nucleic acid is a single guide nucleic acid (e.g., where the activator and the targeter nucleic acids are covalently linked by intervening nucleotides).

The present disclosure features a PAM-modified Cas9 polypeptide, comprising a Cas9 polypeptide that is conjugated to a PAMmer, wherein the PAMmer is a single stranded oligonucleotide comprising: (a) a protospacer adjacent motif (PAM) sequence, and (b) at least one of: (i) an orientation segment, positioned 3' of the PAM sequence, comprising a nucleotide sequence that is complementary to a second target nucleotide sequence in the target nucleic acid, and (ii) a specificity segment, positioned 5' of the PAM sequence, comprising a nucleotide sequence that is complementary to said first target nucleotide sequence.

The present disclosure features a composition comprising: (i) a PAMmer, wherein the PAMmer is a single stranded oligonucleotide comprising: (a) a protospacer adjacent motif (PAM) sequence, and (b) at least one of: (b.i) an orientation segment, positioned 3' of the PAM sequence, comprising a nucleotide sequence that is complementary to a first target nucleotide sequence in a target nucleic acid, and (b.ii) a specificity segment, positioned 5' of the PAM sequence, comprising a nucleotide sequence that is complementary to a second target nucleotide sequence in a target nucleic acid; and at least one of: (ii) a Cas9 polypeptide, or a nucleic acid encoding the same; and (iii) a guide nucleic acid, or a nucleic acid encoding the same, wherein the guide nucleic acid comprises: (a) a targeting segment comprising a nucleotide sequence that is complementary to said first target nucleotide sequence in said single stranded target nucleic acid, and (b) a protein-binding segment comprising two stretches of nucleotides that hybridize with one another to form a double-stranded RNA duplex that interacts with a Cas9 polypeptide. In some cases, the guide nucleic acid is a guide RNA. In some cases, the guide nucleic acid is a DNA/RNA hybrid guide nucleic acid, wherein the targeting segment of the guide nucleic acid comprises DNA. In some cases, the guide nucleic acid is a dual guide nucleic acid, wherein the two stretches of nucleotides that hybridize with one another are present on separate nucleic acid molecules. In some cases, the guide nucleic acid is a single guide nucleic acid, wherein the two stretches of nucleotides that hybridize with one another are present on the same nucleic acid molecule and are covalently linked by intervening nucleotides. In some cases, the PAM sequence is the 5' end of the PAMmer. In some cases, the PAM sequence is GG. In some cases, the PAM sequence is 5'-NGG-3' and N can be any nucleotide. In some cases, 10 or less nucleotides are present in the target nucleic acid between the first and second target sequences. In some cases, 2 or 3 nucleotides are present in the target nucleic acid between the first and second target sequences. In some cases, the Cas9 polypeptide is a variant Cas9 polypeptide having reduced nuclease activity relative to a corresponding wild type Cas9 polypeptide.

The present disclosure features a kit comprising: (i) a guide nucleic acid, or a nucleic acid encoding the same, wherein the guide nucleic acid comprises: (a) a targeting segment comprising a nucleotide sequence that is complementary to a first target sequence in a target nucleic acid, and (b) a protein-binding segment comprising two stretches of nucleotides that hybridize with one another to form a double-stranded RNA duplex that interacts with a Cas9 polypeptide; and (ii) a PAMmer, or a nucleic acid encoding the same, wherein the PAMmer is a single stranded oligonucleotide comprising: (a) a protospacer adjacent motif (PAM) sequence, and (b) at least one of: (b.i) an orientation segment, positioned 3' of the PAM sequence, comprising a nucleotide sequence that is complementary to a second target sequence in the target nucleic acid, and (b.ii) a specificity segment, positioned 5' of the PAM sequence, comprising a nucleotide sequence that is complementary to said first target sequence.

The present disclosure features a library comprising: two or more targeting nucleic acid pairs, wherein each targeting pair comprises: (i) a guide nucleic acid, or a nucleic acid encoding the same, wherein the guide nucleic acid comprises: (a) a targeting segment comprising a nucleotide sequence that is complementary to a first target sequence in a target nucleic acid, and (b) a protein-binding segment comprising two stretches of nucleotides that hybridize with one another to form a double-stranded RNA duplex that interacts with a Cas9 polypeptide; and (ii) a PAMmer, or a nucleic acid encoding the same, wherein the PAMmer is a single stranded oligonucleotide comprising: (a) a protospacer adjacent motif (PAM) sequence, and (b) at least one of: (b.i) an orientation segment, positioned 3' of the PAM sequence, comprising a nucleotide sequence that is complementary to a second target sequence in the target nucleic acid, and (b.ii) a specificity segment, positioned 5' of the PAM sequence, comprising a nucleotide sequence that is complementary to said first target sequence in the target nucleic acid.

BRIEF DESCRIPTION OF THE DRAWINGS

FIG. 5A-5C present binding and cleavage assays testing off-target effects and employing various PAMmers. λ2 (SEQ ID NO:1361); λ3 (SEQ ID NO:1362); λ4 (SEQ ID NO:1363).

FIG. 9A-9B depict the amino acid sequence of a Cas9 polypeptide from *Streptococcus pyogenes* (SEQ ID NO:8). Cas9 has domains homologous to both HNH and RuvC endonucleases. (FIG. 9A) Motifs 1-4 are overlined. (FIG. 9B) Domains 1 and 2 are overlined.

FIG. 10 depicts a multiple sequence alignment of motifs 1-4 of Cas9 proteins from various diverse species. The full length amino sequences from various diverse species are: *Streptococcus pyogenes* (SEQ ID NO:8), *Legionella pneumophila* (SEQ ID NO:17), Gamma proteobacterium (SEQ ID NO:107), *Listeria innocua* (SEQ ID NO:3), *Lactobacillus gasseri* (SEQ ID NO:152), *Eubacterium rectale* (SEQ ID NO:99), *Staphylococcus lugdunensis* (SEQ ID NO:185), *Mycoplasma synoviae* (SEQ ID NO:22), *Mycoplasma mobile* (SEQ ID NO:16), *Wolinella succinogenes* (SEQ ID NO:10), *Flavobacterium columnare* (SEQ ID NO:235), *Fibrobacter succinogenes* (SEQ ID NO:121), *Bacteroides fragilis* (SEQ ID NO:21), *Acidothermus cellulolyticus* (SEQ ID NO:42), and *Bifidobacterium dentium* (SEQ ID NO:131). Motifs 1-4, respectively, for each species are: *Streptococcus pyogenes*: (SEQ ID NO:260-263); *Legionella pneumophila* (SEQ ID NOs. 1552-1555); Gamma proteobacterium (SEQ ID NOs. 1556-1559); *Listeria innocua* (SEQ ID NOs. 1560-1563); *Lactobacillus gasseri* (SEQ ID NOs. 1564-1567); *Eubacterium rectale* (SEQ ID NOs. 1568-1571); *Staphylococcus lugdunensis* (SEQ ID NOs. 1572-1575); *Mycoplasma synoviae* (SEQ ID NOs. 1576-1579); *Mycoplasma mobile* (SEQ ID NOs. 1580-1583); *Wolinella succinogenes* (SEQ ID NOs. 1584-1587); *Flavobacterium columnare* (SEQ ID NOs. 1588-1591); *Fibrobacter succinogenes* (SEQ ID NOs. 1592-1595); *Bacteroides fragilis* (SEQ ID NOs. 1596-1599); *Acidothermus cellulolyticus* (SEQ ID NOs. 1600-1603); and *Bifidobacterium dentium* (SEQ ID NOs. 1604-1607).

(FIG. 11A) multiple sequence alignment of selected tracrRNA orthologues (AlignX, VectorNTI package, Invitrogen) associated with CRISPR/Cas loci of similar architecture and highly similar Cas9 sequences. Black boxes represent shared nucleotides (FIG. 11B) multiple sequence alignment of selected tracrRNA orthologues (AlignX, VectorNTI package, Invitrogen) associated with CRISPR/Cas loci of different architecture and non-closely related Cas9 sequences. Note the sequence similarity of *N. meningitidis* and *P. multocida* tracrRNA orthologues. Black boxes represent shared nucleotides. For more exemplary activator sequences, see SEQ ID NOs:431-562.

FIG. 12A-12B provide alignments of naturally occurring duplex-forming segments of crRNA ("targeter") sequences from various species (*L. innocua* (SEQ ID NO:577); *S. pyogenes* (SEQ ID NO:569); *S. mutans* (SEQ ID NO:574); *S. thermophilus*1 (SEQ ID NO:575); *C. jejuni* (SEQ ID NO:597); *S. pyogenes* (SEQ ID NO:569); *F. novicida* (SEQ ID NO:572); *M. mobile* (SEQ ID NO:571); *N. meningitides* (SEQ ID NO:579); *P. multocida* (SEQ ID NO:570); and *S. thermophilus*2 (SEQ ID NO:576). (A) multiple sequence alignments of exemplary duplex-forming segment of targeter sequences (AlignX, VectorNTI package, Invitrogen) associated with the loci of similar architecture and highly similar Cas9 sequences. (B) multiple sequence alignments of exemplary duplex-forming segment of targeter sequences (AlignX, VectorNTI package, Invitrogen) associated with the loci of different architecture and diverse Cas9 sequences. Black boxes represent shared nucleotides. For more exemplary duplex-forming segments targeter sequences, see SEQ ID NOs:563-679.

Figure 13:
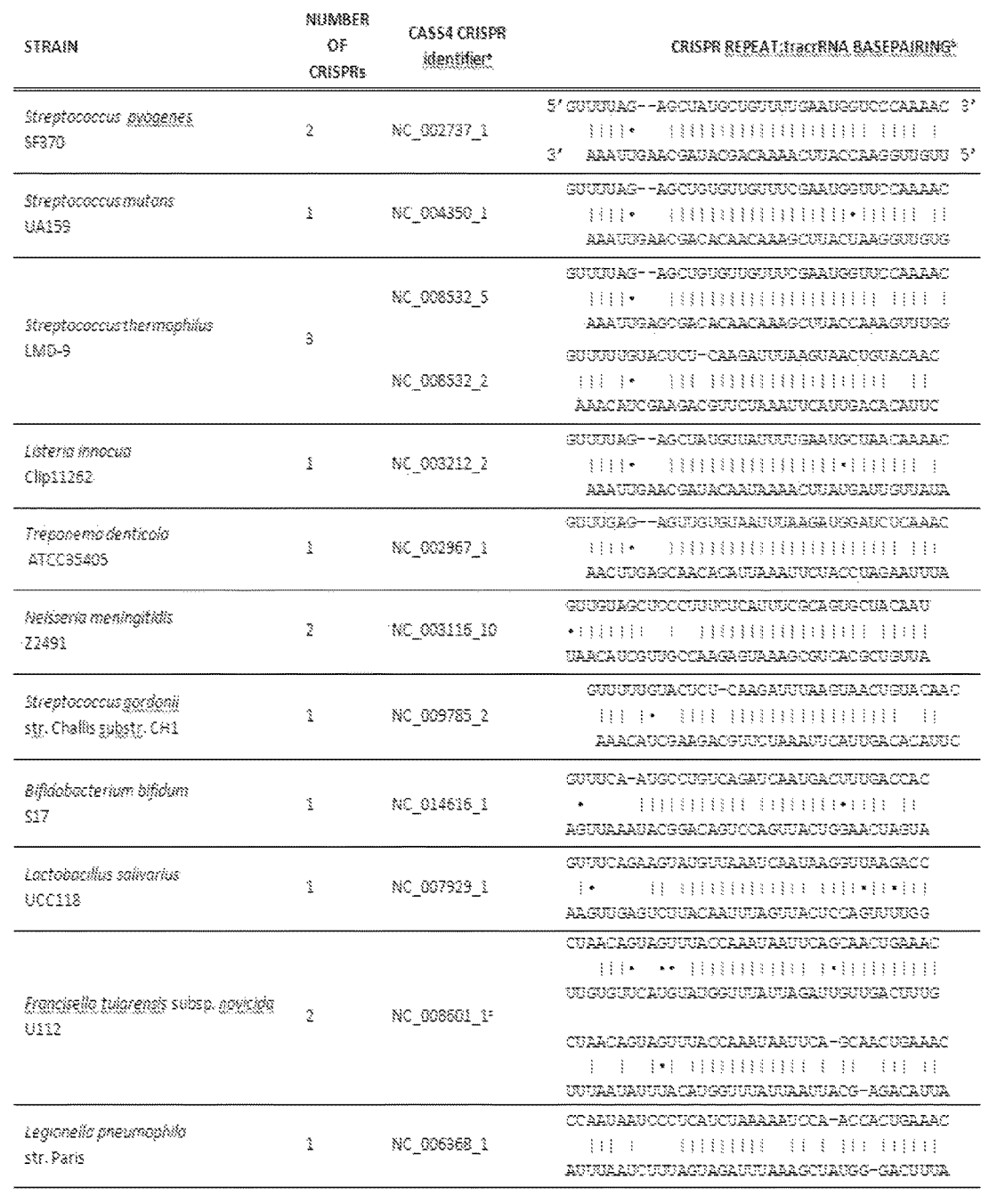

FIG. 13 provides a schematic of hybridization for naturally occurring duplex-forming segments of the crRNA ("targeter") with the duplex-forming segment of the corresponding tracrRNA orthologue ("activator"). Upper sequence, targeter; lower sequence, duplex-forming segment of the corresponding activator. The CRISPR loci belong to the Type II (Nmeni/CASS4) CRISPR/Cas system. Nomenclature is according to the CRISPR database (CRISPR DB). SEQ ID numbers are listed top to bottom: *S. pyogenes* (SEQ ID NOs:569 and 442); *S. mutans* (SEQ ID NOs:574 and 443); *S. thermophilus*1 (SEQ ID NOs:575 and 444); *S. thermophilus*2 (SEQ ID NOs:576 and 445); *L. innocua* (SEQ ID NOs:577 and 446); *T. denticola* (SEQ ID NOs:578 and 448); *N. meningitides* (SEQ ID NOs:579 and 449); *S. gordonii* (SEQ ID NOs:580 and 451); *B. bifidum* (SEQ ID NOs:581 and 452); *L. salivarius* (SEQ ID NOs:582 and 453); *F. tularensis* (SEQ ID NOs:583, 454, 584, and 455); and *L. pneumophila* (SEQ ID NOs:585 and 456). Note that some species contain more than one Type II CRISPR loci. For more exemplary activator sequences, see SEQ ID NOs:431-562. For more exemplary duplex-forming segments of targeter sequences, see SEQ ID NOs:563-679.

FIG. 14 depicts example tracrRNA (activator) and crRNA (targeter) sequences from two species. A degree of interchangeability exists; for example, the *S. pyogenes* Cas9 protein is functional with tracrRNA and crRNA derived from Linnocua. "I" denotes a canonical Watson-Crick base pair while "•" denotes a G-U wobble base pair. "Variable 20nt" or "20nt" represents the targeting segment that is complementary to a target nucleic acid (this region can be up to about 100nt in length). Also shown is the design of a single guide nucleic acid that incorporates features of the targeter and the activator. Cas9 protein sequences from a wide variety of species are set forth as SEQ ID NOs:1-256 and 795-1346. *Streptococcus pyogenes* (top to bottom, SEQ ID NOs: 563, 478, 680); *Listeria innocua* (top to bottom, SEQ ID NOs: 564, 479, 681). The sequences provided are non-limiting examples and are meant to illustrate how single and dual guide nucleic acids can be designed based on targeter and activator sequences from a wide variety of species. Various examples of suitable seuqences from a wide variety of species are set forth as follows (Cas9 protein: SEQ ID NOs:1-259; tracrRNAs: SEQ ID NOs:431-562, or the complements thereof; crRNAs: SEQ ID NOs:563-679, or the complements thereof; and exemplary single guide nucleic acids designed from targeter and activator sequences: SEQ ID NOs:680-682).

FIG. 15A-15D list examples of suitable fusion partners (or fragments thereof) for a subject Cas9 polypeptide (e.g., wild type Cas9, variant Cas9). Examples include, but are not limited to those listed.

FIG. 16A-16D provide experiments directed at determining Cas9 amino acid positions required for cleavage as well as alignments of selected regions of Cas9 polypeptides. (C) Top to bottom (SEQ ID NOs:1364-1375). (D) Top to bottom (SEQ ID NOs:1376-1391).

FIG. 17A-17B provide experiments testing PAMmer the include one or more modified nucleotides.

FIG. 18A-18E provides evidence demonstrating RNA-guided Cas9 cleaving ssRNA targets in the presence of a short PAM presenting DNA oligonucleotide (PAMmer). "PAMmer" (SEQ ID NO: 1471); "Target ssRNA" (SEQ ID NO: 1472).

FIG. 19A-19C present assays testing whether dCas9-gRNA binds ssRNA targets with high affinity in the presence of PAMmers.

FIG. 21A-21H present assays testing whether RNA-guided Cas9 can target non-PAM sites on ssRNA and can be used to isolate GAPDH mRNA from HeLa cells in a tagless manner (H) (Top to bottom, SEQ ID NOs: 1473-1478).

FIG. 24 provides a representative binding experiment demonstrating guide-specific ssRNA binding with 5'-extended PAMmers.

FIG. 25A-25B provide data exploring RNA cleavage efficiencies and binding specificity using PAMmers with variable 5'-extensions.

FIG. 26A-26E provide date related to site-specific biotin labelling of Cas9.

FIG. 29A-29F provide schematics of applications of RCas9 (RNA directed Cas9) for untagged transcript analysis, detection and manipulation.

DEFINITIONS

Figure 1:
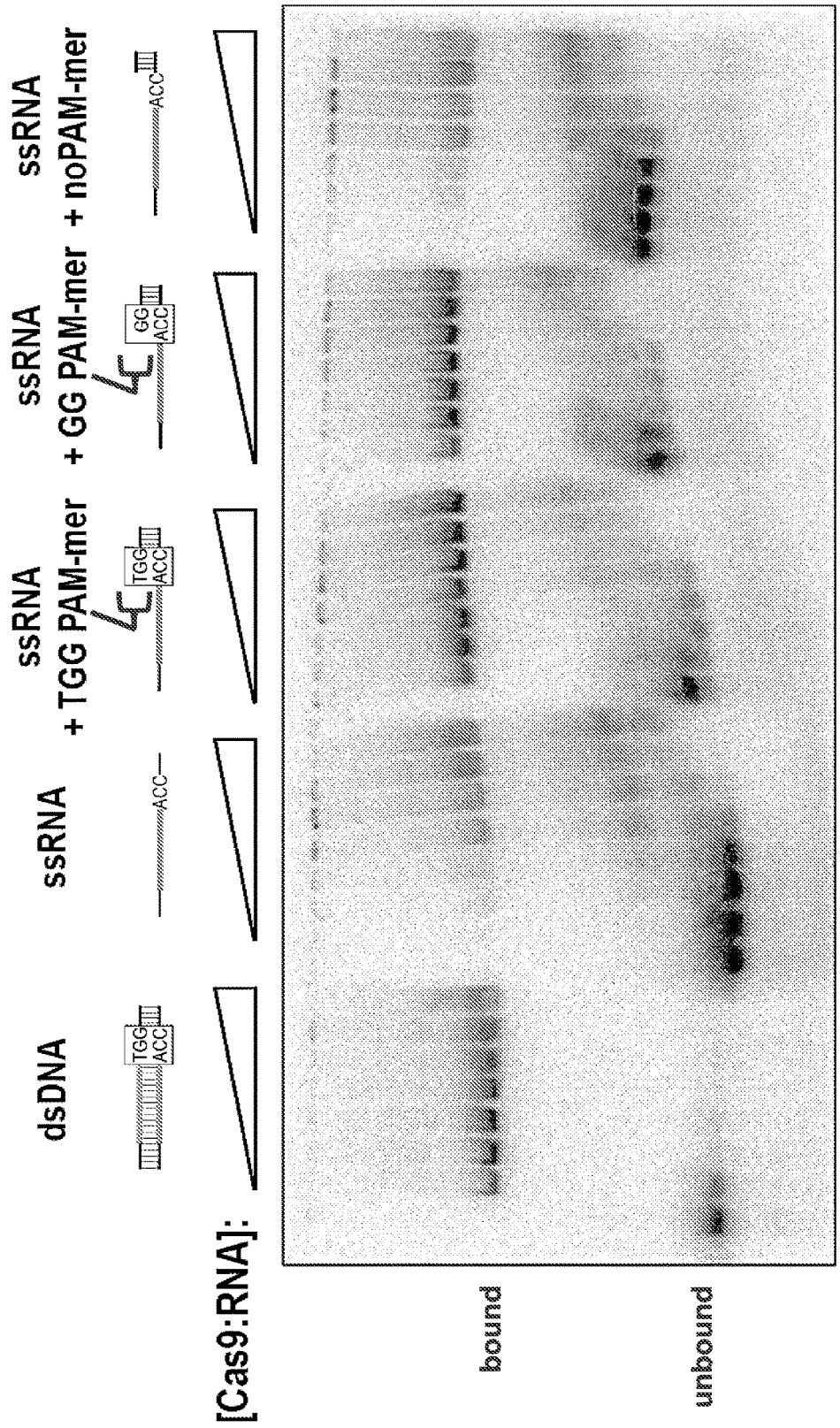
FIG. 1 presents binding assays testing whether Cas9 binds single stranded target nucleic acid molecules (e.g., single stranded RNA (ssRNA)) in the presence of a protospacer adjacent motif (PAM)-containing oligonucleotide ("PAMmer").

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "oligonucleotide" refers to a polynucleotide of between 3 and 100 nucleotides of single- or double-stranded nucleic acid (e.g., DNA, RNA, or a modified nucleic acid). However, for the purposes of this disclosure, there is no upper limit to the length of an oligonucleotide. Oligonucleotides are also known as "oligomers" or "oligos" and may be isolated from genes, transcribed (in vitro and/or in vivo), or chemically synthesized. The terms "polynucleotide" and "nucleic acid" should be understood to include, as applicable to the embodiments being described, single-stranded (such as sense or antisense) and double-stranded polynucleotides.

A "stem-loop structure" refers to a nucleic acid having a secondary structure that includes a region of nucleotides which are known or predicted to form a double strand (step portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. As is known in the art, a stem-loop structure does not require exact base-pairing. Thus, the stem may include one or more base mismatches. Alternatively, the base-pairing may be exact, i.e. not include any mismatches.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a ssRNA target nucleic acid base pairs with a DNA PAMmer, when a DNA target nucleic acid base pairs with an RNA guide nucleic acid, etc.): guanine (G) can also base pair with uracil (U). For example, G/U base-pairing is partially responsible for the degeneracy (i.e., redundancy) of the genetic code in the context of tRNA anti-codon base-pairing with codons in mRNA. Thus, in the context of this disclosure, a guanine (G) (e.g., of a protein-binding segment (dsRNA duplex) of a subject guide nucleic acid molecule; of a target nucleic acid base pairing with a guide nucleic acid and/or a PAMmer, etc.) is considered complementary to both a uracil (U) and to an adenine (A). For example, when a G/U base-pair can be made at a given nucleotide position of a protein-binding segment (e.g., dsRNA duplex) of a subject guide nucleic acid molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). The temperature and wash solution salt concentration may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Exemplary methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a subject Cas9/guide nucleic acid complex and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant (Ka) of less than $10^{-6}$ M, less than $10^{-7}$ M, less than $10^8$ M, less than $10^{-9}$ M, less than $10^{10}$ M, less than $10^{11}$ M, less than $10^{12}$ M, less than $10^{-13}$ M, less than $10^{14}$ M, or less than $10^{-15}$ M. "Affinity" refers to the strength of binding, increased binding affinity being correlated with a lower Ka.

By "binding domain" it is meant a protein domain that is able to bind non-covalently to another molecule. A binding domain can bind to, for example, a DNA molecule (a DNA-binding domain), an RNA molecule (an RNA-binding domain) and/or a protein molecule (a protein-binding domain). In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various methods and computer programs (e.g., BLAST, T-COFFEE, MUSCLE, MAFFT, etc.), available over the world wide web at sites including ncbi.nlm nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g. tRNA, rRNA, microRNA (miRNA), a "non-coding" RNA (ncRNA), a guide nucleic acid, etc.).

A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide nucleic acid) or a coding sequence (e.g., Cas9 polypeptide, or Cas9 polypeptide) and/or regulate translation of an encoded polypeptide.

As used herein, a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is wild type (and naturally occurring).

The term "chimeric" as used herein as applied to a nucleic acid or polypeptide refers to two components that are defined by structures derived from different sources. For example, where "chimeric" is used in the context of a chimeric polypeptide (e.g., a chimeric Cas9 protein), the chimeric polypeptide includes amino acid sequences that are derived from different polypeptides. A chimeric polypeptide may comprise either modified or naturally-occurring polypeptide sequences (e.g., a first amino acid sequence from a modified or unmodified Cas9 protein; and a second amino acid sequence other than the Cas9 protein). Similarly, "chimeric" in the context of a polynucleotide encoding a chimeric polypeptide includes nucleotide sequences derived from different coding regions (e.g., a first nucleotide sequence encoding a modified or unmodified Cas9 protein; and a second nucleotide sequence encoding a polypeptide other than a Cas9 protein).

The term "chimeric polypeptide" refers to a polypeptide which is made by the combination (i.e., "fusion") of two otherwise separated segments of amino sequence, usually through human intervention. A polypeptide that comprises a chimeric amino acid sequence is a chimeric polypeptide. Some chimeric polypeptides can be referred to as "fusion variants."

"Heterologous," as used herein, means a nucleotide or polypeptide sequence that is not found in the native nucleic acid or protein, respectively. For example, in a chimeric Cas9 protein, the RNA-binding domain of a naturally-occurring bacterial Cas9 polypeptide (or a variant thereof) may be fused to a heterologous polypeptide sequence (i.e. a polypeptide sequence from a protein other than Cas9 or a polypeptide sequence from another organism). The heterologous polypeptide sequence may exhibit an activity (e.g., enzymatic activity) that will also be exhibited by the chimeric Cas9 protein (e.g., methyltransferase activity, acetyltransferase activity, kinase activity, ubiquitinating activity, etc.). A heterologous nucleic acid sequence may be linked to a naturally-occurring nucleic acid sequence (or a variant thereof) (e.g., by genetic engineering) to generate a chimeric nucleotide sequence encoding a chimeric polypeptide. As another example, in a fusion variant Cas9 polypeptide, a variant Cas9 polypeptide may be fused to a heterologous polypeptide (i.e. a polypeptide other than Cas9), which exhibits an activity that will also be exhibited by the fusion variant Cas9 polypeptide. A heterologous nucleic acid sequence may be linked to a variant Cas9 polypeptide (e.g., by genetic engineering) to generate a nucleotide sequence encoding a fusion variant polypeptide.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., guide nucleic acid) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

A "target nucleic acid" as used herein is a polynucleotide (e.g., RNA, DNA) that includes a "target site" or "target sequence." The terms "target site" or "target sequence" are used interchangeably herein to refer to a nucleic acid sequence present in a target nucleic acid to which a targeting segment of a subject guide nucleic acid will bind (see FIG. 8A-8F), provided sufficient conditions for binding exist. For example, the target site (or target sequence) 5'-GAGCAUAUC-3' within a target nucleic acid is targeted by (or is bound by, or hybridizes with, or is complementary to) the sequence 5'-GAUAUGCUC-3'. Suitable hybridization conditions include physiological conditions normally present in a cell. For a double stranded target nucleic acid, the strand of the target nucleic acid that is complementary to and hybridizes with the guide nucleic acid is referred to as the "complementary strand"; while the strand of the target nucleic acid that is complementary to the "complementary strand" (and is therefore not complementary to the guide nucleic acid) is referred to as the "noncomplementary strand" or "non-complementary strand". In cases where the target nucleic acid is a single stranded target nucleic acid (e.g., single stranded DNA (ssDNA), single stranded RNA (ssRNA)), the guide nucleic acid is complementary to and hybridizes with single stranded target nucleic acid.

By "Cas9 polypeptide" or "site-directed polypeptide" or "site-directed Cas9 polypeptide" it is meant a polypeptide that binds RNA (e.g., the protein binding segment of a guide nucleic acid) and is targeted to a specific sequence (a target site) in a target nucleic acid. A Cas9 polypeptide as described herein is targeted to a target site by the guide nucleic acid to which it is bound. The guide nucleic acid comprises a sequence that is complementary to a target sequence within the target nucleic acid, thus targeting the bound Cas9 polypeptide to a specific location within the target nucleic acid (the target sequence) (e.g., stabilizing the interaction of Cas9 with the target nucleic acid). In some cases, the Cas9 polypeptide is a naturally-occurring polypeptide (e.g., naturally occurs in bacterial and/or archaeal cells). In other cases, the Cas9 polypeptide is not a naturally-occurring polypeptide (e.g., the Cas9 polypeptide is a variant Cas9 polypeptide, a chimeric polypeptide as discussed below, and the like). Exemplary Cas9 polypeptides are set forth in SEQ ID NOs: 1-259, and 795-1346 as a non-limiting and non-exhaustive list. Naturally occurring Cas9 polypeptides bind a guide nucleic acid, are thereby directed to a specific sequence within a target nucleic acid (a target site), and cleave the target nucleic acid (e.g., cleave dsDNA to generate a double strand break, cleave ssDNA, cleave ssRNA, etc.). A subject Cas9 polypeptide comprises two portions, an RNA-binding portion and an activity portion. An RNA-binding portion interacts with a subject guide nucleic acid. An activity portion exhibits site-directed enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases the activity portion exhibits reduced nuclease activity relative to the corresponding portion of a wild type Cas9 polypeptide. In some cases, the activity portion is enzymatically inactive.

By "cleavage" it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. In certain embodiments, a complex comprising a guide nucleic acid and a Cas9 polypeptide is used for targeted cleavage of a single stranded target nucleic acid (e.g., ssRNA, ssDNA).

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.).

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

A nucleic acid molecule that binds to the Cas9 polypeptide and targets the polypeptide to a specific location within the target nucleic acid is referred to herein as a "guide nucleic acid". When the guide nucleic acid is an RNA molecule, it can be referred to as a "guide RNA" or a "gRNA". A subject guide nucleic acid comprises two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule. For example, in some cases the protein-binding segment (described below) of a guide nucleic acid is one nucleic acid molecule (e.g., one RNA molecule) and the protein-binding segment therefore comprises a region of that one molecule. In other cases, the protein-binding segment (described below) of a guide nucleic acid comprises two separate molecules that are hybridized along a region of complementarity. As an illustrative, non-limiting example, a protein-binding segment of a guide nucleic acid that comprises two separate molecules can comprise (i) base pairs 40-75 of a first molecule (e.g., RNA molecule, DNA/RNA hybrid molecule) that is 100 base pairs in length; and (ii) base pairs 10-25 of a second molecule (e.g., RNA molecule) that is 50 base pairs in length. The definition of "segment," unless otherwise specifically defined in a particular context, is not limited to a specific number of total base pairs, is not limited to any particular number of base pairs from a given nucleic acid molecule, is not limited to a particular number of separate molecules within a complex, and may include regions of nucleic acid molecules that are of any total length and may or may not include regions with complementarity to other molecules.

The first segment (targeting segment) of a guide nucleic acid comprises a nucleotide sequence that is complementary to a specific sequence (a target site) within a target nucleic acid (e.g., a target ssRNA, a target ssDNA, the complementary strand of a double stranded target DNA, etc.). The protein-binding segment (or "protein-binding sequence") interacts with a Cas9 polypeptide. Site-specific binding and/or cleavage of the target nucleic acid can occur at locations determined by base-pairing complementarity between the guide nucleic acid and the target nucleic acid.

The protein-binding segment of a subject guide nucleic acid comprises two complementary stretches of nucleotides that hybridize to one another to form a double stranded RNA duplex (dsRNA duplex).

In some embodiments, a subject nucleic acid (e.g., a guide nucleic acid, a nucleic acid comprising a nucleotide sequence encoding a guide nucleic acid; a nucleic acid encoding a Cas9 polypeptide; a PAMmer, etc.) comprises a modification or sequence (e.g., an additional segment at the 5' and/or 3' end) that provides for an additional desirable feature (e.g., modified or regulated stability; subcellular targeting; tracking, e.g., a fluorescent label; a binding site for a protein or protein complex; etc.). Non-limiting examples include: a 5' cap (e.g., a 7-methylguanylate cap (m7G)); a 3' polyadenylated tail (i.e., a 3' poly(A) tail); a ribozyme sequence (e.g. to allow for self-cleavage and release of a mature molecule in a regulated fashion); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the nucleic acid to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA and/or RNA, including transcriptional activators, transcriptional repressors, DNA methyltransferases, DNA demethylases, histone acetyltransferases, histone deacetylases, and the like); and combinations thereof.

A subject guide nucleic acid and a subject Cas9 polypeptide form a complex (i.e., bind via non-covalent interactions). The guide nucleic acid provides target specificity to the complex by comprising a nucleotide sequence that is complementary to a sequence of a target nucleic acid. The Cas9 polypeptide of the complex provides the site-specific activity. In other words, the Cas9 polypeptide is guided to a target nucleic acid sequence (e.g. a target sequence in a chromosomal nucleic acid; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; etc.) by virtue of its association with the protein-binding segment of the guide nucleic acid.

In some embodiments, a subject guide nucleic acid comprises two separate nucleic acid molecules: an "activator" and a "targeter" (see below) and is referred to herein as a "dual guide nucleic acid", a "double-molecule guide nucleic acid", or a "two-molecule guide nucleic acid." If both molecules of a dual guide nucleic acid are RNA molecules, the dual guide nucleic acid can be referred to as a "dual guide RNA" or a "dgRNA." In some embodiments, the subject guide nucleic acid is a single nucleic acid molecule (single polynucleotide) and is referred to herein as a "single guide nucleic acid", a "single-molecule guide nucleic acid," or a "one-molecule guide nucleic acid." If a single guide nucleic acid is an RNA molecule, it can be referred to as a "single guide RNA" or an "sgRNA." The term "guide nucleic acid" is inclusive, referring to both dual guide nucleic acids and to single guide nucleic acids (e.g., dgRNAs, sgRNAs, etc.).

In some cases, a guide nucleic acid is a DNA/RNA hybrid molecule. In such cases, the protein-binding segment of the guide nucleic acid is RNA and forms an RNA duplex. However, the targeting segment of a guide nucleic acid can be DNA. Thus, if a DNA/RNA hybrid guide nucleic acid is a dual guide nucleic acid, the "targeter" molecule and be a hybrid molecule (e.g., the targeting segment can be DNA and the duplex-forming segment can be RNA). In such cases, the duplex-forming segment of the "activator" molecule can be RNA (e.g., in order to form an RNA-duplex with the duplex-forming segment of the targeter molecule), while nucleotides of the "activator" molecule that are outside of the duplex-forming segment can be DNA (in which case the activator molecule is a hybrid DNA/RNA molecule) or can be RNA (in which case the activator molecule is RNA). If a DNA/RNA hybrid guide nucleic acid is a single guide nucleic acid, then the targeting segment can be DNA, the duplex-forming segments (which make up the protein-binding segment) can be RNA, and nucleotides outside of the targeting and duplex-forming segments can be RNA or DNA.

An exemplary dual guide nucleic acid comprises a crRNA-like ("CRISPR RNA" or "targeter" or "crRNA" or "crRNA repeat") molecule and a corresponding tracrRNA-like ("trans-acting CRISPR RNA" or "activator" or "tracrRNA") molecule. A crRNA-like molecule (targeter) comprises both the targeting segment (single stranded) of the guide nucleic acid and a stretch ("duplex-forming segment") of nucleotides that forms one half of the dsRNA duplex of the protein-binding segment of the guide nucleic acid. A corresponding tracrRNA-like molecule (activator) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the guide nucleic acid. As such, each crRNA-like molecule can be said to have a corresponding tracrRNA-like molecule. The crRNA-like molecule additionally provides the single stranded targeting segment. Thus, a crRNA-like and a tracrRNA-like molecule (as a corresponding pair) hybridize to form a dual guide nucleic acid. The exact sequence of a given crRNA or tracrRNA molecule is characteristic of the species in which the RNA molecules are found. Various suitable activators and targeters are depicted individually, as well as in corresponding complementary pairs in FIG. 11-14 (described in more detail below). A subject dual guide nucleic acid can include any corresponding activator and targeter pair.

The term "activator" is used herein to mean a tracrRNA-like molecule of a dual guide nucleic acid (and of a single guide nucleic acid when the "activator" and the "targeter" are linked together by intervening nucleic acids). The term "targeter" is used herein to mean a crRNA-like molecule of a dual guide nucleic acid (and of a single guide nucleic acid when the "activator" and the "targeter" are linked together by intervening nucleic acids). The term "duplex-forming segment" is used herein to mean the stretch of nucleotides of an activator or a targeter that contributes to the formation of the dsRNA duplex by hybridizing to a stretch of nucleotides of a corresponding activator or targeter molecule. In other words, an activator comprises a duplex-forming segment that is complementary to the duplex-forming segment of the corresponding targeter. As such, an activator comprises a duplex-forming segment while a targeter comprises both a duplex-forming segment and the targeting segment of the guide nucleic acid. A subject single guide nucleic acid can comprise an "activator" and a "targeter" where the "activator" and the "targeter" are covalently linked (e.g., by intervening nucleotides). Therefore, a subject dual guide nucleic acid can be comprised of any corresponding activator and targeter pair.

A "host cell" or "target cell" as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ecto-derm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hESl (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This quiescent state may be temporary, i.e. reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

In some instances, a component (e.g., a nucleic acid component (e.g., a guide nucleic acid, a PAMmer, etc.); a protein component (e.g., a Cas9 polypeptide, a variant Cas9 polypeptide); and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels)(e.g., a fluorescent label) and indirectly detectable labels (indirect labels)(e.g., a binding pair member). A fluorescent label can be any fluorescent lable (e.g., a fluorescent dye (e.g., fluorescein, Texas red, rhodamine, ALEXAFLUOR® labels, and the like), a fluorescent protein (e.g., GFP, EGFP, YFP, RFP, CFP, YFP, cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^3$H, $^{125}$I, $^{35}$S, $^{14}$C, or $^{32}$P); an enzyme (an indirect label)(e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, *lucifer* yellow/anti-*lucifer* yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some cases, when two or more components are labeled, they can be labeled with label moieties that are distinguiahable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions and methods for modifying (binding and/or cleaving) a single stranded target nucleic acid. A method of cleaving includes contacting a singled stranded target nucleic acid with (or introducing into a cell) a Cas9 polypeptide, a guide nucleic acid (e.g., a dual guide RNA, a single guide RNA, an RNA/DNA hybrid guide RNA, etc.), and a PAMmer. A subject PAMmer is a single stranded oligonucleotide having a protospacer adjacent motif (PAM) sequence and at least one of: (i) a specificity segment, positioned 5' of the PAM sequence, having a nucleotide sequence that is complementary to a first target nucleotide sequence in the target nucleic acid (i.e., the target site); and (ii) an orientation segment, positioned 3' of the PAM sequence, having a nucleotide sequence that is complementary to a second target nucleotide sequence in the target nucleic acid (i.e., the orientation site). A method of binding includes contacting a singled stranded target nucleic acid with (or introducing into a cell): (i) a variant Cas9 polypeptide having reduced or undetectable nuclease activity relative to a corresponding wild type Cas9 polypeptide; and (ii) a guide nucleic acid. In some cases, a method of binding includes contacting a singled stranded target nucleic acid with (or introducing into a cell): (i) a variant Cas9 polypeptide having reduced or undetectable nuclease activity relative to a corresponding wild type Cas9 polypeptide; (ii) a guide nucleic acid; and (iii) a PAMmer. In some cases, methods of binding are for visualizing single stranded target nucleic acids using a detectable label. In some cases, methods of binding are for isolating, collecting, and/or analyzing bound single stranded target nucleic acids and/or polypeptides associated with the bound single stranded target nucleic acids.

In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). In some cases, a Cas9 polypeptide is conjugated to a PAMmer. In some cases, a guide nucleic acid is conjugated to a PAMmer. In some cases, a guide nucleic acid is a DNA/RNA hybrid guide nucleic acid where the segment that is complementary to a target nucleic acid (i.e., the targeting segment) has DNA and the segment that interacts with a Cas9 polypeptide (i.e., the protein-binding segment) has RNA. The subject methods can be performed outside of a cell in vitro, inside of a cell in vitro or ex vivo, and/or inside of a cell in vivo. Also provided are kits and libraries for performing the disclosed methods.

Throughout the description below, when referring to the components (e.g., a PAMmer, a guide nucleic acid, a Cas9 polypeptide, etc.) of subject compositions and methods, terms describing the components can also be provided as nucleic acids encoding the component. For example, when a composition or method includes a Cas9 polypeptide, it is understood that the Cas9 can be provided as the actual polypeptide or as a nucleic acid (DNA or RNA) encoding the same. Likewise, when a composition or method includes a PAMmer, it is understood that the PAMmer can be provided as the actual PAMmer or as a nucleic acid (DNA) encoding the same. For example, in some cases a PAMmer is DNA, in some cases a PAMmer is a modified nucleic acid, and in some cases a PAMmer is RNA, in which case the term "PAMmer" can be provided as the actual RNA PAMmer but also can be provided as a DNA encoding the RNA PAMmer. Likewise, when a composition or method includes a guide nucleic acid, it is understood that the guide nucleic acid can be provided as the actual guide nucleic acid or as a nucleic acid (DNA) encoding the same. For example, in some cases a guide nucleic acid is a modified nucleic acid, in some cases a guide nucleic acid is a DNA/RNA hybrid molecule, and in some cases a guide nucleic acid is RNA, in which case the guide nucleic acid can be provided as the actual guide RNA or as a DNA (e.g., plasmid) encoding the guide RNA.

Compositions and Components

The present disclosure provides compositions for binding and/or cleaving a single stranded target nucleic acid. A composition for cleaving includes a PAMmer and at least one of: a guide nucleic acid (e.g., a dual guide RNA, a single guide RNA, an RNA/DNA hybrid guide RNA, etc.), and a Cas9 polypeptide. A composition for binding includes a guide nucleic acid (e.g., a dual guide RNA, a single guide RNA, an RNA/DNA hybrid guide RNA, etc.) and a Cas9 polypeptide. A composition for binding can also include a PAMmer.

FIG. 8A-8D presents a schematic depiction of exemplary embodiments of the present disclosure.

Guide Nucleic Acid

The present disclosure provides a guide nucleic acid that directs the activities of an associated polypeptide (e.g., a Cas9 polypeptide) to a specific target sequence within a target nucleic acid. A subject guide nucleic acid comprises: a first segment (also referred to herein as a "nucleic acid targeting segment", or simply a "targeting segment"); and a second segment (also referred to herein as a "protein-binding segment").

First Segment: Targeting Segment

The first segment of a subject guide nucleic acid comprises a nucleotide sequence that can be complementary to a sequence (a target site) in a target nucleic acid. In other words, the targeting segment of a subject guide nucleic acid can interact with a target nucleic acid (e.g., a single stranded RNA (ssRNA) and/or a single stranded DNA (ssDNA)) in a sequence-specific manner via hybridization (i.e., base pairing). As such, the nucleotide sequence of the targeting segment may vary and can determine the location within the target nucleic acid that the guide nucleic acid and the target nucleic acid will interact. The targeting segment of a subject guide nucleic acid can be modified (e.g., by genetic engineering) to hybridize to any desired sequence (target site) within a target nucleic acid.

The targeting segment can have a length of from about 12 nucleotides to about 100 nucleotides. For example, the targeting segment can have a length of from about 12 nucleotides (nt) to about 80 nt, from about 12 nt to about 50nt, from about 12 nt to about 40 nt, from about 12 nt to about 30 nt, from about 12 nt to about 25 nt, from about 12 nt to about 20 nt, or from about 12 nt to about 19 nt. For example, the targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence (the targeting sequence) of the targeting segment that is complementary to a nucleotide sequence (target site) of the target nucleic acid can have a length of 12 nt or more. For example, the targeting sequence of the targeting segment that is complementary to a target site of the target nucleic acid can have a length of 12 nt or more, 15 nt or more, 18 nt or more, 19 nt or more, 20 nt or more, 25 nt or more, 30 nt or more, 35 nt or more or 40 nt. For example, the targeting sequence of the targeting segment that is complementary to a target sequence of the target nucleic acid can have a length of from about 12 nucleotides (nt) to about 80 nt, from about 12 nt to about 50nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. The nucleotide sequence (the targeting sequence) of the targeting segment that is complementary to a nucleotide sequence (target site) of the target nucleic acid can have a length of 12 nt or more.

In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

The percent complementarity between the targeting sequence of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

Where a method of binding is to be performed, the targeting segment of the guide nucleic acid does not need to have complementarity to the region of the target nucleic acid that will be bound (i.e., the target site). For example, in some such cases, the orientation segment of the PAMmer determines the target site of the target nucleic acid (i.e., in such cases, the target site is not defined by complementarity to the guide nucleic acid). For example, in some cases, for a method of binding, when the PAMmer does not have a specificity segment, the guide nucleic acid need not have complementarity to the target nucleic acid, and the binding of the Cas9 polypeptide to the target nucleic acid is determined by the orientation segment of the PAMmer. In other words, a Cas9 polypeptide:guide nucleic acid complex can bind to a single stranded target nucleic acid when the orientation segment of the PAMmer binds to the target nucleic acid, and the complex does not require that the targeting segment of the guide nucleic acid has complementarity to the target nucleic acid (see FIG. 5A-5C and FIG. 8A-8F).

As another example, in some cases (e.g., for a method of binding), when the PAMmer has a specificity segment that is 10 nucleotides (nt) or less (e.g., 9 nt or less, 8 nt or less, 7 nt or less, 6 nt or less, 5 nt or less, 4 nt or less, 3 nt or less, 2 nt or less, or 1 nt or less), the guide nucleic acid need not have complementarity to the target nucleic acid, and the binding of the Cas9 polypeptide to the target nucleic acid can be determined by the orientation segment of the PAMmer (i.e., the Cas9 polypeptide:guide nucleic acid complex will bind to a single stranded target nucleic acid when the orientation segment of the PAMmer binds to the target nucleic acid).

Second Segment: Protein-Binding Segment

The protein-binding segment of a subject guide nucleic acid interacts with a Cas9 polypeptide. The subject guide nucleic acid guides the bound polypeptide to a specific nucleotide sequence within target nucleic acid via the above mentioned targeting segment. The protein-binding segment of a subject guide nucleic acid comprises two stretches of nucleotides that are complementary to one another. The complementary nucleotides of the protein-binding segment hybridize to form a double stranded RNA duplex (dsRNA) (see FIG. 8A and FIG. 8B).

Figure 8A:
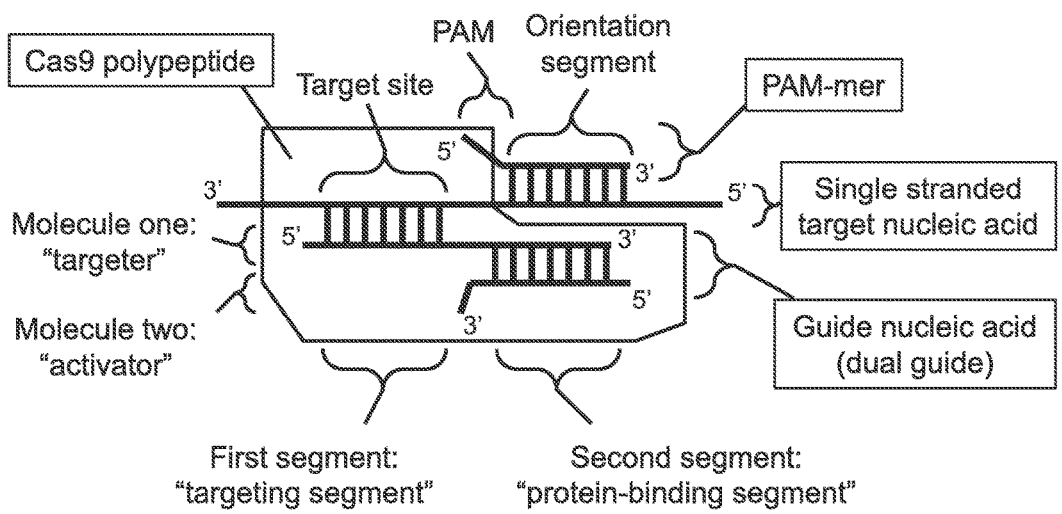
FIG. 8A-8F provide a schematic drawing of exemplary embodiments of subject compositions and methods. (A-B) Each embodiment depicted includes a PAMmer, which is hybridized to a single stranded target nucleic acid; and a guide nucleic acid, which is hybrized to the target nucleic acid and is associated with a Cas9 polypeptide. (C-D) Each embodiment depicted includes a PAMmer having a specificity segment and an orientation segment. The PAM sequence is complementary to the target nucleic acid in 8C, and is not complementary to the target nucleic acid in 8D.
Figure 8B:
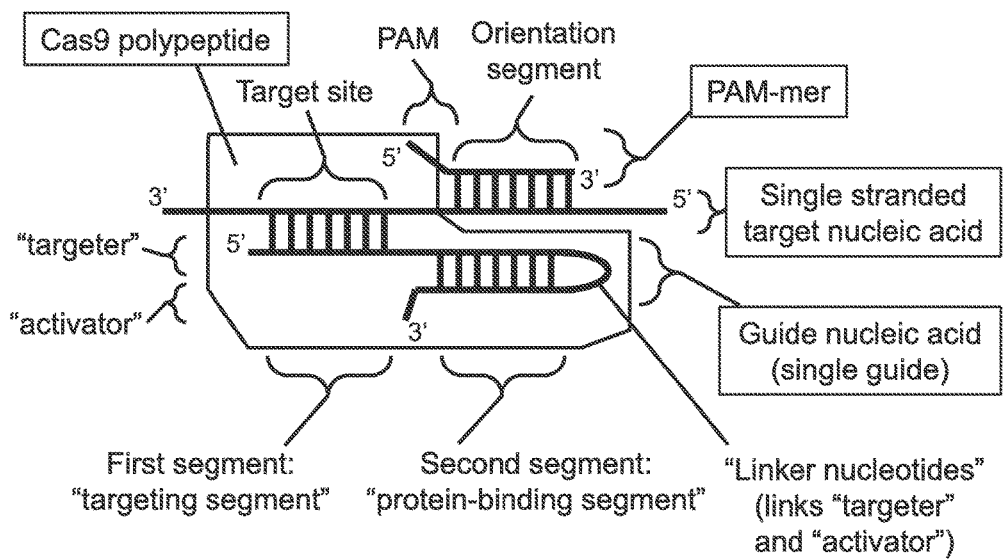
Figure 8C:
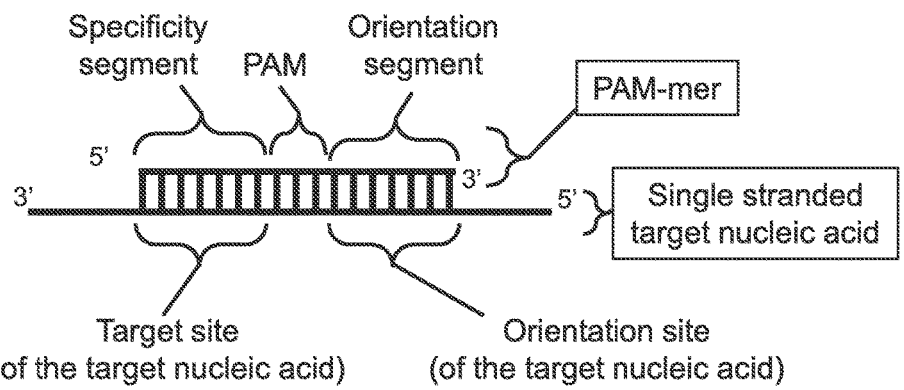
Figure 8D:
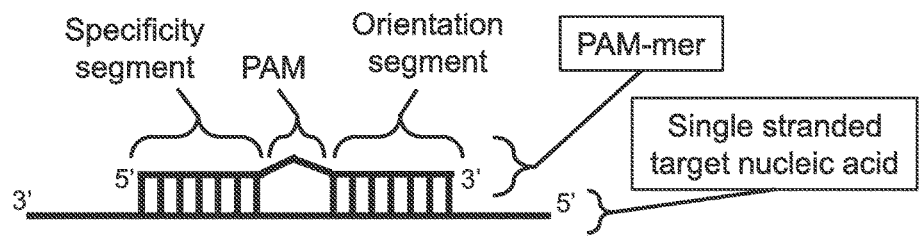

A subject dual guide nucleic acid comprises two separate nucleic acid molecules. Each of the two molecules of a subject dual guide nucleic acid comprises a stretch of nucleotides that are complementary to one another such that the complementary nucleotides of the two molecules hybridize to form the double stranded RNA duplex of the protein-binding segment (FIG. 8A).

In some embodiments, the duplex-forming segment of the activator is 60% or more identical to one of the activator (tracrRNA) molecules set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, the duplex-forming segment of the activator (or the DNA encoding the duplex-forming segment of the activator) can be 65% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) can be 70% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) can be 75% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) can be 80% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) can be 85% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) can be 90% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) can be 95% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) can be 98% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) can be 99% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) can be 100% identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, the duplex-forming segment of the targeter is 60% or more identical to one of the targeter (crRNA) seqeunces set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 contig or more contiguous uous nucleotides, or 20 or more contiguous nucleotides). For example, the duplex-forming segment of the targeter (or the DNA encoding the duplex-forming segment of the targeter) can be 65% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) can be 70% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) can be 75% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) can be 80% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) can be 85% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) can be 90% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) can be 95% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) can be 98% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) can be 99% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) can be 100% identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

A dual guide nucleic acid can be designed to allow for controlled (i.e., conditional) binding of a targeter with an activator. Because a dual guide nucleic acid is not functional unless both the activator and the targeter are bound in a functional complex with Cas9, a dual guide nucleic acid can be inducible (e.g., drug inducible) by rendering the binding between the activator and the targeter to be inducible. As one non-limiting example, RNA aptamers can be used to regulate (i.e., control) the binding of the activator with the targeter. Accordingly, the activator and/or the targeter can include an RNA aptamer sequence.

Aptamers (e.g., RNA aptamers) are known in the art and are generally a synthetic version of a riboswitch. The terms "RNA aptamer" and "riboswitch" are used interchangeably herein to encompass both synthetic and natural nucleic acid sequences that provide for inducible regulation of the structure (and therefore the availability of specific sequences) of the nucleic acid molecule (e.g., RNA, DNA/RNA hybrid, etc.) of which they are part. RNA aptamers usually comprise a sequence that folds into a particular structure (e.g., a hairpin), which specifically binds a particular drug (e.g., a small molecule). Binding of the drug causes a structural change in the folding of the RNA, which changes a feature of the nucleic acid of which the aptamer is a part. As non-limiting examples: (i) an activator with an aptamer may not be able to bind to the cognate targeter unless the aptamer is bound by the appropriate drug; (ii) a targeter with an aptamer may not be able to bind to the cognate activator unless the aptamer is bound by the appropriate drug; and (iii) a targeter and an activator, each comprising a different aptamer that binds a different drug, may not be able to bind to each other unless both drugs are present. As illustrated by these examples, a dual guide nucleic acid can be designed to be inducible.

Examples of aptamers and riboswitches can be found, for example, in: Nakamura et al., Genes Cells. 2012 May; 17(5):344-64; Vavalle et al., Future Cardiol. 2012 May; 8(3):371-82; Citartan et al., Biosens Bioelectron. 2012 Apr. 15; 34(1):1-11; and Liberman et al., Wiley Interdiscip Rev RNA. 2012 May-June; 3(3):369-84; all of which are herein incorporated by reference in their entirety.

Non-limiting examples of nucleotide sequences that can be included in a dual guide nucleic acid include either of the sequences set forth in SEQ ID NOs:431-562, or complements thereof pairing with any sequences set forth in SEQ ID NOs:563-679, or complements thereof that can hybridize to form a protein binding segment.

A subject single guide nucleic acid comprises two stretches of nucleotides (much like a "targeter" and an "activator" of a dual guide nucleic acid) that are complementary to one another, hybridize to form the double stranded RNA duplex (dsRNA duplex) of the protein-binding segment (thus resulting in a stem-loop structure), and are covalently linked by intervening nucleotides ("linkers" or "linker nucleotides"). Thus, a subject single guide nucleic acid (e.g., a single guide RNA) can comprise a targeter and an activator, each having a duplex-forming segment, where the duplex-forming segments of the targeter and the activator hybridize with one another to form a dsRNA duplex. The targeter and the activator can be covalently linked via the 3' end of the targeter and the 5' end of the activator (see FIG. 8B). Alternatively, targeter and the activator can be covalently linked via the 5' end of the targeter and the 3' end of the activator.

The linker of a single guide nucleic acid can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a single guide nucleic acid is 4 nt.

An exemplary single guide nucleic acid comprises two complementary stretches of nucleotides that hybridize to form a dsRNA duplex. In some embodiments, one of the two complementary stretches of nucleotides of the single guide nucleic acid (or the DNA encoding the stretch) is 60% or more identical to one of the activator (tracrRNA) molecules set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, one of the two complementary stretches of nucleotides of the single guide nucleic acid (or the DNA encoding the stretch) is 65% or more identical, 70% or more identical, 75% or more identical, 80% or more identical, 85% or more identical, 90% or more identical, 95% or more identical, 98% or more identical, 99% or more identical or 100% identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, one of the two complementary stretches of nucleotides of the single guide nucleic acid (or the DNA encoding the stretch) is 60% or more identical to one of the targeter (crRNA) sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, one of the two complementary stretches of nucleotides of the single guide nucleic acid (or the DNA encoding the stretch) is 65% or more identical, 70% or more identical, 75% or more identical, 80% or more identical, 85% or more identical, 90% or more identical, 95% or more identical, 98% or more identical, 99% or more identical or 100% identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, one of the two complementary stretches of nucleotides of the single guide nucleic acid (or the DNA encoding the stretch) is 60% or more identical to one of the targeter (crRNA) sequences or activator (tracrRNA) sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, one of the two complementary stretches of nucleotides of the single guide nucleic acid (or the DNA encoding the stretch) can be 65% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide nucleic acid (or the DNA encoding the stretch) can be 70% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide nucleic acid (or the DNA encoding the stretch) can be 75% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides)

One of the two complementary stretches of nucleotides of the single guide nucleic acid (or the DNA encoding the stretch) can be 80% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide nucleic acid (or the DNA encoding the stretch) can be 85% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide nucleic acid (or the DNA encoding the stretch) can be 90% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide nucleic acid (or the DNA encoding the stretch) can be 95% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide nucleic acid (or the DNA encoding the stretch) can be 98% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide nucleic acid (or the DNA encoding the stretch) can be 99% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide nucleic acid (or the DNA encoding the stretch) can be 100% identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

Appropriate cognate pairs of targeters and activators can be routinely determined for SEQ ID NOs:431-679 by taking into account the species name and base-pairing (for the dsRNA duplex of the protein-binding domain) (see FIG. 11A-11B, FIG. 12A-12B, FIG. 13, and FIG. 14 for non-limiting examples of activator sequences, targeter sequences, paired activator/targeter sequences, and single guide nucleic acid sequences designed from corresponding activator/targeter pairs). Any activator/targeter pair can be used as part of subject dual guide nucleic acid or as part of a subject single guide nucleic acid.

In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 60% or more sequence identity (e.g., 65% or more, 70% or more, 75% or more, 80% or more, 85% or more, 90% or more, 95% or more, 98% or more, or 100% sequence identity) with an activator (tracrRNA) molecule set forth in any one of SEQ ID NOs:431-562, and 1535-1544, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 70% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 75% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 80% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 85% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 90% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 95% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 98% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 100% sequence identity with an activator (tracrRNA) molecule set forth in any one of SEQ ID NOs:431-562, and 1535-1544, or a complement thereof.

In some cases, an activator (e.g., a trRNA, trRNA-like molecule, etc.) of a dual guide nucleic acid (e.g., a dual guide RNA) or a single guide nucleic acid (e.g., a single guide RNA) includes 30 or more nucleotides (nt) (e.g., 40 or more, 50 or more, 60 or more, 70 or more, 75 or more nt). In some cases, an activator (e.g., a trRNA, trRNA-like molecule, etc.) of a dual guide nucleic acid (e.g., a dual guide RNA) or a single guide nucleic acid (e.g., a single guide RNA) has a length in a range of from 30 to 200 nucleotides (nt) (e.g., 40 to 200 nucleotides, 50 to 200 nucleotides, 60 to 200 nucleotides, 65 to 200 nucleotides, 70 to 200 nucleotides, 75 to 200 nucleotides, 40 to 150 nucleotides, 50 to 150 nucleotides, 60 to 150 nucleotides, 65 to 150 nucleotides, 70 to 150 nucleotides, 75 to 150 nucleotides, 40 to 100 nucleotides, 50 to 100 nucleotides, 60 to 100 nucleotides, 65 to 100 nucleotides, 70 to 100 nucleotides, or 75 to 100 nucleotides).

The protein-binding segment can have a length of from about 10 nucleotides to about 100 nucleotides. For example, the protein-binding segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

Also with regard to both a subject single guide nucleic acid and to a subject dual guide nucleic acid, the dsRNA duplex of the protein-binding segment can have a length from about 6 base pairs (bp) to about 50 bp. For example, the dsRNA duplex of the protein-binding segment can have a length from about 6 bp to about 40 bp, from about 6 bp to about 30 bp, from about 6 bp to about 25 bp, from about 6 bp to about 20 bp, from about 6 bp to about 15 bp, from about 8 bp to about 40 bp, from about 8 bp to about 30 bp, from about 8 bp to about 25 bp, from about 8 bp to about 20 bp or from about 8 bp to about 15 bp. For example, the dsRNA duplex of the protein-binding segment can have a length from about from about 8 bp to about 10 bp, from about 10 bp to about 15 bp, from about 15 bp to about 18 bp, from about 18 bp to about 20 bp, from about 20 bp to about 25 bp, from about 25 bp to about 30 bp, from about 30 bp to about 35 bp, from about 35 bp to about 40 bp, or from about 40 bp to about 50 bp. In some embodiments, the dsRNA duplex of the protein-binding segment has a length of 36 base pairs. The percent complementarity between the nucleotide sequences that hybridize to form the dsRNA duplex of the protein-binding segment can be 60% or more. For example, the percent complementarity between the nucleotide sequences that hybridize to form the dsRNA duplex of the protein-binding segment can be 65% or more, 70% or more, 75% or more, 80% or more, 85% or more, 90% or more, 95% or more, 98% or more, or 99% or more. In some cases, the percent complementarity between the nucleotide sequences that hybridize to form the dsRNA duplex of the protein-binding segment is 100%.

Hybrid Guide Nucleic Acids

In some cases, a guide nucleic acid is two RNA molecules (dual guide RNA). In some cases, a guide nucleic acid is one RNA molecule (single guide RNA). In some cases, a guide nucleic acid is a DNA/RNA hybrid molecule. In such cases, the protein-binding segment of the guide nucleic acid is RNA and forms an RNA duplex. Thus, the duplex-forming segments of the activator and the targeter is RNA. However, the targeting segment of a guide nucleic acid can be DNA. Thus, if a DNA/RNA hybrid guide nucleic acid is a dual guide nucleic acid, the "targeter" molecule and be a hybrid molecule (e.g, the targeting segment can be DNA and the duplex-forming segment can be RNA). In such cases, the duplex-forming segment of the "activator" molecule can be RNA (e.g., in order to form an RNA-duplex with the duplex-forming segment of the targeter molecule), while nucleotides of the "activator" molecule that are outside of the duplex-forming segment can be DNA (in which case the activator molecule is a hybrid DNA/RNA molecule) or can be RNA (in which case the activator molecule is RNA). If a DNA/RNA hybrid guide nucleic acid is a single guide nucleic acid, then the targeting segment can be DNA, the duplex-forming segments (which make up the protein-binding segment of the single guide nucleic acid) can be RNA, and nucleotides outside of the targeting and duplex-forming segments can be RNA or DNA.

A DNA/RNA hybrid guide nucleic can be useful in some cases, for example, when a target nucleic acid is an RNA. Cas9 normally associates with a guide RNA that hybridizes with a target DNA, thus forming a DNA-RNA duplex at the target site. Therefore, when the target nucleic acid is an RNA, it is sometimes advantageous to recapitulate a DNA-RNA duplex at the target site by using a targeting segment (of the guide nucleic acid) that is DNA instead of RNA. However, because the protein-binding segment of a guide nucleic acid is an RNA-duplex, the targeter molecule is DNA in the targeting segment and RNA in the duplex-forming segment. Hybrid guide nucleic acids can bias Cas9 binding to single stranded target nucleic acids relative to double stranded target nucleic acids.

Exemplary Guide Nucleic Acids

In some embodiments, a suitable guide nucleic acid comprises two separate RNA polynucleotide molecules. In some cases, the first of the two separate RNA polynucleotide molecules (the activator) comprises a nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in SEQ ID NOs:431-562, or a complement thereof. In some cases, the second of the two separate RNA polynucleotide molecules (the targeter) comprises a nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in SEQ ID NOs: 563-679, or a complement thereof.

In some embodiments, a suitable guide nucleic acid is a single RNA polynucleotide and comprises a first nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in SEQ ID NOs:431-562 and a second nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in SEQ ID NOs: 463-679.

In some embodiments, the guide nucleic acid is a dual guide nucleic acid and the targeter comprises the sequence 5'GUUUUAGAGCUA-3' (SEQ ID NO:679) linked at its 5' end to a stretch of nucleotides that are complementary to a target nucleic acid. In some embodiments, the guide nucleic acid is a dual guide nucleic acid and the activator comprises the sequence 5' UAGCAAGUUAAAAUAAGGCUAGU-CCG-3' (SEQ ID NO:397).

In some embodiments, the guide nucleic acid is a single guide nucleic acid and comprises the sequence 5'-GUUUUAGAGCUA-linker-UAG-CAAGUUAAAAUAAGGCUAGUCCG-3' (SEQ ID NO:680) linked at its 5' end to a stretch of nucleotides that are complementary to a target nucleic acid (where "linker" denotes any a linker nucleotide sequence that can comprise any nucleotide sequence). Other exemplary single guide nucleic acids include those set forth in SEQ ID NOs: 680-682.

Stability Control Sequence (e.g., Transcriptional Terminator Segment)

In some embodiments, a guide nucleic acid comprises a stability control sequence. A stability control sequence influences the stability of a nucleic acid (e.g., a guide nucleic acid, a targeter, an activator, etc.). One example of a suitable stability control sequence for use with an RNA is a transcriptional terminator segment (i.e., a transcription termination sequence). A transcriptional terminator segment of a subject guide nucleic acid can have a total length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

In some cases, the transcription termination sequence is one that is functional in a eukaryotic cell. In some cases, the transcription termination sequence is one that is functional in a prokaryotic cell.

Non-limiting examples of nucleotide sequences that can be included in a stability control sequence (e.g., transcriptional termination segment, or in any segment of the guide nucleic acid to provide for increased stability) include sequences set forth in SEQ ID NO:683-696 and, for example, 5'-UAAUCCCACAGCCGCCAGUUCCGCUG-GCGGCAUUUU-5' (SEQ ID NO:795) (a Rho-independent trp termination site).

Additional Sequences

In some embodiments, a guide nucleic acid comprises an additional segment or segments (in some cases at the 5' end, in some cases the 3' end, in some cases at either the 5' or 3' end, in some cases embedded within the sequence (i.e., not at the 5' and/or 3' end), in some cases at both the 5' end and the 3' end, in some cases embedded and at the 5' end and/or the 3' end, etc). For example, a suitable additional segment can comprise a 5' cap (e.g., a 7-methylguanylate cap (m$^7$G)); a 3' polyadenylated tail (i.e., a 3' poly(A) tail); a ribozyme sequence (e.g. to allow for self-cleavage of a guide nucleic acid (or component of a guide nucleic acid, e.g., a targeter, an activator, etc.) and release of a mature PAMmer in a regulated fashion); a riboswitch sequence (e.g., to allow for regulated stability and/or regulated accessibility by proteins and protein complexes); a sequence that forms a dsRNA duplex (i.e., a hairpin)); a sequence that targets an RNA to a subcellular location (e.g., nucleus, mitochondria, chloroplasts, and the like); a modification or sequence that provides for tracking (e.g., a direct label (e.g., direct conjugation to a fluorescent molecule (i.e., fluorescent dye)), conjugation to a moiety that facilitates fluorescent detection, a sequence that allows for fluorescent detection; a modification or sequence that provides a binding site for proteins (e.g., proteins that act on DNA, including transcriptional activators, transcriptional repressors, DNA methyltransferases, DNA demethylases, histone acetyltransferases, histone deacetylases, proteins that bind RNA (e.g., RNA aptemers), labeled proteins, fluorescently labeled proteins, and the like); a modification or sequence that provides for increased, decreased, and/or controllable stability; and combinations thereof.

PAMmer

The present disclosure provides a PAMmer. A subject PAMmer is a single stranded oligonucleotide (as defined above) (e.g., DNA, RNA, a modified nucleic acid (described below), etc.) that hybridizes to a single stranded target nucleic acid (thus converting the single stranded target nucleic acid into a double stranded target nucleic acid at a desired position), and provides a protospacer adjacent motif (PAM) sequence, thus converting the single stranded target nucleic acid into a target for binding and/or cleavge by a Cas9 polypeptide.

In some cases, a PAMmer is a DNA molecule. In some cases, a PAMmer is an RNA molecule. In some cases, a PAMmer is a hybrid DNA/RNA molecule (e.g., in some cases, at least the PAM sequence of the PAMmer is DNA). In some cases the PAMmer has one or more modified nucleic acids (described in more detail below with respect to nucleic acid modifications). In some embodiments, a subject PAMmer has one or more nucleotides that are 2'-O-Methyl modified nucleotides. In some embodiments, a subject PAMmer has one or more 2' Fluoro modified nucleotides. In some embodiments, a subject PAMmer has one or more LNA bases. In some embodiments, a subject PAMmer has one or more nucleotides that are linked by a phosphorothioate bond (i.e., the subject nucleic acid has one or more phosphorothioate linkages). In some embodiments, a subject PAMmer has a 5' cap (e.g., a 7-methylguanylate cap (m7G)). In some embodiments, a subject PAMmer has a combination of modified nucleotides. For example, a subject PAMmer can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage). See FIG. 17A-17B for working examples that utilize PAMmers having one or more modified nucleotides.

A PAMmer includes a PAM sequence and at least one of: an orientation segment (which is positioned 3' of the PAM sequence), and a specificity segment (which is positioned 5' of the PAM sequence). A specificity segment has a nucleotide sequence that is complementary to a first target nucleotide sequence in a target nucleic acid (i.e., the sequence that is targeted by the specificity segment), where the first target nucleotide sequence overlaps (in some cases 100%) with the sequence targeted by the targeting segment of the guide nucleic acid. In other words, the specificity segment is complementary with (and hybridizes to) the target site of the target nucleic acid (see FIG. 8A-8D). In some cases, a PAMmer having a speificity segement is referred to herein as a "5' extended PAMmer." An orientation segment has a nucleotide sequence that is complementary to a second target nucleotide sequence in a target nucleic acid (i.e., the sequence that is targeted by the orientation segment). In some cases, a subject PAMmer includes a PAM sequence and an orientation segment, but does not include a specifity segment. In some cases, a subject PAMmer includes a PAM sequence and a specificity segment, but does not include an orientation segment.

In some cases, a subject PAMmer includes a PAM sequence, an orientation segment, and a specificity segment. The number of nucleotides (nt) present in the PAMmer between a specificity segment and an orientation segment can depend on a number of factors that include, but are not limited to: the length of the PAM sequence (which is present between the specificity segment and the orientation segment); the number of of nucleotides present between the target site and the orientation site of the target nucleic acid; the presence or absence of additional sequences (e.g., aptamers, protein binding sequences, linker nucleotides, stability sequences, etc.) between the specificity segment and the orientation segment; etc. In some embodiments, the number of nucleotides (nt) present in the PAMmer between a specificity segment and an orientation segment is in a range of from 2 nt to 100 nt (e.g., 2 nt to 90 nt, 2 nt to 80 nt, 2 nt to 70 nt, 2 nt to 60 nt, 2 nt to 50 nt, 2 nt to 40 nt, 2 nt to 30 nt, 2 nt to 25 nt, 2 nt to 20 nt, 2 nt to 15 nt, or 2 nt to 10 nt). In some embodiments, the number of nucleotides (nt) present in the PAMmer between the specificity segment and the orientation segment is 100 nt or less (e.g., 90 nt or less, 80 nt or less, 70 nt or less, 60 nt or less, 50 nt or less, 40 nt or less, 30 nt or less, 25 nt or less, 25 nt or less, 20 nt or less, 15 nt or less, or 10 nt or less).

In some embodiments, the PAM sequence is immediately adjacent to the orientation segment, immediately adjacent to the specificity segment, and/or immediately adjacent to both the orientation segment and the specificity segment. In some embodiments, the number of nucleotides (nt) present in the PAMmer between the PAM sequence and the specificity segment of the PAMmer is in a range of from 0 nt to 10 nt (e.g., 0 nt to 9 nt, 0 nt to 8 nt, 0 nt to 7 nt, 0 nt to 6 nt, 0 nt to 5 nt, 0 nt to 4 nt, 0 nt to 3 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 9 nt, 2 nt to 8 nt, 2 nt to 7 nt, 2 nt to 6 nt, 2 nt to 5 nt, 2 nt to 4 nt, or 2 nt to 3 nt). In some embodiments, 10 or less nt (e.g., 9 or less nt, 8 or less nt, 7 or less nt, 6 or less nt, 5 or less nt, 4 or less nt, 3 or less nt, 2 or less nt, 1 or less nt, or no nt) are present in the PAMmer between the PAM sequence and the specificity segment. In some embodiments, the number of nucleotides (nt) present in the PAMmer between the PAM sequence and the orientation segment of the PAMmer is in a range of from 0 nt to 10 nt (e.g., 0 nt to 9 nt, 0 nt to 8 nt, 0 nt to 7 nt, 0 nt to 6 nt, 0 nt to 5 nt, 0 nt to 4 nt, 0 nt to 3 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 9 nt, 2 nt to 8 nt, 2 nt to 7 nt, 2 nt to 6 nt, 2 nt to 5 nt, 2 nt to 4 nt, or 2 nt to 3 nt). In some embodiments, 10 or less nt (e.g., 9 or less nt, 8 or less nt, 7 or less nt, 6 or less nt, 5 or less nt, 4 or less nt, 3 or less nt, 2 or less nt, 1 or less nt, or no nt) are present in the PAMmer between the PAM sequence and the orientation segment.

In some embodiments, a PAMmer has a length (e.g., the PAM sequence and the orientation segment have a combined length) in a range of from 2 nt to 100 nt (e.g., 2 nt to 70 nt, 2 nt to 50 nt, 2 nt to 45 nt, 2 nt to 40 nt, 2 nt to 35 nt, 2 nt to 30 nt, 2 nt to 25 nt, 2 nt to 20 nt, 2 nt to 10 nt, 2 nt to 5 nt, 3 nt to 70 nt, 3 nt to 50 nt, 3 nt to 45 nt, 3 nt to 40 nt, 3 nt to 35 nt, 3 nt to 30 nt, 3 nt to 25 nt, 3 nt to 20 nt, 3 nt to 10 nt, 3 nt to 5 nt, 5 nt to 70 nt, 5 nt to 50 nt, 5 nt to 45 nt, 5 nt to 40 nt, 5 nt to 35 nt, 5 nt to 30 nt, 5 nt to 25 nt, 5 nt to 20 nt, 10 nt to 70 nt, 10 nt to 50 nt, 10 nt to 45 nt, 10 nt to 40 nt, 10 nt to 35 nt, 10 nt to 30 nt, 10 nt to 25 nt, 10 nt to 20 nt, 10 nt to 15 nt, 15 nt to 70 nt, 15 nt to 50 nt, 15 nt to 45 nt, 15 nt to 40 nt, 15 nt to 35 nt, 15 nt to 30 nt, 15 nt to 25 nt, or 15 nt to 20 nt).

PAM Sequence

A wild type Cas9 polypeptide normally has nuclease activity that cleaves a target nucleic acid (e.g., a double stranded DNA (dsDNA)) at a target site defined by the region of complementarity between the targeting segment of the guide nucleic acid and the target nucleic acid. In some cases, site-specific cleavage of the target nucleic acid occurs at locations determined by both (i) base-pairing complementarity between the guide nucleic acid and the target nucleic acid; and (ii) a short motif referred to as the protospacer adjacent motif (PAM) in the target nucleic acid. When a Cas9 polypeptde binds to (in some cases cleaves) a dsDNA target nucleic acid, the PAM sequence that is recognized (bound) by the Cas9 polypeptide is present on the non-complementary strand (the strand that does not hybridize with the targeting segment of the guide nucleic acid) of the target DNA. Thus, when a Cas9 Polypeptide binds to (in some cases cleaves) a single stranded target nucleic acid, no PAM sequence is present because there is no non-complementary strand (see FIG. 8A-8F). A subject PAMmer provides a PAM sequence, which is positioned near the target site (the sequence targeted by the targeting segment of the guide nucleic acid) by the orientation segment and/or the specificity segment of the PAMmer.

Figure 2A:
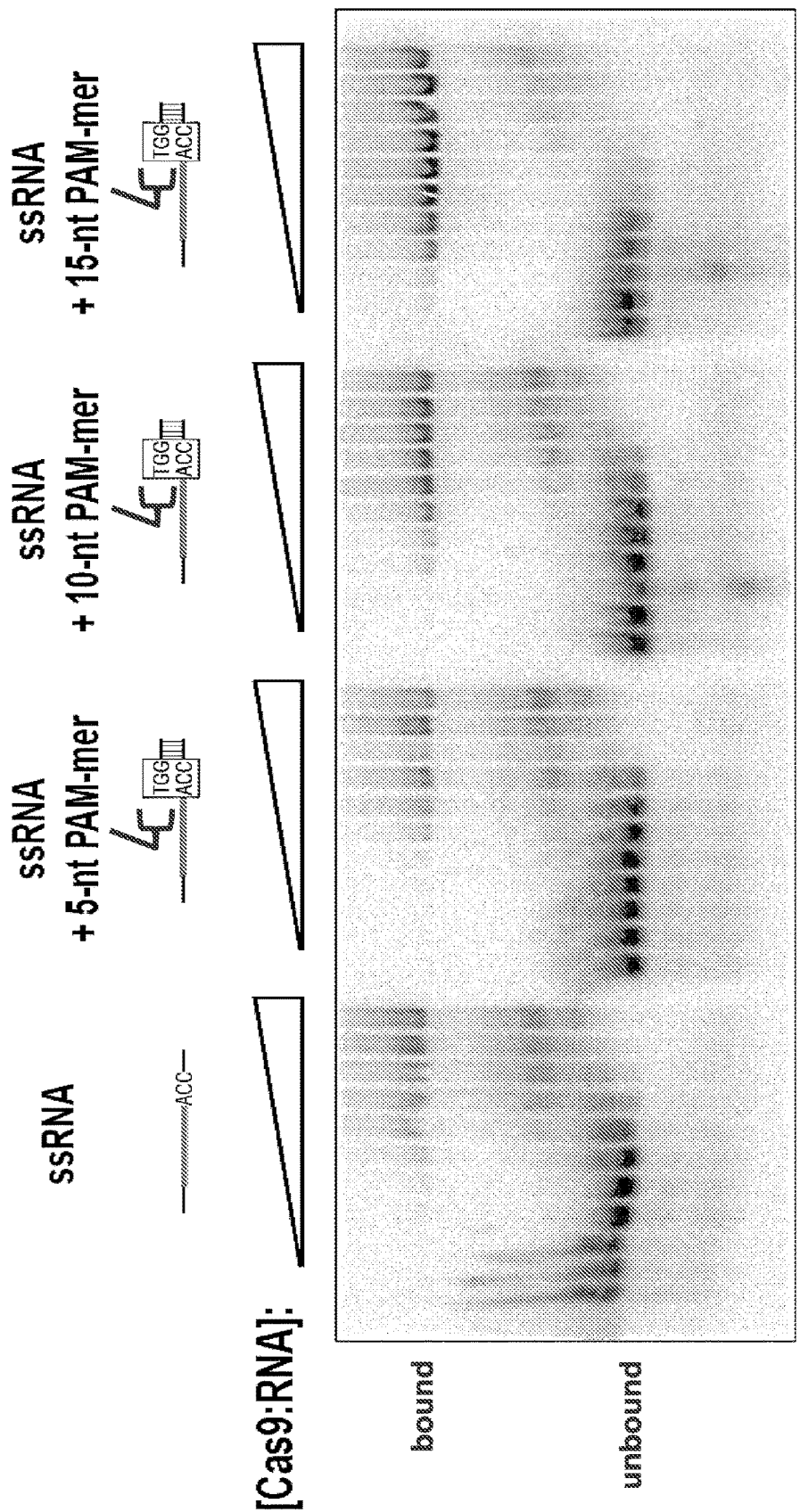
FIG. 2A-2B present binding assays testing whether single stranded target nucleic acid binding is stabilized by PAMmers of increasing length, and whether the PAM sequence itself within the PAMmer needs to be base-paired to the single stranded target nucleic acid.
Figure 2B:
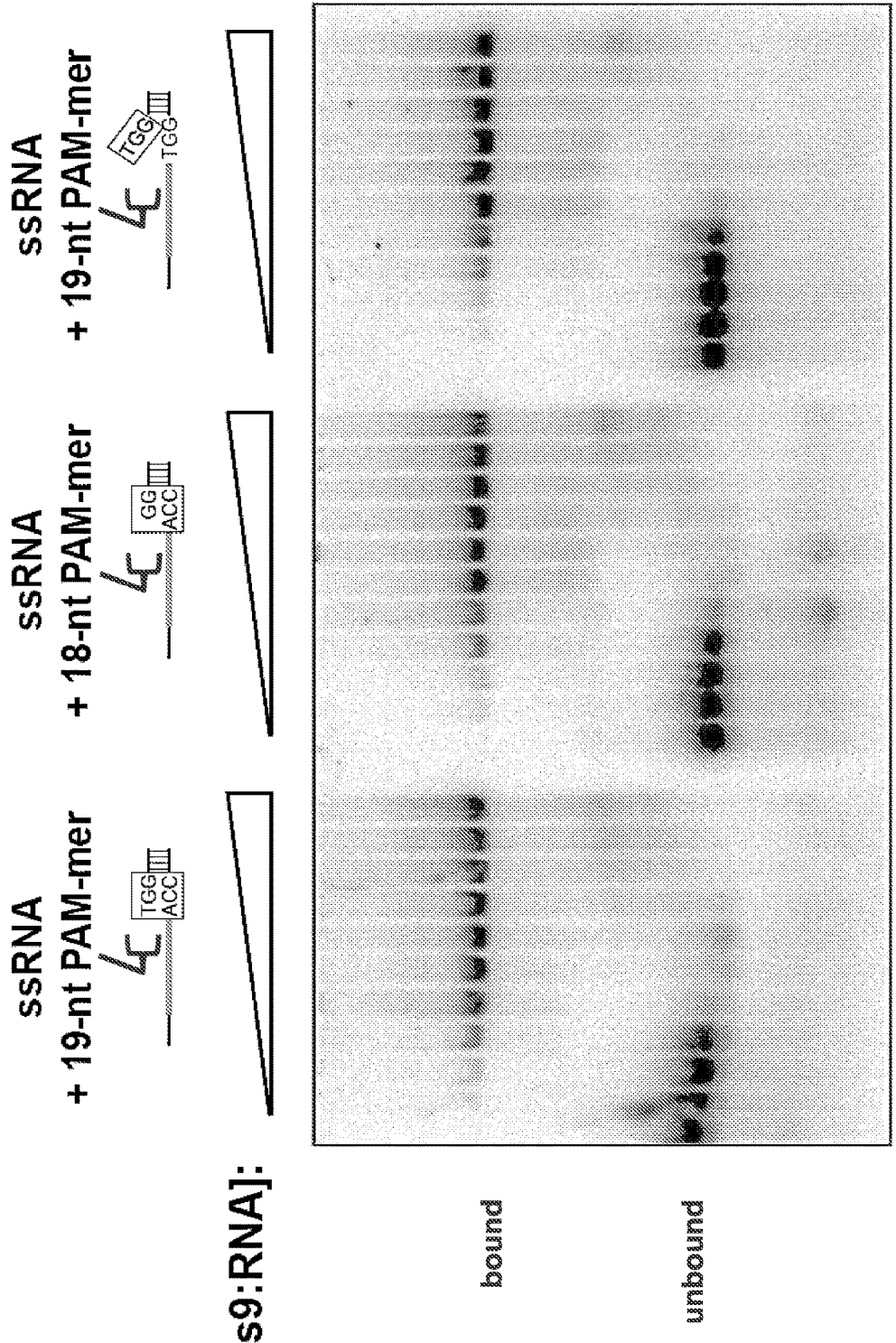
Figure 4A:
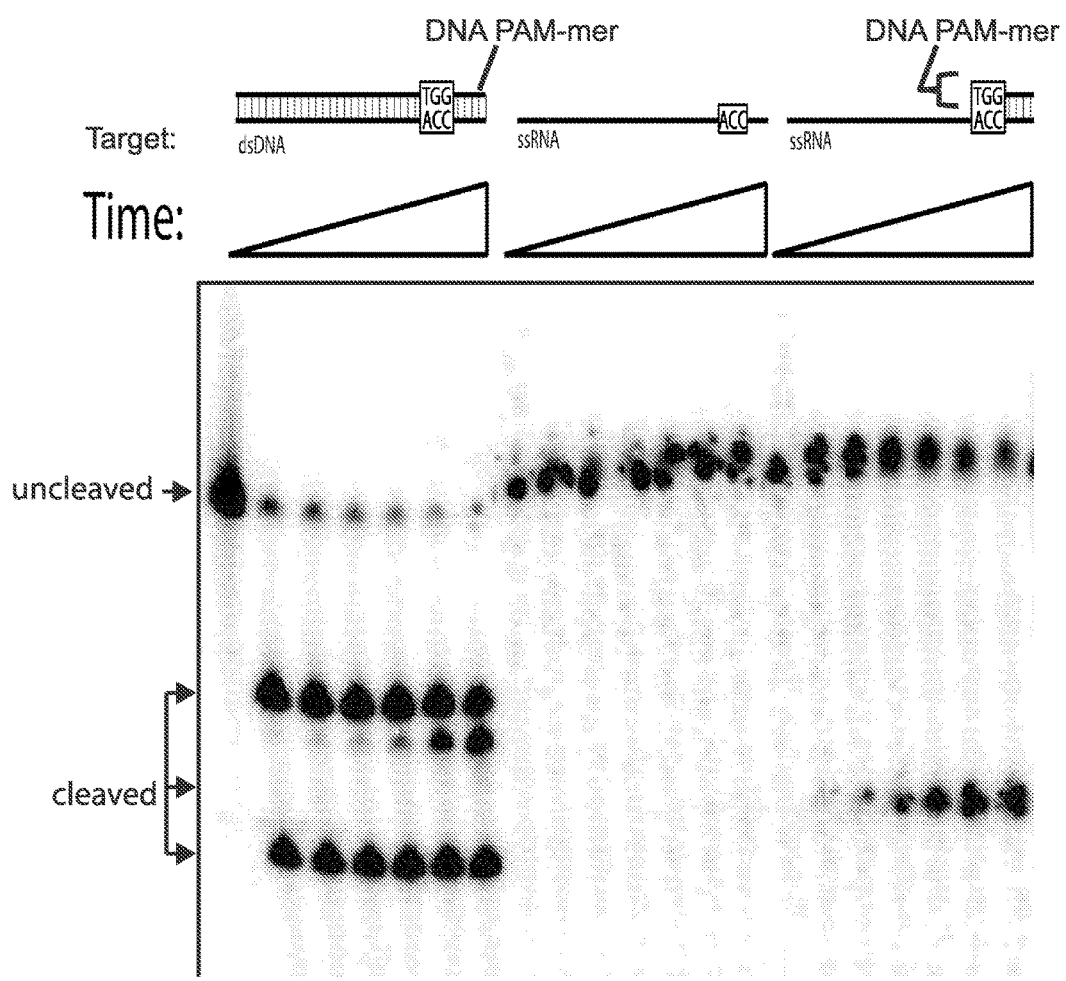
FIG. 4A-4B presents cleavage assays testing whether a DNA oligonucleotide complementary to a single stranded target nucleic acid (e.g., ssRNA), but lacking the PAM, can activate Cas9 for cleavage; and whether a PAMmer having a specificity segment can facilitate Cas9 cleavage.
Figure 6:
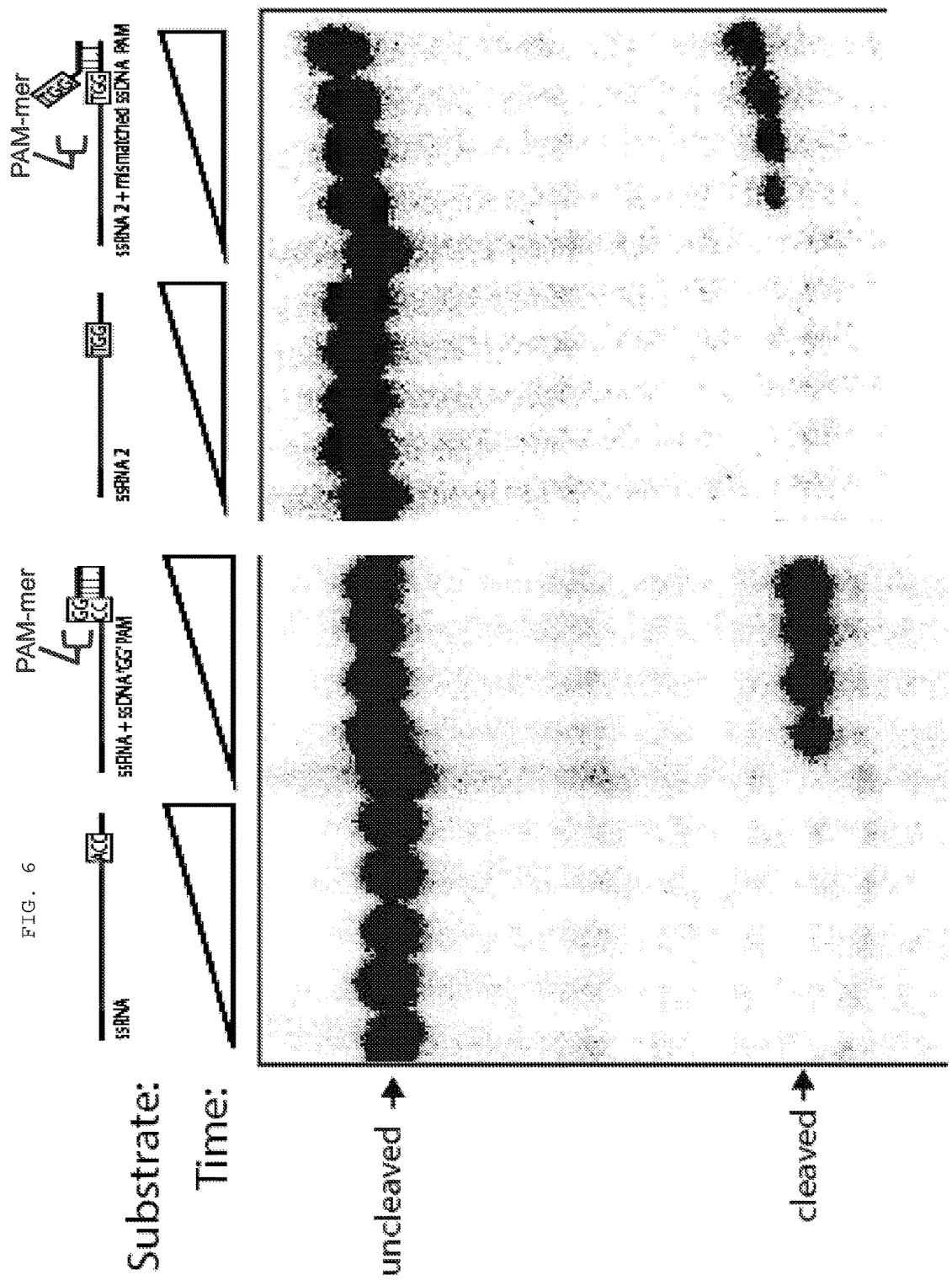
FIG. 6 presents cleavage assays employing various PAMmers.

In some embodiments, the PAM sequence of the PAMmer is complementary to (i.e., hybridizes with) the target nucleic acid (FIG. 1, FIG. 4A). In some embodiments, the PAM sequence of the PAMmer is not complementary to (i.e., does not hybridize with) the target nucleic acid (FIG. 2B, FIG. 6). In some embodiments, a PAM sequence of a PAMmer has a length in a range of from 1 nt to 15 nt (e.g., 1 nt to 14 nt, 1 nt to 13 nt, 1 nt to 12 nt, 1 nt to 11 nt, 1 nt to 10 nt, 1 nt to 9 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 15 nt, 2 nt to 14 nt, 2 nt to 13 nt, 2 nt to 12 nt, 2 nt to 11 nt, 2 nt to 10 nt, 2 nt to 9 nt, 2 nt to 8 nt, 2 nt to 7 nt, 2 nt to 6 nt, 2 nt to 5 nt, 2 nt to 4 nt, 2 nt to 3 nt, 2 nt, or 3 nt).

In some embodiments (e.g., when the Cas9 polypeptide from *S. pyogenes* or a closely related Cas9 is used; see for example, Chylinski et al., RNA Biol. 2013 May; 10(5):726-37; and Jinek et al., Science. 2012 Aug. 17; 337(6096):816-21; both of which are hereby incorporated by reference in their entirety), the PAM sequence of the PAMmer can be GG (5'-GG-3'), or can be 5'-NGG-3', where N is any nucleotide. In some embodiments (e.g., when a Cas9 polypeptide from *Neisseria meningitidis* or a closely related Cas9 is used), the PAM sequence of the PAMmer can be 5'-NNNNGANN-3', 5'-NNNNGTTN-3', 5'-NNNNGNNT-3', 5'-NNNNGTNN-3', 5'-NNNNGNTN-3', or 5'-NNNNGATT-3', where N is any nucleotide. In some embodiments (e.g., when a Cas9 polypeptide from *Streptococcus thermophilus* #1 or a closely related Cas9 is used), the PAM sequence of the PAMmer can be 5'-NNAGAA-3', 5'-NNAGGA-3', 5'-NNGGAA-3', 5'-NNANAA-3', or 5'-NNGGGA-3' where N is any nucleotide. In some embodiments (e.g., when a Cas9 polypeptide from *Treponema denticola* (TD) or a closely related Cas9 is used), the PAM sequence of the PAMmer can be 5'-NAAAAN-3', 5'-NAAAAC-3', 5'-NAAANC-3', 5'-NANAAC-3', or 5'-NNAAAC-3', where N is any nucleotide. As would be known by one of ordinary skill in the art, additional PAM sequences for other Cas9 polypeptides can readily be determined using bioinformatic analysis (e.g, analysis of genomic sequencing data). See Esvelt et al., Nat Methods. 2013 November; 10(11):1116-21, for additional information.

Specificity Segment

A specificity segment can be present or absent in a subject PAMmer (the PAMmer has a specificity segment, an orientation segment, or both a specificity segment and an orientation segment), and when present, the specificity segment is positioned 5' of the PAM seqeunce. In some cases, a PAMmer having a specificity segement is referred to herein as a "5'-extended PAMmer." The specificity segment hybridizes to (i.e., targets) a sequence of a target nucleic that overlaps with the target site such that the PAM sequence is positioned near the target site (i.e., the sequence of the target nucleic acid that is targeted by the targeting segment of the guide nucleic acid). Thus, the PAMmer provides a PAM sequence at any desired location within a target nucleic acid (e.g., by designing the specificity segment of the PAMmer to hybridize to any desired nucleotide sequence of the target nucleic acid).

In cases where a PAMmer is used in a method of cleavage, the targeting segment of the guide nucleic acid (which associates with a Cas9 polypeptide) is complementary to the target nucleic acid, and this is true whether or not the PAMmer has a specificity segment. In cases where a PAMmer is used in a method of binding, the targeting segment of the guide nucleic acid (which associates with a Cas9 polypeptide) is complementary to the target nucleic acid when the PAMmer has a specificity segment, but the targeting segment of the guide nucleic acid need not be complementary to the target nucleic acid when the PAMmer does not have a specificity segment (i.e., when the PAMmer has PAM sequence and an orieintation segment, but not a specificity segment).

A specificity segment can have a length of from 3 nucleotides (nt) to 100 nt (e.g., from 3 nt to 80 nt, from 3 nt to 50nt, from 3 nt to 40 nt, from 5 nt to 40 nt, from 5 nt to 35 nt, from 5 nt to 30 nt, from 5 nt to 25 nt, from 10 nt to 40 nt, from 10 nt to 35 nt, from 10 nt to 30 nt, from 10 nt to 25 nt, from 10 nt to 20 nt, from 12 nt to 40 nt, from 12 nt to 35 nt, from 12 nt to 30 nt, from 12 nt to 25 nt, from 12 nt to 20 nt, from 15 nt to 40 nt, from 15 nt to 35 nt, from 15 nt to 30 nt, from 15 nt to 25 nt, from 15 nt to 20 nt, from 17 nt to 40 nt, from 17 nt to 35 nt, from 17 nt to 30 nt, from 17 nt to 25 nt, from 17 nt to 20 nt, from 18 nt to 40 nt, from 18 nt to 35 nt, from 18 nt to 30 nt, from 18 nt to 25 nt, from 18 nt to 20 nt, from 20 nt to 40 nt, from 20 nt to 35 nt, from 20 nt to 30 nt, or from 20 nt to 25 nt). In some cases, the specificity segment is 20 nucleotides in length. In some cases, the specificity segment is 19 nucleotides in length.

The percent complementarity between the specificity segment and the sequence of the target nucleic acid targeted by the specificity segment (e.g., the target site, i.e., the site targeted by the targeting segment of the guide nucleic acid) can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the specificity segment and the sequence of the target nucleic acid targeted by the specificity segment is 60% or more (e.g., 65% or more, 70% or more, 75% or more, 80% or more, 85% or more, 90% or more, 95% or more, 97% or more, 98% or more, 99% or more, or 100%) over about 10 to 30 contiguous nucleotides (nt) (e.g. 15 to 30 contiguous nt, 15 to 25 contiguous nt, 17 to 30 contiguous t, 17 to 25 contiguous t, or 18 to 22 contiguous nt). In some cases, the percent complementarity between the specificity segment and the sequence of the target nucleic acid targeted by the specificity segment is 60% or more (e.g., 65% or more, 70% or more, 75% or more, 80% or more, 85% or more, 90% or more, 95% or more, 97% or more, 98% or more, 99% or more, or 100%) over 10 or more contiguous nucleotides (nt) (e.g. 12 or more contiguous nt, 15 or more contiguous nt, 17 or more contiguous nt, 18 or more contiguous nt, 19 or more contiguous nt, or 20 or more contiguous nt).

In some cases, the sequence targeted by the specificity segment of a PAMmer is 100% identical to the target site (i.e., the sequence targeted by the targeting segment of the guide nucleic acid). However, the sequence targeted by the specificity segment of a PAMmer need not be 100% identical to the target site. For example, in some cases, the sequence targeted by the specificity segment of a PAMmer overlaps with the sequence targeted by the targeting segment of the guide nucleic acid, but the overlap is not 100%. For example, the sequence targeted by the specificity segment of a PAMmer can be a subset of the target site. In some cases, the sequence targeted by the specificity segment of a PAMmer is shorter than the sequence targeted by the targeting segment of the guide nucleic acid. In some cases, the sequence targeted by the specificity segment of a PAMmer is longer than the sequence targeted by the targeting segment of the guide nucleic acid. In some cases, the sequence targeted by the specificity segment of a PAMmer is the same length as the sequence targeted by the targeting segment of the guide nucleic acid.

In some cases, the sequence targeted by the specificity segment of a PAMmer shares 2 nucleotides (nt) or more with the sequence targeted by the targeting segment of the guide nucleic acid (e.g., 3 nt or more, 5 nt or more, 8 nt or more, 10 nt or more, 12 nt or more, 15 nt or more, 18 nt or more, etc.). In some cases, the sequence targeted by the specificity segment of a PAMmer shares 2 nucleotides (nt) to 30 nt with the sequence targeted by the targeting segment of the guide nucleic acid (e.g., 5 nt to 30 nt, 5 nt to 25 nt, 5 nt to 22 nt, 8 nt to 30 nt, 8 nt to 25 nt, 8 nt to 22 nt, 8 nt to 20 nt, 10 nt to 30 nt, 10 nt to 25 nt, 10 nt to 22 nt, 10 nt to 20 nt, 12 nt to 30 nt, 12 nt to 25 nt, 12 nt to 22 nt, 12 nt to 20 nt, 15 nt to 30 nt, 15 nt to 25 nt, 15 nt to 22 nt, 15 nt to 20 nt, 18 nt to 30 nt, 18 nt to 25 nt, 18 nt to 22 nt, or 18 nt to 20 nt).

Figure 8E:
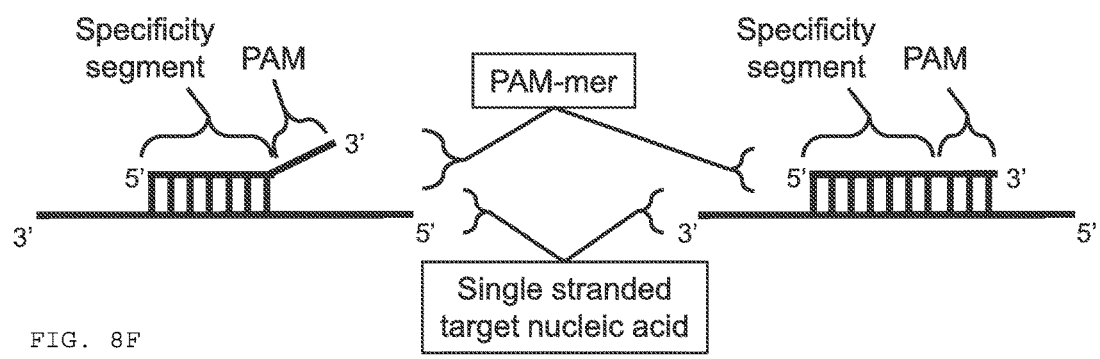

In some embodiments, a PAMmer has a specificity segment, but does not have an orientation segment (i.e., the PAMmer does not have a nucleotide sequence 3' of the PAM sequence that hybridizes with the target nucleic acid) (FIG. 8E). In some such cases, the PAM sequence can be at the 3' end of the PAMmer (i.e., the PAMmer can have 0 nucleotides 3' of the PAM sequence), or the PAMmer can have 1 or more nucleotides (nt) 3' of the PAM sequence (e.g., 2 or more nt, 3 or more nt, 4 or more nt, 5 or more nt, 10 or more nt, 15 or more nt, 20 or more nt, etc.), where the nucleotides 3' of the PAM sequence do not hybridize to the target nucleic acid. In some cases in which a PAMmer does not have an orientation segment, a PAMmer can have a nucleotide sequence, 3' of the PAM sequence, with a length in a range of from 1 nucleotide (nt) to 20 nt (e.g., from 1 nt to 18 nt, from 1 nt to 16 nt, from 1 nt to 14 nt, from 1 nt to 12 nt, from 1 nt to 10 nt, from 1 nt to 9 nt, from 1 nt to 8 nt, from 1 nt to 7 nt, from 1 nt to 6 nt, from 1 nt to 5 nt, from 1 nt to 4 nt, or from 1 nt to 3 nt), where the nucleotides 3' of the PAM sequence do not hybridize to the target nucleic acid. For example, if a PAMmer has nucleotides 3' of the PAM sequence that do hybridize to the target nucleic acid, then the nucleotides that hybridize would be considered an (or part of an) orientation segment.

In some cases, the length of the specificity segment inversely correlates with efficiency of the cleavage reaction and positively correlates with specificity (i.e., reduction of off-target effects). Thus, there can be a trade-off between the desired level of cleavage and the desired level of specificity. The presence (as well as the length) of a specificity segment can be determined based on the particular target nucleic acid, the nature/purpose of the method, and/or the desired outcome. For example, if maximum specificity is desired, but cleavage efficiency is not a concern, then a long specificity segment may be desirable. On the other hand, if maximum cleavage is desired, but specificity is not a concern (e.g., the orientation segment of the PAMmer provides for adequate specificity), then a shorter specificity segment (e.g., no specificity segment) may be desirable.

For methods of binding, the presence of a specificity segment can increase binding specificity. Not to be bound by theory, it is believed that this is because the specificity segment provides an energetic barrier to binding that can be overcome by the presence of a targeting segment in the guide nucleic acid that has complementarity to (i.e., can hybridize with) that target nucleic acid, thus displacing the specificity segment of the PAMmer.

Orientation Segment

An orientation segment can be present or absent in a subject PAMmer (the PAMmer has a specificity segment, an orientation segment, or both a specificity segment and an orientation segment), and when present, the orientation segment is positioned 3' of the PAM seqeunce. The orientation segment hybridizes to (i.e., targets) a sequence of a target nucleic (the orientation site) such that the PAM sequence is positioned near the target site (i.e., the sequence of the target nucleic acid that is targeted by the targeting segment of the guide nucleic acid). Thus, the PAMmer provides a PAM sequence at any desired location within a target nucleic acid (e.g., by designing the orientation segment of the PAMmer to hybridize to any desired nucleotide sequence of the target nucleic acid).

The orientation segment can have a length of from 3 nucleotides (nt) to 100 nt (e.g., from 3 nt to 80 nt, from 3 nt to 50nt, from 3 nt to 40 nt, from 5 nt to 40 nt, from 5 nt to 35 nt, from 5 nt to 30 nt, from 5 nt to 25 nt, from 10 nt to 40 nt, from 10 nt to 35 nt, from 10 nt to 30 nt, from 10 nt to 25 nt, from 10 nt to 20 nt, from 12 nt to 40 nt, from 12 nt to 35 nt, from 12 nt to 30 nt, from 12 nt to 25 nt, from 12 nt to 20 nt, from 15 nt to 40 nt, from 15 nt to 35 nt, from 15 nt to 30 nt, from 15 nt to 25 nt, from 15 nt to 20 nt, from 17 nt to 40 nt, from 17 nt to 35 nt, from 17 nt to 30 nt, from 17 nt to 25 nt, from 17 nt to 20 nt, from 18 nt to 40 nt, from 18 nt to 35 nt, from 18 nt to 30 nt, from 18 nt to 25 nt, from 18 nt to 20 nt, from 20 nt to 40 nt, from 20 nt to 35 nt, from 20 nt to 30 nt, or from 20 nt to 25 nt). In some cases, the orientation segment is 20 nucleotides in length. In some cases, the orientation segment is 19 nucleotides in length.

The percent complementarity between the orientation segment and the sequence of the target nucleic acid targeted by the orientation segment can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the orientation segment and the sequence of the target nucleic acid targeted by the orientation segment is 60% or more (e.g., 65% or more, 70% or more, 75% or more, 80% or more, 85% or more, 90% or more, 95% or more, 97% or more, 98% or more, 99% or more, or 100%) over about 10 to 30 contiguous nucleotides (nt) (e.g. 15 to 30 contiguous nt, 15 to 25 contiguous nt, 17 to 30 contiguous nt, 17 to 25 contiguous nt, or 18 to 22 contiguous nt). In some cases, the percent complementarity between the orientation segment and the sequence of the target nucleic acid targeted by the orientation segment is 60% or more (e.g., 65% or more, 70% or more, 75% or more, 80% or more, 85% or more, 90% or more, 95% or more, 97% or more, 98% or more, 99% or more, or 100%) over 10 or more contiguous nucleotides (nt) (e.g. 12 or more contiguous nt, 15 or more contiguous nt, 17 or more contiguous nt, 18 or more contiguous nt, 19 or more contiguous nt, or 20 or more contiguous nt).

In some cases, the sequence targeted by the orientation segment of a PAMmer is immediately adjacent to the sequence targeted by the targeting segment of the guide nucleic acid. In some embodiments, 10 or less nt (e.g., 9 or less nt, 8 or less nt, 7 or less nt, 6 or less nt, 5 or less nt, 4 or less nt, 3 or less nt, 2 or less nt, 1 or less nt, or no nt) are present in the target nucleic acid between the sequence targeted by the targeting segment of the guide nucleic acid (i.e., the target site) and the sequence targeted by the orientation segment of the PAMmer. In some cases, the sequence of the target nucleic acid that is targeted by the orientation segment of a PAMmer is within 10 or fewer nucleotides (nt) (e.g., 9 or fewer nt, 8 or fewer nt, 7 or fewer nt, 6 or fewer nt, 5 or fewer nt, 4 or fewer nt, 3 or fewer nt, 2 or fewer nt, 1 or fewer nt, or no nt) of the sequence targeted by the targeting segment of the guide nucleic acid. In some embodiments, the number of nucleotides (nt) present in the target nucleic acid between the sequence targeted by the targeting segment of the guide nucleic acid (i.e., the target site) and the sequence targeted by the orientation segment of the PAMmer is in a range of from 0 nt to 10 nt (e.g., 0 nt to 9 nt, 0 nt to 8 nt, 0 nt to 7 nt, 0 nt to 6 nt, 0 nt to 5 nt, 0 nt to 4 nt, 0 nt to 3 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 9 nt, 2 nt to 8 nt, 2 nt to 7 nt, 2 nt to 6 nt, 2 nt to 5 nt, 2 nt to 4 nt, or 2 nt to 3 nt).

Figure 8F:
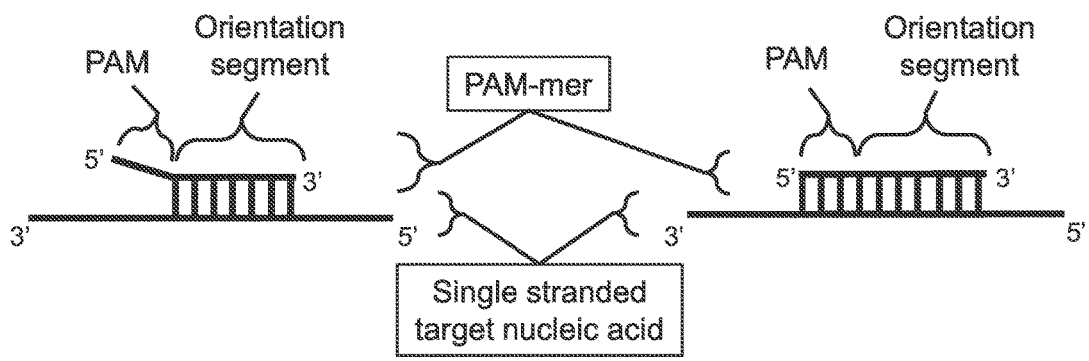
Figure 11A:
FIG. 11A-11B provide alignments of naturally occurring tracrRNA ("activator") sequences from various species (*L. innocua* (SEQ ID NO:268); *S. pyogenes* (SEQ ID NO:267); *S. mutans* (SEQ ID NO:269); *S. thermophilus*1 (SEQ ID NO:270); *M. mobile* (SEQ ID NO:274); *N. meningitides* (SEQ ID NO:272); *P. multocida* (SEQ ID NO:273); *S. thermophilus*2 (SEQ ID NO:271); and *S. pyogenes* (SEQ ID NO:267).
Figure 11B:
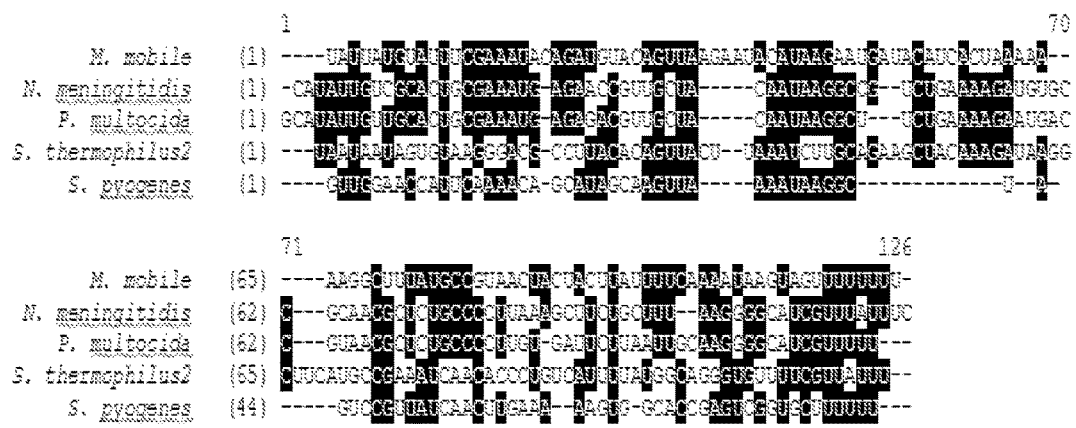

In some cases, a PAMmer has an orientation segment, but does not have a specificity segment (i.e., the PAMmer does not have a nucleotide sequence 5' of the PAM sequence that hybridizes with the target nucleic acid), but does have an orientation segment (FIG. 8F). In some such cases, the PAM sequence can be at the 5' end of the PAMmer (i.e., the PAMmer can have 0 nucleotides 5' of the PAM sequence), or the PAMmer can have 1 or more nucleotides (nt) 5' of the PAM sequence (e.g., 2 or more nt, 3 or more nt, 4 or more nt, 5 or more nt, 10 or more nt, 15 or more nt, 20 or more nt, etc.), where the nucleotides 5' of the PAM sequence do not hybridize to the target nucleic acid. In some cases in which a PAMmer does not have a specificity segment, a PAMmer can have a nucleotide sequence, 5' of the PAM sequence, with a length in a range of from 1 nucleotide (nt) to 20 nt (e.g., from 1 nt to 18 nt, from 1 nt to 16 nt, from 1 nt to 14 nt, from 1 nt to 12 nt, from 1 nt to 10 nt, from 1 nt to 9 nt, from 1 nt to 8 nt, from 1 nt to 7 nt, from 1 nt to 6 nt, from 1 nt to 5 nt, from 1 nt to 4 nt, or from 1 nt to 3 nt), where the nucleotides 5' of the PAM sequence do not hybridize to the target nucleic acid. For example, if a PAMmer has nucleotides 5' of the PAM sequence that do hybridize to the target nucleic acid, then the nucleotides that hybridize would be considered a (or part of a) specificity segment.

In some cases (e.g., those involving methods of binding, where the PAMmer does not have a specificity segment), the target site of the target nucleic acid can be determined by the orientation segment of the PAMmer and not by the targeting segment of the guide nucleic acid. In some cases, the targeting segment of the guide nucleic acid does not have complementarity to a nucleotide sequence of the target nucleic acid. In some cases, the targeting segment of the guide nucleic acid does not have complementarity to a nucleotide sequence of the target nucleic acid that is near (e.g., within 20 or fewer nucleotides (nt), within 30 or fewer nt, within 40 or fewer t, within 50 or fewer nt, within 60 or fewer nt, within 70 or fewer nt, within 80 or fewer nt, within 90 or fewer nt, or within 100 or fewer nt) the orientation site. However, the orientation segment of the PAMmer still positions the PAM sequence of the PAMmer such that the target nucleic acid can still be bound and/or cleaved by a subject Cas9 polypeptide (e.g., see FIG. 5A-5C).

Stability Control Sequence (e.g., Transcriptional Terminator Segment)

In some embodiments, a PAMmer comprises a stability control sequence. A stability control sequence influences the stability of a nucleic acid (e.g., a guide nucleic acid, a targeter, an activator, a PAMmer etc.). One example of a suitable stability control sequence for use with an RNA is a transcriptional terminator segment (i.e., a transcription termination sequence). A transcriptional terminator segment of a subject guide nucleic acid can have a total length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

In some cases, the transcription termination sequence is one that is functional in a eukaryotic cell. In some cases, the transcription termination sequence is one that is functional in a prokaryotic cell.

Non-limiting examples of nucleotide sequences that can be included in a stability control sequence (e.g., transcriptional termination segment, or in any segment of the guide nucleic acid to provide for increased stability) include sequences set forth in SEQ ID NO:683-696 and, for example, 5'-UAAUCCCACAGCCGCCAGUUCCGCUG-GCGGCAUUUU-5' (SEQ ID NO:795) (a Rho-independent trp termination site).

Additional Sequences

In some embodiments, a PAMmer comprises an additional segment or segments (in some cases at the 5' end, in some cases the 3' end, in some cases at either the 5' or 3' end, in some cases embedded within the sequence (i.e., not at the 5' and/or 3' end), in some cases at both the 5' end and the 3' end, in some cases embedded and at the 5' end and/or the 3' end, etc). For example, a suitable additional segment can comprise a 5' cap (e.g., a 7-methylguanylate cap (m$^7$G)); a 3' polyadenylated tail (i.e., a 3' poly(A) tail); a ribozyme sequence (e.g. to allow for self-cleavage of a precursor PAMmer and release of a mature PAMmer in a regulated fashion); a riboswitch sequence (e.g., to allow for regulated stability and/or regulated accessibility by proteins and protein complexes); a sequence that forms a dsRNA duplex (i.e., a hairpin)); a sequence that targets an RNA to a subcellular location (e.g., nucleus, mitochondria, chloroplasts, and the like); a modification or sequence that provides for tracking (e.g., direct conjugation to a fluorescent molecule (i.e., fluorescent dye), conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, proteins that bind RNA (e.g., RNA aptamers), labeled proteins, fluorescently labeled proteins, protein translation components (e.g., initiation factors, elongation factors release factors, etc.), RNA editing enzymes (e.g., RNA deaminases, e.g., adenosine deaminase acting on RNA (ADAR), including A to I and/or C to U editing enzymes), RNA splicing factors (e.g., RS domains), RNA and/or DNA helicases, RNA methylases, RNA-binding proteins, and the like); a modification or sequence that provides for increased, decreased, and/or controllable stability; and combinations thereof.

Cas9 Polypeptides

A subject guide nucleic acid and a subject Cas9 polypeptide form a complex. The guide nucleic acid provides target specificity to the complex by comprising a nucleotide sequence that is complementary to a sequence (the target site) of a target nucleic acid (as noted above). The Cas9 polypeptide of the complex provides the site-specific activity. In other words, the Cas9 polypeptide is guided to a target site within a target nucleic acid sequence (e.g. a chromosomal sequence or an extrachromosomal sequence, e.g. an episomal sequence, a minicircle sequence, a mitochondrial sequence, a chloroplast sequence, etc.) by virtue of its association with the protein-binding segment of the guide nucleic acid (described above).

A subject Cas9 polypeptide can bind and/or modify (e.g., cleave, methylate, demethylate, etc.) a target nucleic acid and/or a polypeptide associated with target nucleic acid (e.g., methylation or acetylation of a histone tail). A Cas9 polypeptide is also referred to herein as a "site-directed polypeptide."

In some cases, the Cas9 polypeptide is a naturally-occurring polypeptide (e.g., naturally occurs in bacterial and/or archaeal cells). In other cases, the Cas9 polypeptide is not a naturally-occurring polypeptide (e.g., the Cas9 polypeptide is a variant Cas9 polypeptide, a chimeric polypeptide as discussed below, and the like).

Exemplary Cas9 polypeptides are set forth in SEQ ID NOs: 1-259, and 795-1346 as a non-limiting and non-exhaustive list of Cas9 endonucleases. Naturally occurring Cas9 polypeptides bind a guide nucleic acid, are thereby directed to a specific sequence within a target nucleic acid (a target site), and cleave the target nucleic acid (e.g., cleave dsDNA to generate a double strand break, cleave ssDNA, cleave ssRNA, etc.). A subject Cas9 polypeptide comprises two portions, an RNA-binding portion and an activity portion. An RNA-binding portion interacts with a subject guide nucleic acid. An activity portion exhibits site-directed enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases the activity portion exhibits reduced nuclease activity relative to the corresponding portion of a wild type Cas9 polypeptide. In some cases, the activity portion is enzymatically inactive.

Assays to determine whether a protein has an RNA-binding portion interacts with a subject guide nucleic acid can be any convenient binding assay that tests for binding between a protein and a nucleic acid. Exemplary binding assays are shown in FIG. 1 and FIG. 2A-2B and include binding assays (e.g., gel shift assays) that include adding a guide nucleic acid and a Cas9 polypeptide to a target nucleic acid. In some cases, a PAMmer is also added (e.g., in some cases when the target nucleic acid is a single stranded nucleic acid).

Assays to determine whether a protein has an activity portion (e.g., to determine if the polypeptide has nuclease activity that cleave a target nucleic acid) can be any convenient nucleic acid cleavage assay that tests for nucleic acid cleavage. Exemplary cleavage assays are shown in FIG. 3, FIG. 4A-4B, FIG. 5A-5C, FIG. 6, and FIG. 7A-7D and include cleavage assays that include adding a guide nucleic acid and a Cas9 polypeptide to a target nucleic acid. In some cases, a PAMmer is also added (e.g., in some cases when the target nucleic acid is a single stranded nucleic acid).

In some cases, a subject Cas9 polypeptide (e.g., a chimeric Cas9 polypeptide) has enzymatic activity that modifies target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In other cases, a subject Cas9 polypeptide (e.g., a chimeric Cas9 polypeptide) has enzymatic activity that modifies a polypeptide (e.g., a histone) associated with target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Many Cas9 orthologs from a wide variety of species have been identified and the protiens share only a few identical amino acids. All identified Cas9 orthologs have the same domain architecture with a central HNH endonuclease domain and a split RuvC/RNaseH domain (See FIG. 9A-9B, FIG. 10, and Table 1). Cas9 proteins share 4 key motifs with a conserved architecture. Motifs 1, 2, and 4 are RuvC like motifs while motif 3 is an HNH-motif. In some cases, a suitable Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence depicted in FIG. 9A (SEQ ID NOs: 260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable Cas9 polypeptide comprises an amino acid sequence having 4 motifs, each of motifs 1-4 having 60% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable Cas9 polypeptide comprises an amino acid sequence having 4 motifs, each of motifs 1-4 having 70% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable Cas9 polypeptide comprises an amino acid sequence having 4 motifs, each of motifs 1-4 having 75% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable Cas9 polypeptide comprises an amino acid sequence having 4 motifs, each of motifs 1-4 having 80% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable Cas9 polypeptide comprises an amino acid sequence having 4 motifs, each of motifs 1-4 having 85% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable Cas9 polypeptide comprises an amino acid sequence having 4 motifs, each of motifs 1-4 having 90% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable Cas9 polypeptide comprises an amino acid sequence having 4 motifs, each of motifs 1-4 having 95% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable Cas9 polypeptide comprises an amino acid sequence having 4 motifs, each of motifs 1-4 having 99% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable Cas9 polypeptide comprises an amino acid sequence having 4 motifs, each of motifs 1-4 having 100% amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable Cas9 polypeptide comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 60% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 70% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 75% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 80% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 85% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 90% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 95% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 99% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 100% amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346.

Any Cas9 protein as defined above can be used as a Cas9 polypeptide or as part of a chimeric Cas9 polypeptide of the subject methods.

In some cases, a suitable Cas9 polypeptide comprises an amino acid sequence having 60% or more, 70% or more, 75% or more, 80% or more, 85% or more, 90% or more, 95% or more, 99% or more or 100% amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 60% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 70% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 75% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 80% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 85% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 90% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 95% or more amino acid sequence identity to the Cas9 amino acid sequence depicted in FIG. 9A-9B (SEQ ID NO:8), or to any of the amino acid sequences set forth as SEQ ID NOs:1-256 and 795-1346.

Any Cas9 protein as defined above can be used as a Cas9 polypeptide or as part of a chimeric Cas9 polypeptide of the subject methods.

In some cases, a suitable Cas9 polypeptide comprises an amino acid sequence having 99% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a suitable Cas9 polypeptide comprises an amino acid sequence having 100% amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a Cas9 polypeptide or as part of a chimeric Cas9 polypeptide of the subject methods.

In some cases, a Cas9 polypeptide comprises 4 motifs (as listed in Table 1 and depicted in FIG. 9A and FIG. 10), at least one with (or each with) amino acid sequences having 75% or more, 80% or more, 85% or more, 90% or more, 95% or more, 99% or more or 100% amino acid sequence identity to each of the 4 motifs listed in Table 1 (SEQ ID NOs:260-263), or to the corresponding portions in any of the amino acid sequences set forth as SEQ ID NOs:1-256 and 795-1346.

As used herein, the term "Cas9 polypeptide" encompasses the term "variant Cas9 polypeptide"; and the term "variant Cas9 polypeptide" encompasses the term "chimeric Cas9 polypeptide."

Variant Cas9 Polypeptides

The present disclosure provides composition and methods include a variant Cas9 polypeptide. A variant Cas9 polypeptide has an amino acid sequence that is different by one amino acid (e.g., has a deletion, insertion, substitution, fusion) (i.e., different by at least one amino acid) when compared to the amino acid sequence of a wild type Cas9 polypeptide. In some instances, the variant Cas9 polypeptide has an amino acid change (e.g., deletion, insertion, or substitution) that reduces the nuclease activity of the Cas9 polypeptide. For example, in some instances, the variant Cas9 polypeptide has less than 50%, less than 40%, less than 30%, less than 20%, less than 10%, less than 5%, or less than 1% of the nuclease activity of the corresponding wild-type Cas9 polypeptide. In some cases, the variant Cas9 polypeptide has no substantial nuclease activity. When a subject Cas9 polypeptide is a variant Cas9 polypeptide that has no substantial nuclease activity, it can be referred to as "dCas9."

In some cases, a variant Cas9 polypeptide has reduced nuclease activity. For example, a variant Cas9 polypeptide suitable for use in a binding method of the present disclosure exhibits less than about 20%, less than about 15%, less than about 10%, less than about 5%, less than about 1%, or less than about 0.1%, of the endonuclease activity of a wild-type Cas9 polypeptide, e.g., a wild-type Cas9 polypeptide comprising an amino acid sequence as depicted in FIG. 9A-9B (SEQ ID NO:8).

In some cases, a variant Cas9 polypeptide can cleave the complementary strand of a target nucleic acid but has reduced ability to cleave the non-complementary strand of a double stranded target nucleic acid. For example, the variant Cas9 polypeptide can have a mutation (amino acid substitution) that reduces the function of the RuvC domain (e.g., "domain 1" of FIG. 9B). As a non-limiting example, in some embodiments, a variant Cas9 polypeptide has a D10A (aspartate to alanine at amino acid position 10 of SEQ ID NO:8) mutation (or the corresponding mutation of any of the proteins presented in SEQ ID NOs:1-256 and 795-1346) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 polypeptide cleaves a double stranded target nucleic acid) (see, for example, Jinek et al., Science. 2012 Aug. 17; 337(6096):816-21).

In some cases, a variant Cas9 polypeptide can cleave the non-complementary strand of a double stranded target nucleic acid but has reduced ability to cleave the complementary strand of the target nucleic acid. For example, the variant Cas9 polypeptide can have a mutation (amino acid substitution) that reduces the function of the HNH domain (RuvC/HNH/RuvC domain motifs, "domain 2" of FIG. 9B). As a non-limiting example, in some embodiments, the variant Cas9 polypeptide has an H840A (histidine to alanine at amino acid position 840) mutation (or the corresponding mutation of any of the proteins set forth as SEQ ID NOs: 1-256 and 795-1346) and can therefore cleave the non-complementary strand of the target nucleic acid but has reduced ability to cleave the complementary strand of the target nucleic acid (thus resulting in a SSB instead of a DSB when the variant Cas9 polypeptide cleaves a double stranded target nucleic acid). Such a Cas9 polypeptide has a reduced ability to cleave a target nucleic acid (e.g., a single stranded target nucleic acid) but retains the ability to bind a target nucleic acid (e.g., a single stranded target nucleic acid).

In some cases, a variant Cas9 polypeptide has a reduced ability to cleave both the complementary and the non-complementary strands of a double stranded target nucleic acid. As a non-limiting example, in some cases, the variant Cas9 polypeptide harbors both the D10A and the H840A mutations (or the corresponding mutations of any of the proteins set forth as SEQ ID NOs:1-256 and 795-1346) such that the polypeptide has a reduced ability to cleave both the complementary and the non-complementary strands of a double stranded target nucleic acid. Such a Cas9 polypeptide has a reduced ability to cleave a target nucleic acid (e.g., a single stranded target nucleic acid) but retains the ability to bind a target nucleic acid (e.g., a single stranded target nucleic acid).

As another non-limiting example, in some cases, the variant Cas9 polypeptide harbors W476A and W1126A mutations (or the corresponding mutations of any of the proteins set forth as SEQ ID NOs:1-256 and 795-1346) such that the polypeptide has a reduced ability to cleave a target nucleic acid (FIG. 16A-16D). Such a Cas9 polypeptide has a reduced ability to cleave a target nucleic acid (e.g., a single stranded target nucleic acid) but retains the ability to bind a target nucleic acid (e.g., a single stranded target nucleic acid).

As another non-limiting example, in some cases, the variant Cas9 polypeptide harbors P475A, W476A, N477A, D1125A, W1126A, and D1127A mutations (or the corresponding mutations of any of the proteins set forth as SEQ ID NOs:1-256 and 795-1346) such that the polypeptide has a reduced ability to cleave a target nucleic acid (FIG. 16A-16D). Such a Cas9 polypeptide has a reduced ability to cleave a target nucleic acid (e.g., a single stranded target nucleic acid) but retains the ability to bind a target nucleic acid (e.g., a single stranded target nucleic acid).

As another non-limiting example, in some cases, the variant Cas9 polypeptide harbors H840A, W476A, and W1126A, mutations (or the corresponding mutations of any of the proteins set forth as SEQ ID NOs:1-256 and 795-1346) such that the polypeptide has a reduced ability to cleave a target nucleic acid. Such a Cas9 polypeptide has a reduced ability to cleave a target nucleic acid (e.g., a single stranded target nucleic acid) but retains the ability to bind a target nucleic acid (e.g., a single stranded target nucleic acid).

As another non-limiting example, in some cases, the variant Cas9 polypeptide harbors H840A, D10A, W476A, and W1126A, mutations (or the corresponding mutations of any of the proteins set forth as SEQ ID NOs:1-256 and 795-1346) such that the polypeptide has a reduced ability to cleave a target nucleic acid. Such a Cas9 polypeptide has a reduced ability to cleave a target nucleic acid (e.g., a single stranded target nucleic acid) but retains the ability to bind a target nucleic acid (e.g., a single stranded target nucleic acid).

As another non-limiting example, in some cases, the variant Cas9 polypeptide harbors, H840A, P475A, W476A, N477A, D1125A, W1126A, and D1127A mutations (or the corresponding mutations of any of the proteins set forth as SEQ ID NOs:1-256 and 795-1346) such that the polypeptide has a reduced ability to cleave a target nucleic acid. Such a Cas9 polypeptide has a reduced ability to cleave a target nucleic acid (e.g., a single stranded target nucleic acid) but retains the ability to bind a target nucleic acid (e.g., a single stranded target nucleic acid).

As another non-limiting example, in some cases, the variant Cas9 polypeptide harbors D10A, H840A, P475A, W476A, N477A, D1125A, W1126A, and D1127A mutations (or the corresponding mutations of any of the proteins set forth as SEQ ID NOs:1-256 and 795-1346) such that the polypeptide has a reduced ability to cleave a target nucleic acid. Such a Cas9 polypeptide has a reduced ability to cleave a target nucleic acid (e.g., a single stranded target nucleic acid) but retains the ability to bind a target nucleic acid (e.g., a single stranded target nucleic acid).

In some cases, when a variant Cas9 polypeptide harbors W476A and W1126A mutations (or the corresponding mutations of any of the proteins set forth as SEQ ID NOs:1-256 and 795-1346); or when the variant Cas9 polypeptide harbors P475A, W476A, N477A, D1125A, W1126A, and D1127A mutations (or the corresponding mutations of any of the proteins set forth as SEQ ID NOs:1-256 and 795-1346), the variant Cas9 polypeptide does not bind efficiently to a PAM sequence. Thus, in some such cases, when such a variant Cas9 polypeptide is used in a method of binding, the method need not include a PAMmer. In other words, in some cases, when such a variant Cas9 polypeptide is used in a method of binding, the method can include a guide nucleic acid, but the method can be performed in the absence of a PAMmer (and the specificity of binding is therefore provided by the targeting segment of the guide nucleic acid).

Other residues can be mutated to achieve the above effects (i.e. inactivate one or the other nuclease portions). As non-limiting examples, residues D10, G12, G17, E762, H840, N854, N863, H982, H983, A984, D986, and/or A987 (or the corresponding mutations of any of the proteins set forth as SEQ ID NOs:1-256 and 795-1346) can be altered (i.e., substituted) (see FIG. 9A-9B, FIG. 10, FIG. 16A-16D, and Table 1 for more information regarding the conservation of Cas9 amino acid residues). Also, mutations other than alanine substitutions are suitable.

In some embodiments, a variant Cas9 polypeptide that has reduced catalytic activity (e.g., when a Cas9 protein has a D10, G12, G17, E762, H840, N854, N863, H982, H983, A984, D986, and/or a A987 mutation, e.g., D10A, G12A, G17A, E762A, H840A, N854A, N863A, H982A, H983A, A984A, and/or D986A), the variant Cas9 polypeptide can still bind to target nucleic acid in a site-specific manner (because it is still guided to a target nucleic acid sequence by a guide nucleic acid) as long as it retains the ability to interact with the guide nucleic acid.

TABLE 1

Table 1 lists 4 motifs that are present in Cas9 sequences from various species (see also FIG. 9A-9B and FIG. 10). The amino acids listed here are from the Cas9 from *S. pyogenes* (SEQ ID NO: 8).

| Motif # | Motif | Amino acids (residue #s) | Highly conserved |
|---|---|---|---|
| 1 | RuvC-like I | IGLDIGTINSVGWAVI (7-21) (SEQ ID NO: 260) | D10, G12, G17 |
| 2 | RuvC-like II | IVIEMARE (759-766) (SEQ ID NO: 261) | E762 |
| 3 | HNH-motif | DVDHIVPQSFLKDDSIDNKVLTRSDKN (837-863) (SEQ ID NO: 262) | H840, N854, N863 |
| 4 | RuvC-like II | HHAHDAYL (982-989) (SEQ ID NO: 263) | H982, H983, A984, D986, A987 |

In addition to the above, a variant Cas9 protein can have the same parameters for sequence identity as described above for Cas9 polypeptides. Thus, in some cases, a suitable variant Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable variant Cas9 polypeptide comprises an amino acid sequence having 4 motifs, each of motifs 1-4 having 60% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable variant Cas9 polypeptide comprises an amino acid sequence having 4 motifs, each of motifs 1-4 having 70% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable variant Cas9 polypeptide comprises an amino acid sequence having 4 motifs, each of motifs 1-4 having 75% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable variant Cas9 polypeptide comprises an amino acid sequence having 4 motifs, each of motifs 1-4 having 80% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable variant Cas9 polypeptide comprises an amino acid sequence having 4 motifs, each of motifs 1-4 having 85% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable variant Cas9 polypeptide comprises an amino acid sequence having 4 motifs, each of motifs 1-4 having 90% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable variant Cas9 polypeptide comprises an amino acid sequence having 4 motifs, each of motifs 1-4 having 95% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable variant Cas9 polypeptide comprises an amino acid sequence having 4 motifs, each of motifs 1-4 having 99% or more amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable variant Cas9 polypeptide comprises an amino acid sequence having 4 motifs, each of motifs 1-4 having 100% amino acid sequence identity to motifs 1-4 of the Cas9 amino acid sequence depicted in FIG. 9A (SEQ ID NOs:260-263, respectively, as depicted in Table 1), or to the corresponding portions in any of the amino acid sequences set forth in SEQ ID NOs:1-256 and 795-1346 (see FIG. 10 for an alignment of motifs 1-4 from divergent Cas9 sequences).

In some cases, a suitable variant Cas9 polypeptide comprises an amino acid sequence having 60% or more, 70% or more, 75% or more, 80% or more, 85% or more, 90% or more, 95% or more, 99% or more, or 100% amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 60% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 70% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 75% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 80% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 85% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 90% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 95% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 99% or more amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 100% amino acid sequence identity to amino acids 7-166 or 731-1003 of the Cas9 amino acid sequence depicted in FIG. 9A-9B (SEQ ID NO:8), or to the corresponding portions in any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 60% or more, 70% or more, 75% or more, 80% or more, 85% or more, 90% or more, 95% or more, 99% or more, or 100% amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 60% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 70% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 75% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 80% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 85% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 90% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 95% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 99% or more amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 100% amino acid sequence identity to the Cas9 amino acid sequence depicted in FIG. 9A-9B (SEQ ID NO:8), or to any of the amino acid sequences set forth as SEQ ID NOs:1-256 and 795-1346. Any Cas9 protein as defined above can be used as a variant Cas9 polypeptide or as part of a chimeric variant Cas9 polypeptide of the subject methods.

Chimeric Polypeptides (Fusion Polypeptides)

In some embodiments, a variant Cas9 polypeptide is a chimeric Cas9 polypeptide (also referred to herein as a fusion polypeptide, e.g., a "Cas9 fusion polypeptide"). A Cas9 fusion polypeptide can bind and/or modify a target nucleic acid (e.g., cleave, methylate, demethylate, etc.) and/or a polypeptide associated with target nucleic acid (e.g., methylation, acetylation, etc., of, for example, a histone tail).

A Cas9 fusion polypeptide is a variant Cas9 polypeptide by virtue of differing in sequence from a wild type Cas9 polypeptide. A Cas9 fusion polypeptide is a Cas9 polypeptide (e.g., a wild type Cas9 polypeptide, a variant Cas9 polypeptide, a variant Cas9 polypeptide with reduced nuclease activity (as described above), and the like) fused to a covalently linked heterologous polypeptide (also referred to as a "fusion partner"). In some cases, a Cas9 fusion polypeptide is a variant Cas9 polypeptide with reduced nuclease activity (e.g., dCas9) fused to a covalently linked heterologous polypeptide. In some cases, the heterologous polypeptide exhibits (and therefore provides for) an activity (e.g., an enzymatic activity) that will also be exhibited by the Cas9 fusion polypeptide (e.g., methyltransferase activity, acetyltransferase activity, kinase activity, ubiquitinating activity, etc.). In some such cases, a method of binding, e.g., where the Cas9 polypeptide is a variant Cas9 polypeptide having a fusion partner (i.e., having a heterologous polypeptide) with an activity (e.g., an enzymatic activity) that modifies the target nucleic acid, the method can also be considered to be a method of modifying the target nucleic acid. In some cases, a method of binding a target nucleic acid (e.g., a single stranded target nucleic acid) can result in modification of the target nucleic acid. Thus, in some cases, a method of binding a target nucleic acid (e.g., a single stranded target nucleic acid) can be a method of modifying the target nucleic acid.

In some cases, the heterologous sequence provides for subcellular localization, i.e., the heterologous sequence is a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a variant Cas9 does not include a NLS so that the protein is not targeted to the nucleus (which can be advantageous, e.g., when the target nucleic acid is an RNA that is present in the cyosol). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some embodiments, the heterologous sequence can provide for increased or decreased stability (i.e., the heterologous sequence is a stability control peptide, e.g., a degron, which in some cases is controllable (e.g., a temperature sensitive or drug controllable degron sequence, see below). In some embodiments, the heterologous sequence can provide for increased or decreased transcription from the target nucleic acid (i.e., the heterologous sequence is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g., to provide the ability of a Cas9 fusion polypeptide to bind to another protein of interest, e.g., a DNA or histone modifying protein, a transcription factor or transcription repressor, a recruiting protein, an RNA modification enzyme, an RNA-binding protein, a translation initiation factor, an RNA splicing factor, etc.). A heterologous nucleic acid sequence may be linked to another nucleic acid sequence (e.g., by genetic engineering) to generate a chimeric nucleotide sequence encoding a chimeric polypeptide.

A subject Cas9 fusion polypeptide (Cas9 fusion protein) can have multiple (1 or more, 2 or more, 3 or more, etc.) fusion partners in any combination of the above. As an illustrative example, a Cas9 fusion protein can have a heterologous sequence that provides an activity (e.g., for transcription modulation, target modification, modification of a protein associated with a target nucleic acid, etc.) and can also have a subcellular localization sequence. In some cases, such a Cas9 fusion protein might also have a tag for ease of tracking and/or purification (e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). As another illustrative example, a Cas9 protein can have one or more NLSs (e.g., two or more, three or more, four or more, five or more, 1, 2, 3, 4, or 5 NLSs). In some cases a fusion partner (or multiple fusion partners) (e.g., an NLS, a tag, a fusion partner providing an activity, etc.) is locataed at or near the C-terminus of Cas9. In some cases a fustion partner (or multiple fusion partners) (e.g., an NLS, a tag, a fusion partner providing an activity, etc.) is located at the N-terminus of Cas9. In some cases a Cas9 has a fustion partner (or multiple fusion partners)(e.g., an NLS, a tag, a fusion partner providing an activity, etc.) at both the N-terminus and C-terminus.

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled in part by the degron sequence. In some cases, a suitable degron is constitutive such that the degron exerts its influence on protein stability independent of experimental control (i.e., the degron is not drug inducible, temperature inducible, etc.) In some cases, the degron provides the variant Cas9 polypeptide with controllable stability such that the variant Cas9 polypeptide can be turned "on" (i.e., stable) or "off" (i.e., unstable, degraded) depending on the desired conditions. For example, if the degron is a temperature sensitive degron, the variant Cas9 polypeptide may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non-functional (i.e., "off", degraded) above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g., Dohmen et al., Science, 1994. 263(5151): p. 1273-1276: Heat-inducible degron: a method for constructing temperature-sensitive mutants; Schoeber et al., Am J Physiol Renal Physiol. 2009 January; 296(1):F204-11: Conditional fast expression and function of multimeric TRPV5 channels using Shield-1; Chu et al., Bioorg Med Chem Lett. 2008 Nov. 15; 18(22):5941-4: Recent progress with FKBP-derived destabilizing domains; Kanemaki, Pflugers Arch. 2012 Dec. 28: Frontiers of protein expression control with conditional degrons; Yang et al., Mol Cell. 2012 Nov. 30; 48(4):487-8: Titivated for destruction: the methyl degron; Barbour et al., Biosci Rep. 2013 Jan. 18; 33(1).: Characterization of the bipartite degron that regulates ubiquitin-independent degradation of thymidylate synthase; and Greussing et al., J Vis Exp. 2012 Nov. 10; (69): Monitoring of ubiquitin-proteasome activity in living cells using a Degron (dgn)-destabilized green fluorescent protein (GFP)-based reporter protein; all of which are hereby incorporated in their entirety by reference).

Exemplary degron sequences have been well-characterized and tested in both cells and animals Thus, fusing Cas9 (e.g., wild type Cas9; variant Cas9; variant Cas9 with reduced nuclease activity, e.g., dCas9; and the like) to a degron sequence produces a "tunable" and "inducible" Cas9 polypeptide. Any of the fusion partners described herein can be used in any desirable combination. As one non-limiting example to illustrate this point, a Cas9 fusion protein (i.e., a chimeric Cas9 polypeptide) can comprise a YFP sequence for detection, a degron sequence for stability, and transcription activator sequence to increase transcription of the target nucleic acid. A suitable reporter protein for use as a fusion partner for a Cas9 polypeptide (e.g., wild type Cas9, variant Cas9, variant Cas9 with reduced nuclease function, etc.), includes, but is not limited to, the following exemplary proteins (or functional fragment thereof): his3, β-galatosidase, a fluorescent protein (e.g., GFP, RFP, YFP, cherry, tomato, etc., and various derivatives thereof), luciferase, β-glucuronidase, and alkaline phosphatase. Furthermore, the number of fusion partners that can be used in a Cas9 fusion protein is unlimited. In some cases, a Cas9 fusion protein comprises one or more (e.g. two or more, three or more, four or more, or five or more) heterologous sequences.

Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying nucleic acid directly (e.g., methylation of DNA or RNA) or at modifying a nucleic acid-associated polypeptide (e.g., a histone, a DNA binding protein, and RNA binding protein, and the like). Further suitable fusion partners include, but are not limited to boundary elements (e.g., CTCF), proteins and fragments thereof that provide periphery recruitment (e.g., Lamin A, Lamin B, etc.), and protein docking elements (e.g., FKBP/FRB, Pil1/Aby1, etc.).

Examples of various additional suitable fusion partners (or fragments thereof) for a subject variant Cas9 polypeptide include, but are not limited to those listed in FIG. 15A-15D and are also described in the PCT patent applications: WO2010075303, WO2012068627, and WO2013155555 which are hereby incorporated by reference in their entirety.

Suitable fusion partners include, but are not limited to, a polypeptide that provides an activity that indirectly increases transcription by acting directly on the target nucleic acid or on a polypeptide (e.g., a histone, a DNA-binding protein, an RNA-binding protein, an RNA editing protein, etc.) associated with the target nucleic acid. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

Additional suitable fusion partners include, but are not limited to, a polypeptide that directly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.).

Non-limiting examples of fusion partners to accomplish increased or decreased transcription are listed in FIG. 15B-15D and include transcription activator and transcription repressor domains (e.g., the Krüppel associated box (KRAB or SKD); the Mad mSIN3 interaction domain (SID); the ERF repressor domain (ERD), etc). In some such cases, a Cas9 fusion protein is targeted by the guide nucleic acid to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of fusion partners for use when targeting ssRNA target nucleic acids are listed in FIG. 15A and include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a fusion partner can include the entire protein or in some cases can include a fragment of the protein (e.g., a functional domain).

In some embodiments, the heterologous sequence can be fused to the C-terminus of the Cas9 polypeptide. In some embodiments, the heterologous sequence can be fused to the N-terminus of the Cas9 polypeptide. In some embodiments, the heterologous sequence can be fused to an internal portion (i.e., a portion other than the N- or C-terminus) of the Cas9 polypeptide.

In addition to the fusion partners listed in FIG. 15A the fusion partner of a chimeric Cas9 polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable fusion partner is a PUF RNA-binding domain, which is described in more detail in WO2012068627.

Some RNA splicing factors that can be used (in whole or as fragments thereof) as fusion partners for a Cas9 polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cω-elements that are located in either the core exon region or the exon extension region (i.e., between the two alternative 5' splice sites). For more examples, see WO2010075303.

In some embodiments, a Cas9 polypeptide (e.g., a wild type Cas9, a variant Cas9, a variant Cas9 with reduced nuclease activity, etc.) can be linked to a fusion partner via a peptide spacer.

Nucleic Acids Encoding a PAMmer and/or a Guide Nucleic Acid, and/or a Cas9 Polypeptide The present disclosure provides compositions and methods that include a PAMmer and at least one of: a guide nucleic acid, and a Cas9 polypeptide (e.g., a wilde type Cas9 polypeptide, a variant Cas9 polypeptide, a chimeric Cas9 polypeptide, and the like). In some cases, a subject PAMmer, and/or guide nucleic acid, and/or a Cas9 polypeptide is provded as a nucleic acid encoding one or more of a PAMmer and/or guide nucleic acid, and/or a Cas9 polypeptide. In some embodiments, a subject nucleic acid is an expression vector, e.g., a recombinant expression vector. As such, In some embodiments, a subject method involves contacting a target nucleic acid (e.g., a single stranded target nucleic acid) or introducing into a cell (or a population of cells) a PAMmer (or a nucleic acid comprising a nucleotide sequence encoding a PAMmer) and at least one of: a guide nucleic acid (or a nucleic acid comprising a nucleotide sequence encoding a guide nucleic acid), and a Cas9 polypeptide (or a nucleic acid comprising a nucleotide sequence encoding a Cas9 polypeptide). In some embodiments a cell comprising a target nucleic acid is in vitro and/or ex vivo. In some embodiments a cell comprising a target nucleic acid is in vivo. Suitable nucleic acids comprising nucleotide sequences encoding a PAMmer, a guide nucleic acid, and/or a Cas9 polypeptide include expression vectors, where an expression vector comprising a nucleotide sequence encoding a PAMmer and/or a guide nucleic acid and/or a Cas9 polypeptide is a "recombinant expression vector."

In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

In some embodiments, a nucleotide sequence encoding a PAMmer, and/or a guide nucleic acid and/or a Cas9 polypeptide is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a PAMmer, and/or a guide nucleic acid and/or a Cas9 polypeptide is operably linked to multiple control elements that allow expression of the nucleotide sequence encoding a PAMmer, and/or a guide nucleic acid and/or a Cas9 polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, green fluorescent protein, etc.) that are fused to the Cas9 polypeptide, thus resulting in a chimeric polypeptide.

In some embodiments, a nucleotide sequence encoding a guide nucleic acid and/or a Cas9 polypeptide is operably linked to an inducible promoter. In some embodiments, a nucleotide sequence encoding a guide nucleic acid and/or a Cas9 polypeptide is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a subject Cas9 polypeptide in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn, et al. (2010) Nat. Med. 16(10):1161-1166); a serotonin receptor promoter (see, e.g., GenBank S62283); a tyrosine hydroxylase promoter (TH) (see, e.g., Oh et al. (2009) Gene Ther 16:437; Sasaoka et al. (1992) Mol. Brain Res. 16:274; Boundy et al. (1998) J. Neurosci. 18:9989; and Kaneda et al. (1991) Neuron 6:583-594); a GnRH promoter (see, e.g., Radovick et al. (1991) Proc. Natl. Acad. Sci. USA 88:3402-3406); an L7 promoter (see, e.g., Oberdick et al. (1990) Science 248:223-226); a DNMT promoter (see, e.g., Bartge et al. (1988) Proc. Natl. Acad. Sci. USA 85:3648-3652); an enkephalin promoter (see, e.g., Comb et al. (1988) EMBO J. 17:3793-3805); a myelin basic protein (MBP) promoter; a Ca2+-calmodulin-dependent protein kinase II-alpha (CamKIIa) promoter (see, e.g., Mayford et al. (1996) Proc. Natl. Acad. Sci. USA 93:13250; and Casanova et al. (2001) Genesis 31:37); a CMV enhancer/platelet-derived growth factor-β promoter (see, e.g., Liu et al. (2004) Gene Therapy 11:52-60); and the like.

Adipocyte-specific spatially restricted promoters include, but are not limited to aP2 gene promoter/enhancer, e.g., a region from −5.4 kb to +21 bp of a human aP2 gene (see, e.g., Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (see, e.g., Knight et al. (2003) Proc. Natl. Acad. Sci. USA 100:14725); a fatty acid translocase (FAT/CD36) promoter (see, e.g., Kuriki et al. (2002) Biol. Pharm. Bull. 25:1476; and Sato et al. (2002) J. Biol. Chem. 277:15703); a stearoyl-CoA desaturase-1 (SCD1) promoter (Tabor et al. (1999) J. Biol. Chem. 274:20603); a leptin promoter (see, e.g., Mason et al. (1998) Endocrinol. 139: 1013; and Chen et al. (1999) Biochem. Biophys. Res. Comm 262:187); an adiponectin promoter (see, e.g., Kita et al. (2005) Biochem. Biophys. Res. Comm 331:484; and Chakrabarti (2010) Endocrinol. 151:2408); an adipsin promoter (see, e.g., Platt et al. (1989) Proc. Natl. Acad. Sci. USA 86:7490); a resistin promoter (see, e.g., Seo et al. (2003) Molec. Endocrinol. 17:1522); and the like.

Cardiomyocyte-specific spatially restricted promoters include, but are not limited to control sequences derived from the following genes: myosin light chain-2, α-myosin heavy chain, AE3, cardiac troponin C, cardiac actin, and the like. Franz et al. (1997) Cardiovasc. Res. 35:560-566; Robbins et al. (1995) Ann. N.Y. Acad. Sci. 752:492-505; Linn et al. (1995) Circ. Res. 76:584-591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Smooth muscle-specific spatially restricted promoters include, but are not limited to an SM22a promoter (see, e.g., Akyürek et al. (2000) Mol. Med. 6:983; and U.S. Pat. No. 7,169,874); a smoothelin promoter (see, e.g., WO 2001/018048); an α-smooth muscle actin promoter; and the like. For example, a 0.4 kb region of the SM22a promoter, within which lie two CArG elements, has been shown to mediate vascular smooth muscle cell-specific expression (see, e.g., Kim, et al. (1997) Mol. Cell. Biol. 17, 2266-2278; Li, et al., (1996) J. Cell Biol. 132, 849-859; and Moessler, et al. (1996) Development 122, 2415-2425).

Photoreceptor-specific spatially restricted promoters include, but are not limited to, a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225); and the like.

Methods of introducing a nucleic acid into a host cell are known in the art, and any known method can be used to introduce a nucleic acid (e.g., an expression construct) into a cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

Contacting cells with a PAMmer, and/or guide nucleic acid, and/or Cas9 polypeptide may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Conditions that promote the survival of cells are typically permissive of the subject cleavage and binding methods In some embodiments, a Cas9 polypeptide can be codon optimized. In some cases, a codon optimized Cas9 polypeptide is a variant Cas9 polypeptide. In some cases, a codon optimized Cas9 polypeptide is a chimeric Cas9 polypeptide. Codon optimization is known in the art and entails the mutation of foreign-derived DNA to mimic the codon preferences of the intended host organism or host cell while encoding the same protein. Thus, the codons are changed, but the encoded protein remains unchanged. For example, if the intended target cell was a human cell, a human codon optimized Cas9 (or Cas9 variant) would be a suitable Cas9 polypeptide. As another non-limiting example, if the intended host cell were a mouse cell, than a mouse codon optimized Cas9 (or variant, e.g., enzymatically inactive variant) would be a suitable Cas9 polypeptide. While codon optimization is not required, it is acceptable and may be preferable in certain cases.

In some embodiments, a guide nucleic acid and/or a Cas9 polypeptide and/or PAMmer can be provided as RNA. In such cases, the guide nucleic acid and/or the RNA encoding the Cas9 polypeptide and/or the PAMmer can be produced by direct chemical synthesis or may be transcribed in vitro from a DNA (e.g., encoding the guide nucleic acid, the PAMmer, and/or the Cas9 polypeptide). Methods of synthesizing RNA from a DNA template are well known in the art. In some cases, the guide nucleic acid and/or the PAMmer and/or the RNA encoding the Cas9 polypeptide will be synthesized in vitro using an RNA polymerase enzyme (e.g., T7 polymerase, T3 polymerase, SP6 polymerase, etc.). Once synthesized, the RNA may directly contact a target nucleic acid or may be introduced into a cell by any of the well-known techniques for introducing nucleic acids into cells (e.g., microinjection, electroporation, transfection, etc). In some cases, a PAMmer is a DNA oligonucleotide and can produced using any convient method (e.g., chemical synthesis).

Nucleotides encoding a guide nucleic acid (introduced either as DNA or RNA) and/or a Cas9 polypeptide (introduced as DNA or RNA) and/or a PAMmer (introduced either as DNA or RNA) may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008) Efficient gene targeting in *Drosophila* by direct embryo injection with zinc-finger nucleases. PNAS 105(50):19821-19826. Alternatively, nucleic acids encoding a guide nucleic acid and/or a Cas9 polypeptide and/or a chimeric Cas9 polypeptide and/or a PAMmer may be provided on DNA vectors. Many vectors, e.g. plasmids, cosmids, minicircles, phage, viruses, etc., useful for transferring nucleic acids into target cells are available. The vectors comprising the nucleic acid(s) may be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as MMLV, HIV-1, ALV, etc.

Vectors may be provided directly to the subject cells. In other words, the cells are contacted with vectors comprising the nucleic acid encoding guide nucleic acid and/or a Cas9 polypeptide and/or a chimeric Cas9 polypeptide and/or a PAMmer such that the vectors are taken up by the cells. Methods for contacting cells with nucleic acid vectors that are plasmids, including electroporation, calcium chloride transfection, microinjection, and lipofection are well known in the art. For viral vector delivery, the cells are contacted with viral particles comprising the nucleic acid encoding a guide nucleic acid and/or a Cas9 polypeptide and/or a chimeric Cas9 polypeptide and/or a PAMmer. Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the nucleic acid encoding the reprogramming factors into packaging cell lines and of collecting the viral particles that are generated by the packaging lines are well known in the art. Nucleic acids can also introduced by direct micro-injection (e.g., injection of RNA into a zebrafish embryo).

Vectors used for providing the nucleic acids encoding guide nucleic acid and/or a Cas9 polypeptide and/or a chimeric Cas9 polypeptide and/or a PAMmer to the subject cells will typically comprise suitable promoters for driving the expression, that is, transcriptional activation, of the nucleic acid of interest. In other words, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a guide nucleic acid and/or a Cas9 polypeptide and/or a chimeric Cas9 polypeptide and/or a PAMmer to the subject cells may include nucleic acid sequences that encode for selectable markers in the target cells, so as to identify cells that have taken up the guide nucleic acid and/or a Cas9 polypeptide and/or a chimeric Cas9 polypeptide and/or a PAMmer.

A subject guide nucleic acid and/or a Cas9 polypeptide and/or a chimeric Cas9 polypeptide may instead be used to contact DNA or introduced into cells as RNA. Methods of introducing RNA into cells are known in the art and may include, for example, direct injection, transfection, or any other method used for the introduction of DNA.

A subject Cas9 polypeptide may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, the subject Cas9 polypeptide may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO:268). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A. 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A subject Cas9 polypeptide may be produced in vitro or by eukaryotic cells or by prokaryotic cells, and it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are guide nucleic acids, PAMmers, and Cas9 polypeptides that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc) or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The Cas9 polypeptides may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The Cas9 polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein.

To induce cleavage or any desired modification to a target nucleic acid, or any desired modification to a polypeptide associated with target nucleic acid, the guide nucleic acid and/or the Cas9 polypeptide and/or the PAMmer, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different guide nucleic acids that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

Nucleic Acid Modifications

In some embodiments, a subject nucleic acid (e.g., a guide nucleic acid, a PAMmer, etc.) has one or more modifications, e.g., a base modification, a backbone modification, etc, to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

In some cases, 2% or more of the nucleotides of a subject nucleic acid (e.g., a guide nucleic acid, a PAMmer, etc.) are modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject nucleic acid are modified). In some cases, 2% or more of the nucleotides of a subject PAMmer are modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject PAMmer are modified). In some cases, 2% or more of the nucleotides of a subject guide nucleic acid are modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject guide nucleic acid are modified).

In some cases, the number of nucleotides of a subject nucleic acid nucleic acid (e.g., a guide nucleic acid, a PAMmer, etc.) that are modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject PAMmer that are modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject guide nucleic acid that are modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a subject nucleic acid (e.g., a guide nucleic acid, a PAMmer, etc.) are modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject nucleic acid are modified). In some cases, one or more of the nucleotides of a subject PAMmer are modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject PAMmer are modified). In some cases, one or more of the nucleotides of a subject guide nucleic acid are modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject guide nucleic acid are modified).

In some cases, 99% or less of the nucleotides of a subject nucleic acid (e.g., a guide nucleic acid, a PAMmer, etc.) are modified (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid are modified). In some cases, 99% or less of the nucleotides of a subject PAMmer are modified (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject PAMmer are modified). In some cases, 99% or less of the nucleotides of a subject guide nucleic acid are modified (e.g., 99% or less, 95% or less, 90% or less, 85% or less, 80% or less, 75% or less, 70% or less, 65% or less, 60% or less, 55% or less, 50% or less, or 45% or less of the nucleotides of a subject guide nucleic acid are modified).

In some cases, the number of nucleotides of a subject nucleic acid nucleic acid (e.g., a guide nucleic acid, a PAMmer, etc.) that are modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject PAMmer that are modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject guide nucleic acid that are modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a subject nucleic acid (e.g., a guide nucleic acid, a PAMmer, etc.) are modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid are modified). In some cases, 20 or fewer of the nucleotides of a subject PAMmer are modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject PAMmer are modified). In some cases, 20 or fewer of the nucleotides of a subject guide nucleic acid are modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject guide nucleic acid are modified).

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stable with respect to attack by single-stranded ribonucleases and is typically 5 to 10-fold less susceptible to DNases than DNA. It is commonly used in antisense oligos as a means to increase stability and binding affinity to the target message.

In some cases, 2% or more of the nucleotides of a subject nucleic acid (e.g., a guide nucleic acid, a PAMmer, etc.) are 2'-O-Methyl modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject nucleic acid are 2'-O-Methyl modified). In some cases, 2% or more of the nucleotides of a subject PAMmer are 2'-O-Methyl modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject PAMmer are 2'-O-Methyl modified). In some cases, 2% or more of the nucleotides of a subject guide nucleic acid are 2'-O-Methyl modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject guide nucleic acid are 2'-O-Methyl modified).

In some cases, the number of nucleotides of a subject nucleic acid nucleic acid (e.g., a guide nucleic acid, a PAMmer, etc.) that are 2'-O-Methyl modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject PAMmer that are 2'-O-Methyl modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject guide nucleic acid that are 2'-O-Methyl modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a subject nucleic acid (e.g., a guide nucleic acid, a PAMmer, etc.) are 2'-O-Methyl modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject nucleic acid are 2'-O-Methyl modified). In some cases, one or more of the nucleotides of a subject PAMmer are 2'-O-Methyl modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject PAMmer are 2'-O-Methyl modified). In some cases, one or more of the nucleotides of a subject guide nucleic acid are 2'-O-Methyl modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject guide nucleic acid are 2'-O-Methyl modified).

In some cases, 99% or less of the nucleotides of a subject nucleic acid (e.g., a guide nucleic acid, a PAMmer, etc.) are 2'-O-Methyl modified (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid are 2'-O-Methyl modified). In some cases, 99% or less of the nucleotides of a subject PAMmer are 2'-O-Methyl modified (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject PAMmer are 2'-O-Methyl modified) . In some cases, 99% or less of the nucleotides of a subject guide nucleic acid are 2'-O-Methyl modified (e.g., 99% or less, 95% or less, 90% or less, 85% or less, 80% or less, 75% or less, 70% or less, 65% or less, 60% or less, 55% or less, 50% or less, or 45% or less of the nucleotides of a subject guide nucleic acid are 2'-O-Methyl modified).

In some cases, the number of nucleotides of a subject nucleic acid nucleic acid (e.g., a guide nucleic acid, a PAMmer, etc.) that are 2'-O-Methyl modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject PAMmer that are 2'-O-Methyl modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject guide nucleic acid that are 2'-O-Methyl modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a subject nucleic acid (e.g., a guide nucleic acid, a PAMmer, etc.) are 2'-O-Methyl modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid are 2'-O-Methyl modified). In some cases, 20 or fewer of the nucleotides of a subject PAMmer are 2'-O-Methyl modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject PAMmer are 2'-O-Methyl modified) . In some cases, 20 or fewer of the nucleotides of a subject guide nucleic acid are 2'-O-Methyl modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject guide nucleic acid are 2'-0-Methyl modified).

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

In some cases, 2% or more of the nucleotides of a subject nucleic acid (e.g., a guide nucleic acid, a PAMmer, etc.) are 2' Fluoro modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject nucleic acid are 2' Fluoro modified). In some cases, 2% or more of the nucleotides of a subject PAMmer are 2' Fluoro modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject PAMmer are 2' Fluoro modified). In some cases, 2% or more of the nucleotides of a subject guide nucleic acid are 2' Fluoro modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject guide nucleic acid are 2' Fluoro modified).

In some cases, the number of nucleotides of a subject nucleic acid nucleic acid (e.g., a guide nucleic acid, a PAMmer, etc.) that are 2' Fluoro modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject PAMmer that are 2' Fluoro modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject guide nucleic acid that are 2' Fluoro modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a subject nucleic acid (e.g., a guide nucleic acid, a PAMmer, etc.) are 2' Fluoro modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject nucleic acid are 2' Fluoro modified). In some cases, one or more of the nucleotides of a subject PAMmer are 2' Fluoro modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject PAMmer are 2' Fluoro modified). In some cases, one or more of the nucleotides of a subject guide nucleic acid are 2' Fluoro modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject guide nucleic acid are 2' Fluoro modified).

In some cases, 99% or less of the nucleotides of a subject nucleic acid (e.g., a guide nucleic acid, a PAMmer, etc.) are 2' Fluoro modified (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid are 2' Fluoro modified). In some cases, 99% or less of the nucleotides of a subject PAMmer are 2' Fluoro modified (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject PAMmer are 2' Fluoro modified). In some cases, 99% or less of the nucleotides of a subject guide nucleic acid are 2' Fluoro modified (e.g., 99% or less, 95% or less, 90% or less, 85% or less, 80% or less, 75% or less, 70% or less, 65% or less, 60% or less, 55% or less, 50% or less, or 45% or less of the nucleotides of a subject guide nucleic acid are 2' Fluoro modified).

In some cases, the number of nucleotides of a subject nucleic acid nucleic acid (e.g., a guide nucleic acid, a PAMmer, etc.) that are 2' Fluoro modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject PAMmer that are 2' Fluoro modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject guide nucleic acid that are 2' Fluoro modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a subject nucleic acid (e.g., a guide nucleic acid, a PAMmer, etc.) are 2' Fluoro modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid are 2' Fluoro modified). In some cases, 20 or fewer of the nucleotides of a subject PAMmer are 2' Fluoro modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject PAMmer are 2' Fluoro modified). In some cases, 20 or fewer of the nucleotides of a subject guide nucleic acid are 2' Fluoro modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject guide nucleic acid are 2' Fluoro modified).

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

In some cases, the number of nucleotides of a subject nucleic acid nucleic acid (e.g., a guide nucleic acid, a PAMmer, etc.) that have an LNA base is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject PAMmer that have an LNA base is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject guide nucleic acid that have an LNA base is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a subject nucleic acid (e.g., a guide nucleic acid, a PAMmer, etc.) have an LNA base (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject nucleic acid have an LNA base). In some cases, one or more of the nucleotides of a subject PAMmer have an LNA base (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject PAMmer have an LNA base). In some cases, one or more of the nucleotides of a subject guide nucleic acid have an LNA base (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject guide nucleic acid have an LNA base).

In some cases, 99% or less of the nucleotides of a subject nucleic acid (e.g., a guide nucleic acid, a PAMmer, etc.) have an LNA base (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid have an LNA base). In some cases, 99% or less of the nucleotides of a subject PAMmer have an LNA base (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject PAMmer have an LNA base). In some cases, 99% or less of the nucleotides of a subject guide nucleic acid have an LNA base (e.g., 99% or less, 95% or less, 90% or less, 85% or less, 80% or less, 75% or less, 70% or less, 65% or less, 60% or less, 55% or less, 50% or less, or 45% or less of the nucleotides of a subject guide nucleic acid have an LNA base).

In some cases, the number of nucleotides of a subject nucleic acid nucleic acid (e.g., a guide nucleic acid, a PAMmer, etc.) that have an LNA base is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject PAMmer that have an LNA base is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject guide nucleic acid that have an LNA base is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a subject nucleic acid (e.g., a guide nucleic acid, a PAMmer, etc.) have an LNA base (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid have an LNA base). In some cases, 20 or fewer of the nucleotides of a subject PAMmer have an LNA base (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject PAMmer have an LNA base). In some cases, 20 or fewer of the nucleotides of a subject guide nucleic acid have an LNA base (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject guide nucleic acid have an LNA base).

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some cases, the number of nucleotides of a subject nucleic acid nucleic acid (e.g., a guide nucleic acid, a PAMmer, etc.) that have a phosphorothioate linkage is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject PAMmer that have a phosphorothioate linkage is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject guide nucleic acid that have a phosphorothioate linkage is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a subject nucleic acid (e.g., a guide nucleic acid, a PAMmer, etc.) have a phosphorothioate linkage (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject nucleic acid have a phosphorothioate linkage). In some cases, one or more of the nucleotides of a subject PAMmer have a phosphorothioate linkage (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject PAMmer have a phosphorothioate linkage). In some cases, one or more of the nucleotides of a subject guide nucleic acid have a phosphorothioate linkage (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject guide nucleic acid have a phosphorothioate linkage).

In some cases, 99% or less of the nucleotides of a subject nucleic acid (e.g., a guide nucleic acid, a PAMmer, etc.) have a phosphorothioate linkage (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid have a phosphorothioate linkage). In some cases, 99% or less of the nucleotides of a subject PAMmer have a phosphorothioate linkage (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject PAMmer have a phosphorothioate linkage). In some cases, 99% or less of the nucleotides of a subject guide nucleic acid have a phosphorothioate linkage (e.g., 99% or less, 95% or less, 90% or less, 85% or less, 80% or less, 75% or less, 70% or less, 65% or less, 60% or less, 55% or less, 50% or less, or 45% or less of the nucleotides of a subject guide nucleic acid have a phosphorothioate linkage).

In some cases, the number of nucleotides of a subject nucleic acid nucleic acid (e.g., a guide nucleic acid, a PAMmer, etc.) that have a phosphorothioate linkage is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject PAMmer that have a phosphorothioate linkage is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject guide nucleic acid that have a phosphorothioate linkage is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a subject nucleic acid (e.g., a guide nucleic acid, a PAMmer, etc.) have a phosphorothioate linkage (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid have a phosphorothioate linkage). In some cases, 20 or fewer of the nucleotides of a subject PAMmer have a phosphorothioate linkage (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject PAMmer have a phosphorothioate linkage). In some cases, 20 or fewer of the nucleotides of a subject guide nucleic acid have a phosphorothioate linkage (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject guide nucleic acid have a phosphorothioate linkage).

In some embodiments, a subject nucleic acid (e.g., a guide nucleic acid, a PAMmer, etc.) has one or more nucleotides that are 2'-O-Methyl modified nucleotides. In some embodiments, a subject nucleic acid (e.g., a guide nucleic acid, a PAMmer, etc.) has one or more 2' Fluoro modified nucleotides. In some embodiments, a subject nucleic acid (e.g., a guide nucleic acid, a PAMmer, etc.) has one or more LNA bases. In some embodiments, a subject nucleic acid (e.g., a guide nucleic acid, a PAMmer, etc.) has one or more nucleotides that are linked by a phosphorothioate bond (i.e., the subject nucleic acid has one or more phosphorothioate linkages). In some embodiments, a subject nucleic acid (e.g., a guide nucleic acid, a PAMmer, etc.) has a 5' cap (e.g., a 7-methylguanylate cap (m7G)).

In some embodiments, a subject nucleic acid (e.g., a guide nucleic acid, a PAMmer, etc.) has a combination of modified nucleotides. For example, a subject nucleic acid (e.g., a guide nucleic acid, a PAMmer, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage). See, e.g., FIG. 17A-17B and FIG. 21A-21H for working examples that utilize subject nucleic acids having one or more modified nucleotides. A subject nueclceic acid can have any combination of modifications. For example, a subject nueclceic acid can have any combination of the above described modifications.

In some embodiments, a subject guide nucleic acid has one or more nucleotides that are 2'-O-Methyl modified nucleotides. In some embodiments, a subject guide nucleic acid has one or more 2' Fluoro modified nucleotides. In some embodiments, a subject guide nucleic acid has one or more LNA bases. In some embodiments, a subject guide nucleic acid has one or more nucleotides that are linked by a phosphorothioate bond (i.e., the subject nucleic acid has one or more phosphorothioate linkages). In some embodiments, a subject guide nucleic acid has a 5' cap (e.g., a 7-methylguanylate cap (m7G)).

In some embodiments, a subject guide nucleic acid has a combination of modified nucleotides. For example, a subject guide nucleic acid can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage). A subject guide nucleic acid can have any combination of modifications. For example, a subject guide nucleic acid can have any combination of the above described modifications.

In some embodiments, a subject PAMmer has one or more nucleotides that are 2'-O-Methyl modified nucleotides. In some embodiments, a subject PAMmer has one or more 2' Fluoro modified nucleotides. In some embodiments, a subject PAMmer has one or more LNA bases. In some embodiments, a subject PAMmer has one or more nucleotides that are linked by a phosphorothioate bond (i.e., the subject nucleic acid has one or more phosphorothioate linkages). In some embodiments, a subject PAMmer has a 5' cap (e.g., a 7-methylguanylate cap (m7G)).

In some embodiments, a subject PAMmer has a combination of modified nucleotides. For example, a subject PAMmer can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage). See, e.g., FIG. 17A-17B and FIG. 21A-21H for working examples that utilize PAMmers having one or more modified nucleotides. A subject PAMmer can have any combination of modifications. For example, a subject PAMmer can have any combination of the above described modifications.

Modified Backbones and Modified Internucleoside Linkages

Examples of suitable nucleic acids containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —$CH_2$—NH—O—$CH_2$—, —$CH_2$—N($CH_3$)—O—$CH_2$-(known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (e.g., Koshkin et al., Tetrahedron, 1998, 54, 3607-3630). LNAs and preparation thereof are also described in WO 98/39352 and WO 99/14226, as well as U.S. applications 20120165514, 20100216983, 20090041809, 20060117410, 20040014959, 20020094555, and 20020086998.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_n O_m CH_3$, $O(CH_2)_n OCH_3$, $O(CH_2)_n NH_2$, $O(CH_2)_n CH_3$, $O(CH_2)_n ONH_2$, and $O(CH_2)_n ON((CH_2)_n CH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylamino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy $CH_2$ $CH_2$ $CH_2NH_2$), allyl (—$CH_2$—CH═$CH_2$), —O-allyl (—O—$CH_2$—CH═$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3', 2': 4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937.

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some cases, a PTD attached to another molecule facilitates entry of the molecule into the nucleus (e.g., in some cases, a PTD includes a nuclear localization signal). In some embodiments, a PTD is covalently linked to the amino terminus of an exogenous polypeptide (e.g., a Cas9 polypeptide). In some embodiments, a PTD is covalently linked to the carboxyl terminus of an exogenous polypeptide (e.g., a Cas9 polypeptide). In some embodiments, a PTD is covalently linked to the amino terminus and to the carboxyl terminus of an exogenous polypeptide (e.g., a Cas9 polypeptide). In some embodiments, a PTD is covalently linked to a nucleic acid (e.g., a guide nucleic acid, a polynucleotide encoding a guide nucleic acid, a polynucleotide encoding a Cas9 polypeptide, etc.). Exemplary PTDs include but are not limited to a minimal undecapeptide protein transduction domain (corresponding to residues 47-57 of HIV-1 TAT comprising YGRKKRRQRRR; SEQ ID NO:264); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an *Drosophila* Antennapedia protein transduction domain (Noguchi et al. (2003) Diabetes 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:265); Transportan GWTLNSAGYLLGKINLKALAALAKKIL (SEQ ID NO:266); KALAWEAKLAKALAKA-LAKHLAKALAKALKCEA (SEQ ID NO:267); and RQIKIWFQNRRMKWKK (SEQ ID NO:268). Exemplary PTDs include but are not limited to, YGRKKRRQRRR (SEQ ID NO:264), RKKRRQRRR (SEQ ID NO:269); an arginine homopolymer of from 3 arginine residues to 50 arginine residues; Exemplary PTD domain amino acid sequences include, but are not limited to, any of the following: YGRKKRRQRRR (SEQ ID NO:264); RKKRRQRR (SEQ ID NO:270); YARAAARQARA (SEQ ID NO:271); THRLPRRRRRR (SEQ ID NO:272); and GGRRAR-RRRRR (SEQ ID NO:273). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Additional Examples

Additional targeters, activators, Cas9 polypeptides (including variant Cas9 polypeptides), and methods of using the same, can be found in the literature (see, for example, Chylinski et al., RNA Biol. 2013 May; 10(5):726-37; Jinek et al., Science. 2012 Aug. 17; 337(6096):816-21; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et. al., Genome Res. 2013 Oct. 31; Chen et. al., Nucleic Acids Res. 2013 Nov. 1; 41(20):e19; Cheng et. al., Cell Res. 2013 October; 23(10):1163-71; Cho et. al., Genetics. 2013 November; 195(3):1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; *Mali* et. al., Nat Methods. 2013 October; 10(10):957-63; Nakayama et. al., Genesis. 2013 December; 51(12):835-43; Ran et. al., Nat Protoc. 2013 November; 8(11):2281-308; Ran et. al., Cell. 2013 Sep. 12; 154(6):1380-9; Upadhyay et. al., G3 (Bethesda). 2013 Dec. 9; 3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; all of which are hereby incorporated by reference in their entirety).

Methods

The present disclosure provides methods for cleaving a single stranded target nucleic acid (and/or modifying a polypeptide associated with a single stranded target nucleic acid). The present disclosure provides methods for binding a single stranded target nucleic acid (and/or modifying a polypeptide associated with a single stranded target nucleic acid). Generally, a subject method of cleaving involves contacting a single stranded target nucleic acid with (e.g., by introducing into a cell) a subject PAMmer, a guide nucleic acid, and a Cas9 polypeptide (e.g., a wild type Cas9 polypeptide, a variant Cas9 polypeptide, a variant Cas9 polypeptide with reduced nuclease activity, etc.). Generally, a subject method of binding involves contacting a single stranded target nucleic acid with (e.g., by introducing into a cell), a guide nucleic acid and a Cas9 polypeptide (e.g., a wild type Cas9 polypeptide, a variant Cas9 polypeptide, a variant Cas9 polypeptide with reduced nuclease activity, etc.). In some cases, a method of binding also includes contacting a single stranded target nucleic acid with a subject PAMmer. In some cases, the PAMmer has a specificity segment and does not have an orientation segment. In some cases, the PAMmer has an orientation segment and does not have a specificity segment. In some cases, the PAMmer has a specificity segment and an orientation segment.

In some embodiments of the subject methods, the target nucleic acid is inside of a cell (which can be referred to as a "host cell" or a "target cell"). In some cases, the method involves contacting a cell with (e.g., introducing into a cell) a subject PAMmer (or a nucleic acid encoding the same), and/or guide nucleic acid (or a nucleic acid encoding the same), and/or Cas9 polypeptide (or a nucleic acid encoding the same). In some embodiments of the subject methods, the host cell provides one or more of the components (e.g., the cell can be genetically modified to express a Cas9 polypeptide and/or a guide nucleic acid (or a component of a dual guide nucleic acid) and/or a PAMmer). In some such cases, the methods therefore include adding those components not provided by the host cell. For example, if the host cell is genetically modified to express a Cas9 polypeptide, the method can include introducing into the cell a guide nucleic acid and/or a PAMmer (which would therefore constitute a method of contacting a target nucleic acid with a Cas9 polypeptide, a guide nucleic acid, and/or a PAMmer).

As discussed above, a subject guide nucleic acid and a subject Cas9 polypeptide form a complex. The guide nucleic acid provides target specificity to the complex by comprising a nucleotide sequence that is complementary to a sequence of a target nucleic acid. The Cas9 polypeptide of the complex provides the site-specific activity. When the target nucleic acid is a single stranded target nucleic acid, a PAMmer provides a PAM sequence that activates the Cas9 polypeptide. In some embodiments, a subject complex cleaves a target nucleic acid.

In some cases, the Cas9 polypeptide exhibits nuclease activity that cleaves target nucleic acid at a target nucleic acid sequence (target site) defined by: (i) the region of complementarity between the guide nucleic acid and the target nucleic acid; and/or (ii) the region of complementarity between the target nucleic acid and the orientation segment of the PAMmer. A Cas9 polypeptide is activated by the presense of a PAM sequence adjacent to the target site and a single stranded target nucleic acid does not have a PAM sequence. As defined and discussed above, a subject PAMmer facilitates the cleavage of a single stranded target nucleic acid by providing a PAM sequence (anchored into an appropriate position by the orientation segment and/or the specificity segment of the PAMmer, see FIG. 8A-8F).

In some embodiments, when the method is a method of binding, the target nucleic acid can be contacted with a variant Cas9 polypeptide that has reduced nuclease activity (as described above). Such a Cas9 polypeptide can still bind to target nucleic acids in a sequence-specific manner, but the binding does not result in cleavage of the target nucleic acid. Thus, methods of binding can be used to isolate, collect, and/or analyze single stranded target nucleic acids in a sequence-specific manner A Cas9 polypeptide (e.g., a variant Cas9 polypeptide that has reduced nuclease activity) can bind to a single stranded target nucleic acid in the presence of a guide nucleic acid, in the absence of a PAMmer. However, in some cases, a PAMmer increases the efficiency of biding between the complex and the target nucleic acid. As such, in some cases, a method of binding a single stranded target nucleic acid does not include a PAMmer. In some cases, a method of binding a single stranded target nucleic acid does include a PAMmer.

Where the method is a method of binding, in some cases, the targeting segment of the guide nucleic does not need to have complementarity to the region of the target nucleic acid that will be bound (i.e., the target site). For example, in some such cases, the orientation segment of the PAMmer determines the target site of the target nucleic acid (i.e., in such cases, the target site is not defined by complementarity to the guide nucleic acid). For example, in some cases, for a method of binding, when the PAMmer does not have a specificity segment, the guide nucleic acid need not have complementarity to the target nucleic acid, and the binding of the Cas9 polypeptide to the target nucleic acid is determined by the orientation segment of the PAMmer. In other words, a Cas9 polypeptide:guide nucleic acid complex can bind to a single stranded target nucleic acid when the orientation segment of the PAMmer binds to the target nucleic acid, and the complex does not require that the targeting segment of the guide nucleic acid has complementarity to the target nucleic acid (see FIG. 5A-5C and 8A-8F). Without being bound by theory, this is believed to be because the target is a single stranded target and no strand needs to be displaced from the target site (which is not the case when a PAMmer has a specificity segment). This can be advantageous, for example, when simultaneously targeting multiple different single stranded target nucleic acids because one would need only to provide the appropriate PAMmers (each having a PAM sequence and an orientation segment of interest), but would not need to provide multiple different matched (i.e., cognate) guide nucleic acids because the same guide nucleic acid will allow for binding of all targeted single stranded target nucleic acids (because the PAMmers provided that target specificity via the orientation segments).

As another example, in some cases (e.g., for a method of binding), when the PAMmer has a specificity segment that is 10 nucleotides (nt) or less (e.g., 9 nt or less, 8 nt or less, 7 nt or less, 6 nt or less, 5 nt or less, 4 nt or less, 3 nt or less, 2 nt or less, or 1 nt or less), the guide nucleic acid need not have complementarity to the target nucleic acid, and the binding of the Cas9 polypeptide to the target nucleic acid can be determined by the orientation segment of the PAMmer (i.e., the Cas9 polypeptide:guide nucleic acid complex will bind to a single stranded target nucleic acid when the orientation segment of the PAMmer binds to the target nucleic acid).

In some cases, in addition to contacting a target nucleic acid with a guide nucleic acid, a variant Cas9 (with reduced nuclease activity) (which produces a variant-Cas9/target complex), and/or a PAMmer (which can increase the efficiency of binding of a Cas9 polypeptide (e.g. a variant Cas9 polypeptide):guide nucleic acid complex with a target nucleic acid), a subject method further includes isolating the variant-Cas9/target complex, and collecting and/or analyzing the single stranded target nucleic acid and/or a polypeptide (or polypeptides) associated with the single stranded target nucleic acid. In some cases, the method includes, prior to collecting and/or analyzing, releasing the single stranded target nucleic acid from the variant-Cas9/target complex. In some cases, variant-Cas9/target complex, once formed, self dissociates. For example, in some cases, the variant Cas9 polypeptide has a fusion parnter (e.g., a fusion partner having enzymatic activity) that modifies the target nucleic acid, and once modified the variant-Cas9/target complex dissociates.

A variant-Cas9/target complex can be isolated by any convenient method. For example, the variant-Cas9/target complex can be isolated by immunoprecipitation (e.g., using an antibody against the Cas9 polypeptide and/or using a labeled Cas9 polypeptide)(various labels are described above). As one non-limiting example, the Cas9 polypeptide can be labeled with biotin then immobilized on a solid support (e.g. agarose-streptavidin), and the RNA can be isolated and/or analyzed (e.g., via column chromatography, via RNA purification and sequencing, etc.). In some cases, the target nucleic acid will also be bound by other nucleic acids and/or proteins there were present prior to contacting with a Cas9 polypeptide. In some such cases, after a subject binding method is performed, the target nucleic acid remains bound to the other nucleic acids and/or proteins (e.g., proteins and/or nucleic acids of a cell that normally interact with the target nucleic acid). As such, a subject binding method can be used to study the molecules (e.g., nucleic acids and/or proteins) that interact with any target nucleic acid of interest.

In addition, a method of binding can be used to visualize the target nucleic acid (e.g., visualize the subcellular distribution of a target nucleic acid). Because the Cas9/guide nucleic acid/PAMmer form a complex at a targeted site of a target single stranded nucleic acid, any one of the components (the Cas9 polypeptide, the guide nucleic acid, the PAMmer, etc.) can be detectably labeled (i.e., can have an indirect and/or direct label moiety, defined above) in order to visualize the complex. The term "detectable label" includes directly and/or indirectly detectable labels. In some cases, a guide nucleic acid and/or a PAMmer can have a label moiety that can be indirectly detected (an RNA aptamer, a nucleic acid sequence that is bound by a labeled protein, biotin, etc.) and/or directly detected (e.g., a fluorescent dye).

In some instances, one or more components (e.g, a target nucleic acid, a PAMmer, a guide nucleic acid, and/or a Cas9 polypeptide) is labeled with (e.g., linked to) a donor molecule, while another component is labeled with (e.g., linked to) an acceptor molecule, and detection of an association between the labeled components is by fluorescence resonance energy transfer (also referred to as "Förster resonance energy transfer" or "FRET").

FRET is phenomenon wherein excitation of one emissive dye is transferred to another without emission of a photon. A FRET pair consists of a donor chromophore and an acceptor chromophore (where the acceptor chromophore may be a quencher molecule). The emission spectrum of the donor and the absorption spectrum of the acceptor must overlap, and the two molecules must be in close proximity The distance between donor and acceptor at which 50% of donors are deactivated (transfer energy to the acceptor) is defined by the Förster radius, which is typically 10-100 angstroms. Changes in the emission spectrum comprising FRET pairs can be detected, indicating changes in the number of that are in close proximity (i.e., within 100 angstroms of each other). This will typically result from the binding or dissociation of two molecules, one of which is labeled with a FRET donor and the other of which is labeled with a FRET acceptor, wherein such binding brings the FRET pair in close proximity.

Binding of such molecules will result in an increased emission of the acceptor and/or quenching of the fluorescence emission of the donor. FRET pairs (donor/acceptor) suitable for use include, but are not limited to, EDANS/fluorescein, IAEDANS/fluorescein, fluorescein/tetramethylrhodamine, fluorescein/Cy 5, IEDANS/DABCYL, fluorescein/QSY-7, fluorescein/LC Red 640, fluorescein/Cy 5.5 and fluorescein/LC Red 705. In addition, a fluorophore/quantum dot donor/acceptor pair can be used. EDANS is (5-((2-Aminoethyl)amino)naphthalene-1-sulfonic acid); IAEDANS is 5-({2-[(iodoacetyl)amino]ethyl}amino)naphthalene-1-sulfonic acid); DABCYL is 4-(4-dimethylaminophenyl) diazenylbenzoic acid.

Cy3, Cy5, Cy 5.5, and the like, are cyanines. For example, Cy3 and Cy5 are reactive water-soluble fluorescent dyes of the cyanine dye family Cy3 dyes are red (~550 nm excitation, 570 nm emission and therefore appear green), while Cy5 is fluorescent in the red region (~650/670 nm) but absorbs in the orange region (~649 nm). Alexa Fluor dyes, Dylight, IRIS Dyes, Seta dyes, SeTau dyes, SRfluor dyes and Square dyes dyes can also be used.

In another aspect of FRET, an emissive donor molecule and a nonemissive acceptor molecule ("quencher") may be employed. In this application, emission of the donor will increase when quencher is displaced from close proximity to the donor and emission will decrease when the quencher is brought into close proximity to the donor. Useful quenchers include, but are not limited to, DABCYL, QSY 7 and QSY 33. Useful fluorescent donor/quencher pairs include, but are not limited to EDANS/DABCYL, Texas Red/DABCYL, BODIPY/DABCYL, Lucifer yellow/DABCYL, coumarin/DABCYL and fluorescein/QSY 7 dye.

In some instances, one or more components (e.g., a target nucleic acid, a PAMmer, a guide nucleic acid, and/or a Cas9 polypeptide) is labeled with (e.g., linked to, fused with, bound by, etc.) a first member of a split fluorophore, while another component is labeled with (e.g., linked to, fused with, bound by, etc.) a second member of a split fluorophore, and detection of the fluorophore can occur when the first and second split fluorophores are brought into close proximity For example, in some cases, a Cas9 polypeptide (or a guide nucleic acid) can be labeled with a first member of a split fluorophore and the corresponding PAMmer can be labeled with a second member of the split fluorophore such that, when the Cas9/guide nucleic acid complex is brought into close proximity to the corresponding PAMmer (which occurs when both are binding to (associated with) the target nucleic acid), a signal can be detected. Any convenient split fluorophore can be used. For more information related to split fluorophores (e.g., a split-GFP), refer to Cabantous et al., Sci Rep. 2013 Oct. 4; 3:2854. doi: 10.1038/srep02854, which is hereby incorporated by reference in its entirety.

Multiple Guide Nucleic Acids and/or PAMmers

In some embodiments, multiple guide nucleic acids and multiple PAMmers are used to simultaneously cleave and/or bind multiple different target nucleic acids or multiple different locations on the same target nucleic. For example, for methods of binding, each targeting pair (a PAMmer and a guide nucleic acid) can have a detectable label that is distinguishable from another targeting pair, and thus, multiple different target nucleic acids can be simultaneously bound (e.g., visualized). In some embodiments, two or more guide nucleic acids (and PAMmers) target the same gene or transcript or locus. In some embodiments, two or more guide nucleic acids (and PAMmers) target different unrelated target nucleic acids. In some embodiments, two or more guide nucleic acids (and PAMmers) target different, but related target nucleic acids.

Because the guide nucleic acids and PAMmers are small and robust multiple guide nucleic acids and/or multiple PAMmers (e.g., when a PAMmer is transcribed from DNA) can be simultaneously present on the same expression vector and can even be under the same transcriptional control if so desired. In some embodiments, two or more (e.g., 3 or more, 4 or more, 5 or more, 10 or more, 15 or more, 20 or more, 25 or more, 30 or more, 35 or more, 40 or more, 45 or more, or 50 or more) guide nucleic acids (and/or PAMmers) are simultaneously expressed in a target cell (from the same or different vectors). The expressed guide nucleic acids (and/or PAMmers) can be differentially recognized by Cas9 proteins from different bacteria, such as *S. pyogenes, S. thermophilus, L. innocua,* and *N. meningitidis.*

In some cases (e.g., when a PAMmer is DNA or a modified nucleic acid (i.e., is not transcribed from DNA)), the PAMmer(s) can be introduced directly (e.g., transfected into a cell), which is also the case when using a single PAMmer (and/or a single guide nucleic acid).

To express multiple guide nucleic acids (and/or PAMmers), an artificial RNA processing system mediated by the Csy4 endoribonuclease can be used. Multiple guide nucleic acids can be concatenated into a tandem array on a precursor transcript (e.g., expressed from a U6 promoter), and separated by Csy4-specific RNA sequence. Co-expressed Csy4 protein cleaves the precursor transcript into multiple guide nucleic acids (and/or PAMmers). Advantages for using an RNA processing system include: first, there is no need to use multiple promoters; second, since all guide nucleic acids (and/or PAMmers) are processed from a precursor transcript, their concentrations are normalized for similar Cas9-binding.

Csy4 is a small endoribonuclease (RNase) protein derived from bacteria *Pseudomonas aeruginosa*. Csy4 specifically recognizes a minimal 17-bp RNA hairpin, and exhibits rapid (<1 min) and highly efficient (>99.9% or more) RNA cleavage. Unlike most RNases, the cleaved RNA fragment remains stable and functionally active. The Csy4-based RNA cleavage can be repurposed into an artificial RNA processing system. In this system, the 17-bp RNA hairpins are inserted between multiple RNA fragments that are transcribed as a precursor transcript from a single promoter. Co-expression of Csy4 is effective in generating individual RNA fragments.

In some embodiments (e.g., in some cases where the Cas9 polypeptide is a chimeric Cas9 polypeptide), a subject complex modifies a target polypeptide associated with target nucleic acid (e.g., a histone, a DNA-binding protein, an RNA-binding protein, an RNA editing protein etc.), leading to, for example, protein methylation, protein acetylation, protein ubiquitination, and the like. The target nucleic acid may be, for example, a single stranded nucleic acid outside of a cell in vitro, a single stranded nucleic acid inside of a cell in vitro, a single stranded nucleic acid inside of a cell ex vivo, or a single stranded nucleic acid inside of a cell in vivo. The nuclease activity cleaves single stranded target nucleic acid, causing degradation of, and a reduction in the levels of, the target nucleic acid.

For methods of cleaving and/or binding a single stranded target nucleic acid, in some cases, different Cas9 proteins (i.e., Cas9 proteins from various species) may be advantageous to use in the various provided methods in order to capitalize on various enzymatic characteristics of the different Cas9 proteins (e.g., for different PAM sequence preferences; for increased or decreased enzymatic activity; for an increased or decreased level of cellular toxicity; etc.). Cas9 proteins from various species (see SEQ ID NOs:1-256 and 795-1346) may require different PAM sequences. Thus, for a particular Cas9 protein of choice, the PAM sequence requirement may be different than the PAM sequences described above (e.g., 5'-NGG-3', GG, etc.).

In some embodiments, a subject guide nucleic acid and a subject Cas9 polypeptide are used as an inducible system for shutting off gene expression in cells. For example, in some cases, nucleic acids encoding an appropriate guide nucleic acid and/or an appropriate Cas9 polypeptide and/or a PAMmer can be incorporated into the chromosome of a target cell and are under control of an inducible promoter. When the guide nucleic acid and/or the PAMmer and/or the site-directed polypeptide are induced, the target nucleic acid is cleaved (or otherwise modified) at the location of interest, when the PAMmer, the guide nucleic acid and the Cas9 polypeptide are present and bind the single stranded target nucleic acid. As such, in some cases, cells are engineered to include nucleic acid sequences encoding an appropriate Cas9 polypeptide in the genome and/or an appropriate guide nucleic acid (e.g., on a plasmid, e.g., under control of an inducible promoter), allowing experiments in which the expression of any targeted gene (expressed from a separate plasmid introduced into the cell) could be controlled by inducing expression of the guide nucleic acid and the site-directed polypeptide. The PAMmer can be provided by the experimenter if the PAMmer is a DNA (or a modified nucleic acid), and can be transcribed in the cell if the PAMmer is an RNA.

In some cases, the Cas9 polypeptide has enzymatic activity that modifies target nucleic acid in ways other than introducing strand cleavage. Enzymatic activity of interest that may be used to modify target nucleic acid (e.g., by fusing a heterologous polypeptide with enzymatic activity to a Cas9 polypeptide, thereby generating a chimeric Cas9 polypeptide) includes, but is not limited methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, the Cas9 polypeptide has activity that modulates the production of a protein encoded by a single stranded target nucleic acid (e.g., mRNA) (e.g., by cleaving and thereby degrading the mRNA). In some cases, the subject method is used to cleave a targeted coding-RNA (protein-encoding gene) and/or a targeted non-coding RNA (e.g., tRNA, rRNA, snoRNA, siRNA, miRNA, long ncRNA, etc.).

In some cases, the Cas9 polypeptide has enzymatic activity that modifies a polypeptide associated with a target nucleic acid (e.g. a histone, a DNA-binding protein, an RNA-binding protein, an RNA editing protein and the like). In some embodiments, the enzymatic activity is methyltransferase activity, demethylase activity, acetyltransferase activity, deacetylase activity, kinase activity, phosphatase activity, ubiquitin ligase activity (i.e., ubiquitination activity), deubiquitinating activity, adenylation activity, deadenylation activity, SUMOylating activity, deSUMOylating activity, ribosylation activity, deribosylation activity, myristoylation activity, demyristoylation activity glycosylation activity (e.g., from O-GlcNAc transferase) or deglycosylation activity. The enzymatic activities listed herein catalyze covalent modifications to proteins. Such modifications are known in the art to alter the stability or activity of the target protein (e.g., phosphorylation due to kinase activity can stimulate or silence protein activity depending on the target protein).

Target Cells of Interest

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA). Because the guide nucleic acid provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens* C. Agardh, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.).

Any type of cell may be of interest (e.g. a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. In some cases, the primary cell lines are maintained for fewer than 10 passages in vitro. Target cells are in many embodiments unicellular organisms, or are grown in culture.

If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% or more DMSO, 50% or more serum, and about 40% buffered medium, or some other such solution as is commonly used in the art to preserve cells at such freezing temperatures, and thawed in a manner as commonly known in the art for thawing frozen cultured cells.

Introducing Components into a Target Cell

A guide nucleic acid (or a nucleic acid comprising a nucleotide sequence encoding same), a PAMmer (or a nucleic acid comprising a nucleotide sequence encoding same), and/or a Cas9 polypeptide (or a nucleic acid comprising a nucleotide sequence encoding same) can be introduced into a host cell by any of a variety of well-known methods. Similarly, where a subject method involves introducing into a host cell a nucleic acid comprising a nucleotide sequence encoding a variant Cas9 polypeptide, such a nucleic acid can be introduced into a host cell by any of a variety of well-known methods.

Methods of introducing a nucleic acid into a host cell are known in the art, and any known method can be used to introduce a nucleic acid (e.g., an expression construct) into a stem cell or progenitor cell. Suitable methods include, include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like. For methods of cleaving and/or binding a single stranded target nucleic acid, in some cases, the Cas9 polypeptide is provided as a nucleic acid (e.g., an mRNA, a DNA, a plasmid, an expression vector, etc.) that encodes the Cas9 protein. In some cases, the Cas9 polypeptide is provided directly as a protein. As one non-limiting example, fungi (e.g., yeast) can be transformed with exogenous protein and/or nucleic acid using spheroplast transformation (see Kawai et al., Bioeng Bugs. 2010 November-December; 1(6):395-403: "Transformation of *Saccharomyces cerevisiae* and other fungi: methods and possible underlying mechanism"; and Tanka et al., Nature. 2004 Mar. 18; 428(6980):323-8: "Conformational variations in an infectious protein determine prion strain differences"; both of which are herein incorporated by reference in their entirety). Thus, a Cas9 polypeptide (e.g., Cas9) can be incorporated into a spheroplast (with or without nucleic acid encoding a guide nucleic acid and with or without a donor polynucleotide) and the spheroplast can be used to introduce the content into a yeast cell. A Cas9 polypeptide can be introduced into a cell (provided to the cell) by any convenient method; such methods are known to those of ordinary skill in the art. As another non-limiting example, a Cas9 polypeptide can be injected directly into a cell (e.g., with or without nucleic acid encoding a guide nucleic acid and with or without a donor polynucleotide), e.g., a cell of a zebrafish embryo, the pronucleus of a fertilized mouse oocyte, etc.

Genetically Modified Host Cells

In some embodiments, a genetically modified host cell has been genetically modified with an exogenous nucleic acid comprising a nucleotide sequence encoding a Cas9 polypeptide (e.g., a naturally occurring Cas9; a modified, i.e., mutated or variant, Cas9; a chimeric Cas9; etc.). Single stranded nucleic acids of the genetically modified host cell can be targeted for modification by introducing into the cell a guide nucleic acid (or a DNA encoding a guide nucleic acid, which determines the genomic location/sequence to be modified) and a PAMmer (or a nucleic acid encoding a PAMmer). In some embodiments, the nucleotide sequence encoding a Cas9 polypeptide is operably linked to an inducible promoter (e.g., heat shock promoter, Tetracycline-regulated promoter, Steroid-regulated promoter, Metal-regulated promoter, estrogen receptor-regulated promoter, etc.). In some embodiments, the nucleotide sequence encoding a Cas9 polypeptide is operably linked to a spatially restricted and/or temporally restricted promoter (e.g., a tissue specific promoter, a cell type specific promoter, etc.). In some embodiments, the nucleotide sequence encoding a Cas9 polypeptide is operably linked to a constitutive promoter.

In some embodiments, a subject genetically modified host cell is in vitro. In some embodiments, a subject genetically modified host cell is in vivo. In some embodiments, a subject genetically modified host cell is a prokaryotic cell or is derived from a prokaryotic cell. In some embodiments, a subject genetically modified host cell is a bacterial cell or is derived from a bacterial cell. In some embodiments, a subject genetically modified host cell is an archaeal cell or is derived from an archaeal cell. In some embodiments, a subject genetically modified host cell is a eukaryotic cell or is derived from a eukaryotic cell. In some embodiments, a subject genetically modified host cell is a plant cell or is derived from a plant cell. In some embodiments, a subject genetically modified host cell is an animal cell or is derived from an animal cell. In some embodiments, a subject genetically modified host cell is an invertebrate cell or is derived from an invertebrate cell. In some embodiments, a subject genetically modified host cell is a vertebrate cell or is derived from a vertebrate cell. In some embodiments, a subject genetically modified host cell is a mammalian cell or is derived from a mammalian cell. In some embodiments, a subject genetically modified host cell is a rodent cell or is derived from a rodent cell. In some embodiments, a subject genetically modified host cell is a human cell or is derived from a human cell.

The present disclosure further provides progeny of a subject genetically modified cell, where the progeny can comprise the same exogenous nucleic acid or polypeptide as the subject genetically modified cell from which it was derived. The present disclosure further provides a composition comprising a subject genetically modified host cell.

In other aspects of the disclosure, a PAMmer, and/or guide nucleic acid, and/or Cas9 polypeptide are employed to modify single stranded nucleic acid (ssRNA, ssDNA) in vivo, for purposes such as gene therapy, e.g. to treat a disease or as an antiviral, antipathogenic, or anticancer therapeutic, or for biological research. In in vivo embodiments, a PAMmer, and/or guide nucleic acid, and/or Cas9 polypeptide are administered directly to the individual. A PAMmer, and/or guide nucleic acid, and/or Cas9 polypeptide may be administered by any of a number of well-known methods in the art for the administration of peptides, small molecules and nucleic acids to a subject. A PAMmer, and/or guide nucleic acid, and/or Cas9 polypeptide can be incorporated into a variety of formulations. More particularly, a PAMmer, and/or guide nucleic acid, and/or Cas9 polypeptide of the present disclosure can be formulated into pharmaceutical compositions by combination with appropriate pharmaceutically acceptable carriers or diluents.

Pharmaceutical preparations are compositions that include one or more of a PAMmer, and/or guide nucleic acid, and/or Cas9 polypeptide present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which an agent (e.g., one or more of a PAMmer, and/or guide nucleic acid, and/or Cas9 polypeptide) is formulated for administration to a mammal Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the a PAMmer, and/or guide nucleic acid, and/or Cas9 polypeptide can be achieved in various ways, including oral, buccal, rectal, parenteral, intraperitoneal, intradermal, transdermal, intratracheal, intraocular, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin The potential for using BBB opening to target specific agents to brain tumors is also an option. A BBB disrupting agent can be co-administered with the therapeutic compositions of the present disclosure when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the methods of the present disclosure, to facilitate transport across the endothelial wall of the blood vessel. Alternatively, drug delivery of therapeutics agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversably affixed (see e.g. US Application Nos. 20080081064 and 20090196903, incorporated herein by reference).

Typically, an effective amount of a PAMmer, and/or guide nucleic acid, and/or Cas9 polypeptide are provided. As discussed above with regard to ex vivo methods, an effective amount or effective dose of a PAMmer, and/or guide nucleic acid, and/or Cas9 polypeptide in vivo is the amount sufficient to induce a 2 fold (or greater) reduction in the amount of intact target nucleic acid (for methods of cleaving) relative to a negative control, e.g. a cell contacted with an empty vector or irrelevant polypeptide. The amount of intact target nucleic acid may be measured by any convenient method, e.g. as described above and known in the art. The calculation of the effective amount or effective dose of a PAMmer, and/or guide nucleic acid, and/or Cas9 polypeptide to be administered is within the skill of one of ordinary skill in the art. The final amount to be administered will be dependent upon the route of administration and upon the nature of the disorder or condition that is to be treated.

The effective amount given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, a PAMmer, and/or guide nucleic acid, and/or Cas9 polypeptide may be obtained from a suitable commercial source. As a general proposition, the total pharmaceutically effective amount of a PAMmer, and/or guide nucleic acid, and/or Cas9 polypeptide administered parenterally per dose will be in a range that can be measured by a dose response curve.

Therapies based on the a PAMmer, and/or guide nucleic acid, and/or Cas9 polypeptide, i.e. preparations of a PAMmer, and/or guide nucleic acid, and/or Cas9 polypeptide to be used for therapeutic administration, must be sterile. Sterility is readily accomplished by filtration through sterile filtration membranes (e.g., 0.2 µm membranes). Therapeutic compositions generally are placed into a container having a sterile access port, for example, an intravenous solution bag or vial having a stopper pierceable by a hypodermic injection needle. The therapies based on a PAMmer, and/or guide nucleic acid, and/or Cas9 polypeptide may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., National Food (NF) grade, generally analytical grade, and more typically pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under Good Manufacturing Practices (GMP) conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Compositions

The present disclosure provides a composition comprising a PAMmer and at least one of: a subject guide nucleic acid and a subject Cas9 polypeptide. In some cases, the Cas9 polypeptide is a variant Cas9 polypeptide. In some cases, the Cas9 polypeptide is a chimeric Cas9 polypeptide. A subject composition is useful for carrying out a method of the present disclosure, e.g., a method for cleaving a single stranded target nucleic acid; a method for binding a single stranded target nucleic acid; etc.

Compositions Comprising a Guide Nucleic Acid

The present disclosure provides a composition comprising a subject PAMmer and at least one of: a guide nucleic acid and a Cas9 polypeptide. The composition can comprise, in addition, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), MES sodium salt, 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a nuclease inhibitor; and the like. For example, in some cases, a subject composition comprises a subject guide nucleic acid and a buffer for stabilizing nucleic acids.

In some embodiments, PAMmer and/or a guide nucleic acid and/or a Cas9 polypeptide is present in a subject composition is pure, e.g., 75% or more, 80% or more, 85% or more, 90% or more, 95% or more, 98% or more, 99% or more, or more than 99% or more pure, where "% or more purity" means that guide nucleic acid is the recited percent free from other macromolecules, or contaminants that may be present during the production of the PAMmer and/or a guide nucleic acid and/or a Cas9 polypeptide.

Kits

The present disclosure provides kits for carrying out a subject method. A subject kit can include one or more of: a Cas9 polypeptide; a nucleic acid comprising a nucleotide encoding a Cas9 polypeptide; a PAMmer; a nucleic acid comprising a nucleotide sequence encoding a PAMmer; a guide nucleic acid; a nucleic acid comprising a nucleotide sequence encoding a guide nucleic acid; an activator; a nucleic acid comprising a nucleotide sequence encoding an activator; a targeter; and a nucleic acid comprising a nucleotide sequence encoding a targeter; all of which are described in detail above.

A kit may comprise a complex that comprises two or more of: a Cas9 polypeptide; nucleic acid comprising a nucleotide encoding a Cas9 polypeptide; a PAMmer; a nucleic acid comprising a nucleotide sequence encoding a PAMmer; a guide nucleic acid; a nucleic acid comprising a nucleotide sequence encoding a guide nucleic acid; an activator; a nucleic acid comprising a nucleotide sequence encoding an activator; a targeter; and a nucleic acid comprising a nucleotide sequence encoding a targeter.

The present disclosure provides a kit for carrying out a subject method. A subject kit comprises: a subject PAMmer, or a nucleic acid comprising a nucleotide sequence encoding the PAMmer; and a subject guide nucleic acid, or a nucleic acid comprising a nucleotide sequence encoding the guide nucleic acid. In some cases, the nucleic acid comprising a nucleotide sequence encoding the guide nucleic acid further comprises a nucleotide sequence encoding a Cas9 polypeptide (e.g. a wild type Cas9 polypeptide, a variant Cas9 polypeptide that exhibits reduced nuclease activity relative to wild-type Cas9; a chimeric Cas9 polypeptide, and the like).

In some embodiments of any of the above kits, the kit comprises an activator or a targeter. In some embodiments of any of the above kits, the kit comprises a single guide nucleic acid. In some embodiments of any of the above kits, the kit comprises a PAMmer. In some embodiments of any of the above kits, the kit comprises two or more guide nucleic acids (e.g., dual and/or single guide nucleic acids). In some embodiments of any of the above kits, the kit comprises two or more PAMmers. In some embodiments of any of the above kits, a guide nucleic acid (e.g., including two or more guide nucleic acids) and/or a PAMmer can be provided as an array (e.g., an array of RNA molecules, an array of DNA molecules, e.g., encoding the guide nucleic acid(s) and/or PAMmers, etc.). Such kits can be useful, for example, for use in conjunction with the above described genetically modified host cells that comprise a subject Cas9 polypeptide. In some embodiments of any of the above kits, the kit further comprises a donor polynucleotide to effect the desired genetic modification. Components of a subject kit can be in separate containers; or can be combined in a single container.

Any of the above-described kits can further include one or more additional reagents, where such additional reagents can be selected from: a dilution buffer; a reconstitution solution; a wash buffer; a control reagent; a control expression vector or RNA polynucleotide; a reagent for in vitro production of the Cas9 polypeptide from DNA, and the like.

In some cases, a subject kit further comprises a variant Cas9 polypeptide that exhibits reduced nuclease activity relative to wild-type Cas9.

In some cases, a subject kit further comprises a nucleic acid comprising a nucleotide sequence encoding a variant Cas9 polypeptide that exhibits reduced nuclease activity relative to wild-type Cas9.

A subject kit can further include one or more additional reagents, where such additional reagents can be selected from: a buffer; a wash buffer; a control reagent; a control expression vector or RNA polynucleotide; a reagent for in vitro production of a Cas9 polypeptide from DNA; and the like. In some cases, a Cas9 polypeptide included in a subject kit is a wild type Cas9 polypepitde. In some cases, a Cas9 polypeptide included in a subject kit is a variant Cas9 polypepitde. In some cases, a Cas9 polypeptide included in a subject kit is a fusion variant Cas9 polypeptide.

Components of a subject kit can be in separate containers; or can be combined in a single container.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Libraries

The present disclosure provides a library of two or more PAMmers. The present disclosure provides a library of two or more targeting pairs, where a targeting pair is a guide nucleic acid and a cognate PAMmer. Thus, each targeting pair is associate wth (targets) one target site of a single stranded target nucleic acid. The guide nucleic acids and/or PAMmers can be present in the library as nucleic acids (e.g., recombinant expression vectors) comprising nucleotides encoding guide nucleic acids and/or PAMmers.

A subject library can comprise from about 2 targeting pairs to about $10^{12}$ targeting pairs; e.g., a subject library can comprise from about 2 targeting pairs to about $10^2$ targeting pairs, from about $10^2$ targeting pairs to about $10^3$ targeting pairs, from about $10^3$ targeting pairs to about $10^5$ targeting pairs, from about $10^5$ targeting pairs to about $10^7$ targeting pairs, from about $10^7$ targeting pairs to about $10^9$ targeting pairs, or from about $10^9$ targeting pairs to about $10^{12}$ targeting pairs.

A "targeting pair" of a subject library differs from other members of the library in the nucleotide sequence of the targeting segment of the guide nucleic acid as well as the orientation segment and/or the specificity segment of the PAMmer. Thus, e.g., each targeting pair of a subject library can comprise a guide nucleic acid with the same or substantially the same nucleotide sequence of the protein-binding segment as all other members of the library. In this way, the library can comprise members that bind to different target nucleic acids.

Utility

A method for cleaving and/or binding a single-stranded target nucleic acid according to the present disclosure finds use in a variety of applications, which are also provided. Applications include research applications; diagnostic applications; industrial applications; and treatment applications. Applications include, e.g., determining the effect (e.g., in a target cell) of reducing the presence of a target nucleic acid (e.g., mRNA, tRNA, rRNA, microRNA, ncRNA, lncRNA, etc.) (i.e., target-selected and target-specific RNA degradation); and/or treating an individual by degrading a particular targeted single stranded DNA or single stranded RNA.

As described above, applications also include (e.g., when using a binding method to visualize a target nucleic acid) the visualization and subcellular localization of specific single stranded target nucleic acids (e.g., in real time) (e.g., multi-color RNA imaging inside of a cell). Also as described above, applications include (e.g., when using a binding method to collect and/or analyze single stranded target nucleic acid) RNA-protein pulldown assays from living cells (e.g., in vitro, ex vivo, and/or in vivo). As described above, applications include (e.g, when a binding method is used to isolate and/or collect and/or analyze target nucleic acid) the identification of target nucleic acid-associated proteins (e.g., via mass spectrometry analysis), or even purification of intact target RNA:protein complexes and subsequent biochemical or biophysical studies.

A subject cleaving method can be used for drug discovery and target validation. High through-put genomic analysis can be carried out using a subject cleaving method, in which only the targeting segment of the guide nucleic acid and the orientation segment of the PAMmer needs to be varied, while the protein-binding segment of the guide nucleic acid (in some cases) can be held constant. A library (e.g., a subject library) comprising a plurality of nucleic acids used in the genomic analysis can include, for example: a promoter operably linked to a guide nucleic acid-encoding nucleotide sequence, where each nucleic acid can include a different targeting segment, and a common protein-binding segment. Applications include large-scale phenotyping and gene-to-function mapping.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

In FIGS. 1-6 of the following working examples, a subject PAMmer is schematized above or below the appropriate experimental lanes and the PAM sequence is boxed (also refer to FIG. 8A-D).

Example 1: Use of Cas9 to Cleave a Single Stranded RNA (ssRNA)

The working examples demonstrate that a Cas9 polypeptide associated with a guide nucleic acid can bind and cleave single stranded RNA (ssRNA) target sequences. Single stranded target nucleic binding is stabilized by including a short PAM-containing oligonucleotide ('PAMmer') that hybridizes to the single stranded target nucleic acid (e.g, RNA and/or DNA) downstream of the region that is recognized sequence-specifically through base-pairing with the guide nucleic acid. Inclusion of the PAMmer also activates Cas9 to cleave the singled stranded target nucleic acid using the same HNH nuclease domain that cleaves double stranded target nucleic acid (dsDNA).

Figure 3:
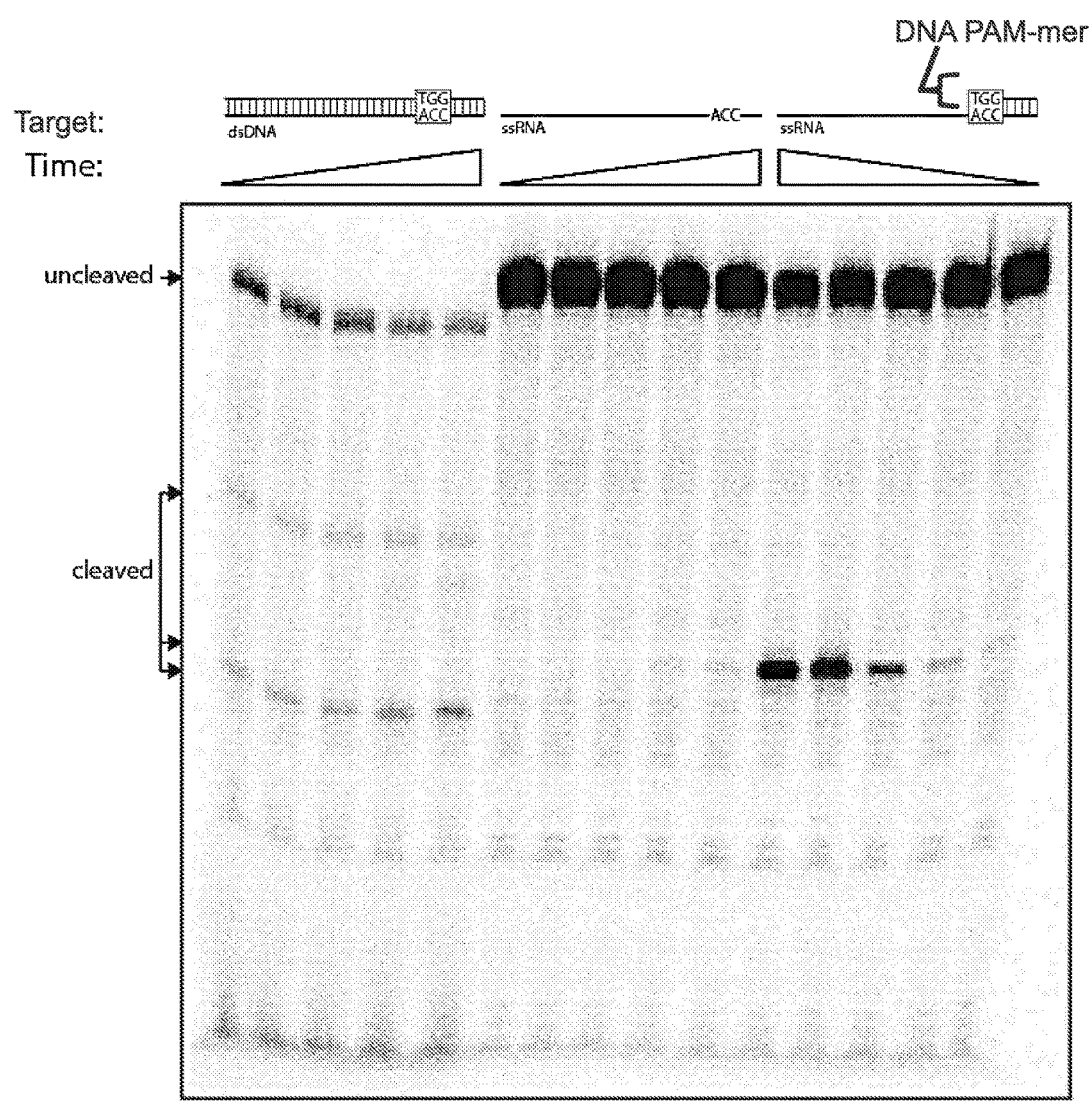
FIG. 3 presents cleavage assays testing whether Cas9 can cleave a single stranded RNA (ssRNA) target nucleic acid when used in combination with a PAMmer.
Figure 4B:
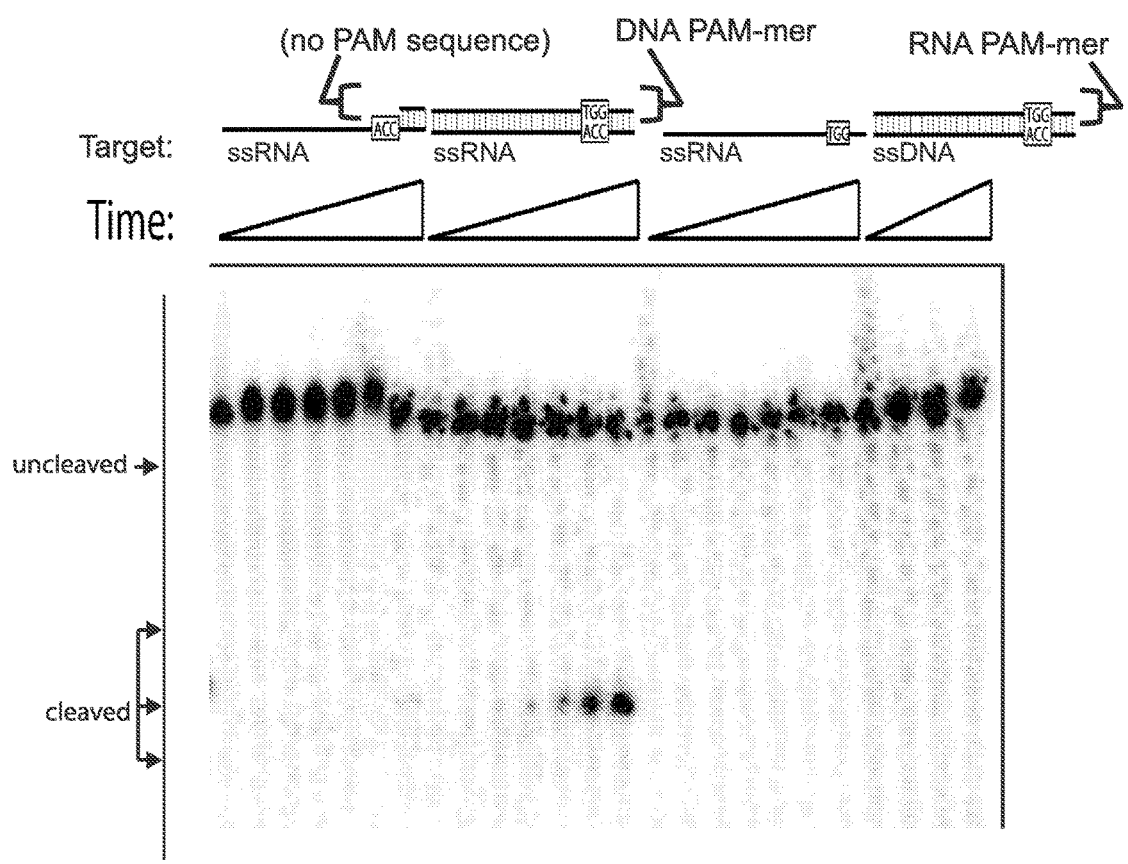

The working examples demonstrate that Cas9 complexed with guide nucleic acid binds target RNA and that PAMmers increase the affinity of this interaction (FIG. 1); that longer PAMmers lead to higher affinity binding, and that the 5'-NGG-3' PAM itself does not need to base-pair with target nucleic acid for this effect (FIG. 2A-2B); that PAMmers activate Cas9 complexed with guide nucleic acid to cleave target RNA (FIG. 3); that this activating effect is dependent on the PAM sequence, and is not recovered with just flanking RNA:DNA duplex (FIG. 4A-4B).

The working examples demonstrate that Cas9 can be used to target single stranded nucleic acids. This is useful for multiple applications, including (but not limited to) in vivo RNA imaging/localization, RNA-protein analysis through the affinity purification of specific RNA molecules via Cas9, and programmable cleavage/degradation of target RNAs in vitro or in vivo.

FIG. 1. Specific single-stranded RNA binding by Cas9 is the absence or presence of a PAM-containing DNA oligonucleotide ('PAMmer'). Binding assays were performed with S. pyogenes Cas9 (complexed with a guide nucleic acid) in the presence of ~1 nM 5'-$^{32}$P-labeled double-stranded DNA, single-stranded RNA or single-stranded RNA in the presence of a DNA oligonucleotide containing a TGG PAM, GG PAM, or no PAM at its 5' end. Cas9 was held constant at 300 nM and the guide nucleic acid was titrated from 0.3 nM to 300 nM. Reactions were resolved on a 5% native polyacrylamide gel containing 5 mM MgCl$_2$ and visualized using a phoshorimager.

FIG. 2A-2B. Specific single-stranded RNA binding by Cas9 is the absence or presence of PAMmers of variable length. (FIG. 2A-2B) Binding assays were performed with S. pyogenes Cas9 (complexed with a guide nucleic acid) in the presence of ~1 nM 5'-$^{32}$P-labeled single-stranded RNA or single-stranded RNA in the presence of PAMmers containing increasing lengths downstream of the TGG sequence. These experiments demonstrate that longer PAMmers lead to higher affinity binding, likely as a consequence of increased stability of the PAMmer:ssRNA hybrid duplex. The PAM itself does not need to base-pair with target RNA for high-affinity binding by Cas9:RNA (bottom gel, right side). Cas9 was held constant at 300 nM and the guide nucleic acid was titrated from 0.01 nM to 300 nM. Reactions were resolved on a 5% native polyacrylamide gel containing 5 mM MgCl$_2$ and visualized using a phoshorimager. The PAM sequence itself within the PAMmer need not be base-paired to the target nucleic acid. Thus, this strategy can be used to target non PAM-containing sites within a target nucleic acid.

FIG. 3. Specific single-stranded RNA cleavage by Cas9 is activated by the addition of a PAMmer having a PAM sequence. Cleavage assays were performed with 100 nM S. pyogenes Cas9 (complexed with a guide nucleic acid) in the presence of ~1 nM 5'-$^{32}$P-labeled double-stranded DNA, single-stranded RNA or single-stranded RNA pre-annealed with a DNA oligonucleotide containing a TGG PAM sequence. Time points were taken at 0, 1, 5, 60 and 120 min and immediately quenched with formamide-EDTA buffer. Quenched samples were resolved on a 12% urea-polyacrylamide gel electrophoresis (PAGE) gel and visualized using a phosphorimager.

FIG. 4A-4B. Specific single-stranded RNA cleavage by Cas9 is activated by the addition of a PAMmer having a PAM sequence, but not by a PAMmer without a PAM sequence. (FIG. 4A-4B) Cleavage assays were performed with 100 nM S. pyogenes Cas9 (complexed with a guide nucleic acid) in the presence of ~1 nM 5'-$^{32}$P-labeled double-stranded DNA, single-stranded RNA or single-stranded RNA pre-annealed with various DNA oligonucleotides. Time points were taken at 0, 1, 2, 5, 10, 30 and 60 min and immediately quenched with formamide-EDTA buffer. Quenched samples were resolved on a 12% urea-PAGE gel and visualized using a phoshoimager. A ssDNA target nucleic acid was not cleaved when an RNA PAMmer was used. However, ssRNA and ssDNA target nucleic acids were both cleaved when a DNA PAMmer was used (also see FIG. 6).

Figure 5A:
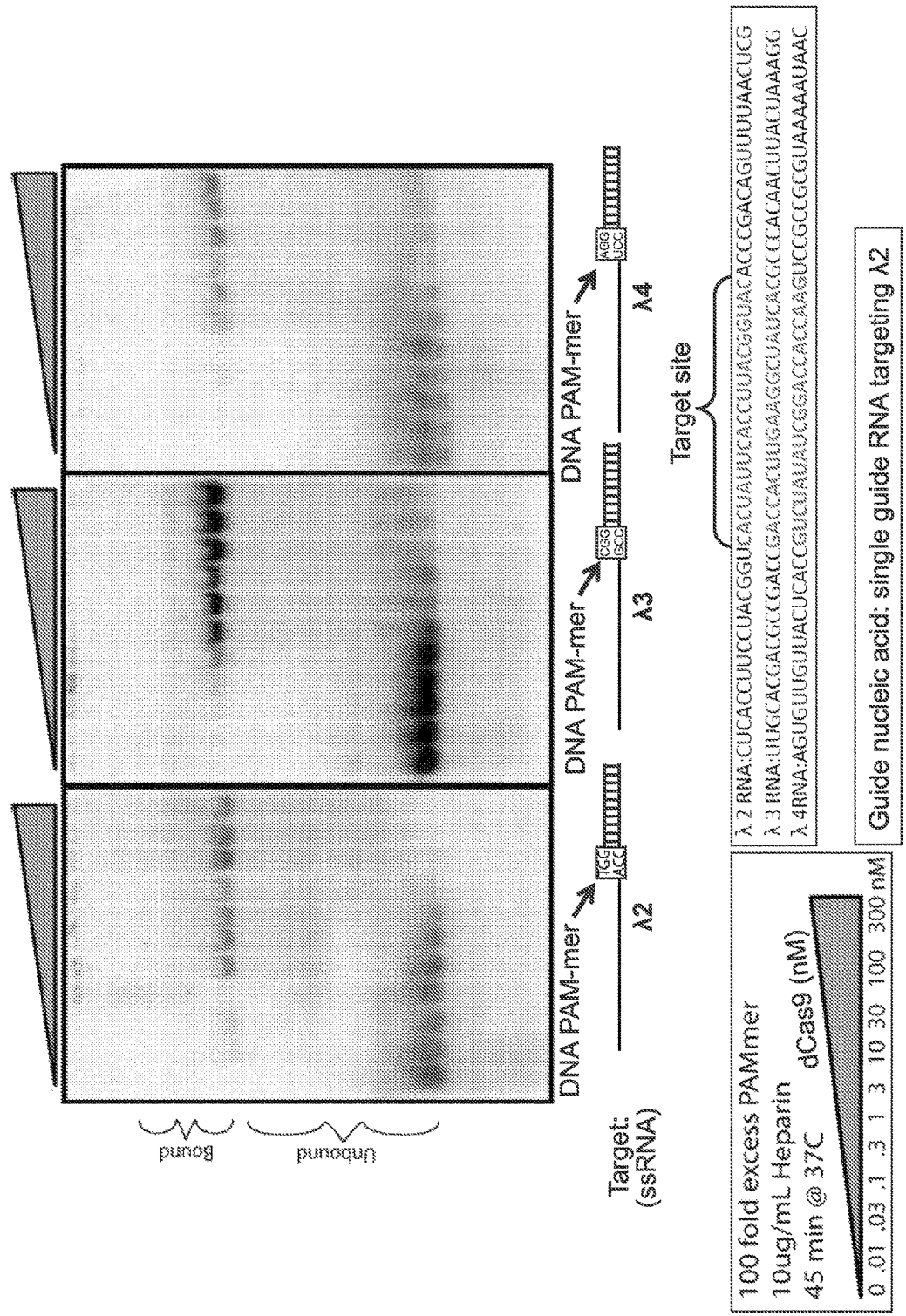
Figure 5B:
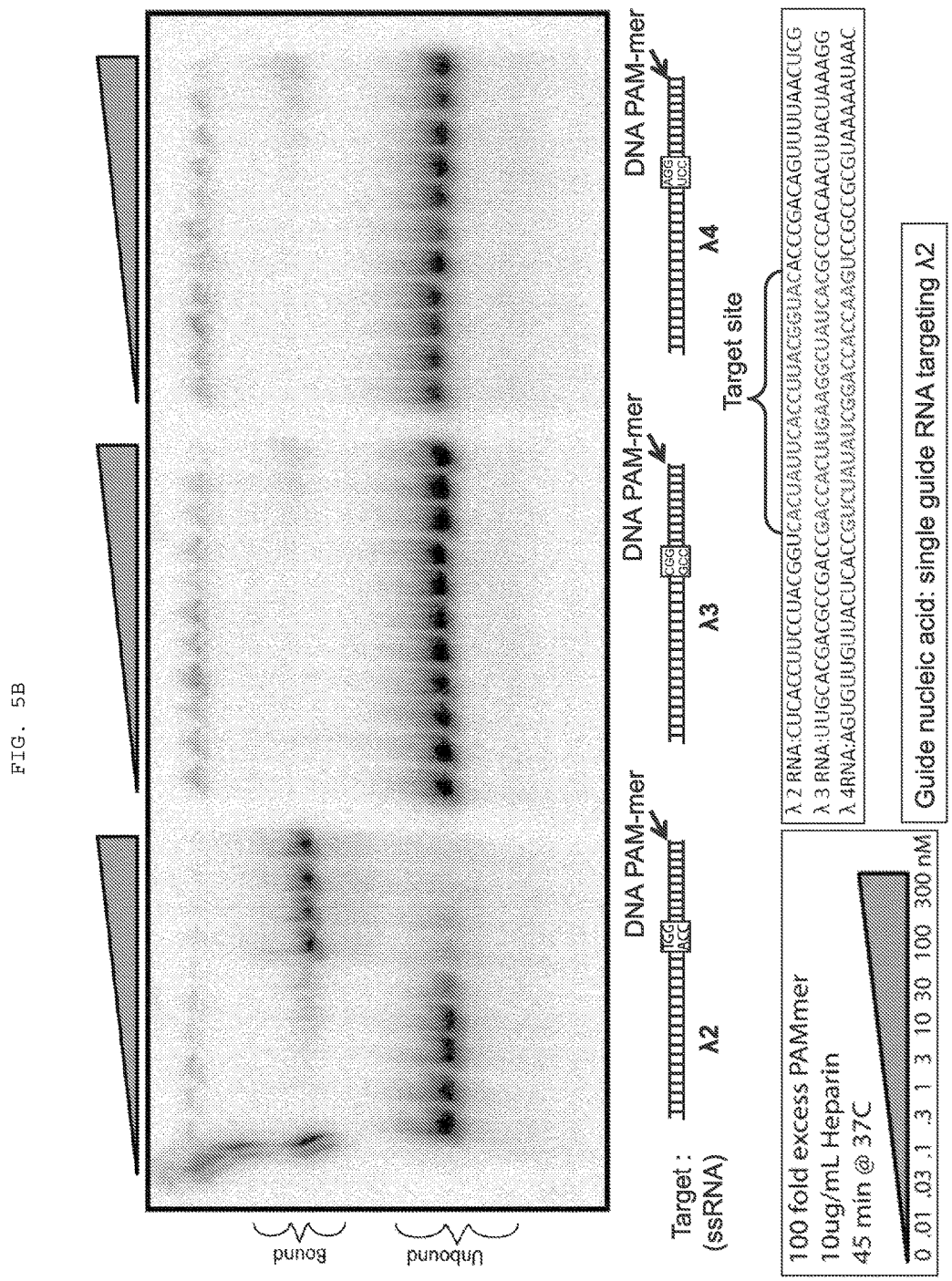

FIG. 5A-5C. (FIG. 5A) Cas9 programmed with guide RNA was incubated with four different target ssRNA sequences; each reaction contained a 100-fold excess of complementary PAMmer (without a specificity segment) specific to each target ssRNA. Cas9 binds each of the targets with similar affinity, despite the fact that the guide RNA is complementary only to the λ2 target. These data indicate that, under these conditions, the affinity of Cas9 for these targets is dominated by presentation of the PAMmer, and not by sequence complementarity between the guide RNA and target RNA. Thus, when the PAMmer does not have a specificity segment (i.e., the PAMmer has a PAM sequence and an orientation segment), the binding of a Cas9 polypeptide:guide nucleic acid complex does not require complementarity between the targeting segment of the guide nucleic acid and the target nucleic acid. (FIG. 5B) The experiment from FIG. 5A was repeated, except that the PAMmers each contained a specificity segment at the 5' end (the specificity segment was positioned 5' of the PAM sequence, as depicted). The target nucleic acids were 55 nucleotide (nt) ssRNA and the PAMmers were each 55 nt (with a 20 nt specificity segment) DNA, such that an RNA:DNA duplex was formed. When Cas9 was complexed with λ2 guide RNA (i.e., the specificity segment of the guide RNA was complementary to the λ2 target ssRNA, but not the λ3 or λ4 targets). Only the λ2 target could be melted open and recognized, presumably via base pairing between guide RNA and target RNA, while the off-targets (λ3 and λ4) were unbound. These experiments demonstrate that when the PAMmer includes a specificity segment, increased specificity for the target nucleic acid can be achieved. Not to be bound by theory, this is presumably because the target duplex (PAMmer bound to the target single stranded nucleic acid) must be unwound before initiating base-pairing to the target ssRNA. Thus, in some instances when the PAMmer has a specificity segment, the binding of a Cas9 polypeptide: guide nucleic acid complex to a single stranded target nucleic acid requires complementarity between the targeting segment of the guide nucleic acid and the target nucleic acid. (FIG. 5C) Cleavage assays were performed with 100 nM S. pyogenes Cas9 (complexed with a guide nucleic acid) in the presence of ~1 nM double-stranded DNA, single-stranded RNA or single-stranded RNA pre-annealed with a PAMmer (a DNA oligonucleotide containing a TGG PAM sequence (as depicted)). Time points were taken at 0, 5, 10, 30, and 60 minutes, at 37° C. and immediately quenched with formamide-EDTA buffer. Quenched samples were resolved on a 12% urea-PAGE gel and visualized using a phosphorimager. These data show that when the PAMmer does not have a specificity segment (i.e., the PAMmer has a PAM sequence and an orientation segment), the cleavage of a single stranded target nucleic acid by a Cas9 polypeptide does require complementarity between the targeting segment of the guide nucleic acid and the target nucleic acid (although binding does not have this requirement, see FIG. 5A).

FIG. 6. Cas9 can be activated by a PAM-containing oligonucleotide in which the TGG PAM sequence is mismatched with the target RNA. Cleavage assays were performed with 100 nM S. pyogenes Cas9 (complexed with a guide nucleic acid) in the presence of −1 nM 5'-$^{32}$P-labeled single-stranded RNA, single-stranded RNA pre-annealed with various DNA oligonucleotides, or single-stranded RNA. Time points were taken at 0, 5, 10, 30 and 60 min and immediately quenched with formamide-EDTA buffer. Quenched samples were resolved on a 12% urea-PAGE gel and visualized using a phoshoimager. The results show that the PAM sequence in the PAMmer need not base-pair with the single stranded target nucleic acid (ssRNA in this case) for nuclease activation, indicating that non-PAM containing nucleic acid sequences can be targeted.

Example 2: Use of Cas9 to Cleave and/or Bind a Single Stranded DNA (ssDNA)

Materials and Methods

Wild-type Cas9 from S. pyogenes was purified. crRNAs (42 nucleotides in length) were either ordered synthetically (Integrated DNA Technologies) or transcribed in vitro with T7 polymerase using single-stranded DNA templates. tracrRNA was also transcribed in vitro and contained nucleotides 15-87 following the numbering scheme used previously. crRNA:tracrRNA duplexes were prepared by mixing equimolar concentrations of each RNA in Hybridization Buffer (20 mM Tris-HCl pH 7.5, 100 mM KCl, 5 mM MgCl$_2$), heating to 95° C. for 30 seconds, and slow-cooling.The substrates were prepared by 5'-radiolabeling only the target strand, hybridizing it to a 10× excess of the indicated unlabeled complementary strand, and gel purifying the partial/full duplex by 10% native gel electrophoresis. Cas9:RNA complexes were reconstituted prior to cleavage and binding experiments by incubating Cas9 and the crRNA:tracrRNA duplex for 10 min at 37° C. in Reaction Buffer. Cleavage assays were conducted in reaction buffer at room temperature and analyzed by 10% denaturing polyacrylamide gel electrophoresis and phosphorimaging. Aliquots were removed at each time point and quenched by the addition of gel loading buffer supplemented with 25 mM EDTA (at 1X). Reactions contained ~1 nM radiolabeled DNA substrate and 100 nM Cas9:RNA Results In the absence of a PAMmer, a ssDNA substrate was cleaved more than two orders of magnitude slower than a double-stranded DNA (dsDNA) substrate (FIG. 7A and FIG.

Figure 7A:
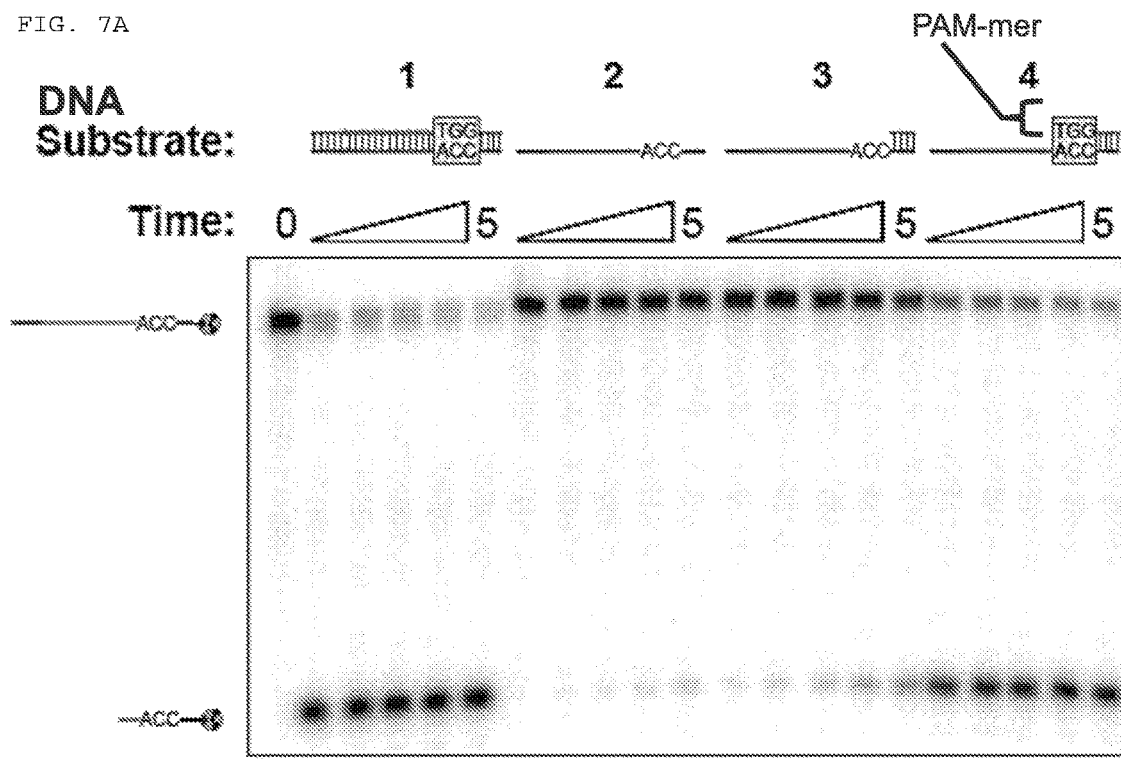
FIG. 7A-7D present assays testing whether Cas9 can cleave and/or bind a single stranded DNA (ssDNA) target nucleic acid when used in combination with a PAMmer.
Figure 7B:
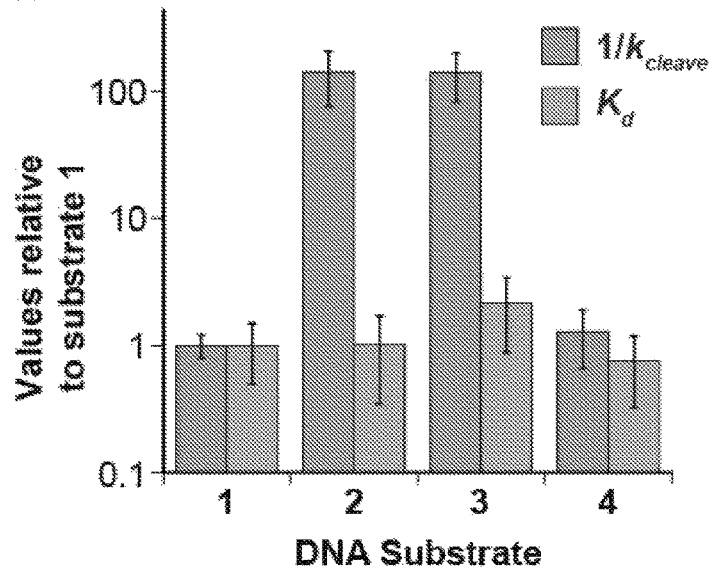
Figure 7C:
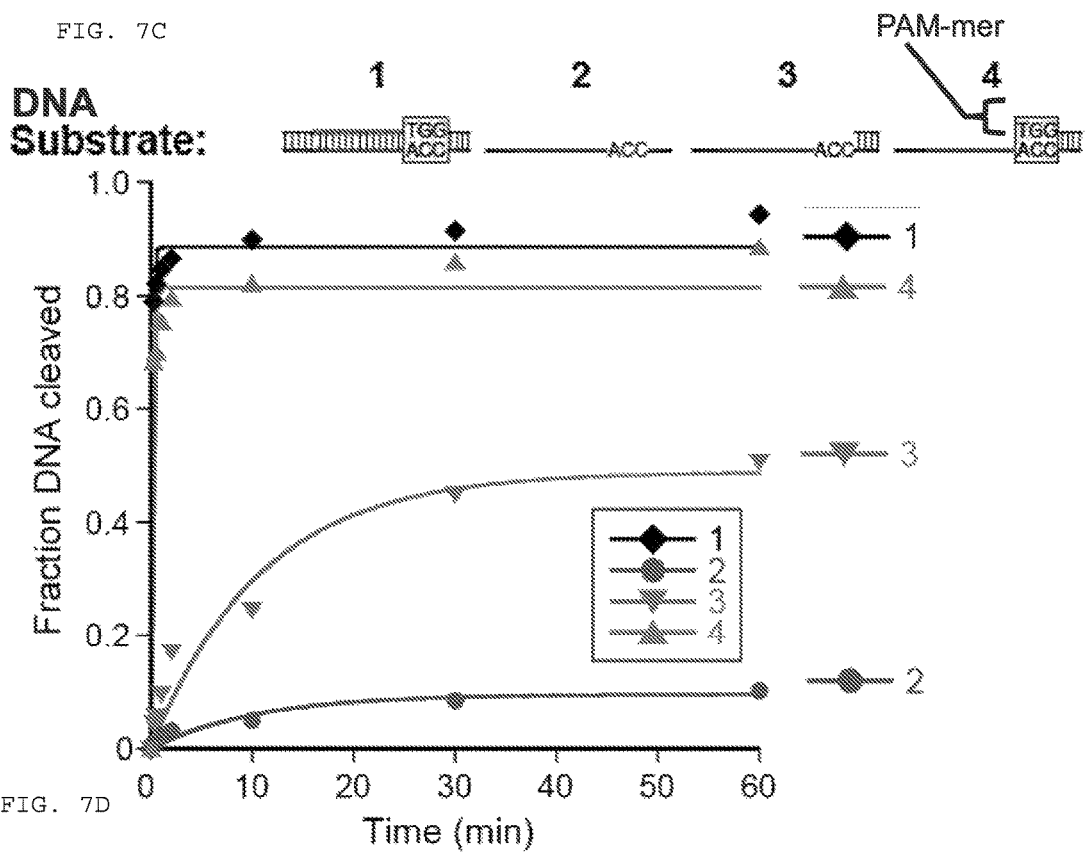
Figure 7D:
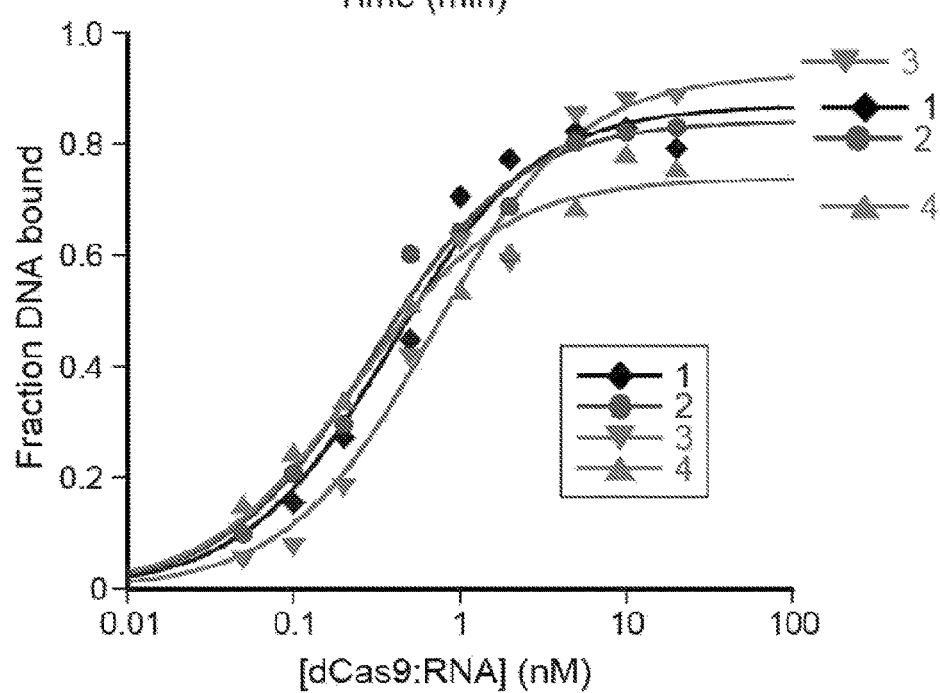

7B), despite the fact that dCas9:RNA (dCas9 complexed with a guide nucleic acid) bound both the dsDNA and ssDNA substrates with similar affinities (FIG. 7B).

Substrates were prepared with varying lengths of dsDNA at the 3' flanking sequence (FIG. 7A). Cleavage assays revealed that the ssDNA target strand could be activated for cleavage in the presence of flanking dsDNA that extended across the PAM sequence (i.e., the presence of a PAMmer), but that this activating effect was lost when the dsDNA was truncated immediately before the PAM sequence (FIG. 7A and FIG. 7B). Binding experiments confirmed these results were not a consequence of discrimination at the level of binding (FIG. 7B). Rather, the presence of the 5'-NGG-3' PAM on the non-target strand was critical for a step of the reaction that occurred after binding. Quantification of cleavage assays can be seen in FIG. 7C. For binding experiments (quantified in FIG. 7D), substrates were gel purified after annealing the radiolabelled target strand to a 10× excess of cold complement. Binding reactions contained ~0.1 nM DNA and increasing concentrations of dCas9-RNA, and were incubated at 37° C. for 1 h before being resolved by 5% native PAGE. The quantified data were fit with standard binding isotherms (solid lines). Results from three independent experiments yielded apparent Kd values of 0.27±0.14 nM (substrate 1), 0.28±0.12 nM (substrate 2), 0.59±0.18 nM (substrate 3) and 0.21±0.06 nM (substrate 4).

Example 3: Variant Cas9 Polypeptides with Reduced Nuclease Activity

Materials and Methods
PAM Recognition by SpyCas9 Involves Two Tryptophan-Containing Flexible Loops To gain insight into PAM sequence binding by *S. pyogenes* Cas9 ("SpyCas9"), the SpyCas9 RuvC nuclease domain structure was compared to to that of the RuvC Holliday junction resolvase-substrate complex (PDB entry 4LD0). RuvC structures were then superpositioned to model the likely trajectory of the non-target DNA strand in the SpyCas9 holoenzyme. The DNA strand is located along the length of the nuclease lobe cleft in an orientation that would position the 3' end of the DNA, and hence the PAM, at the junction of the two lobes, in the vicinity of the Arg-rich segment and the Topo-homology domain.

Figure 16A:
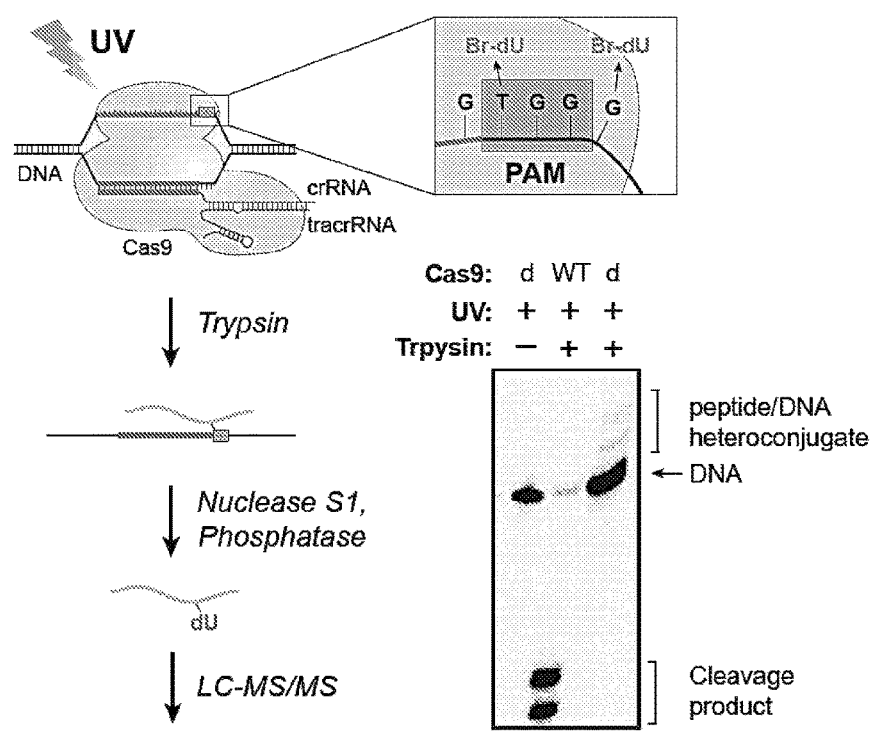

To directly identify regions of Cas9 involved in PAM binding, catalytically inactive SpyCas9 (D10A/H840A), along with a crRNA:tracrRNA guide RNA, was bound to DNA targets carrying a photoactivatable 5-bromodeoxyuridine (Br-dU) nucleotide adjacent to either end of the GG PAM motif on the non-target strand (FIG. 16A). Following UV irradiation and trypsin digestion, covalent peptide-DNA crosslinks were detected (FIG. 16A), whereas a DNA substrate containing Br-dU on the target strand opposite the PAM failed to produce a crosslink After treatment with nuclease and phosphatase to digest cross-linked DNA, nano-HPLC MS/MS was performed to identify tryptic peptides containing an extra mass resulting from covalent dU or p-dU adducts (FIG. 16A). The nucleotide immediately 5' to the GG motif cross-linked to residue W476$^{Spy}$, whereas the residue immediately 3' to the motif cross-linked to residue W1126$^{Spy}$. Both tryptophans are located in disordered regions of the SpyCas9 structure that are ~30 A apart. W476$^{Spy}$ resides in a 53-aa loop at the edge of the alpha helical lobe underneath the Arg-rich region, whereas W1126$^{Spy}$ is in a 33-aa loop that connects the RuvC domain and the Topo-homology domain. These tryptophan residues are conserved among Type II-A Cas9 proteins that utilize the same NGG PAM to cleave target DNA in vitro, but are absent from the *Neisseria meningitidis* and *Streptococcus thermophilus* Type II-C Cas9 proteins, which are known to recognize different PAMs (FIG. 16C, FIG. 16D).

Figure 16B:
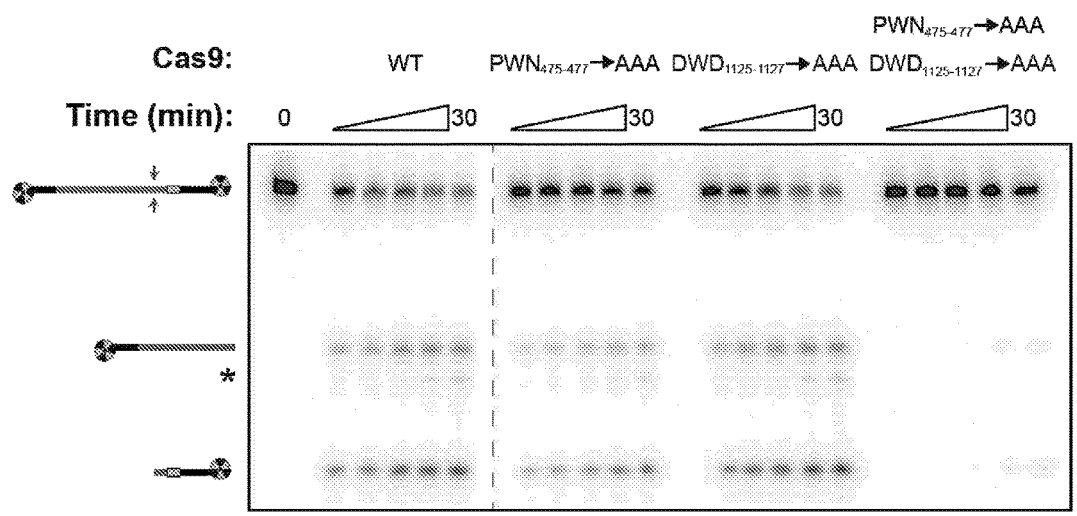
Figure 16C:
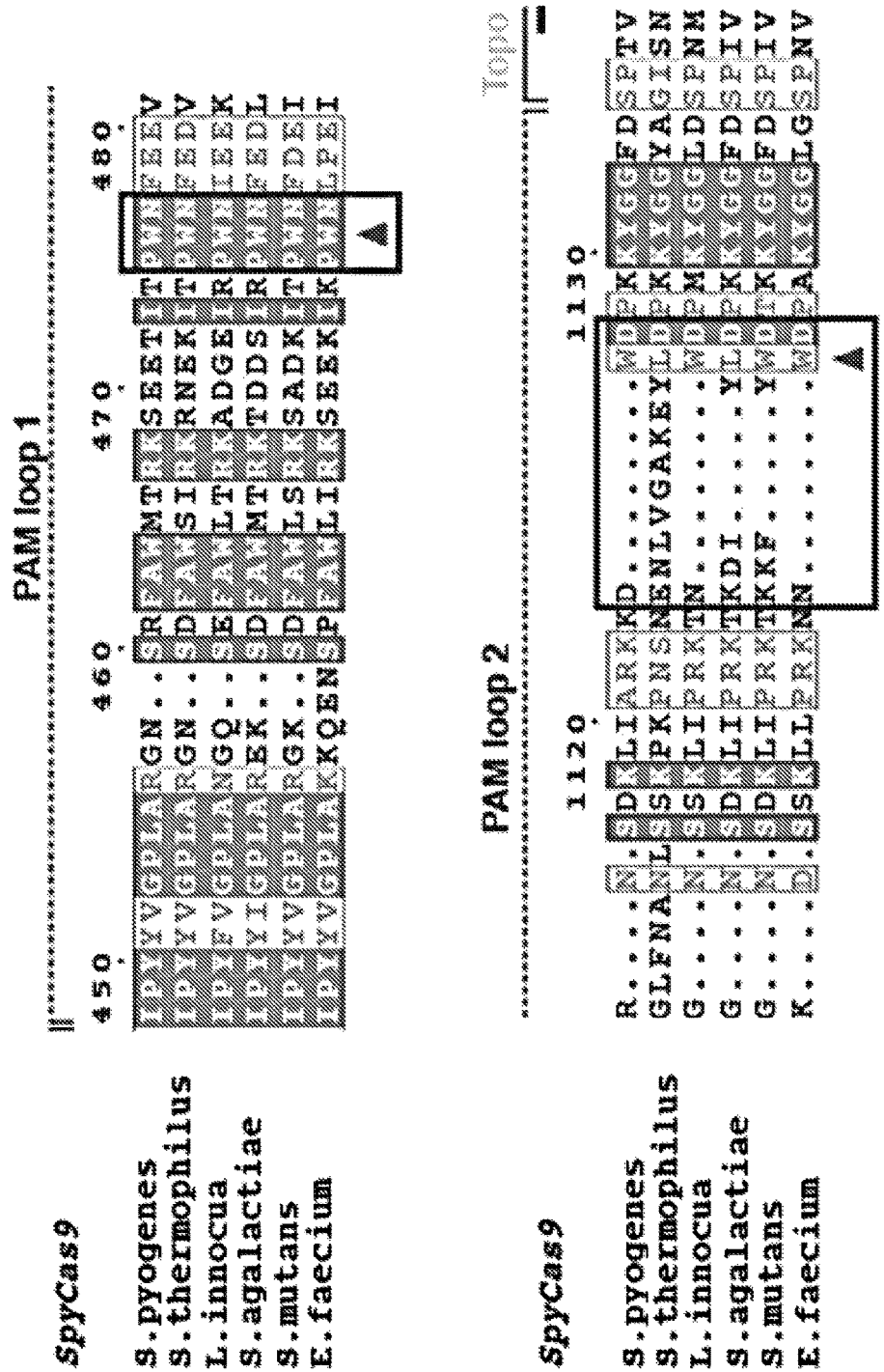

To test the roles of both loops in DNA target recognition and cleavage, triple alanine substitutions of residues 475$^{Spy}$-477$^{Spy}$ (P-W-N) and 1125$^{Spy}$-1127$^{Spy}$ (D-W-D) (of S. *Pyogenes* Cas9) were made and cleavage assays were performed with double-stranded DNA targets (FIG. 16B). SpyCas9 mutated in residues 1125$^{Spy}$-1127$^{Spy}$ showed wild-type cleavage activity, whereas mutations in residues 475$^{Spy}$-477$^{Spy}$ caused a subtle but reproducible decrease of activity compared to wild-type. Remarkably, mutating both loops simultaneously almost completely abolished SpyCas9 activity under the conditions tested (FIG. 16D). These data demonstrate that at least one tryptophan is necessary to promote the DNA cleavage reaction. The spatial constraints of crosslink formation and the distance of both tryptophan residues from either nuclease domain argue against a direct catalytic role of these residues, and instead suggest that they are involved in PAM binding.

FIG. 16A-16D. Crosslinking data identify a PAM binding region adjacent to the active-site cleft. (A) Cartoon (left) showing the design and workflow of crosslinking experiments with DNA substrates containing 5-bromodeoxyuridine (Br-dU) nucleotides for LC-MS/MS analysis. The guide/target sequence is depicted in red and the PAM is highlighted in yellow. The denaturing polyacrylamide gel (right) demonstrates the generation of covalent peptide-DNA adducts with Br-dUI and catalytically inactive Spy-Cas9 (dCas9) following UV irradiation and trypsin digestion. (B) DNA cleavage activity assays with SpyCas9 constructs containing mutations in residues identified by crosslinking and LC-MS/MS experiments. (C) Multiple sequence alignments of selected portions of Cas9 proteins associated with Type II-A CRISPR loci. Primary sequences of Cas9 proteins from *Streptococcus pyogenes* (GI 15675041), *Streptococcus thermophilus* LMD-9 (GI 116628213), *Listeria innocua* Clip 11262 (GI 16801805), *Streptococcus agalactiae* A909 (GI 76788458), *Streptococcus mutans* UA159 (GI 24379809), and *Enterococcus faecium* 1,231,408 (GI 257893735) were aligned using MAFFT. The alignment was generated in ESPript using default settings. Triangles indicate the tryptophan residues involved in PAM binding based on SpyCas9 crosslinking assay. (D) Multiple sequence alignment of selected portions of Type II-A and II-C Cas9 orthologs. The primary sequences of Cas9 orthologs were aligned using CLUST-ALW. The alignment was generated in ESPript using default settings. Triangles indicate the tryptophan residues involved in PAM binding based on SpyCas9 crosslinking assay. Accession numbers for each Cas9 ortholog are as follows: Ana (*Actinomyces naeslundii* str. Howell 279, EJN84392.1), Nme (*Neisseria meningitidis*, WP_019742773.1), Cje (*Campylobacter jejuni*, WP_002876341.1), Tde (*Treponema denticola*, WP_002676671.1), Sth (*Streptococcus thermophilus* LMD-9, YP_820832.1), Smu (*Streptococcus mutans*, WP_019803776.1), Sag (*Streptococcus agalactiae*, WP_001040088.1), and Spy (*Streptococcus pyogenes*, YP_282132.1).

Example 4: Use of PAMmers Having One or More Modified Nucleotides

Figure 17B:
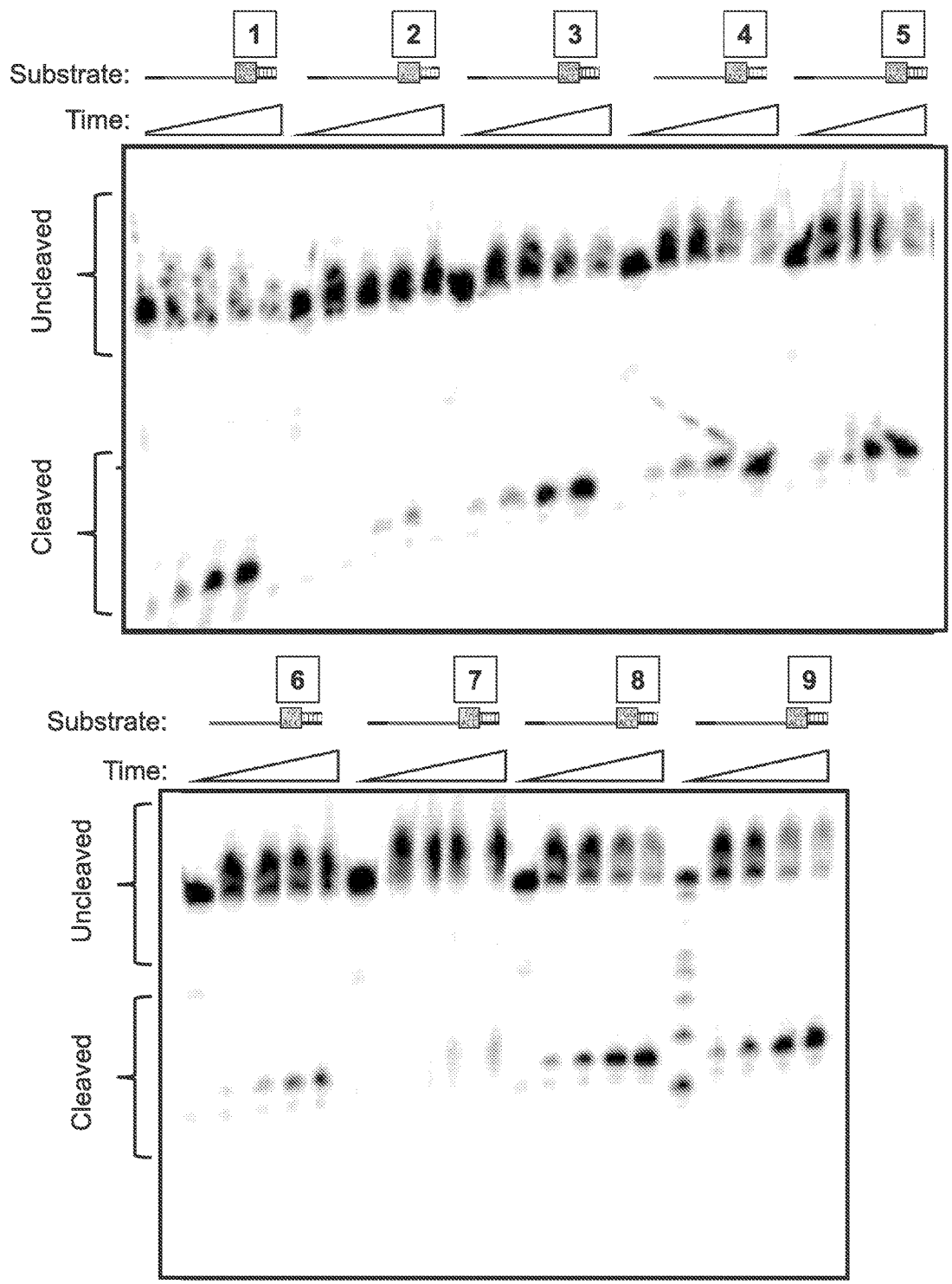

Experiments were carried out as described above for binding and cleaving, and further details are provided in FIG. 17A-17B. The data show that PAMmers having modified nucleotides can be successfuly used in the subject methods, as assayed by both binding assays (FIG. 17A) and cleavage assays (FIG. 17B). The target nucleic acid is a single stranded RNA. For both FIG. 17A and FIG. 17B, the number associated with each panel (lower left in FIG. 17A; above and to the right in FIG. 17B) refers to the PAMmer that was used (see key below). Note: the gel in FIG. 17B has "smiling", but "uncleaved" and "cleaved" substrates are clearly labeled as such.

Legend for FIG. 17A and FIG. 17B

```
(1) ssDNA PAMmer:
                                    (SEQ ID NO: 1466)
TGGGCTGTCAAAATTGAGC;

(2) 2'OMe/ssDNA PAMmer:
                                    (SEQ ID NO: 1545)
mGmGmGmCmUmGmUmCmAmAAATFGAGC,
where mN is 2'OMe modified nucleotide N;

(3) 2'OMe/ssDNA PAMmer:
                                    (SEQ ID NO: 1514)
mUGGGCTGTCAAAATTGAGmC,
where mN is 2'OMe modified nucleotide N;

(4) phosphorothioate ssDNA PAMmer:
                                    (SEQ ID NO: 1546)
G*G*G*C*T*G*T*C*A*AAATTGAGC,
where * is a phosphorothioate linkage;

(5) phosphorothioate ssDNA PAMmer:
                                    (SEQ ID NO: 1547)
T*GGGCTGTCAAAATTGAG*C,
where * is a phosphorothioate linkage;

(6) 2'F/ssDNA PAMmer:
                                    (SEQ ID NO: 1548)
fGfGfGfCfTfGfTfCfAfAAATTGAGC,
where fN is a 2'F modified nucleotide N;

(7) LNA/ssDNA PAMmer:
                                    (SEQ ID NO: 1549)
+G+G+GCTG+T+C+AAAATTGAGC,
where +N is a LNA nucleotide N:

(8) 2'F/ssDNA PAMmer:
                                    (SEQ ID NO: 1550)
fUGGGCTGTCAAAATTGAGfC,
where fN is a 2'F modified nucleotide N; and (9) LNA/ssDNA PAMmer:
                                    (SEQ ID NO: 1551)
+TGGGCTGTCAAAATTGAG+C,
where +N is a LNA nucleotide N.
```

Example 5: Programmable RNA Recognition and Cleavage by CRISPR/Cas9

The CRISPR-associated protein Cas9 is an RNA-guided DNA endonuclease that uses RNA-DNA complementarity to identify target sites for sequence-specific double-stranded DNA (dsDNA) cleavage. In its native context, Cas9 acts on DNA substrates exclusively because both binding and catalysis require recognition of a shortDNAsequence, known as the protospacer adjacent motif (PAM), next to and on the strand opposite the twenty-nucleotide target site in dsDNA. Cas9 has proven to be a versatile tool for genome engineering and gene regulation in a large range of prokaryotic and eukaryotic cell types, and in whole organisms, but it has been thought to be incapable of targeting RNA5. The experiments herein demonstrate that Cas9 binds with high affinity to single-stranded RNA (ssRNA) targets matching the Cas9-associated guide RNA sequence when the PAM is presented in trans as a separate DNA oligonucleotide. Furthermore, PAM-presenting oligonucleotides (PAMmers) stimulate site-specific endonucleolytic cleavage of ssRNA targets, similar to PAM-mediated stimulation of Cas9-catalysed DNA cleavage. Using PAMmers, Cas9 can be specifically directed to bind or cut RNA targets while avoiding corresponding DNA sequences. This strategy enables the isolation of a specific endogenous messenger RNA from cells. These results reveal a fundamental connection between PAM binding and substrate selection by Cas9, and highlight the utility of Cas9 for programmable transcript recognition without the need for tags.

Figure 18A:
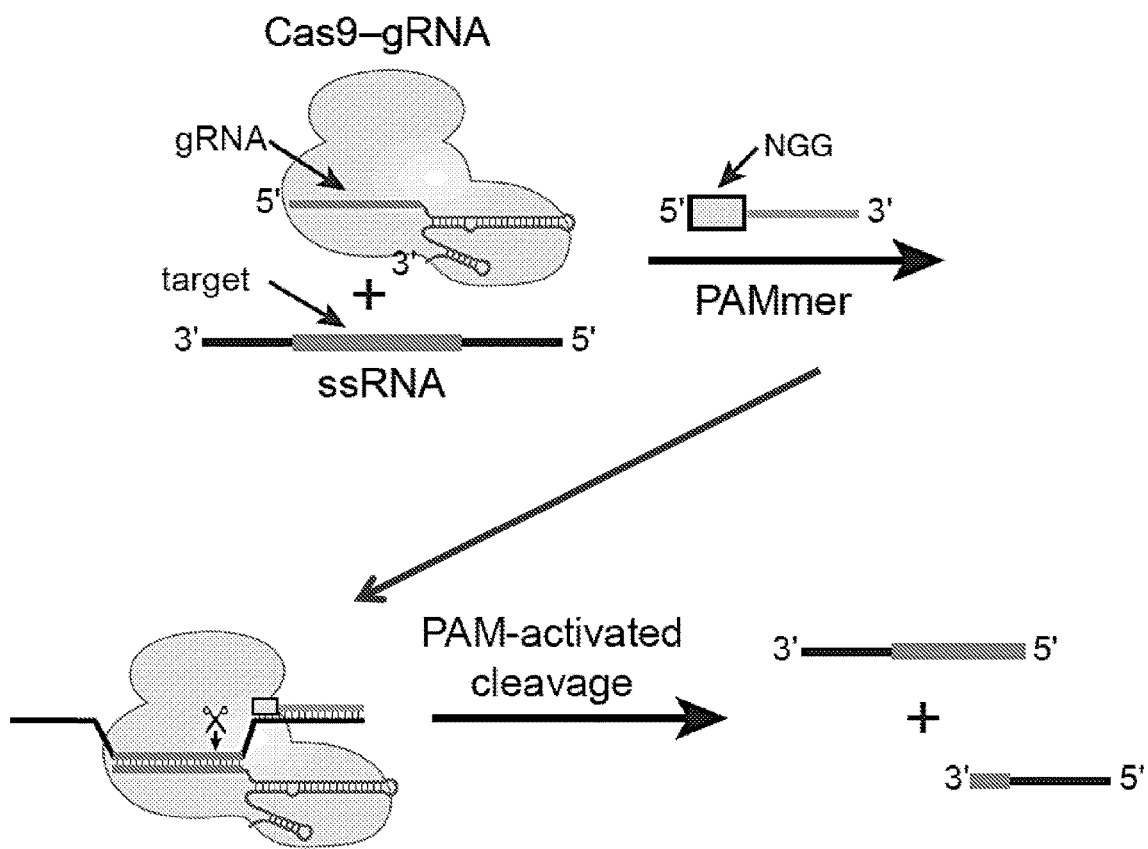

CRISPR-Cas immune systems must discriminate between self and nonself to avoid an autoimmune response. In type I and II systems, foreign DNA targets that contain adjacent PAM sequences are targeted for degradation, whereas potential targets inCRISPR loci of the host do not contain PAMs and are avoided by RNA-guided interference complexes. Single-molecule and bulk biochemical experiments showed that PAMs act both to recruit Cas9-guide-RNA (Cas9-gRNA) complexes to potential target sites and to trigger nuclease domain activation. Cas9 from *Streptococcus pyogenes* recognizes a 5'-NGG-3' PAM on the non-target (displaced) DNA strand, suggesting that PAM recognition may stimulate catalysis through allosteric regulation. Based on the observations that single-stranded DNA (ssDNA) targets can be activated for cleavage by a separate PAMmer, a similar strategy was contemplated for enabling Cas9 to cleave ssRNA targets in a programmable fashion (FIG. 18A). Using *S. pyogenes* Cas9 and dual-guideRNAs (Methods), in vitro cleavage experiments were performed using a panel of RNA and DNA targets (FIG. 18B and Table 2). Deoxyribonucleotide PAMmers specifically activated Cas9 to cleave ssRNA (FIG. 18C), an effect that required a 5'-NGG-3' or 5'-GG-3' PAM. RNA cleavage was not observed using ribonucleotide-based PAMmers, suggesting that Cas9 may recognize the local helical geometry and/or deoxyribose moieties within the PAM. Consistent with this hypothesis, dsRNA targets were not cleavable and RNA-DNA heteroduplexes could only be cleaved when the non-target strand was composed of deoxyribonucleotides. Notably, Cas9 cleaved the ssRNA target strand between positions 4 and 5 of the base-paired gRNA-target-RNA hybrid (FIG. 18D), in contrast to the cleavage between positions 3 and 4 observed for dsDNA. This is probably due to subtle differences in substrate positioning. However, a significant reduction in the pseudo-first-order cleavage rate constant of PAMmer-activated ssRNA as compared to ssDNA was not observed (FIG. 22).

FIG. 18A-18C demonstrates RNA-guided Cas9 cleaving ssRNA targets in the presence of a short PAM presenting DNA oligonucleotide (PAMmer). FIG. 18A, Schematic depicting the approach used to target ssRNA for programmable, sequence-specific cleavage. FIG. 18B, The panel of nucleic acid substrates examined in this study. Substrate elements are coloured as follows: DNA, grey; RNA, black; guide-RNA target sequence, red; DNA PAM, yellow; mutated DNA PAM, blue; RNA PAM, orange. The 18-nucleotide 'GG PAMmer' contains only a GG dinucleotide PAM sequence. nt, nucleotide. FIG. 18C, Representative cleavage assay for 5'-radiolabelled nucleic acid substrates using Cas9-gRNA, numbered as in b. FIG. 18D, Cas9-gRNA cleavage site mapping assay for substrate 3. T1 and OH2 denote RNase T1 and hydrolysis ladders, respectively; the sequence of the target ssRNA is shown at right. Sites of G cleavage by RNase T1 are shown at left. Site of Cas9 cleavage (G24) shown at right. E, Representative ssRNA cleavage assay in the presence of PAMmers of increasing length, numbered as in B.

Figure 22:
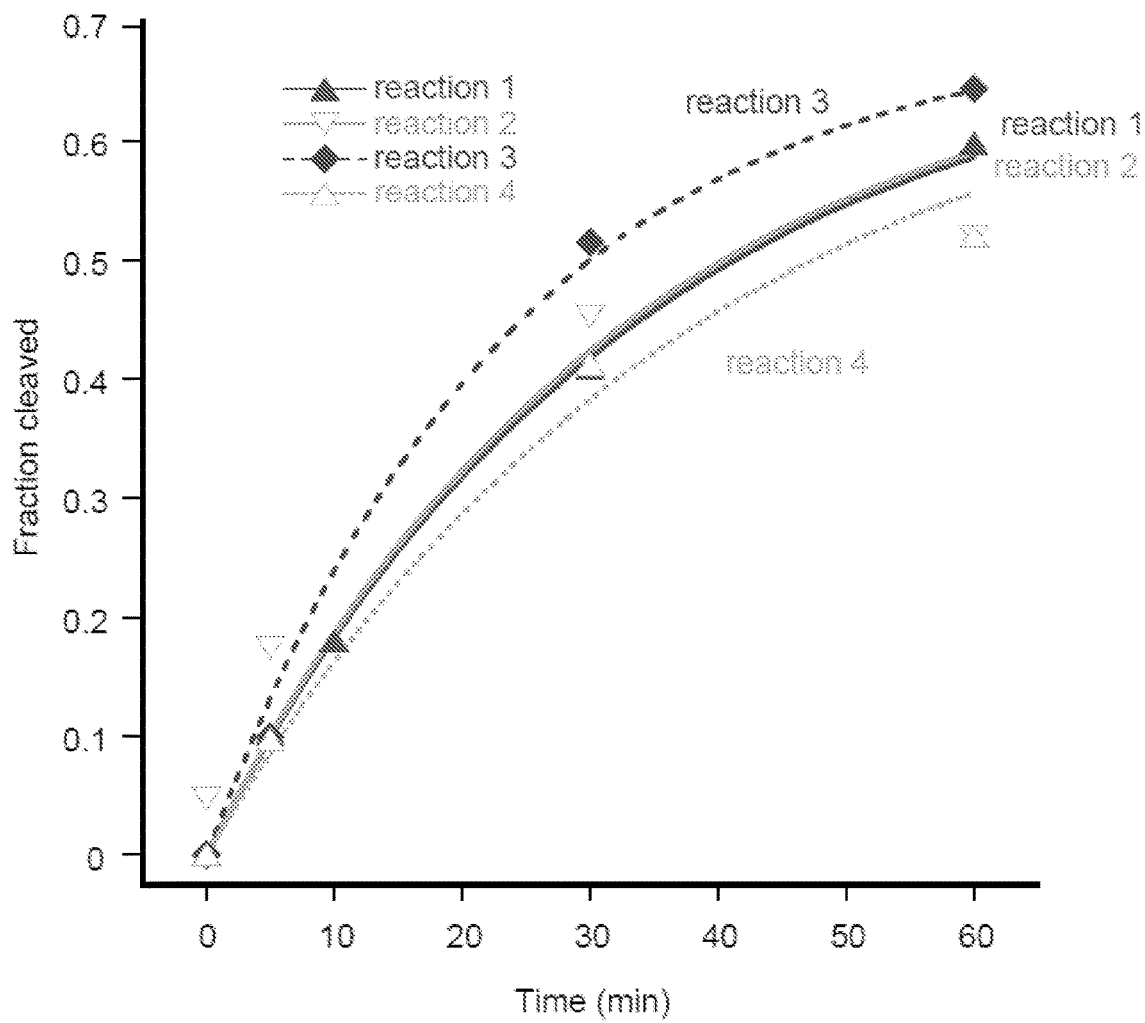
FIG. 22 depicts quantified data for cleavage of ssRNA by Cas9-gRNA in the presence of a 19-nucleotide PAMmer.

FIG. 22 depicts quantified data for cleavage of ssRNA by Cas9-gRNA in the presence of a 19-nucleotide PAMmer. Cleavage assays were conducted as described in the Methods, and the quantified data were fitted with single-exponential decays. Results from four independent experiments yielded an average apparent pseudo-first-order cleavage rate constant (mean±s.d.) of 0.032±0.007 min This is slower than the rate constant determined previously for ssDNA in the presence of the same 19-nucleotide PAMmer (7.3±3.2 min$^{-1}$).

Figure 23:
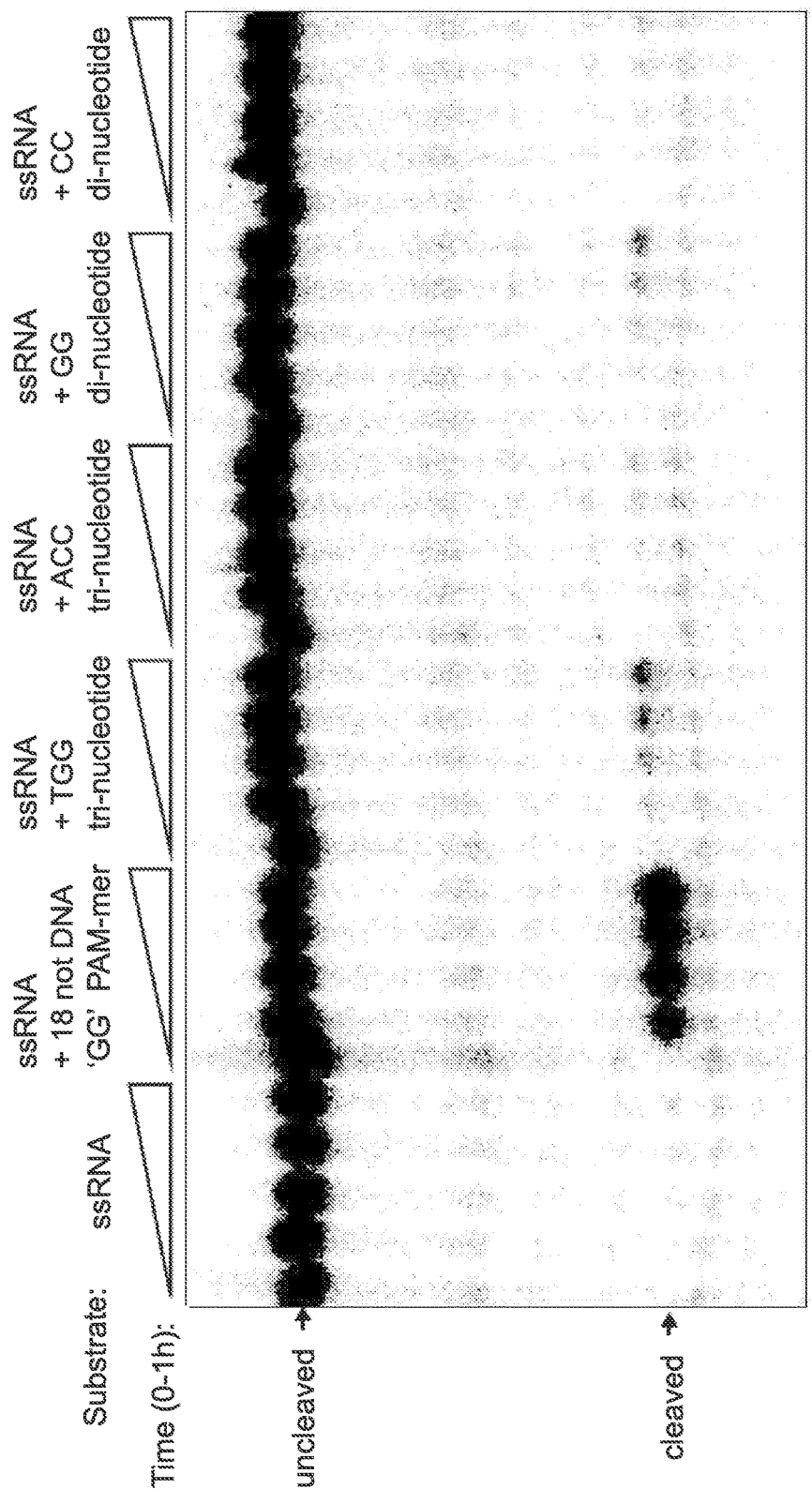
FIG. 23 provides data showing that RNA cleavage is marginally stimulated by di- and tri-deoxyribonucleotides.

By varying PAMmer length, it was next tested whether PAMmer nuclease activation depends on the stability of the hybridized PAMmer-ssRNA duplex. ssRNA cleavage was lost when the predicted melting temperature for the duplex decreased below the temperature used in the experiments (FIG. 18E). In addition, large molar excesses of di- or tri-deoxyribonucleotides in solution were poor activators of Cas9 cleavage (FIG. 23). Collectively, these data demonstrate that hybrid substrate structures composed of ssRNA and deoxyribonucleotide-based PAMmers that anneal upstream of the RNA target sequence can be cleaved efficiently by RNA-guided Cas9.

FIG. 23 demonstrates that RNA cleavage is marginally stimulated by di- and tri-deoxyribonucleotides. Cleavage reactions contained ~1 nM 5'-radiolabelled target ssRNA and no PAMmer (left), 100 nM 18-nt PAMmer (second from left), or 1 mM of the indicated di- or tri-nucleotide (remaining lanes). Reaction products were resolved by 12% denaturing polyacrylamide gel electrophoresis (PAGE) and visualized by phosphorimaging.

Figure 19B:
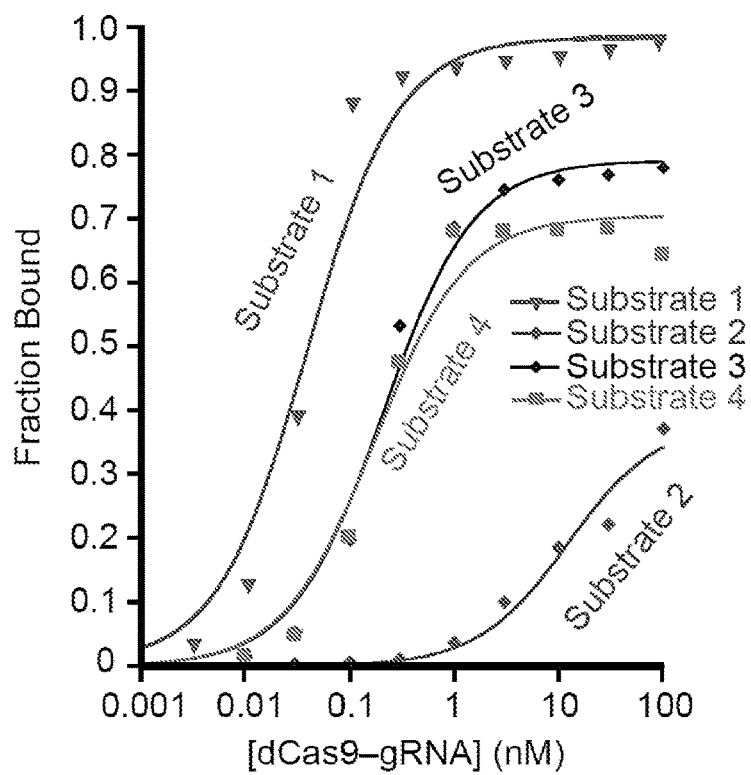

The binding affinity of catalytically inactive dCas9 (Cas9 (D10A;H840A))-gRNA for ssRNA targets with and without PAMmers was then tested using a gel mobility shift assay. Notably, whereas the previous results showed that ssDNA and PAMmer-activated ssDNA targets are bound with indistinguishable affinity, PAMmer-activated ssRNA targets were bound >500-fold tighter than ssRNA alone (FIG. 19A-19B). A recent crystal structure of Cas9 bound to a ssDNA target revealed deoxyribose-specific van der Waals interactions between the protein and the DNA backbone, suggesting that energetic penalties associated with ssRNA binding must be attenuated by favourable compensatory binding interactions with the provided PAM. The equilibrium dissociation constant measured for a PAMmer-ssRNA substrate was within five fold of that for dsDNA (FIG. 19B), and this high-affinity interaction again required a cognate deoxyribonucleotide 5'-GG-3' PAM (FIG. 19A). Tight binding also scaled with PAMmer length (FIG. 19C), consistent with the cleavage data presented above.

Figure 19C:
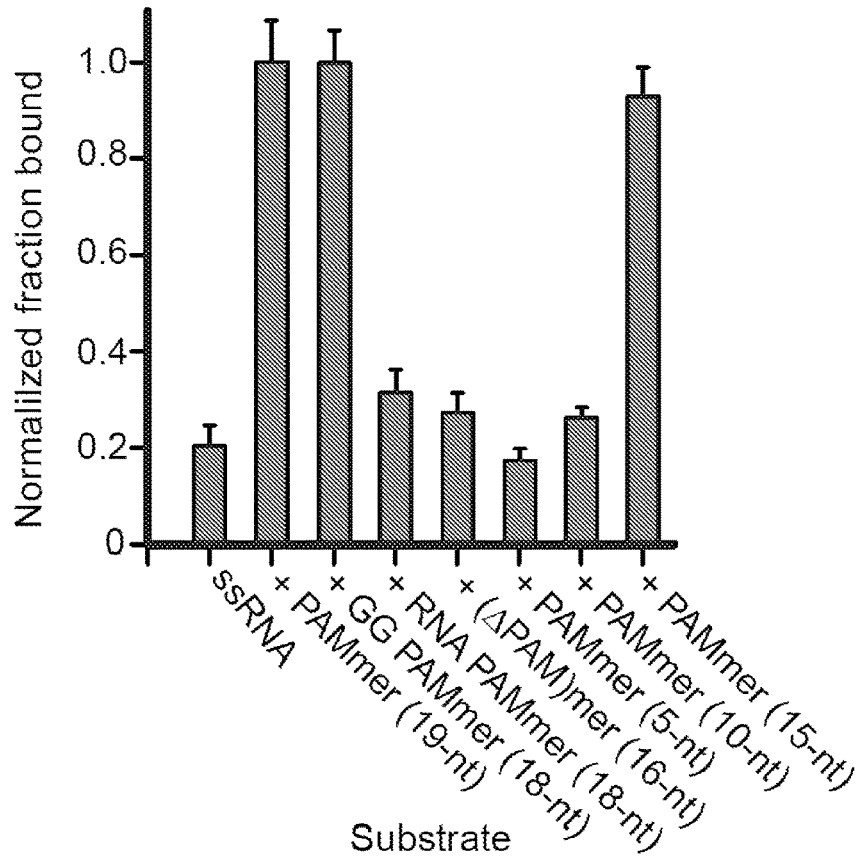

FIG. 19A-19C demonstrates that dCas9-gRNA binds ssRNA targets with high affinity in the presence of PAMmers. FIG. 19A, Representative electrophoretic mobility shift assay for binding reactions with dCas9-gRNA and a panel of 5'-radiolabelled nucleic acid substrates, numbered as in FIG. 18B. FIG. 19B, Quantified binding data for substrates 1-4 from a fitted with standard binding isotherms. Measured dissociation constants from three independent experiments (mean±s.d.) were 0.036±0.003 nM (substrate 1), >100 nM (substrate 2), 0.20±0.09 nM (substrate 3) and 0.18±0.07 nM (substrate 4). c, Relative binding data for 1 nM dCas9-gRNA and 5'-radiolabelled ssRNA with a panel of different PAMmers. The data are normalized to the amount of binding observed at 1 nM dCas9-gRNA with a 19-nucleotide (nt) PAMmer; error bars represent the standard deviation from three independent experiments.

Figure 20A:
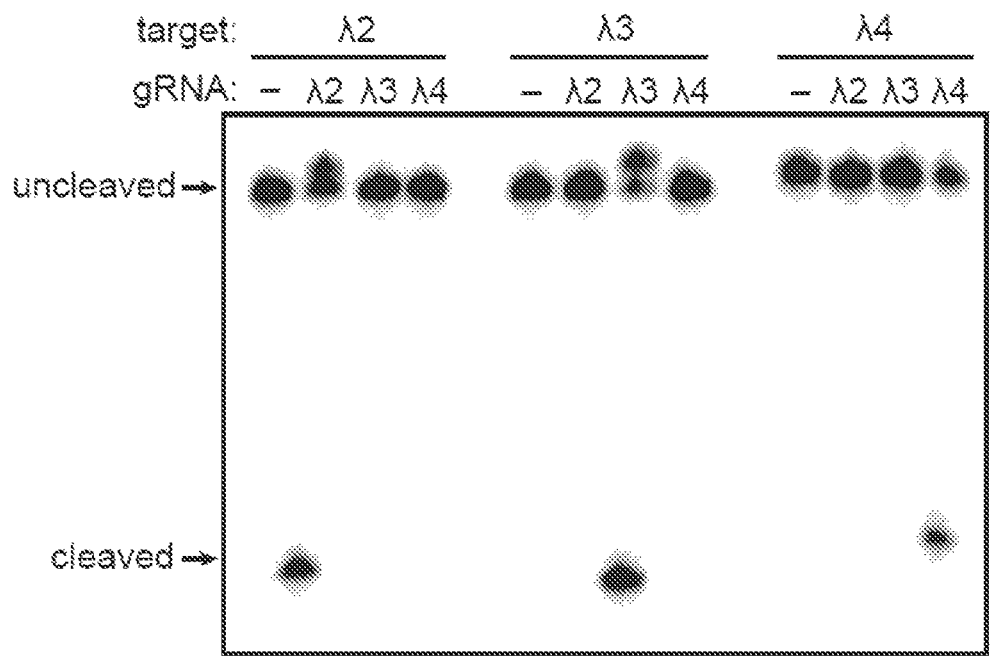
FIG. 20A-20D present assays testing whether 5'-extended PAMmers are required for specific target ssRNA binding.
Figure 20B:
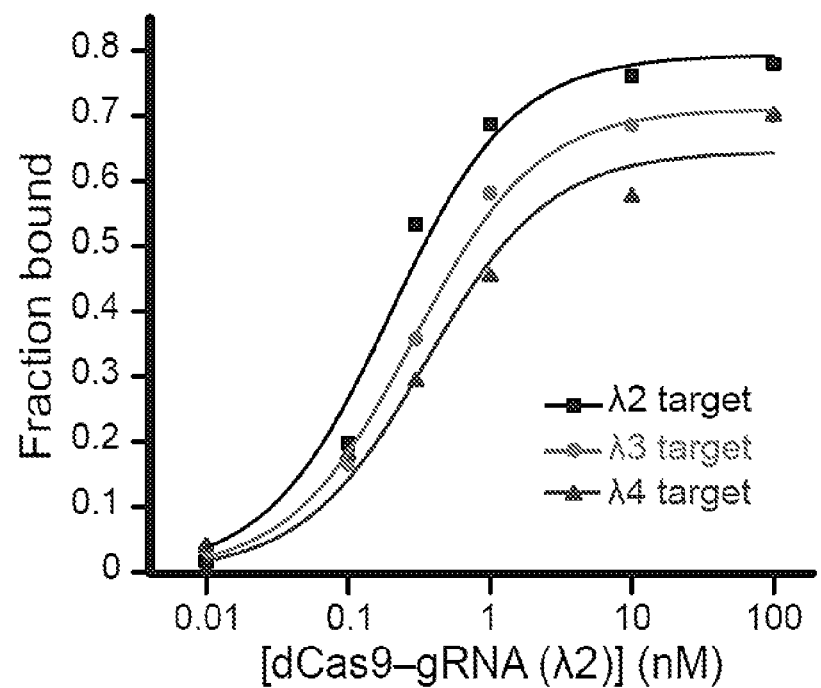

It is known that Cas9 possesses an intrinsic affinity for RNA, but sequence specificity of the interaction had not been explored. Thus, to verify the programmable nature of PAMmer-mediated ssRNA cleavage by Cas9-gRNA, three distinct guideRNAs ($\lambda 2$, $\lambda 3$, and $\lambda 4$; each targeting 20-nucleotide sequences within $\lambda 2$, $\lambda 3$, and $\lambda 4$ RNAs, respectively) were prepared and their corresponding ssRNA targets were efficiently cleaved using complementary PAMmers without any detectable cross-reactivity (FIG. 20A). This result indicates that complementary RNA-RNA base pairing is critical in these reactions. Notably however, dCas9 programmed with the $\lambda 2$ guide RNA bound all three PAMmer-ssRNA substrates with similar affinity (FIG. 20B). This observation suggests that high-affinity binding in this case may not require correct base pairing between the guide RNA and the ssRNA target, particularly given the compensatory role of the PAMmer.

Figure 20C:
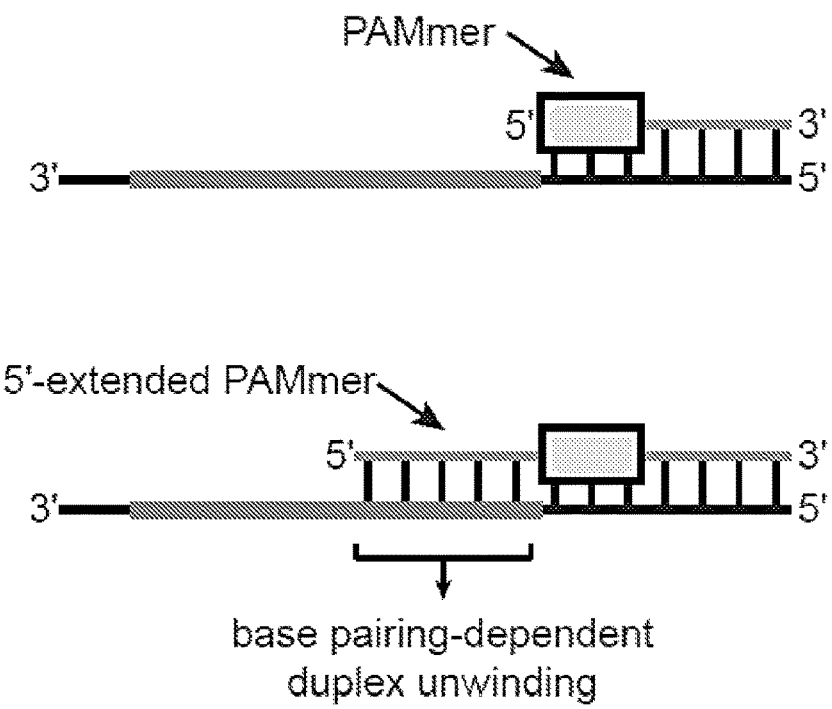
Figure 20D:
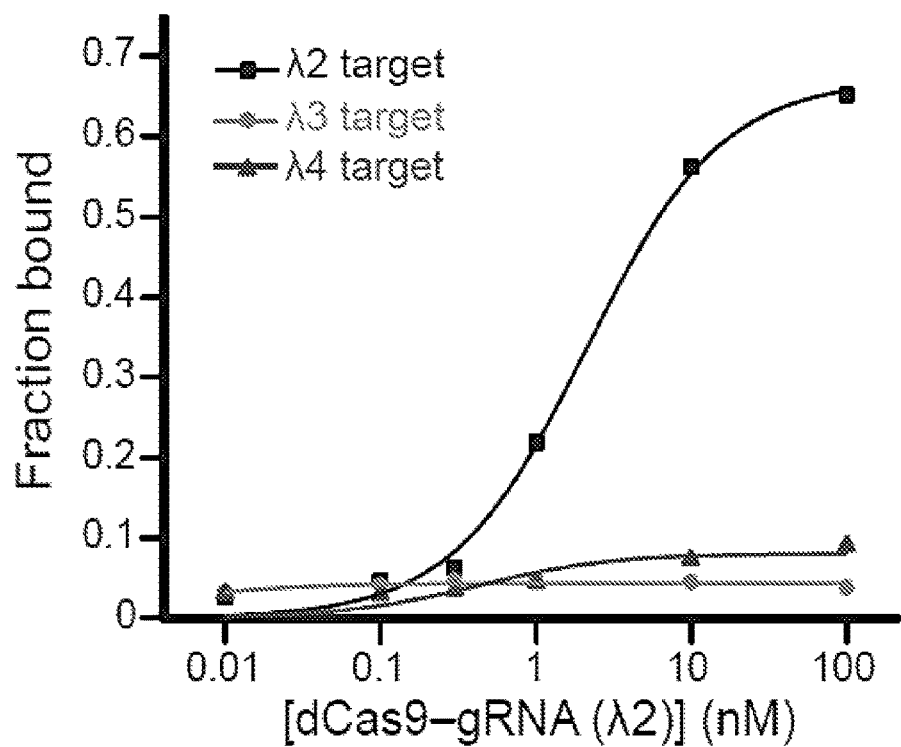

FIG. 20A-20D shows that 5'-extended PAMmers are required for specific target ssRNA binding. FIG. 20A, Cas9 programmed with either $\lambda 2$-, $\lambda 3$- or $\lambda 4$-targeting gRNAs exhibits sequence-specific cleavage of 5'-radiolabelled $\lambda 2$, $\lambda 3$, and $\lambda 4$ target ssRNAs, respectively, in the presence of cognate PAMmers. FIG. 20B, dCas9 programmed with a $\lambda 2$-targeting gRNA exhibits similar binding affinity to $\lambda 2$, $\lambda 3$, and $\lambda 4$ target ssRNAs in the presence of cognate PAMmers. Dissociation constants from three independent experiments (mean±s.d.) were 0.20±0.09 nM ($\lambda 2$), 0.33±0.14 nM ($\lambda 3$) and 0.53±0.21 nM ($\lambda 4$). FIG. 20C, Schematic depicting the approach used to restore gRNA-mediated ssRNA binding specificity, which involves 5'-extensions to the PAMmer that cover part or all of the target sequence. FIG. 20D, dCas9 programmed with a $\lambda 2$-targeting gRNA specifically binds the ssRNA but not and $\lambda 4$ ssRNAs in the presence of complete 5'-extended PAMmers. Dissociation constants from three independent experiments (mean±s.d.) were 3.3±1.2 nM ($\lambda 2$) and 0.100 nM ($\lambda 3$ and $\lambda 4$).

During dsDNA targeting by Cas9-gRNA, duplex melting proceeds directionally from the PAM and requires the formation of complementary RNA-DNA base pairs to offset the energetic costs associated with dsDNA unwinding. It was therefore tested whether binding specificity for ssRNA substrates would be recovered using PAMmers containing 5'-extensions that create a partially double-stranded target region requiring unwinding (FIG. 20C).Use of a 5'-extended PAMmer enabled dCas9 bearing the $\lambda 2$ guide sequence to bind sequence selectively to the PAMmer-ssRNA target. The $\lambda 3$ and $\lambda 4$ PAMmer-ssRNA targets were not recognized (FIG. 20D and FIG. 24), although a tenfold reduction in overall ssRNA substrate binding affinity was observed. By systematically varying the length of the 5' extension, it was found that PAMmers containing 2-8 additional nucleotides upstream of the 5'-NGG-3' offer a good compromise between gains in binding specificity and concomitant losses in binding affinity and cleavage efficiency (FIG. 25A-25B).

FIG. 24 depicts a representative binding experiment demonstrating guide-specific ssRNA binding with 5'-extended PAMmers. Gel shift assays were conducted as described in the Methods section below. Binding reactions contained Cas9 programmed with $\lambda 2$ gRNA and either (on-target), (off-target) or (off-target) ssRNA in the presence of short cognate PAMmers or cognate PAMmers with complete 5'-extensions, as indicated. The presence of a cognate 5'-extended PAMmer abrogated off-target binding. Three independent experiments were conducted to produce the data shown in FIG. 20B, 20D.

Figure 25B:
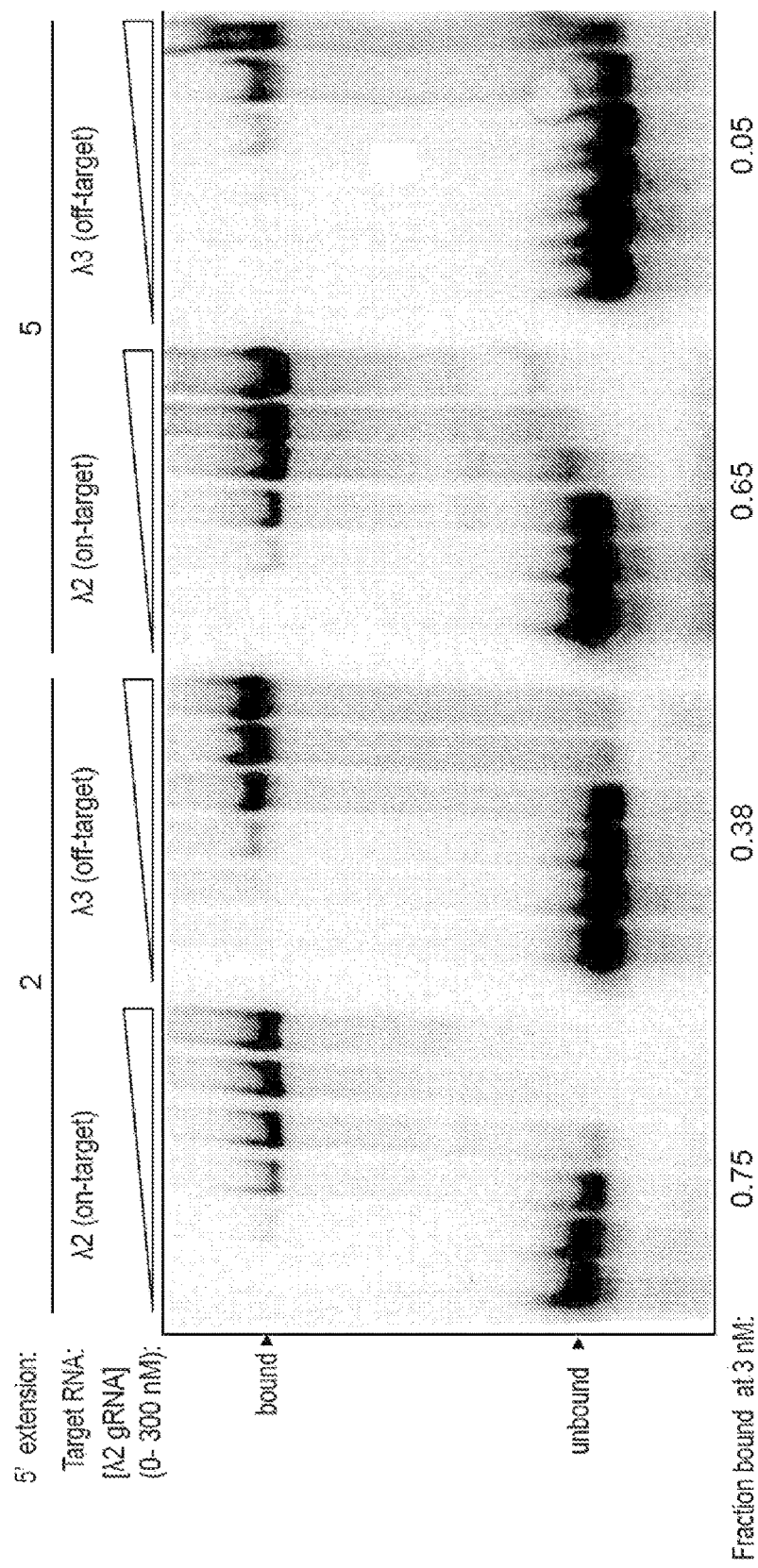
Figure 25B:
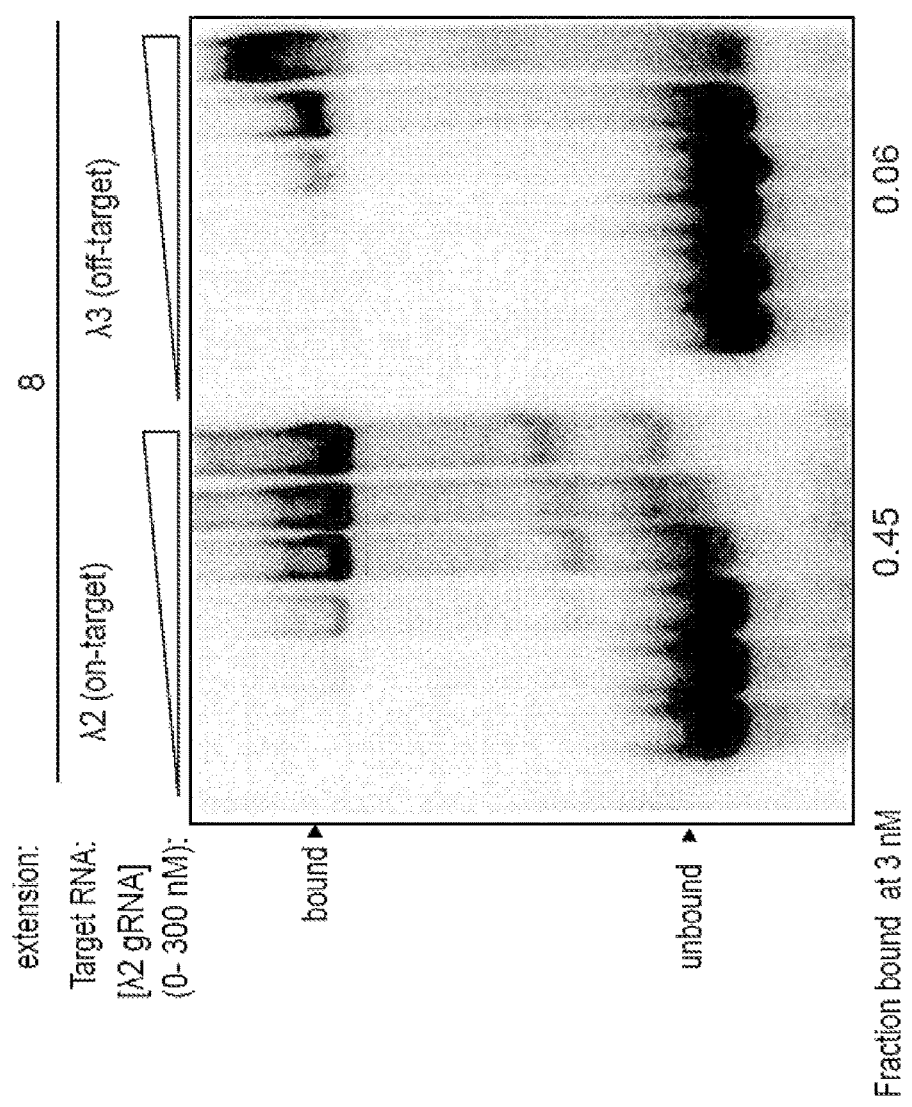
Figure 25B:
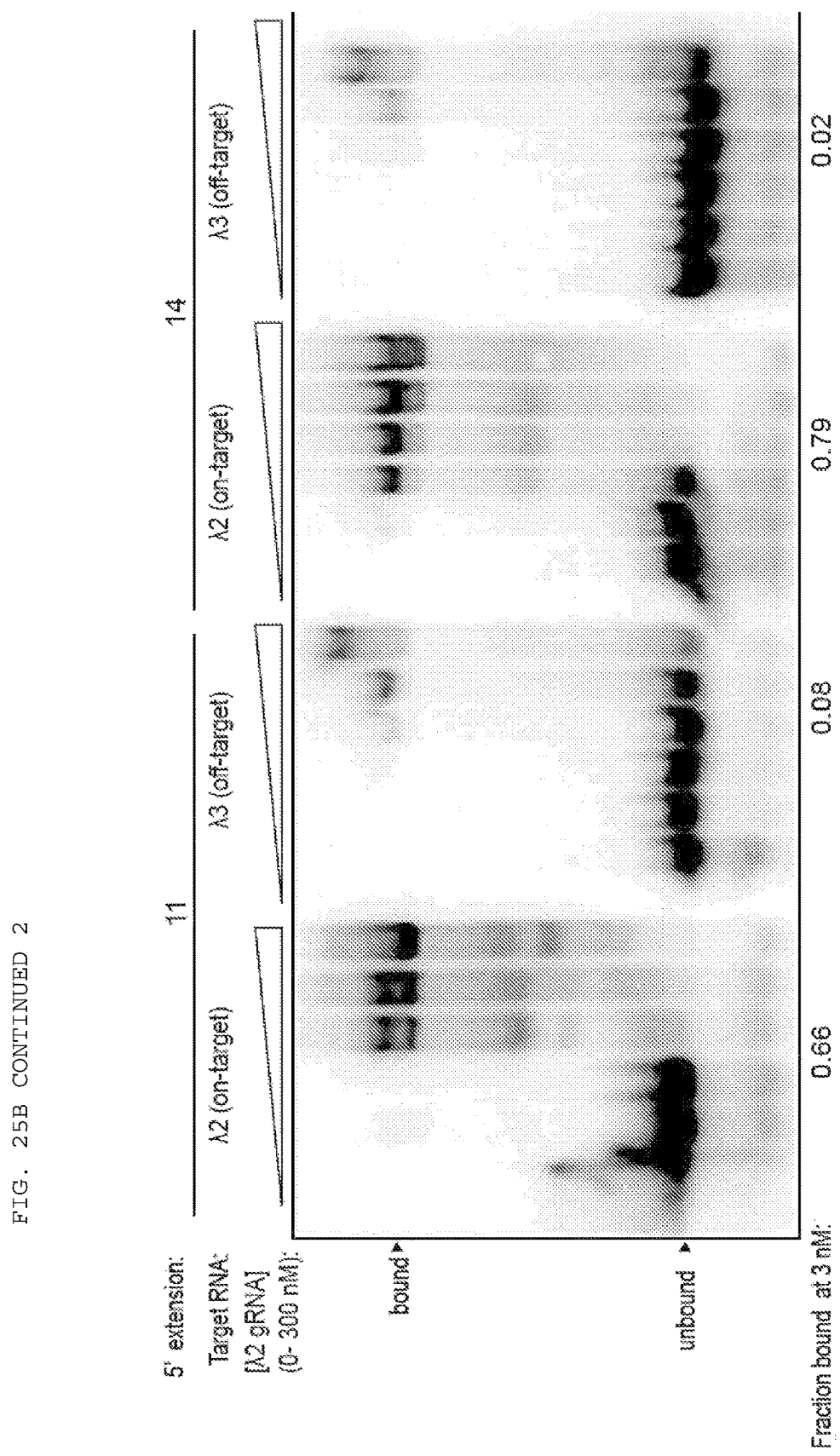
Figure 25B:
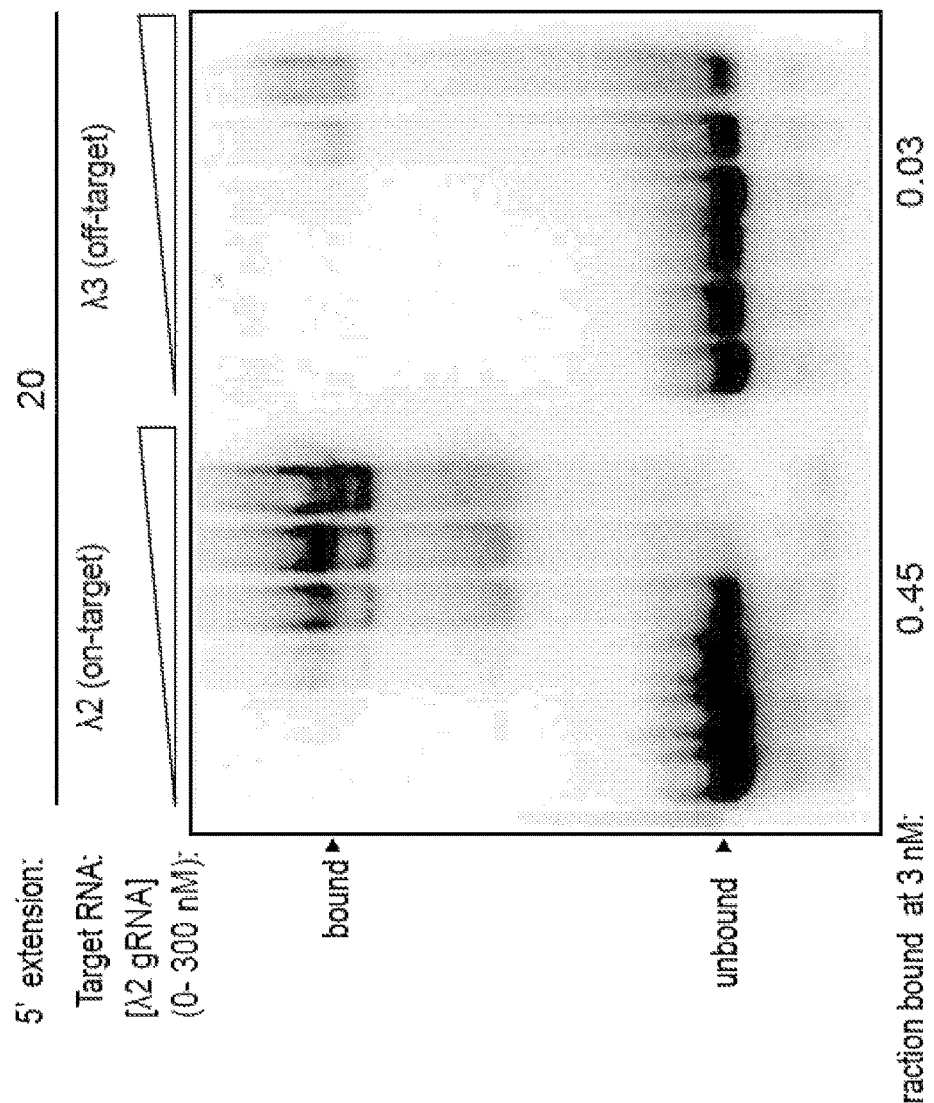

FIG. 25A-25B depicts exploration of RNA cleavage efficiencies and binding specificity using PAMmers with variable 5'-extensions. FIG. 25A, Cleavage assays were conducted as described in the methods section below. Reactions contained Cas9 programmed with λ2 gRNA and λ2 ssRNA targets in the presence of PAMmers with 5'-extensions of variable length. The ssRNA cleavage efficiency decreased as the PAMmer extended further into the target region, as indicated by the fraction of RNA cleaved after 1 h. FIG. 25B, Binding assays were conducted as described in the Methods section below, using mostly the same panel of 5'-extended PAMmers as in a. Binding reactions contained Cas9 programmed with λ2 gRNA and either (on-target) or λ3 (off-target) ssRNA in the presence of cognate PAMmers with 5'-extensions of variable length. The binding specificity increased as the PAMmer extends further into the target region, as indicated by the fraction of 3 (off-target) ssRNA bound at 3 nM Cas9-gRNA. PAMmers with 5' extensions also caused a slight reduction in the relative binding affinity of (on-target) ssRNA.

Figure 21A:
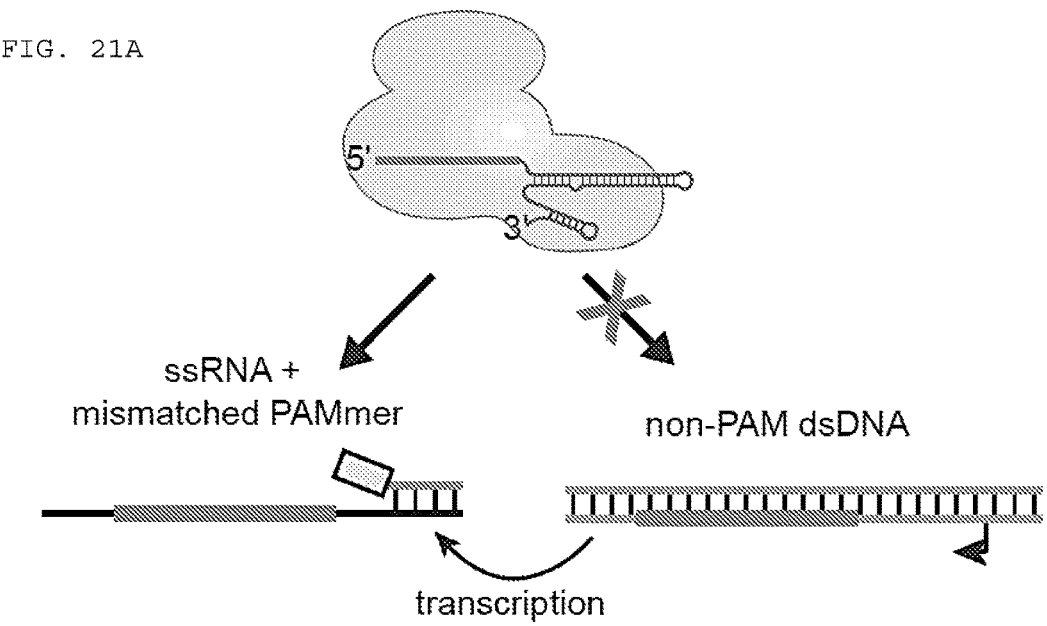
Figure 21B:
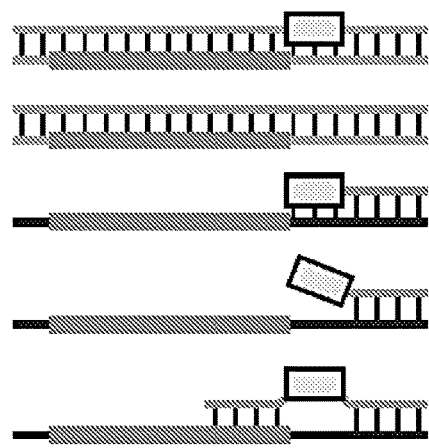
Figure 21C:
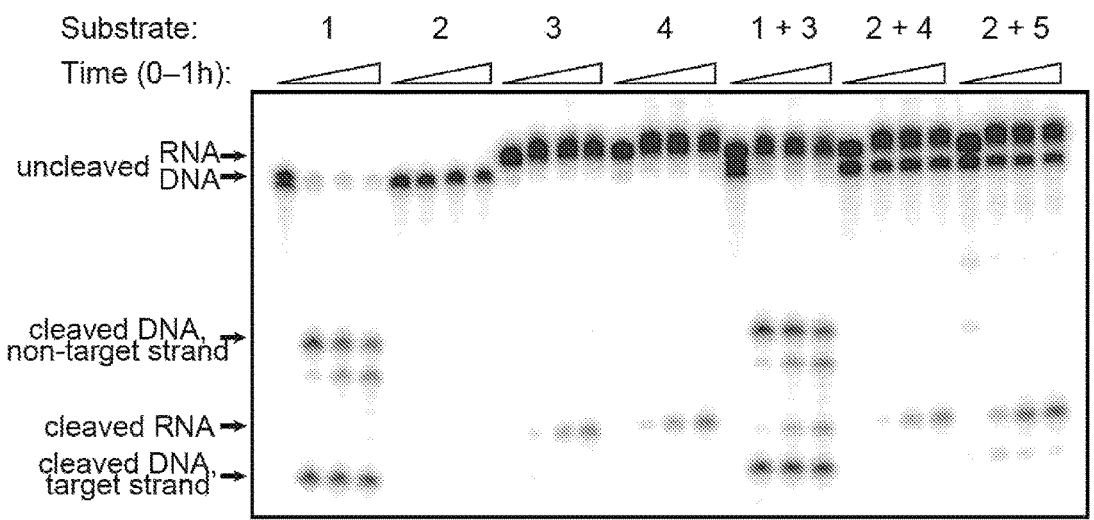

It was next investigated whether nuclease activation by PAMmers requires base pairing between the 5'-NGG-3' and corresponding nucleotides on the ssRNA. Prior studies have shown that DNA substrates containing a cognate PAM that is mismatched with the corresponding nucleotides on the target strand are cleaved as efficiently as a fully base-paired PAM. This could enable targeting of RNA while precluding binding or cleavage of corresponding genomic DNA sites lacking PAMs (FIG. 21A). To test this possibility, it was first demonstrated that Cas9-gRNA cleaves PAMmer-ssRNA substrates regardless of whether the PAM is base paired (FIG. 21B-21C). When Cas9-RNA was incubated with both a PAMmer-ssRNA substrate and the corresponding dsDNA template containing a cognate PAM, both targets were cleaved. In contrast, when a dsDNA target lacking a PAM was incubated together with aPAMmer-ssRNA substrate bearing a mismatched 5'-NGG-3' PAM, Cas9-gRNA selectively targeted the ssRNA for cleavage (FIG. 21C). The same result was obtained using a mismatched PAMmer with a 5' extension (FIG. 21C), demonstrating that this general strategy enables the specific targeting of RNA transcripts while effectively eliminating any targeting of their corresponding dsDNA template loci.

Figure 21D:
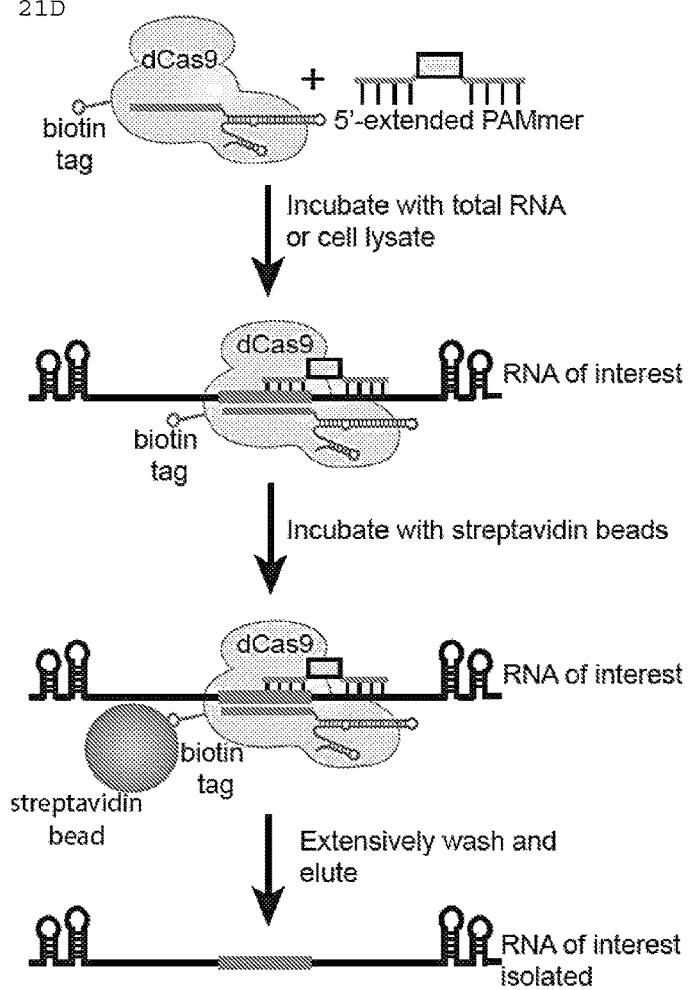

It was next tested whether Cas9-mediated RNA targeting could be applied in tagless transcript isolation from HeLa cells (FIG. 21D). The immobilization of Cas9 on a solid-phase resin is described in the Methods section below (see also FIG. 26). As a proof of concept, GAPDH mRNA was first isolated from HeLa total RNA using biotinylated dCas9, gRNAs and PAMmers (Table 2) that target four non-PAM-adjacent sequences within exons 5-7 (FIG. 21E). A substantial enrichment of GAPDH mRNA relative to control b-actin mRNA was observed by northern blot analysis, but no enrichment using a non-targeting gRNA or dCas9 alone was observed (FIG. 21F).

FIG. 21 shows that RNA-guided Cas9 can target non-PAM sites on ssRNA and can be used to isolate GAPDH mRNA from HeLa cells in a tagless manner FIG. 21A, Schematic of the approach designed to avoid cleavage of template DNA by targeting non-PAM sites in the ssRNA target. FIG. 21B, The panel of nucleic acid substrates tested in c. FIG. 21C, Cas9-gRNA cleaved ssRNA targets with equal efficiency when the 5'-NGG-3' of the PAMmer was mismatched with the ssRNA. This strategy enables selective cleavage of ssRNA in the presence of non-PAM target dsDNA. FIG. 21D, Schematic of the dCas9 RNA pull-down experiment. FIG. 21E, GAPDH mRNA transcript isoform 3 (GAPDH-003) shown schematically, with exons common to all GAPDH protein-coding transcripts in red and gRNA/PAMmer targets G1-G4 indicated. kb, kilobase pairs. FIG. 21F, Northern blot showing that gRNAs and corresponding 5'-extended PAMmers enabled tagless isolation of GAPDH mRNA from HeLa total RNA; b-actin mRNA is shown as a control. FIG. 21G, Northern blot showing tagless isolation of GAPDH mRNA from HeLa cell lysate with varying 2'-OMe-modified PAMmers. RNase H cleavage is abrogated with v4 and v5 PAMmers; b-actin mRNA is shown as a control. u, unmodified PAMmer (G1). v1-v5, increasingly 2'-OMe-modified PAMmers (G1), see g for PAMmer sequences. FIG. 21H, Sequences of unmodified and modified GAPDH PAMmers used in g; 2'-OMe-modified nucleotides are shown in red.

Figures 26B, 26C:
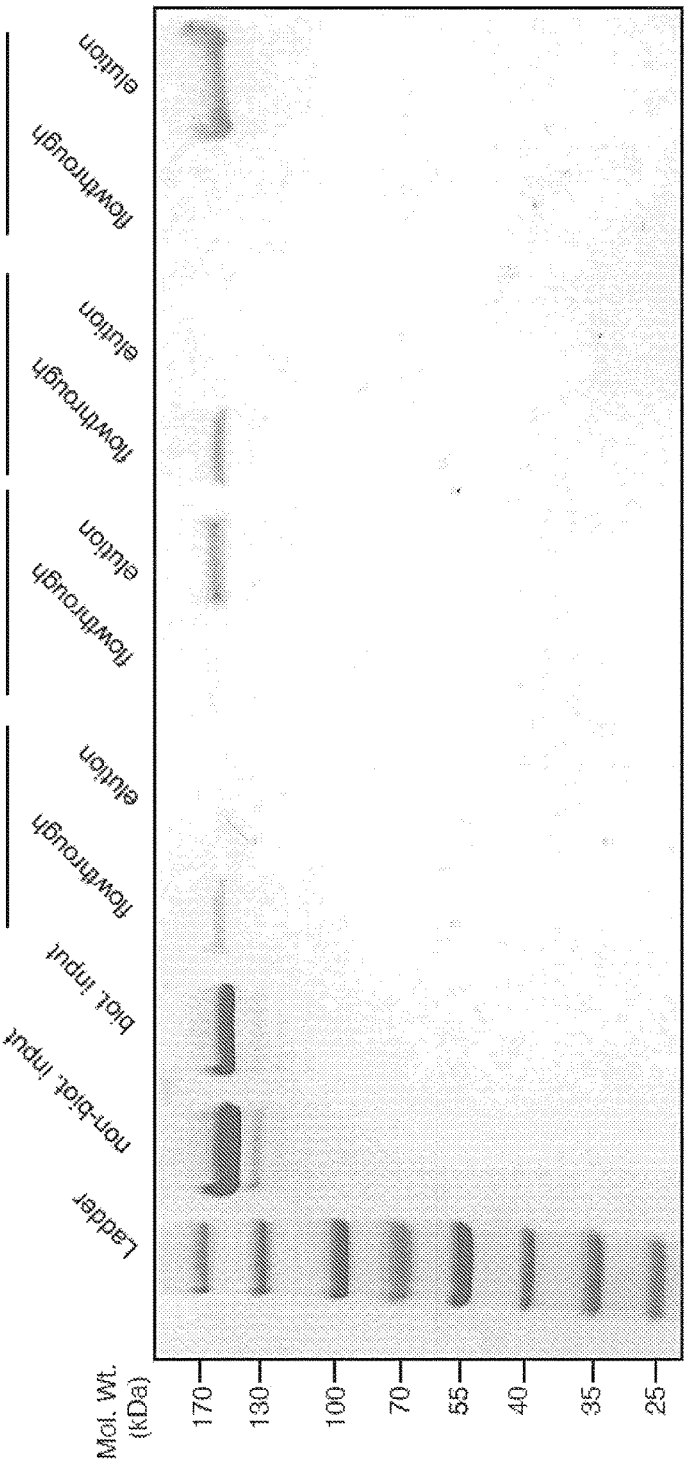
Figure 26D:
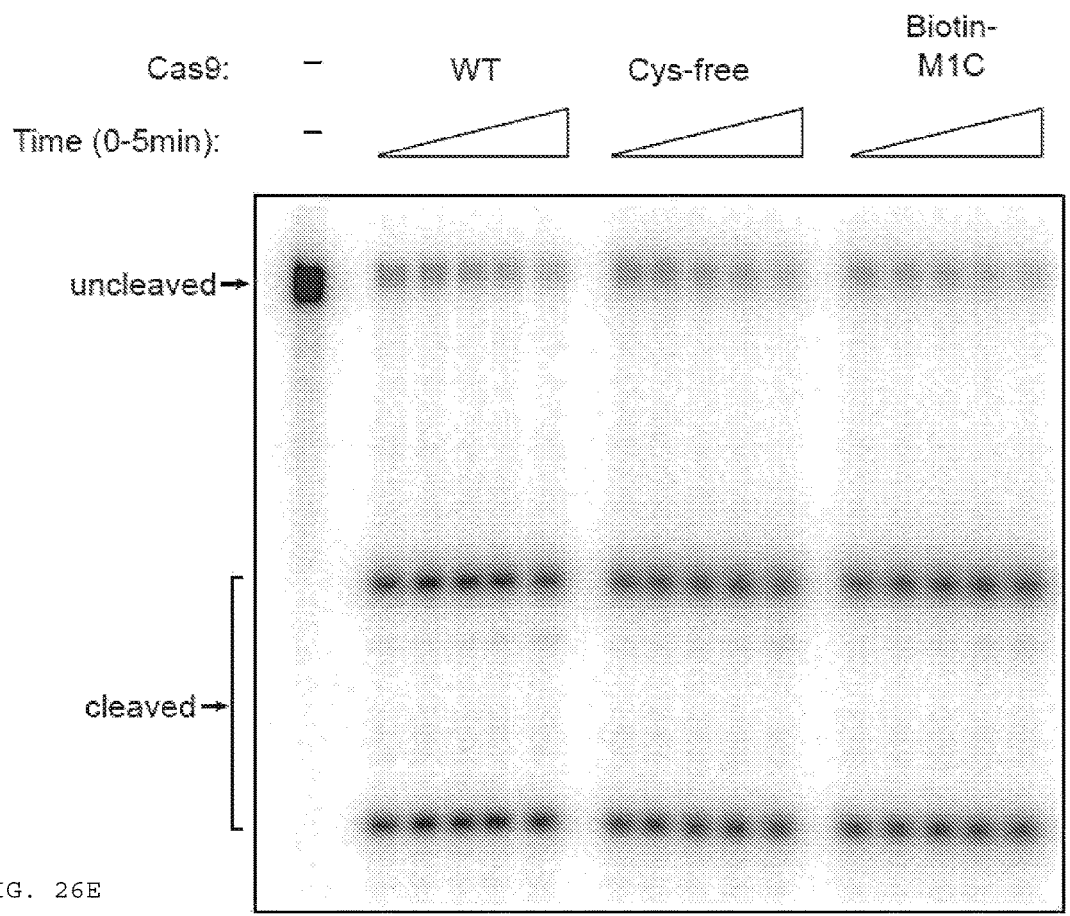
Figure 26E:
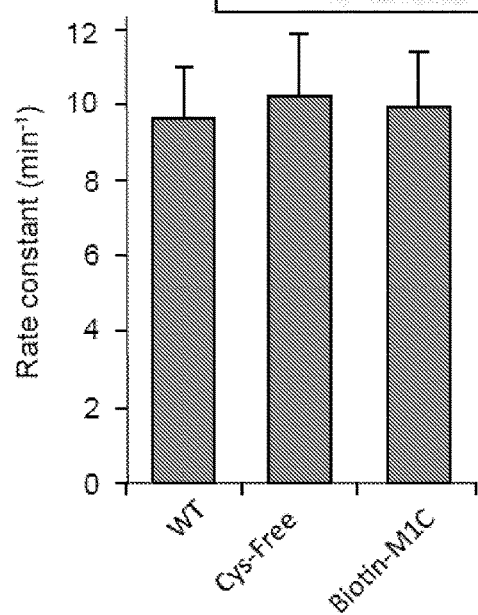

FIG. 26A-26E provides date related to site-specific biotin labelling of Cas9. FIG. 26A, In order to introduce a single biotin moiety on Cas9, the solvent accessible, non-conserved amino-terminal methionine was mutated to a cysteine (M1C; red text) and the naturally occurring cysteine residues were mutated to serine (C80S and C574S; bold text). This enabled cysteine-specific labelling with EZ-link Maleimide-PEG2-biotin through an irreversible reaction between the reduced sulphydryl group of the cysteine and the maleimide group present on the biotin label. Mutations of dCas9 are also indicated in the domain schematic. FIG. 26B, Mass spectrometry analysis of the Cas9 biotin-labelling reaction confirmed that successful biotin labelling only occurred when the M1C mutation was present in the Cys-free background (C80S;C574S). The mass of the Maleimide-PEG2-biotin reagent is 525.6 Da. FIG. 26C, Streptavidin bead binding assay with biotinylated (biot.) or non-biotinylated (non-biot.) Cas9 and streptavidin agarose or streptavidin magnetic beads. Cas9 only remained specifically bound to the beads after biotin labelling. FIG. 26D, Cleavage assays were conducted as described in the Methods and resolved by denaturing PAGE. Reactions contained 100 nM Cas9 programmed with λ2 gRNA and ~1 nM 5'-radiolabelled dsDNA target. FIG. 26E, Quantified cleavage data from triplicate experiments were fitted with single-exponential decays to calculate the apparent pseudo-first-order cleavage rate constants (average±standard deviation). Both Cys-free and biotin-labelled Cas9 (M1C) retained wild-type activity.

Figure 27:
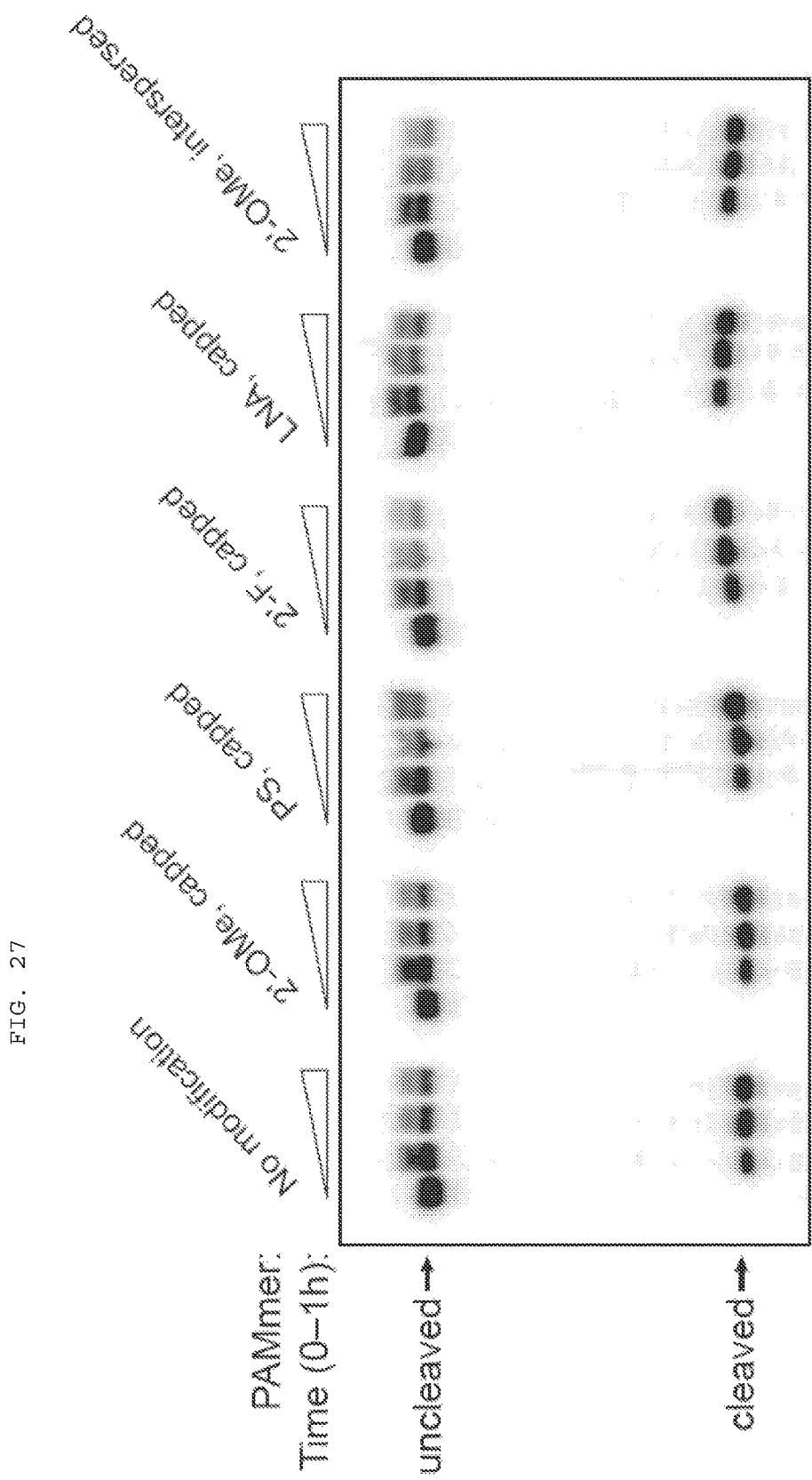
FIG. 27 provides data showing that RNA-guided Cas9 can utilize chemically modified PAMmers.

This approach was then used to isolate endogenous GAPDH transcripts from HeLa cell lysate under physiological conditions. In initial experiments, Cas9-gRNA captured two GAPDH-specific RNA fragments rather than the full-length mRNA (FIG. 21G). Based on the sizes of these bands, it was surmised that RNA-DNA heteroduplexes formed between the mRNA and PAMmer were cleaved by cellular RNaseH. Previous studies have shown that modified DNA oligonucleotides can abrogate RNaseH activity, and it was therefore investigated whether Cas9 would tolerate chemical modifications to the PAMmer. A wide range of modifications (locked nucleic acids, 2'-OMe and 2'-F ribose moieties) still enabled PAMmer-mediated nuclease activation (FIG. 27). Furthermore, by varying the pattern of 2'-OMe modifications in the PAMmer, RNase-H-mediated cleavage could be completely eliminated during the pull-down and intact GAPDH mRNA was successfully isolated (FIG. 21G-21H). Notably, specific isolation of GAPDH mRNA in the absence of any PAMmer occurred, albeit with lower efficiency, suggesting that Cas9-gRNA can bind to GAPDH mRNA through direct RNA-RNA hybridization (FIG. 21F-21G and FIG. 28A-28B). These experiments demonstrate that RNA guided Cas9 can be used to purify endogenous untagged RNA transcripts. In contrast to current oligonucleotide-mediated RNA-capture methods, this approach works well under physiological salt conditions and does not require crosslinking or large sets of biotinylated probes.

FIG. 27 depicts data showing that RNA-guided Cas9 can utilize chemically modified PAMmers. Nineteen-nucleotide PAMmer derivatives containing various chemical modifications on the 5' and 3' ends (capped) or interspersed throughout the strand still activated Cas9 for cleavage of ssRNA targets. These types of modification are often used to increase the in vivo half-life of short oligonucleotides by preventing exo- and endonuclease-mediated degradation. Cleavage assays were conducted as described in the Methods. PS, phosphorothioate bonds; LNA, locked nucleic acid.

Figure 28A:
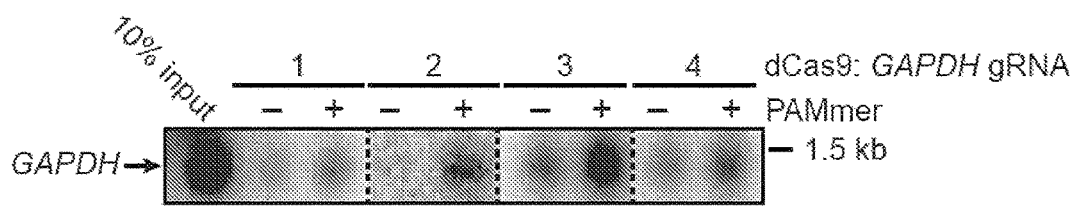
FIG. 28A-28B provide data showing that Cas9 programmed with GAPDH-specific gRNAs can pull down GAPDH mRNA in the absence of PAMmers.
Figure 28B:
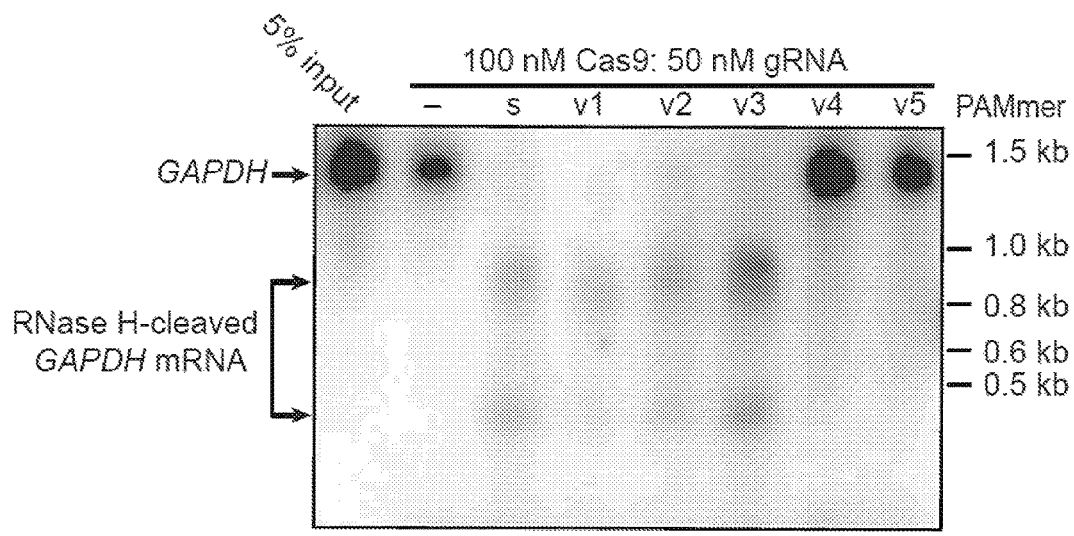

FIG. 28A-28B depicts data showing that Cas9 programmed with GAPDH-specific gRNAs can pull down GAPDH mRNA in the absence of PAMmers. FIG. 28A, Northern blot showing that, in some cases, Cas9-gRNA is able to pull down detectable amounts of GAPDH mRNA from total RNA without requiring a PAMmer. FIG. 28B, Northern blot showing that Cas9-gRNA G1 is also able to pull down quantitative amounts of GAPDH mRNA from HeLa cell lysate without requiring a PAMmer. s, standard; v1-5, increasingly 2'-OMe-modified PAMmers. See FIG. 21G for PAMmer sequences.

The data herein demonstrate the ability to re-direct the dsDNA targeting capability of CRISPR/Cas9 for RNA-guided ssRNA binding and/or cleavage (which can be referred to as RCas9, an RNA-targeting Cas9). Examples of uses for compositions and methods described herein include, but are not limited to those schematized in FIG. 29A-29F. Although certain engineered proteins such as PPR proteins and Pumilio/FBF (PUF) repeats show promise as platforms for sequence-specific RNA targeting, these strategies require re-designing the protein for every new RNA sequence of interest. In contrast to these systems, the molecular basis for RNA recognition by RCas9 is now clear and requires only the design and synthesis of a matching gRNA and complementary PAMmer. The ability to recognize endogenous RNAs within complex mixtures with high affinity and in a programmable manner allows for direct transcript detection, analysis and manipulation without the need for genetically encoded affinity tags.

Figure 29A:
Figure 29B:
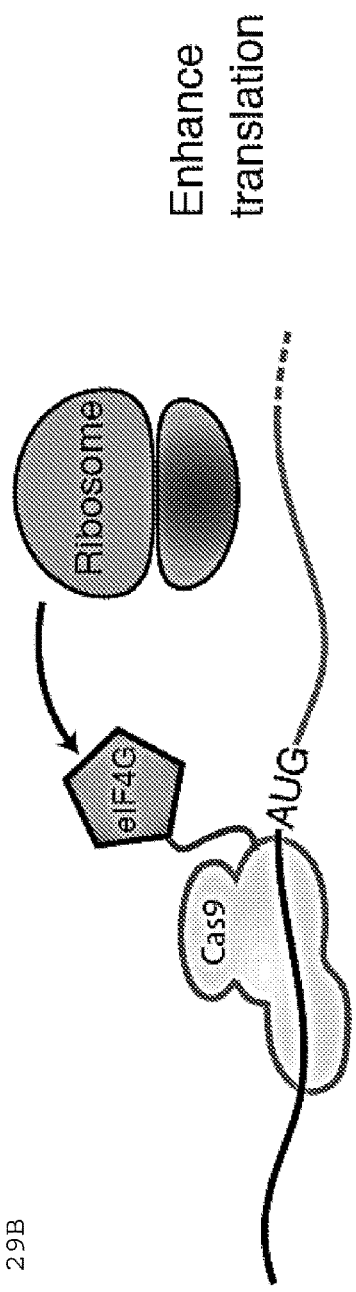
Figure 29C:
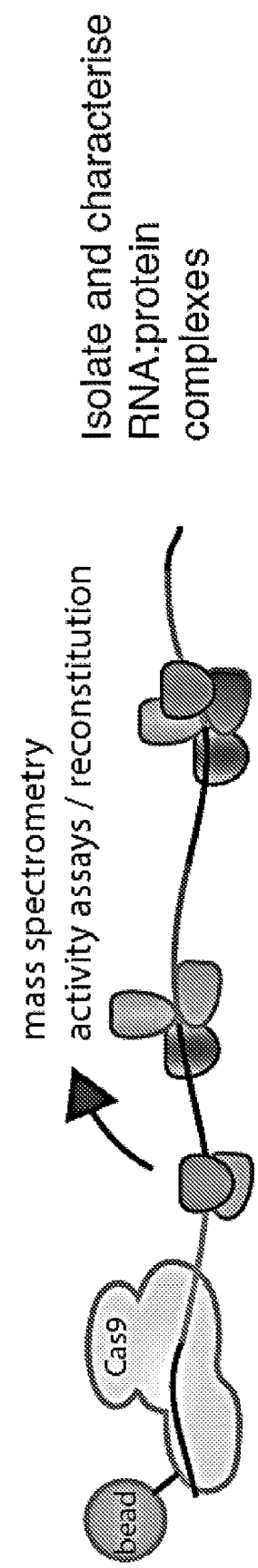

FIG. 29A-29F depicts schematics of example applications of RCas9 (RNA directed Cas9) for untagged transcript analysis, detection and manipulation. FIG. 29A, Catalytically active RCas9 can be used to target and cleave RNA targets, particularly those for which RNA-interference-mediated repression/degradation is not possible. FIG. 29B, Tethering the eukaryotic initiation factor eIF4G to a catalytically inactive dRCas9 targeted to the 5' untranslated region of an mRNA can drive translation. FIG. 29C, dRCas9 tethered to beads can be used to specifically isolate RNA or native RNA-protein complexes of interest from cells for downstream analysis or assays including identification of bound-protein complexes, probing of RNA structure under native protein-bound conditions, and enrichment of rare transcripts for sequencing analysis. FIG. 29D, dRCas9 tethered to RNA deaminase or N6-mA methylase domains could direct site-specific A-to-I editing or methylation of RNA, respectively. FIG. 29E, dRCas9 fused to a U1 recruitment domain (arginine- and serine-rich (RS) domain) can be programmed to recognize a splicing enhancer site and thereby promote the inclusion of a targeted exon. FIG. 29F, dRCas9 tethered to a fluorescent protein such as GFP can be used to observe RNA localization and transport in living cells.

Materials and Methods

Cas9 and Nucleic Acid Preparation

Wild-typeCas9 and catalytically inactive dCas9 (Cas9 (D10A;H840A)) from *S. pyogenes* were purified as previously described (Jinek et al., Science. 2012 Aug. 17; 337 (6096):816-21). Forty two-nucleotide crRNAs were either ordered synthetically (IntegratedDNATechnologies) or transcribed in vitro with T7 polymerase using single-stranded DNA templates. Using the previously described numbering scheme (Jinek et al., Science. 2012 Aug. 17; 337(6096):816-21), tracrRNA was transcribed in vitro and contained nucleotides 15-87. Single-guide RNAs (sgRNAs) targeting 1-RNAs were transcribed in vitro from linearized plasmids and contain full-length crRNA and tracrRNA connected via a GAAA tetraloop insertion. GAPDH mRNA-targeting sgRNAs were transcribed in vitro from dsDNA PCR products. Target ssRNAs (55-56 nucleotides) were transcribed in vitro using single-stranded DNA templates. Sequences of all nucleic acid substrates used in this study can be found in Table 2.

All RNAs were purified using 10-15% denaturing polyacrylamide gel electrophoresis (PAGE). Duplexes of crRNA and tracrRNA were prepared by mixing equimolar concentrations of each RNA in hybridization buffer (20 mM Tris-HCl, pH7.5, 100 mM KCl, 5 mM $MgCl_2$), heating to 95° C. for 30 s and slow cooling. Fully double-stranded DNA/RNA substrates (substrates 1, 8-10 in FIG. 1 and substrates 1 and 2 in FIG. 4A-4B) were prepared by mixing equimolar concentrations of each nucleic acid strand in hybridization buffer, heating to 95° C. for 30 s, and slow cooling. RNA, DNA and chemically modified PAMmers were synthesized commercially (Intergrated DNA Technologies). DNA and RNA substrates were 5'-radiolabelled using $[\gamma\text{-}^{32}P]$ATP (PerkinElmer) and T4 polynucleotide kinase (New England Biolabs). Double-stranded DNA and dsRNA substrates (FIGS. 1c and 4c) were 5'-radiolabelled on both strands, whereas only the target ssRNA was 5'-radiolabelled in other experiments.

Cleavage Assays

Cas9-gRNA complexes were reconstituted before cleavage experiments by incubating Cas9 and the crRNA-tracrRNA duplex for 10 min at 37° C. in reaction buffer (20 mM Tris-HCl, pH7.5, 75 mM KCl, 5 mM $MgCl_2$, 1 mM dithiothreitol (DTT), 5% glycerol). Cleavage reactions were conducted at 37° C. and contained 1 nM 5'-radiolabelled target substrate, 100 nM Cas9-RNA, and 100 nM PAMmer, where indicated. Aliquots were removed at each time point and quenched by the addition of RNA gel-loading buffer (95% deionized formamide, 0.025% (w/v) bromophenol blue, 0.025% (w/v) xylene cyanol, 50 mM EDTA (pH 8.0), 0.025% (w/v) SDS). Samples were boiled for 10 min at 95° C. before being resolved by 12% denaturing PAGE. Reaction products were visualized by phosphorimaging and quantified with ImageQuant (GE Healthcare).

RNA Cleavage Site Mapping.

A hydrolysis ladder (OH2) was obtained by incubating, 25 nM 5'-radiolabelled λ2 target ssRNA in hydrolysis buffer (25 mM CAPS (N-cyclohexyl-3-aminopropanesulphonic acid), pH 10.0, 0.25 mM EDTA) at 95° C. for 10 min, before quenching on ice. An RNase T1 ladder was obtained by incubating, 25 nM 5'-radiolabelled λ2 target ssRNA with 1 U RNase T1 (New England Biolabs) for 5 min at 37° C. in RNase T1 buffer (20 mM sodium citrate, pH 5.0, 1 mM EDTA, 2 M urea, 0.1 mg/ml yeast transfer RNA). The reaction was quenched by phenol/chloroform extraction before adding RNA gel-loading buffer. All products were resolved by 15% denaturing PAGE.

Electrophoretic Mobility Shift Assays.

In order to avoid dissociation of the Cas9-gRNA complex at low concentrations during target ssRNA binding experiments, binding reactions contained a constant excess of dCas9 (300 nM), increasing concentrations of sgRNA, and 0.1-1 nM of target ssRNA. The reaction buffer was supplemented with 10 mg/ml heparin in order to avoid non-specific association of apo-dCas9 with target substrates. Reactions were incubated at 37° C. for 45 min before being resolved by 8% native PAGE at 4° C. (0.53 TBE buffer with 5 mM $MgCl_2$). RNA and DNA were visualized by phosphorimaging, quantified with ImageQuant (GE Healthcare), and analyzed with Kaleidagraph (Synergy Software).

Cas9 Biotin Labelling

To ensure specific labelling at a single residue on Cas9, two naturally occurring cysteine residues were mutated to serine (C80S and C574S) and a cysteine point mutant was introduced at residue Met 1. To attach the biotin moiety, 10 mM wild-type Cas9 or dCas9 was reacted with a 50-fold molar excess of EZ-LinkMaleimide-PEG2-Biotin (Thermo Scientific) at 25° C. for 2h. The reaction was quenched by the addition of 10 mM DTT, and unreacted Maleimide-PEG2-Biotin was removed using a Bio-Gel P-6 column (Bio-Rad). Labelling was verified using a streptavidin bead binding assay, where 8.5 pmol of biotinylated Cas9 or non-biotinylatedCas9 was mixed with either 25 ml streptavidin-agarose (Pierce Avidin Agarose; Thermo Scientific) or 25 ml streptavidin magnetic beads (DynabeadsMyOne StreptavidinCl; Life Technologies). Samples were incubated in Cas9 reaction buffer at room temperature for 30 min, followed by three washes with Cas9 reaction buffer and elution in boiling SDS-PAGE loading buffer. Elutions were analyzed using SDS-PAGE. Cas9 M1C biotinylation was also confirmed using mass spectroscopy performed in the QB3/ChemistryMass Spectrometry Facility at UC Berkeley. Samples of intact Cas9 proteins were analyzed using an Agilent 1200 liquid chromatograph equipped with a Viva C8 (100 mm 31 0 mm, 5 mm particles, Restek) analytical column and connected in-line with an LTQOrbitrapXLmass spectrometer (Thermo Fisher Scientific). Mass spectra were recorded in the positive ionmode. Mass spectral deconvolution was performed using ProMass software (Novatia).

GAPDH mRNA Pull-Down

Total RNAwas isolated from HeLa-S3 cells using Trizol reagent according to the manufacturer's instructions (Life Technologies). Cas9-sgRNA complexes were reconstituted before pull-down experiments by incubating a twofold molar excess of Cas9 with sgRNA for 10 min at 37° C. in reaction buffer. HeLa total RNA (40 μg) or HeLa lysate (~5×10$^6$ cells) was added to reaction buffer with 40U RNasin (Promega), PAMmer (5 mM) and the biotin-dCas9 (50 nM)-sgRNA (25 nM) in a total volume of 100 ml and incubated at 37° C. for 1 h. This mixture was then added to 25 ml magnetic streptavidin beads (Dynabeads MyOne Streptavidin C1; Life Technologies) pre-equilibrated in reaction buffer and agitated at 4° C. for 2 h. Beads were then washed six times with 300 ml wash buffer (20mMTris-HCl, pH7.5, 150 mM NaCl, 5 mM $MgCl_2$, 0.1% Triton X-100, 5% glycerol, 1 mM DTT, 10 mg/ml heparin) Immobilized RNA was eluted by heating beads at 70° C. in the presence of DEPC-treated water and a phenol/chloroform mixture. Eluates were then treated with an equal volume of glyoxal loading dye (Life Technologies) and heated at 50° C. for 1 h before separation via 1% BPTE agarose gel (30 mM Bis-Tris, 10 mM PIPES, 10 mM EDTA, pH 6.5). Following Northern blot transfers, membranes were crosslinked using UV radiation and incubated in pre-hybridization buffer (UltraHYB Ultrasensitive Hybridization Buffer; Life Technologies) for 1 h at 46° C. before hybridization. Radioactive northern probes were synthesized using random priming of GAPDH and β-actin partial cDNAs (for cDNA primers, see Table 2) in the presence of [α-$^{32}$P]dATP (PerkinElmer), using a Prime-It II Random Primer Labelling kit (Agilent Technologies). Hybridization was carried out for 3 h in pre-hybridization buffer at 46° C. followed by two washes with 23×SSC (300 mM NaCl, 30 mM trisodiumcitrate, pH 7, 0.5% (w/v) SDS) for 15 min at 46° C. Membranes were imaged using a phosphorscreen.

TABLE 2

RNA and DNA substrates used in Example 5 (all sequence are 5' to 3' unless otherwise denoted).

| Description | Sequence[a] | Used in: | SEQ ID NO: |
|---|---|---|---|
| Oligo for preparing dsDNA T7 promoter, in vitro transcription | TAATACGACTCACTATA | NA | 1404 |
| λ2-targeting crRNA | GUGAUAAGUGGAAUGCCAUGGUUUUAGAGCUAUGCUGUUUUG | FIG. 18C-E, 20A, 21C-D, 22, 23, 25A | 1407 |
| λ3-targeting crRNA | CUGGUGAACUUCCGAUAGUGGUUUUAGAGCUAUGCUGUUUUG | FIG. 20A | 1408 |
| λ4-targeting crRNA | CAGATATAGCCTGGTGGTTCGUUUUAGAGCUAUGCUGUUUUG | FIG. 20A | 1409 |
| ssDNA T7 template[b]: tracrRNA | AAAAAGCACCGACTCGGTGCCACTTTTTCAAGTTGATAACGGACTAGCCTTATTTTAACTTGCTATGCTGTCCTATAGTGAGTCGTATTA | NA | 1415 |

TABLE 2-continued

RNA and DNA substrates used in Example 5 (all sequence are 5' to 3' unless otherwise denoted).

| Description | Sequence[a] | Used in: | SEQ ID NO: |
|---|---|---|---|
| tracrRNA (nt 15-87) | GGACAGCAUAGCAAGUUAAAAUAAGGCUAGUCCGUUAUCAACUUGAAAAAGUGGCACCGAGUCGGUGCUUUUU | FIG. 18C-E, 20A, 21C-D, 22, 23, 25A | 1416 |
| λ2-targeting sgRNA T7 template[c] | TAATACGACTCACTATAGGTGATAAGTGGAATGCCATGGTTTTAGAGCTATGCTGTTTTGGAAACAAAACAGCATAGCAAGTTAAAATAAGGCTAGTCCGTTATCAACTTGAAAAAGTGGCACCGAGTCGGTGCTTTTTTT | NA | 1479 |
| λ2-targeting sgRNA | GGUGAUAAGUGGAAUGCCAUGGUUUUAGAGCUAUGCUGUUUUGGAAACAAAACAGCAUAGCAAGUUAAAAUAAGGCUAGUCCGUUAUCAACUUGAAAAAGUGGCACCGAGUCGGUGCUUUUUUU | FIG. 19, 20B, D, 24, 25B | 1480 |
| λ2 target dsDNA duplex | 5'-GAGTGGAAGGATGCCAGTGATAAGTGGAATGCCATGTGGGCTGTCAAAATTGAGC-3' 3'-CTCACCTTCCTACGGTCACTATTCACCTTACGGTACACCCGACAGTTTTAACTCG-5' | FIG. 18C, 19A, 25C | 1419 1420 |
| λ2 ssDNA target strand (used to make heteroduplex DNA:RNA) | 3'-CTCACCTTCCTACGGTCACTATTCACCTTACGGTACACCCGACAGTTTTAACTCG-5' | FIG. 18C, 19A, | 1481 |
| λ2 ssDNA non-target strand (used to make heteroduplex DNA:RNA) | GAGTGGAAGGATGCCAGTGATAAGTGGAATGCCATGTGGGCTGTCAAAATTGAGC | FIG. 18C, 19, 20D, 24 | 1463 |
| λ2 ssRNA target strand T7 template | GAGTGGAAGGATGCCAGTGATAAGTGGAATGCCATGTGGGCTGTCAAAATTGAGCCTATAGTGAGTCGTATTA | NA | 1482 |
| λ2 ssRNA target strand | 3'-CUCACCUUCCUACGGUCACUAUUCACCUUACGGUACACCCGACAGUUUUAACUCGG-5' | FIG. 18C-E, 19-25 | 1483 |
| λ2 ssRNA non-target strand T7 template | GCTCAATTTTGACAGCCCACATGGCATTCCACTTATCACTGGCATCCTTCCACTCCTATAGTGAGTCGTATTA | NA | 1484 |
| λ2 ssRNA non-target strand (used to make dsRNA) | GGAGUGGAAGGAUGCCAGUGAUAAGUGGAAUGCCAUGUGGGCUGUCAAAAUUGAGC | FIG. 18C, 19A | 1485 |
| 19 at λ2 DNA PAMmer | TGGGCTGTCAAAATTGAGC | FIG. 18C-E, 19, 20A-B, 22-25 | 1466 |
| 18 nt λ2 "GG" PAMmer | GGGCTGTCAAAATTGAGC | FIG. 18C, 19 | 1486 |
| 19 nt λ2 DNA mutated PAMmer | ACCGCTGTCAAAATTGAGC | FIG. 18C, 19C | 1487 |
| 16 nt λ2 DNA "PAM-less" PAMmer | GCTGTCAAAATTGAGC | FIG. 18C, 19C | 1465 |
| 18 nt λ2 RNA PAMmer | GGGCUGUCAAAAUUGAGC | FIG. 18C, 19A | 1488 |

TABLE 2-continued

RNA and DNA substrates used in Example 5 (all sequence are 5' to 3' unless otherwise denoted).

| Description | Sequence<sup>a</sup> | Used in: | SEQ ID NO: |
|---|---|---|---|
| 5 nt λ2 DNA PAMmer | TGGGC | FIG. 18E, 19C | |
| 10 nt λ2 DNA PAMmer | TGGGCTGTCA | FIG. 18E, 19C | 1489 |
| 15 nt λ2 DNA PAMmer | TGGGCTGTCAAAATT | FIG. 18E, 19C | 1490 |
| λ3 ssRNA target strand T7 template | AACGTGCTCCGGCTGGTGGTGAACTTCCG ATAGTGCGGGTGTTGAATGATTTCCTATAG TGAGTCGTATTA | NA | 1491 |
| λ3 ssRNA target strand | 3'-UUGCACGACGCCGACCGACCACUUGAAG GCUAUCACGCCCACAACUUACUAAAGG-5' | FIG. 20A, B, D, 24, 25B | 1492 |
| λ4 ssRNA target strand T7 template | TCACAACAATGAGTGGCAGATATAGCCTGG TGGTTCAGGCGGCGCATTTTTATTGCCTAT AGTGAGTCGTATTA | NA | 1493 |
| λ4 ssRNA target strand | 3'-AGUGUUGUUACUCACCGUCUAUAUCGGA CCACCAAGUCCGCCGCGUAAAAAUAACG G-5' | FIG. 20A, B, D, 24 | 1494 |
| λ3 ssDNA non-target strand | AACGTGCTGCGCiCTGGCTGGTGAACTTCCG ATAGTGCGGGTGTTGAATGATTTCC | FIG. 20D, 24 | 1421 |
| λ4 ssDNA non-target strand | TCACAACAATGAGTGGCAGATATAGCCTGG TGGTTCAGGCGGCGCATTTTTATTG | FIG. 20D, 24 | 1423 |
| 19 nt λ3 DNA PAMmer | CGGGTGTTGAATGATTTCC | FIG. 20A, B, D, 24, 25 | 1495 |
| 19 nt λ4 DNA PAMmer | AGGCGGCGCATTTTTATTG | FIG. 20A, B, D, 24 | 1496 |
| 21 nt λ2 5'-extended DNA PAMmer | TGTGGGCTGTCAAAATTGAGC | FIG. 21C, 25A, B | 1497 |
| 21 nt λ3 5'-extended DNA PAMmer | TGCGGGTGTTGAATGATTTCC | 25B | 1498 |
| 24 nt λ2 5'-extended DNA PAMmer | CCATGTGGGCTGTCAAAATTGAGC | 25A, B | 1499 |
| 24 nt λ3 5'-extended DNA PAMmer | TAGTGCGGGTGTTGAATGATTTCC | 25B | 1500 |
| 27 nt λ2 5'-extended DNA PAMmer | ATGCCATGTGGGCTGTCAAAATTGAGC | FIG. 21F, G, 25A, B | 1501 |
| 27 nt λ3 5'-extended DNA PAMmer | CGATAGTGCGGGTGTTGAATGATTTCC | 25B | 1502 |

TABLE 2-continued

RNA and DNA substrates used in Example 5 (all sequence are 5' to 3' unless otherwise denoted).

| Description | Sequence[a] | Used in: | SEQ ID NO: |
|---|---|---|---|
| 30 nt λ2 5'-extended DNA PAMmer | GGAATGCCATGTGGGCTGTCAAAATTGAGC | 25A, B | 1503 |
| 30 nt λ3 5'-extended DNA PAMmer | TTCCGATAGTGCGGGTGTTGAATGATTTCC | 25B | 1504 |
| 33 nt λ2 5'-extended DNA PAMmer | AGTGGAATGCCATGTGGGCTGTCAAAATTGAGC | 25A, B | 1505 |
| 33 nt λ3 5'-extended DNA PAMmer | AACTTCCGATAGTGCGGGTGTTGAATGATTTCC | 25B | 1506 |
| 36 nt λ2 5'-extended DNA PAMmer | ATAAGTGGAATGCCATGTGGGCTGTCAAAATTGAGG | 25A | 1507 |
| 39 nt λ2 5'-extended DNA PAMmer | GTGATAAGTGGAATGCCATGTGGGCTGTCAAAATTGAGC | 25A, B | 1508 |
| 39 nt λ3 5'-extended DNA PAMmer | CTGGTGAACTTCCGATAGTGCGGGTGTTGAATGATTTGC | 25B | 1509 |
| non-PAM λ2 dsDNA | 5'-GAGTGGAAGGATGCCAGTGATAAGTGGAATGCCATGACCCCTGTCAAAATTGAGC-3'<br>3'-CTCACCTTCCTACGGTCACTATTCACCTTACGGTACTGGCGACAGTTTTAACTCG-5' | FIG. 21C | 1510<br>1511 |
| non-PAM λ2 ssRNA target strand T7 template | GAGTGGAAGGATGCCAGTGATAAGTGGAATGCCATGACCGCTGTCAAAATTGAGCCTATAGTGAGTCGTATTA | NA | 1512 |
| non-PAM λ2 ssRNA target strand | 3'-CUCACCUUCCUACGGUCACUAUUCACCUUACGGUACUGGCGACAGUUUUAACUCGG-5' | FIG. 21C | 1513 |
| λ2 2'OMe capped PAMmer[d] | *UGGGCTGTCAAAATTGAG *C | 27 | 1514 |
| λ2 PS capped PAMmer[d] | **T*GG**GCTGTCAAAATTGAG*C | 27 | 1515 |
| λ2 2'F capped PAMmer[d] | *UGGGCTGTCAAAATTGAG*C | 27 | 1516 |
| λ2 LNA capped PAMmer[d] | *TGGGCTGTGAAAATTGAG*C | 27 | 1517 |
| λ2 19 nt 2'OMe interspersed PAMmer[d] | *UGGGC*UGTCA*AAATT*GAG*C | 27 | 1518 |

TABLE 2-continued

RNA and DNA substrates used in Example 5 (all sequence are 5' to 3' unless otherwise denoted).

| Description | Sequence[a] | Used in: | SEQ ID NO: |
|---|---|---|---|
| GAPDH-targeting sgRNA 1 T7 template[e] | TAATACGACTCACTATAGGGGCAGAGATG ATGACCCTGTTTAAGAGCTATGGTGGAAAC AGCATAGCAAGTTTAAATAAGGCTAGTCCG TTATCAAGTTGAAAAAGTGGCACGGAGTCG GTGCTTTTTTT | FIG. 21F, G, 28 | 1519 |
| GAPDH-targeting sgRNA 1 | GGGGCAGAGAUGAUGACCCUGUUUAAGA GCUAUGCUGGAAACAGCAUAGCAAGUUUA AAUAAGGCUAGUCCGUUAUCAACUUGAAA AAGUGGCACCGAGUCGGUGCUUUUUUU | FIG. 21F, G, 28 | 1520 |
| GAPDH-targeting sgRNA 2 T7 template[e] | TAATACGACTCACTATAGGCCAAAGTTGT CATGGATGACGTTTAAGAGCTATGCTGGAA ACAGGATAGCAAGTTTAAATAAGGCTAGTC CGTTATCAACTTGAAAAAGTGGCACCGAGT CGGTGCTTTTTTT | FIG. 21F, 28 | 1521 |
| GAPDH-targeting sgRNA 2 | GGCCAAAGUUGUCAUGGAUGACGUUUAA GAGCUAUGCUGGAAACAGCAUAGCAAGUU UAAAUAAGGCUAGUCCGUUAUCAACUUGA AAAGUGGCACCGAGUCGGUGCUUUUUUU | FIG. 21F, 28 | 1522 |
| GAPDH-targeting sgRNA 3 T7 template[e] | TAATACGACTCACTATAGGCCAAAGTTGT CATGGATGACGTTTAAGAGCTATGCTGGAA ACAGCATAGCAAGTTTAAATAAGGCTAGTC CGTTATCAACTTGAAAAAGTGGCACCGAGT CGGTGCTTTTTTT | FIG. 2IF, 28 | 1521 |
| GAPDH-targeting sgRNA 3 | GGAUGUCAUCAUAUUUGGCAGOGUUUAA GAGCUAUGCUGGAAACAGCAUAGCAAGUU UAAAUAAGGCUAGUCCGUUAUCAACUUGA AAAGlJGGCACCGAGUCGGUGCUUUUUUUU | FIG. 2IF, 28 | 1523 |
| GAPDH-targeting sgRNA 4 T7 template[e] | TAATACGACTCACTATAGGATGTCATCAT ATTTGGCAGGGTTTAAGAGCTATGCTGGAA ACAGCATAGCAAGTTTAAATAAGGCTAGTC CGTTATCAACTTGAAAAAGTGGCACCGAGT CGGTGCTTTTTTT | FIG. 21F, 28 | 1524 |
| GAPDH-targeting sgRNA 4 | GGATGTCATCATATTTGGCAGGGTTTAAGA GCTATGCTGGAAACAGCATAGCAAGTTTAA ATAAGGCTAGTCCGTTATCAACTTGAAAAA GTGGCACCGAGTCGGTGCTTTTTTT | FIG. 21F, 28 | 1525 |
| GAPDH PAMmer 1 | ATGACCCTTGGGGCTCCCCCCTGCAAA | FIG. 21, F, G, 28 | 1526 |
| GAPDH PAMmer 2 | TGGATGACCGGGGCCAGGGGTGCTAAG | FIG. 21F, 28 | 1527 |
| GAPDH PAMmer 3 | TTGGCAGGTGGTTCTAGACGGCAGGTC | FUG. 21F, 28 | 1528 |
| GAPDH PAMmer 4 | CCCCAGCGTGGAAGGTGGAGGAGTGGG | FIG. 21F. 28 | 1529 |
| GAPDH PAMmer 1 2'OMe v1 | A*UGACC*CTAGG*GGCTC*CCCCC*UGCAA *A | FIG. 21G, 28 | 1474 |
| GAPDH PAMmer 1 2'OMe v2 | *ATG*ACCC*UAGG*GGCT*CCCC*CCTG*CA A*A | FIG. 21G, 28 | 1475 |
| GAPDH PAMmer 1 2'OMe v3 | *ATG*ACC*CU*AGG*GGC*UCC*CCC*CTG* CAA*A | FIG. 21G, 28 | 1476 |
| GAPDH PAMmer 1 2'OMe v4 | *AT*GA*CC*CT*AGG*GG*CT*CC*CC*CC*U G*CA*AA | FIG. 21G, 28 | 1477 |

TABLE 2-continued

RNA and DNA substrates used in Example 5 (all sequence are 5' to 3' unless otherwise denoted).

| Description | Sequence$^a$ | Used in: | SEQ ID NO: |
|---|---|---|---|
| GAPDH PAMmer 1 2'OMe v5 | *AT*GA*CC*CT*AG*GG*GC*TC*CC*CC*CU*GC*AA*A | FIG. 21G, 28 | 1530 |
| GAPDH cDNA primer Fwd | CTCACTGTTCTCTCCCTCCGC | FIG. 21G, F | 1531 |
| GAPDH cDNA primer Rev | AGGGGTCTACATGGCAACTG | FIG. 21G, F | 1532 |
| β-actin cDNA primer Fwd | AGAAAATCTGGCACCACACC | FIG. 21G, F | 1533 |
| β-actin cDNA primer Rev | GGAGTACTTGCGCTCAGGAG | FIG. 21G, F | 1534 |

*Guide crRNA sequences and complementary DNA target strand sequences are shown in red. PAM sites (5'-NGG-3') are highlighted in yellow on the non-target strand when adjacent to the target sequence or in the PAMmer oligonucleotides.
†The T7 promoter is indicated in bold (or reverse complement of), as well as 5' G or GG included in the ssRNA product by T7 polymerase.
NA, not applicable.
‡ sgRNA template obtained from pIDT, subsequently linearised by AflII for run-off transcription.
§ Positions of modifications depicted with asterisks preceding each modified nucleotide in each case (except for PS linkages which are depicted between bases)
PS: phosphorothioate bond
LNA: locked nucleic acid While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10494620B2). An electronic copy of the "Sequence Listing" will also be available from the USPTO upon request and payment of the fee set forth in 37 CFR 1.19(b)(3).

What is claimed is:

1. A method of binding a single-stranded-target RNA without cleaving the single-stranded target RNA, the method comprising:
   contacting the single stranded target RNA with:
   (a) a variant Cas9 polypeptide comprising one or more amino acid substitutions in the HNH domain such that the variant Cas9 polypeptide binds but does not cleave the single-stranded target RNA; and
   (b) a guide nucleic acid that comprises: i) a first segment that comprises a nucleotide sequence that is complementary to a first target sequence in the single stranded target RNA; and ii) a second segment that forms a double-stranded RNA duplex and interacts with the variant Cas9 polypeptide,
   wherein the first segment is 5' of the second segment, and wherein said contacting produces a variant-Cas9/target complex.

2. The method according to claim 1, further comprising contacting the single-stranded target RNA with a PAMmer, wherein the PAMmer is a single stranded oligonucleotide comprising:
   (a) a protospacer adjacent motif (PAM) sequence, and
   (b) at least one of:
      (i) an orientation segment, positioned 3' of the PAM sequence, comprising a nucleotide sequence that is complementary to a second target nucleotide sequence in the single stranded target RNA; and
      (ii) a specificity segment, positioned 5' of the PAM sequence, comprising a nucleotide sequence that is complementary to said first target nucleotide sequence.

3. The method according to claim 2, wherein the PAMmer comprises a detectable label.

4. The method according to claim 2, wherein the PAMmer comprises the orientation segment and the specificity segment.

5. The method according to claim 1, wherein the one or more amino acid substitutions are substitutions of one or both of an amino acid corresponding to H840 of SEQ ID NO:8 and D10 of SEQ ID NO:8.

6. The method according to claim 1, wherein said one or more amino acid substitutions include at least one of:
   (i) an H to A substitution at an amino acid position that corresponds to position H840 of SEQ ID NO: 8;
   (ii) D to A and H to A substitutions at amino acid positions that correspond to position D10 and H840, respectively, of SEQ ID NO: 8.

7. The method according to claim 1, wherein the variant Cas9 polypeptide comprises a detectable label.

8. The method according to claim 7, wherein the detectable label of the variant Cas9 polypeptide is a directly detectable label.

9. The method according to claim 7, wherein the detectable label of the variant Cas9 polypeptide is an indirectly detectable label.

10. The method according to claim 7, wherein the detectable label is a fluorescent protein.

11. The method according to claim 7, wherein the detectable label is a fluorescent dye.

12. The method according to claim 1, wherein the guide nucleic acid comprises a detectable label.

13. The method according to claim 12, wherein the detectable label of the guide nucleic acid is a directly detectable label.

14. The method according to claim 12, wherein the detectable label of the guide nucleic acid is an indirectly detectable label.

15. The method according to claim 12, wherein the detectable label of the guide nucleic acid is a nucleotide sequence that specifically binds a labeling protein.

16. The method according to claim 1, wherein the variant Cas9 polypeptide comprises a fusion partner with an enzymatic activity, and wherein the single stranded target RNA is modified as a result of said contacting.

17. The method according to claim 1, further comprising:
   isolating the variant-Cas9/target complex;
   releasing the single stranded target RNA from the variant-Cas9/target complex; and
   collecting and/or analyzing the released single stranded target RNA and/or a polypeptide that may be associated with the single stranded target RNA.

18. The method according to claim 1, wherein the target ssRNA is selected from: mRNA, rRNA, tRNA, non-coding RNA (ncRNA), long non-coding RNA (lncRNA), and microRNA (miRNA).

19. The method according to claim 1, wherein the single stranded target RNA is a viral RNA.

20. The method according to claim 1, wherein said contacting is in a cell in vitro or ex vivo.

21. The method according to claim 1, wherein said contacting is in a cell in vivo.

22. The method according to claim 1, wherein the guide nucleic acid is a single guide RNA.

* * * * *